US010967057B2

(12) United States Patent
Yu et al.

(10) Patent No.: US 10,967,057 B2

(45) Date of Patent: Apr. 6, 2021

(54) ZIKA VIRAL ANTIGEN CONSTRUCTS

(71) Applicant: GlaxoSmithKline Biologicals, S.A., Rixensart (BE)

(72) Inventors: Dong Yu, Rockville, MD (US); Mayuri Sharma, Rockville, MD (US)

(73) Assignee: GLAXOSMITHKLINE BIOLOGICALS S.A., Rixensart (BE)

(*) Notice: Subject to any disclaimer, the term of this patent is extended or adjusted under 35 U.S.C. 154(b) by 0 days.

(21) Appl. No.: 16/306,081

(22) PCT Filed: Jun. 1, 2017

(86) PCT No.: PCT/IB2017/053242

§ 371 (c)(1),
(2) Date: Nov. 30, 2018

(87) PCT Pub. No.: WO2017/208191

PCT Pub. Date: Dec. 7, 2017

(65) Prior Publication Data

US 2019/0134184 A1 May 9, 2019

Related U.S. Application Data

(60) Provisional application No. 62/485,081, filed on Apr. 13, 2017, provisional application No. 62/394,769, filed on Sep. 15, 2016, provisional application No. 62/344,417, filed on Jun. 2, 2016.

(51) Int. Cl.

| | |
|---|---|
| ***A61K 39/12*** | (2006.01) |
| ***A61K 39/39*** | (2006.01) |
| ***C12N 15/85*** | (2006.01) |
| ***C12N 15/86*** | (2006.01) |
| ***C07K 14/18*** | (2006.01) |
| ***A61P 31/14*** | (2006.01) |
| *A61K 39/00* | (2006.01) |

(52) U.S. Cl.

CPC .............. *A61K 39/12* (2013.01); *A61K 39/39* (2013.01); *A61P 31/14* (2018.01); *C07K 14/1825* (2013.01); *C12N 15/85* (2013.01); *C12N 15/86* (2013.01); *A61K 2039/53* (2013.01); *A61K 2039/55555* (2013.01); *A61K 2039/55566* (2013.01); *C12N 2770/24134* (2013.01); *C12N 2770/36134* (2013.01); *C12N 2770/36143* (2013.01); *C12N 2770/36144* (2013.01); *Y02A 50/30* (2018.01)

(58) Field of Classification Search

None

See application file for complete search history.

(56) References Cited

U.S. PATENT DOCUMENTS 10,124,055 B2 * 11/2018 Ciaramella ............ A61K 48/00

* cited by examiner

*Primary Examiner* — Benjamin P Blumel

(74) *Attorney, Agent, or Firm* — Birch, Stewart, Kolasch & Birch, LLP

(57) ABSTRACT

Compounds useful as components of immunogenic compositions for the induction of an immunogenic response in a subject against viral infection, methods for their use in treatment, and processes for their manufacture are provided herein. The compounds comprise a nucleic acid construct comprising a sequence which encodes a Zika virus antigen. A particular embodiment is a nucleic acid-based vaccine construct encoding a polypeptide comprising a full-length Zika virus prME antigen. A particular embodiment is a self-replicating RNA molecule comprising a construct encoding a polypeptide comprising a full-length Zika virus prME antigen.

23 Claims, 16 Drawing Sheets

Figure 1:
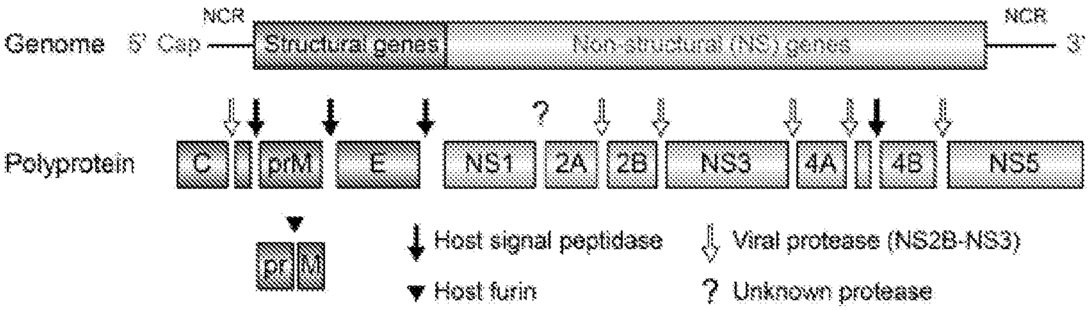

Specification includes a Sequence Listing.

FIG.3A

```
                ◄──────────────────────────────────Capsid(C)──────────────
Uganda          MKNPKEEIRRIRIVNMLKRGVARVNPLGGLKRLPAGLLLGHGPIRMVLAILAFLRFTAIK  60
Micronesia      MKNPKEEIRRIRIVNMLKRGVARVSPFGGLKRLPAGLLLGHGPIRMVLAILAFLRFTAIK  60
Natal           MKNPKKKSGGFRIVNMLKRGVARVSPFGGLKRLPAGLLLGHGPIRMVLAILAFLRFTAIK  60
Salvador        MKNPKKKSGGFRIVNMLKRGVARVSPFGGLKRLPAGLLLGHGPIRMVLAILAFLRFTAIK  60
KU365777        MKNPKKKSGGFRIVNMLKRGVARVSPFGGLKRLPAGLLLGHGPIRMVLAILAFLRFTAIK  60
KU365778        MKNPKKKSGGFRIVNMLKRGVARVSPFGGLKRLPAGLLLGHGPIRMVLAILAFLRFTAIK  60
KU365779        MKNPKKKSGGFRIVNMLKRGVARVSPFGGLKRLPAGLLLGHGPIRMVLAILAFLRFTAIK  60
KU365780        MKNPKKKSGGFRIVNMLKRGVARVSPFGGLKRLPAGLLLGHGPIRMVLAILAFLRFTAIK  60
French          MKNPKKKSGGFRIVNMLKRGVARVSPFGGLKRLPAGLLLGHGPIRMVLAILAFLRFTAIK  60
Sao             MKNPKKKSGGFRIVNMLKRGVARVSPFGGLKRLPAGLLLGHGPIRMVLAILAFLRFTAIK  60
                *****::   :*************.*:*********************************

                ───────────────Capsid(C) ─────────────────►◄─prM Signal Sequence
Uganda          PSLGLINRWGSVGKKEAMEIIKKFKKDLAAMLRIINARKERKRRGADTSIGIIGLLLTTA  120
Micronesia      PSLGLINRWGSVGKKEAMEIIKKFKKDLAAMLRIINARKEKKRRGTDTSVGIVGLLLTTA  120
Natal           PSLGLINRWGSVGKKEAMEIIKKFKKDLAAMLRIINARKEKKRRGADTSVGIVGLLLTTA  120
Salvador        PSLGLINRWGSVGKKEAMEIIKKFKKDLAAMLRIINARKEKKRRGADTSVGIVGLLLTTA  120
KU365777        PSLGLINRWGSVGKKEAMEIIKKFKKDLAAMLRIINARKEKKRRGADTSVGIVGLLLTTA  120
KU365778        PSLGLINRWGSVGKKEAMEIIKKFKKDLAAMLRIINARKEKKRRGADTSVGIVGLLLTTA  120
KU365779        PSLGLINRWGSVGKKEAMEIIKKFKKDLAAMLRIINARKEKKRRGADTSVGIVGLLLTTA  120
KU365780        PSLGLINRWGSVGKKEAMEIIKKFKKDLAAMLRIINARKEKKRRGADTSVGIVGLLLTTA  120
French          PSLGLINRWGSVGKKEAMEIIKKFKKDLAAMLRIINARKEKKRRGADTSVGIVGLLLTTA  120
Sao             PSLGLINRWGSVGKKEAMEIIKKFKKDLAAMLRIINARKEKKRRGADTSVGIVGLLLTTA  120
                ****************************************:****:***:**:*******

                ─►◄──────────────────────────────Pre-Membrane(prM)────────
Uganda          MAAEITRRGSAYYMYLDRSDAGKAISFATTLGVNKCHVQIMDLGHMCDATMSYECPMLDE  180
Micronesia      MAVEVTRRGSAYYMYLDRSDAGEAISFPTTLGMNKCYIQIMDLGHMCDATMSYECPMLDE  180
Natal           MAAEVTRRGSAYYMYLDRNDAGEAISFPTTLGMNKCYIQIMDLGHMCDATMSYECPMLDE  180
Salvador        MAAEVTRRGSAYYMYLDRNDAGEAISFPTTLGMNKCYIQIMDLGHMCDATMSYECPMLDE  180
KU365777        MAAEVTRRGSAYYMYLDRNDAGEAISFPTTLGMNKCYIQIMDLGHMCDATMSYECPMLDE  180
KU365778        MAAEVTRRGSAYYMYLDRNDAGEAISFPTTLGMNKCYIQIMDLGHMCDATMSYECPMLDE  180
KU365779        MAAEVTRRGSAYYMYLDRNDAGEAISFPTTLGMNKCYIQIMDLGHMCDATMSYECPMLDE  180
KU365780        MAAEVTRRGSAYYMYLDRNDAGEAISFPTTLGMNKCYIQIMDLGHMCDATMSYECPMLDE  180
French          MAAEVTRRGSAYYMYLDRNDAGEAISFPTTLGMNKCYIQIMDLGHMCDATMSYECPMLDE  180
Sao             MAAEVTRRGSAYYMYLDRNDAGEAISFPTTLGMNKCYIQIMDLGHMCDATMSYECPMLDE  180
                **.*:*************.***:**** ****:***::**********************

                ───────────────────────────────────────────────(prM)──────
Uganda          GVEPDDVDCWCNTTSTWVVYGTCHHKKGEARRSRRAVTLPSHSTRKLQTRSQTWLESREY  240
Micronesia      GVEPDDVDCWCNTTSTWVVYGTCHHKKGEARRSRRAVTLPSHSTRKLQTRSQTWLESREY  240
Natal           GVEPDDVDCWCNTTSTWVVYGTCHHKKGEARRSRRAVTLPSHSTRKLQTRSQTWLESREY  240
Salvador        GVEPDDVDCWCNTTSTWVVYGTCHHKKGEARRSRRAVTLPSHSTRKLQTRSQTWLESREY  240
KU365777        GVEPDDVDCWCNTTSTWVVYGTCHHKKGEARRSRRAVTLPSHSTRKLQTRSQTWLESREY  240
KU365778        GVEPDDVDCWCNTTSTWVVYGTCHHKKGEARRSRRAVTLPSHSTRKLQTRSQTWLESREY  240
KU365779        GVEPDDVDCWCNTTSTWVVYGTCHHKKGEARRSRRAVTLPSHSTRKLQTRSQTWLESREY  240
KU365780        GVEPDDVDCWCNTTSTWVVYGTCHHKKGEARRSRRAVTLPSHSTRKLQTRSQTWLESREY  240
French          GVEPDDVDCWCNTTSTWVVYGTCHHKKGEARRSRRAVTLPSHSTRKLQTRSQTWLESREY  240
Sao             GVEPDDVDCWCNTTSTWVVYGTCHHKKGEARRSRRAVTLPSHSTRKLQTRSQTWLESREY  240
                ************************************************************
```

FIG.3B

```
            -prM--------►◄-Signal Sequence---------------------------►◄-Envelope(E)
Uganda      TKHLIKVENWIFRNPGFALVAVAIAWLLGSSTSQKVIYLVMILLIAPAYSIRCIGVSNRD  300
Micronesia  TKHLIRVENWIFRNPGFALAAAAIAWLLGSSTSQKVIYLVMILLIAPAYSIRCIGVSNRD  300
Natal       TKHLIRVENWIFRNPGFALAAAAIAWLLGSSTSQKVIYLVMILLIAPAYSIRCIGVSNRD  300
Salvador    TKHLIRVENWIFRNPGFALAAAAIAWLLGSSTSQKVIYLVMILLIAPAYSIRCIGVSNRD  300
KU365777    TKHLIRVENWIFRNPGFALAAAAIAWLLGSSTSQKVIYLVMILLIAPAYSIRCIGVSNRD  300
KU365778    TKHLIRVENWIFRNPGFALAAAAIAWLLGSSTSQKVIYLVMILLIAPAYSIRCIGVSNRD  300
KU365779    TKHLIRVENWIFRNPGFALAAAAIAWLLGSSTSQKVIYLVMILLIAPAYSIRCIGVSNRD  300
KU365780    TKHLIRVENWIFRNPGFALAAAAIAWLLGSSTSQKVIYLVMILLIAPAYSIRCIGVSNRD  300
French      TKHLIRVENWIFRNPGFALAAAAIAWLLGSSTSQKVIYLVMILLIAPAYSIRCIGVSNRD  300
Sao         TKHLIRVENWIFRNPGFALAAAAIAWLLGSSTSQKVIYLVMILLIAPAYSIRCIGVSNRD  300
            *****:*************.*.**************************************

            ----------------------------------------------(E)-------
Uganda      FVEGMSGGTWVDVVLEHGGCVTVMAQDKPTVDIELVTTTVSNMAEVRSYCYEASISDMAS  360
Micronesia  FVEGMSGGTWVDVVLEHGGCVTVMAQDKPAVDIELVTTTVSNMAEVRSYCYEASISDMAS  360
Natal       FVEGMSGGTWVDVVLEHGGCVTVMAQDKPTVDIELVTTTVSNMAEVRSYCYEASISDMAS  360
Salvador    FVEGMSGGTWVDVVLEHGGCVTVMAQDKPTVDIELVTTTVSNMAEVRSYCYEASISDMAS  360
KU365777    FVEGMSGGTWVDVVLEHGGCVTVMAQDKPTVDIELVTTTVSNMAEVRSYCYEASISDMAS  360
KU365778    FVEGMSGGTWVDVVLEHGGCVTVMAQDKPTVDIELVTTTVSNMAEVRSYCYEASISDMAS  360
KU365779    FVEGMSGGTWVDVVLEHGGCVTVMAQDKPTVDIELVTTTVSNMAEVRSYCYEASISDMAS  360
KU365780    FVEGMSGGTWVDVVLEHGGCVTVMAQDKPTVDIELVTTTVSNMAEVRSYCYEASISDMAS  360
French      FVEGMSGGTWVDVVLEHGGCVTVMAQDKPTVDIELVTTTVSNMAEVRSYCYEASISDMAS  360
Sao         FVEGMSGGTWVDIVLEHGGCVTVMAQDKPTVDIELVTTTVSNMAEVRSYCYEASISDMAS  360
            ************:****************:******************************

            ----------------------------------------------(E)-------
Uganda      DSRCPTQGEAYLDKQSDTQYVCKRTLVDRGWGNGCGLFGKGSLVTCAKFTCSKKMTGKSI  420
Micronesia  DSRCPTQGEAYLDKQSDTQYVCKRTLVDRGWGNGCGLFGKGSLVTCAKFACSKKMTGKSI  420
Natal       DSRCPTQGEAYLDKQSDTQYVCKRTLVDRGWGNGCGLFGKGSLVTCAKFACSKKMTGKSI  420
Salvador    DSRCPTQGEAYLDKQSDTQYVCKRTLVDRGWGNGCGLFGKGSLVTCAKFACSKKMTGKSI  420
KU365777    DSRCPTQGEAYLDKQSDTQYVCKRTLVDRGWGNGCGLFGKGSLVTCAKFACSKKMTGKSI  420
KU365778    DSRCPTQGEAYLDKQSDTQYVCKRTLVDRGWGNGCGLFGKGSLVTCAKFACSKKMTGKSI  420
KU365779    DSRCPTQGEAYLDKQSDTQYVCKRTLVDRGWGNGCGLFGKGSLVTCAKFACSKKMTGKSI  420
KU365780    DSRCPTQGEAYLDKQSDTQYVCKRTLVDRGWGNGCGLFGKGSLVTCAKFACSKKMTGKSI  420
French      DSRCPTQGEAYLDKQSDTQYVCKRTLVDRGWGNGCGLFGKGSLVTCAKFACSKKMTGKSI  420
Sao         DSRCPTQGEAYLDKQSDTQYVCKRTLVDRGWGNGCGLFGKGSLVTCAKFACSKKMTGKSI  420
            *************************************************:**********

            ----------------------------------------------(E)-------
Uganda      QPENLEYRIMLSVHGSQHSGMI----GYETDEDRAKVEVTPNSPRAEATLGGFGSLGLDC  476
Micronesia  QPENLEYRIMLSVHGSQHSGMIVNDTGHETDENRAKVEITPNSPRAEATLGGFGSLGLDC  480
Natal       QPENLEYRIMLSVHGSQHSGMIVNDTGHETDENRAKVEITPNSPRAEATLGGFGSLGLDC  480
Salvador    QPENLEYRIMLSVHGSQHSGMIVNDTGHETDENRAKVEITPNSPRAEATLGGFGSLGLDC  480
KU365777    QPENLEYRIMLSVHGSQHSGMIVNDTGHETDENRAKVEITPNSPRAEATLGGFGSLGLDC  480
KU365778    QPENLEYRIMLSVHGSQHSGMIVNDTGHETDENRAKVEITPNSPRAEATLGGFGSLGLDC  480
KU365779    QPENLEYRIMLSVHGSQHSGMIVNDTGHETDENRAKVEITPNSPRAEATLGGFGSLGLDC  480
KU365780    QPENLEYRIMLSVHGSQHSGMIVNDTGHETDENRAKVEITPNSPRAEATLGGFGSLGLDC  480
French      QPENLEYRIMLSVHGSQHSGMIVNDTGHETDENRAKVEITPNSPRAEATLGGFGSLGLDC  480
Sao         QPENLEYRIMLSVHGSQHSGMIVNDTGHETDENRAKVEITPNSPRAEATLGGFGSLGLDC  480
            **********************    *:****:*****:*********************
```

*FIG.3C*

```
                                                                    (E)
Uganda        EPRTGLDFSDLYYLTMNNKHWLVHKEWFHDIPLPWHAGADTGTPHWNNKEALVEFKDAHA  536
Micronesia    EPRTGLDFSDLYYLTMNNKHWLVHKEWFHDIPLPWHAGADTGTPHWNNKEALVEFKDAHA  540
Natal         EPRTGLDFSDLYYLTMNNKHWLVHKEWFHDIPLPWHAGADTGTPHWNNKEALVEFKDAHA  540
Salvador      EPRTGLDFSDLYYLTMNNKHWLVHKEWFHDIPLPWHAGADTGTPHWNNKEALVEFKDAHA  540
KU365777      EPRTGLDFSDLYYLTMNNKHWLVHKEWFHDIPLPWHAGADTGTPHWNNKEALVEFKDAHA  540
KU365778      EPRTGLDFSDLYYLTMNNKHWLVHKEWFHDIPLPWHAGADTGTPHWNNKEALVEFKDAHA  540
KU365779      EPRTGLDFSDLYYLTMNNKHWLVHKEWFHDIPLPWHAGADTGTPHWNNKEALVEFKDAHA  540
KU365780      EPRTGLDFSDLYYLTMNNKHWLVHKEWFHDIPLPWHAGADTGTPHWNNKEALVEFKDAHA  540
French        EPRTGLDFSDLYYLTMNNKHWLVHKEWFHDIPLPWHAGADTGTPHWNNKEALVEFKDAHA  540
Sao           EPRTGLDFSDLYYLTMNNKHWLVHKEWFHDIPLPWHAGADTGTPHWNNKEALVEFKDAHA  540
              ************************************************************

                                                                    (E)
Uganda        KRQTVVVLGSQEGAVHTALAGALEAEMDGAKGRLFSGHLKCRLKMDKLRLKGVSYSLCTA  596
Micronesia    KRQTVVVLGSQEGAVHTALAGALEAEMDGAKGRLSSGHLKCRLKMDKLRLKGVSYSLCTA  600
Natal         KRQTVVVLGSQEGAVHTALAGALEAEMDGAKGRLSSGHLKCRLKMDKLRLKGVSYSLCTA  600
Salvador      KRQTVVVLGSQEGAVHTALAGALEAEMDGAKGRLSSGHLKCRLKMDKLRLKGVSYSLCTA  600
KU365777      KRQTVVVLGSQEGAVHTALAGALEAEMDGAKGRLSSGHLKCRLKMDKLRLKGVSYSLCTA  600
KU365778      KRQTVVVLGSQEGAVHTALAGALEAEMDGAKGRLSSGHLKCRLKMDKLRLKGVSYSLCTA  600
KU365779      KRQTVVVLGSQEGAVHTALAGALEAEMDGAKGRLSSGHLKCRLKMDKLRLKGVSYSLCTA  600
KU365780      KRQTVVVLGSQEGAVHTALAGALEAEMDGAKGRLSSGHLKCRLKMDKLRLKGVSYSLCTA  600
French        KRQTVVVLGSQEGAVHTALAGALEAEMDGAKGRLSSGHLKCRLKMDKLRLKGVSYSLCTA  600
Sao           KRQTVVVLGSQEGAVHTALAGALEAEMDGAKGRLSSGHLKCRLKMDKLRLKGVSYSLCTA  600
              ********************************** *************************

                                                                    (E)
Uganda        AFTFTKVPAETLHGTVTVEVQYAGTDGPCKIPVQMAVDMQTLTPVGRLITANPVITESTE  656
Micronesia    AFTFTKIPAETLHGTVTVEVQYAGTDGPCKVPAQMAVDMQTLTPVGRLITANPVITESTE  660
Natal         AFTFTKIPAETLHGTVTVEVQYAGTDGPCKVPAQMAVDMQTLTPVGRLITANPVITESTE  660
Salvador      AFTFTKIPAETLHGTVTVEVQYAGTDGPCKVPAQMAVDMQTLTPVGRLITANPVITESTE  660
KU365777      AFTFTKIPAETLHGTVTVEVQYAGTDGPCKVPAQMAVDMQTLTPVGRLITANPVITESTE  660
KU365778      AFTFTKIPAETLHGTVTVEVQYAGTDGPCKVPAQMAVDMQTLTPVGRLITANPVITESTE  660
KU365779      AFTFTKIPAETLHGTVTVEVQYAGTDGPCKVPAQMAVDMQTLTPVGRLITANPVITESTE  660
KU365780      AFTFTKIPAETLHGTVTVEVQYAGTDGPCKVPAQMAVDMQTLTPVGRLITANPVITESTE  660
French        AFTFTKIPAETLHGTVTVEVQYAGTDGPCKVPAQMAVDMQTLTPVGRLITANPVITESTE  660
Sao           AFTFTKIPAETLHGTVTVEVQYAGTDGPCKVPAQMAVDMQTLTPVGRLITANPVITESTE  660
              ******:***********************:*.***************************

                                                                    (E)
Uganda        NSKMMLELDPPFGDSYIVIGVGDKKITHHWHRSGSTIGKAFEATVRGAKRMAVLGDTAWD  716
Micronesia    NSKMMLELDPPFGDSYIVIGVGEKKITHHWHRSGSTIGKAFEATVRGAKRMAVLGDTAWD  720
Natal         NSKMMLELDPPFGDSYIVIGVGEKKITHHWHRSGSTIGKAFEATVRGAKRMAVLGDTAWD  720
Salvador      NSKMMLELDPPFGDSYIVIGVGEKKITHHWHRSGSTIGKAFEATVRGAKRMAVLGDTAWD  720
KU365777      NSKMMLELDPPFGDSYIVIGVGEKKITHHWHRSGSTIGKAFEATVRGAKRMAVLGDTAWD  720
KU365778      NSKMMLELDPPFGDSYIVIGVGEKKITHHWHRSGSTIGKAFEATVRGAKRMAVLGDTAWD  720
KU365779      NSKMMLELDPPFGDSYIVIGVGEKKITHHWHRSGSTIGKAFEATVRGAKRMAVLGDTAWD  720
KU365780      NSKMMLELDPPFGDSYIVIGVGEKKITHHWHRSGSTIGKAFEATVRGAKRMAVLGDTAWD  720
French        NSKMMLELDPPFGDSYIVIGVGEKKITHHWHRSGSTIGKAFEATVRGAKRMAVLGDTAWD  720
Sao           NSKMMLELDPPFGDSYIVIGVGEKKITHHWHRSGSTIGKAFEATVRGAKRMAVLGDTAWD  720
              **********************:*************************************
```

FIG.3D

```
                ———————————————————————————————————————————————(E)—————————
Uganda          FGSVGGVFNSLGKGIHQIFGAAFKSLFGGMSWFSQILIGTLLVWLGLNTKNGSISLTCLA  776
Micronesia      FGSVGGALNSLGKGIHQIFGAAFKSLFGGMSWFSQILIGTLLVWLGLNTKNGSISLTCLA  780
Natal           FGSVGGALNSLGKGIHQIFGAAFKSLFGGMSWFSQILIGTLLMWLGLNTKNGSISLMCLA  780
Salvador        FGSVGGALNSLGKGIHQIFGAAFKSLFGGMSWFSQILIGTLLMWLGLNTKNGSISLMCLA  780
KU365777        FGSVGGALNSLGKGIHQIFGAAFKSLFGGMSWFSQILIGTLLMWLGLNTKNGSISLMCLA  780
KU365778        FGSVGGALNSLGKGIHQIFGAAFKSLFGGMSWFSQILIGTLLMWLGLNTKNGSISLMCLA  780
KU365779        FGSVGGALNSLGKGIHQIFGAAFKSLFGGMSWFSQILIGTLLMWLGLNTKNGSISLMCLA  780
KU365780        FGSVGGALNSLGKGIHQIFGAAFKSLFGGMSWFSQILIGTLLMWLGLNTKNGSISLMCLA  780
French          FGSVGGALNSLGKGIHQIFGAAFKSLFGGMSWFSQILIGTLLMWLGLNTKNGSISLMCLA  780
Sao             FGSVGGALNSLGKGIHQIFGAAFKSLFGGMSWFSQILIGTLLMWLGLNTKNGSISLMCLA  780
                ******.:**********************************:************* ***

                ——(E)————>
Uganda          LGGVMIFLSTAVSAD  791
Micronesia      LGGVLIFLSTAVSAD  795
Natal           LGGVLIFLSTAVSAD  795
Salvador        LGGVLIFLSTAVSAD  795
KU365777        LGGVLIFLSTAVSAD  795
KU365778        LGGVLIFLSTAVSAD  795
KU365779        LGGVLIFLSTAVSAD  795
KU365780        LGGVLIFLSTAVSAD  795
French          LGGVLIFLSTAVSAD  795
Sao             LGGVLIFLSTAVSAD  795
                ****:**********
```

FIG.4A

```
                    ◄──────────────────────────────────Capsid(C)──────────
Natal               MKNPKKKSGGFRIVNMLKRGVARVSPFGGLKRLPAGLLLGHGPIRMVLAILAFLRFTAIK
Salvador            MKNPKKKSGGFRIVNMLKRGVARVSPFGGLKRLPAGLLLGHGPIRMVLAILAFLRFTAIK
KU365777            MKNPKKKSGGFRIVNMLKRGVARVSPFGGLKRLPAGLLLGHGPIRMVLAILAFLRFTAIK
KU365778            MKNPKKKSGGFRIVNMLKRGVARVSPFGGLKRLPAGLLLGHGPIRMVLAILAFLRFTAIK
KU365779            MKNPKKKSGGFRIVNMLKRGVARVSPFGGLKRLPAGLLLGHGPIRMVLAILAFLRFTAIK
KU365780            MKNPKKKSGGFRIVNMLKRGVARVSPFGGLKRLPAGLLLGHGPIRMVLAILAFLRFTAIK
Sao                 MKNPKKKSGGFRIVNMLKRGVARVSPFGGLKRLPAGLLLGHGPIRMVLAILAFLRFTAIK
                    ************************************************************

                    ───────────────Capsid(C)      ──────────────►◄─prM    Signal
Sequence
Natal               PSLGLINRWGSVGKKEAMEIIKKFKKDLAAMLRIINARKEKKRRGADTSVGIVGLLLTTA
Salvador            PSLGLINRWGSVGKKEAMEIIKKFKKDLAAMLRIINARKEKKRRGADTSVGIVGLLLTTA
KU365777            PSLGLINRWGSVGKKEAMEIIKKFKKDLAAMLRIINARKEKKRRGADTSVGIVGLLLTTA
KU365778            PSLGLINRWGSVGKKEAMEIIKKFKKDLAAMLRIINARKEKKRRGADTSVGIVGLLLTTA
KU365779            PSLGLINRWGSVGKKEAMEIIKKFKKDLAAMLRIINARKEKKRRGADTSVGIVGLLLTTA
KU365780            PSLGLINRWGSVGKKEAMEIIKKFKKDLAAMLRIINARKEKKRRGADTSVGIVGLLLTTA
Sao                 PSLGLINRWGSVGKKEAMEIIKKFKKDLAAMLRIINARKEKKRRGADTSVGIVGLLLTTA
                    ************************************************************

                    ─►◄───────────────────────────────Pre-Membrane(prM)───────
Natal               MAAEVTRRGSAYYMYLDRNDAGEAISFPTTLGMNKCYIQIMDLGHMCDATMSYECPMLDE
Salvador            MAAEVTRRGSAYYMYLDRNDAGEAISFPTTLGMNKCYIQIMDLGHMCDATMSYECPMLDE
KU365777            MAAEVTRRGSAYYMYLDRNDAGEAISFPTTLGMNKCYIQIMDLGHMCDATMSYECPMLDE
KU365778            MAAEVTRRGSAYYMYLDRNDAGEAISFPTTLGMNKCYIQIMDLGHMCDATMSYECPMLDE
KU365779            MAAEVTRRGSAYYMYLDRNDAGEAISFPTTLGMNKCYIQIMDLGHMCDATMSYECPMLDE
KU365780            MAAEVTRRGSAYYMYLDRNDAGEAISFPTTLGMNKCYIQIMDLGHMCDATMSYECPMLDE
Sao                 MAAEVTRRGSAYYMYLDRNDAGEAISFPTTLGMNKCYIQIMDLGHMCDATMSYECPMLDE
                    ************************************************************

                    ───────────────────────────────────────────────(prM)──────
Natal               GVEPDDVDCWCNTTSTWVVYGTCHHKKGEARRSRRAVTLPSHSTRKLQTRSQTWLESREY
Salvador            GVEPDDVDCWCNTTSTWVVYGTCHHKKGEARRSRRAVTLPSHSTRKLQTRSQTWLESREY
KU365777            GVEPDDVDCWCNTTSTWVVYGTCHHKKGEARRSRRAVTLPSHSTRKLQTRSQTWLESREY
KU365778            GVEPDDVDCWCNTTSTWVVYGTCHHKKGEARRSRRAVTLPSHSTRKLQTRSQTWLESREY
KU365779            GVEPDDVDCWCNTTSTWVVYGTCHHKKGEARRSRRAVTLPSHSTRKLQTRSQTWLESREY
KU365780            GVEPDDVDCWCNTTSTWVVYGTCHHKKGEARRSRRAVTLPSHSTRKLQTRSQTWLESREY
Sao                 GVEPDDVDCWCNTTSTWVVYGTCHHKKGEARRSRRAVTLPSHSTRKLQTRSQTWLESREY
                    ************************************************************

                    ─prM────────►◄─SignalSequence─────────────────►◄─Envelope(E)
Natal               TKHLIRVENWIFRNPGFALAAAAIAWLLGSSTSQKVIYLVMILLIAPAYSIRCIGVSNRD
Salvador            TKHLIRVENWIFRNPGFALAAAAIAWLLGSSTSQKVIYLVMILLIAPAYSIRCIGVSNRD
KU365777            TKHLIRVENWIFRNPGFALAAAAIAWLLGSSTSQKVIYLVMILLIAPAYSIRCIGVSNRD
KU365778            TKHLIRVENWIFRNPGFALAAAAIAWLLGSSTSQKVIYLVMILLIAPAYSIRCIGVSNRD
KU365779            TKHLIRVENWIFRNPGFALAAAAIAWLLGSSTSQKVIYLVMILLIAPAYSIRCIGVSNRD
KU365780            TKHLIRVENWIFRNPGFALAAAAIAWLLGSSTSQKVIYLVMILLIAPAYSIRCIGVSNRD
Sao                 TKHLIRVENWIFRNPGFALAAAAIAWLLGSSTSQKVIYLVMILLIAPAYSIRCIGVSNRD
                    ************************************************************
```

*FIG.4B*

```
                ---------------------------------------------------(E)------
Natal           FVEGMSGGTWVDVVLEHGGCVTVMAQDKPTVDIELVTTTVSNMAEVRSYCYEASISDMAS
Salvador        FVEGMSGGTWVDVVLEHGGCVTVMAQDKPTVDIELVTTTVSNMAEVRSYCYEASISDMAS
KU365777        FVEGMSGGTWVDVVLEHGGCVTVMAQDKPTVDIELVTTTVSNMAEVRSYCYEASISDMAS
KU365778        FVEGMSGGTWVDVVLEHGGCVTVMAQDKPTVDIELVTTTVSNMAEVRSYCYEASISDMAS
KU365779        FVEGMSGGTWVDVVLEHGGCVTVMAQDKPTVDIELVTTTVSNMAEVRSYCYEASISDMAS
KU365780        FVEGMSGGTWVDVVLEHGGCVTVMAQDKPTVDIELVTTTVSNMAEVRSYCYEASISDMAS
Sao             FVEGMSGGTWVDIVLEHGGCVTVMAQDKPTVDIELVTTTVSNMAEVRSYCYEASISDMAS
                ************:***********************************************

                ---------------------------------------------------(E)------
Natal           DSRCPTQGEAYLDKQSDTQYVCKRTLVDRGWGNGCGLFGKGSLVTCAKFACSKKMTGKSI
Salvador        DSRCPTQGEAYLDKQSDTQYVCKRTLVDRGWGNGCGLFGKGSLVTCAKFACSKKMTGKSI
KU365777        DSRCPTQGEAYLDKQSDTQYVCKRTLVDRGWGNGCGLFGKGSLVTCAKFACSKKMTGKSI
KU365778        DSRCPTQGEAYLDKQSDTQYVCKRTLVDRGWGNGCGLFGKGSLVTCAKFACSKKMTGKSI
KU365779        DSRCPTQGEAYLDKQSDTQYVCKRTLVDRGWGNGCGLFGKGSLVTCAKFACSKKMTGKSI
KU365780        DSRCPTQGEAYLDKQSDTQYVCKRTLVDRGWGNGCGLFGKGSLVTCAKFACSKKMTGKSI
Sao             DSRCPTQGEAYLDKQSDTQYVCKRTLVDRGWGNGCGLFGKGSLVTCAKFACSKKMTGKSI
                ************************************************************

                ---------------------------------------------------(E)------
Natal           QPENLEYRIMLSVHGSQHSGMIVNDTGHETDENRAKVEITPNSPRAEATLGGFGSLGLDC
Salvador        QPENLEYRIMLSVHGSQHSGMIVNDTGHETDENRAKVEITPNSPRAEATLGGFGSLGLDC
KU365777        QPENLEYRIMLSVHGSQHSGMIVNDTGHETDENRAKVEITPNSPRAEATLGGFGSLGLDC
KU365778        QPENLEYRIMLSVHGSQHSGMIVNDTGHETDENRAKVEITPNSPRAEATLGGFGSLGLDC
KU365779        QPENLEYRIMLSVHGSQHSGMIVNDTGHETDENRAKVEITPNSPRAEATLGGFGSLGLDC
KU365780        QPENLEYRIMLSVHGSQHSGMIVNDTGHETDENRAKVEITPNSPRAEATLGGFGSLGLDC
Sao             QPENLEYRIMLSVHGSQHSGMIVNDTGHETDENRAKVEITPNSPRAEATLGGFGSLGLDC
                ************************************************************

                ---------------------------------------------------(E)------
Natal           EPRTGLDFSDLYYLTMNNKHWLVHKEWFHDIPLPWHAGADTGTPHWNNKEALVEFKDAHA
Salvador        EPRTGLDFSDLYYLTMNNKHWLVHKEWFHDIPLPWHAGADTGTPHWNNKEALVEFKDAHA
KU365777        EPRTGLDFSDLYYLTMNNKHWLVHKEWFHDIPLPWHAGADTGTPHWNNKEALVEFKDAHA
KU365778        EPRTGLDFSDLYYLTMNNKHWLVHKEWFHDIPLPWHAGADTGTPHWNNKEALVEFKDAHA
KU365779        EPRTGLDFSDLYYLTMNNKHWLVHKEWFHDIPLPWHAGADTGTPHWNNKEALVEFKDAHA
KU365780        EPRTGLDFSDLYYLTMNNKHWLVHKEWFHDIPLPWHAGADTGTPHWNNKEALVEFKDAHA
Sao             EPRTGLDFSDLYYLTMNNKHWLVHKEWFHDIPLPWHAGADTGTPHWNNKEALVEFKDAHA
                ************************************************************

                ---------------------------------------------------(E)------
Natal           KRQTVVVLGSQEGAVHTALAGALEAEMDGAKGRLSSGHLKCRLKMDKLRLKGVSYSLCTA
Salvador        KRQTVVVLGSQEGAVHTALAGALEAEMDGAKGRLSSGHLKCRLKMDKLRLKGVSYSLCTA
KU365777        KRQTVVVLGSQEGAVHTALAGALEAEMDGAKGRLSSGHLKCRLKMDKLRLKGVSYSLCTA
KU365778        KRQTVVVLGSQEGAVHTALAGALEAEMDGAKGRLSSGHLKCRLKMDKLRLKGVSYSLCTA
KU365779        KRQTVVVLGSQEGAVHTALAGALEAEMDGAKGRLSSGHLKCRLKMDKLRLKGVSYSLCTA
KU365780        KRQTVVVLGSQEGAVHTALAGALEAEMDGAKGRLSSGHLKCRLKMDKLRLKGVSYSLCTA
Sao             KRQTVVVLGSQEGAVHTALAGALEAEMDGAKGRLSSGHLKCRLKMDKLRLKGVSYSLCTA
                ************************************************************
```

*FIG.4C*

```
                ——————————————————————————————————————————————————(E)———————
Natal           AFTFTKIPAETLHGTVTVEVQYAGTDGPCKVPAQMAVDMQTLTPVGRLITANPVITESTE
Salvador        AFTFTKIPAETLHGTVTVEVQYAGTDGPCKVPAQMAVDMQTLTPVGRLITANPVITESTE
KU365777        AFTFTKIPAETLHGTVTVEVQYAGTDGPCKVPAQMAVDMQTLTPVGRLITANPVITESTE
KU365778        AFTFTKIPAETLHGTVTVEVQYAGTDGPCKVPAQMAVDMQTLTPVGRLITANPVITESTE
KU365779        AFTFTKIPAETLHGTVTVEVQYAGTDGPCKVPAQMAVDMQTLTPVGRLITANPVITESTE
KU365780        AFTFTKIPAETLHGTVTVEVQYAGTDGPCKVPAQMAVDMQTLTPVGRLITANPVITESTE
Sao             AFTFTKIPAETLHGTVTVEVQYAGTDGPCKVPAQMAVDMQTLTPVGRLITANPVITESTE
                ************************************************************

                ——————————————————————————————————————————————————(E)———————
Natal           NSKMMLELDPPFGDSYIVIGVGEKKITHHWHRSGSTIGKAFEATVRGAKRMAVLGDTAWD
Salvador        NSKMMLELDPPFGDSYIVIGVGEKKITHHWHRSGSTIGKAFEATVRGAKRMAVLGDTAWD
KU365777        NSKMMLELDPPFGDSYIVIGVGEKKITHHWHRSGSTIGKAFEATVRGAKRMAVLGDTAWD
KU365778        NSKMMLELDPPFGDSYIVIGVGEKKITHHWHRSGSTIGKAFEATVRGAKRMAVLGDTAWD
KU365779        NSKMMLELDPPFGDSYIVIGVGEKKITHHWHRSGSTIGKAFEATVRGAKRMAVLGDTAWD
KU365780        NSKMMLELDPPFGDSYIVIGVGEKKITHHWHRSGSTIGKAFEATVRGAKRMAVLGDTAWD
Sao             NSKMMLELDPPFGDSYIVIGVGEKKITHHWHRSGSTIGKAFEATVRGAKRMAVLGDTAWD
                ************************************************************

                ——————————————————————————————————————————————————(E)———————
Natal           FGSVGGALNSLGKGIHQIFGAAFKSLFGGMSWFSQILIGTLLMWLGLNTKNGSISLMCLA
Salvador        FGSVGGALNSLGKGIHQIFGAAFKSLFGGMSWFSQILIGTLLMWLGLNTKNGSISLMCLA
KU365777        FGSVGGALNSLGKGIHQIFGAAFKSLFGGMSWFSQILIGTLLMWLGLNTKNGSISLMCLA
KU365778        FGSVGGALNSLGKGIHQIFGAAFKSLFGGMSWFSQILIGTLLMWLGLNTKNGSISLMCLA
KU365779        FGSVGGALNSLGKGIHQIFGAAFKSLFGGMSWFSQILIGTLLMWLGLNTKNGSISLMCLA
KU365780        FGSVGGALNSLGKGIHQIFGAAFKSLFGGMSWFSQILIGTLLMWLGLNTKNGSISLMCLA
Sao             FGSVGGALNSLGKGIHQIFGAAFKSLFGGMSWFSQILIGTLLMWLGLNTKNGSISLMCLA
                ************************************************************

                ——(E)————————
Natal           LGGVLIFLSTAVSAD
Salvador        LGGVLIFLSTAVSAD
KU365777        LGGVLIFLSTAVSAD
KU365778        LGGVLIFLSTAVSAD
KU365779        LGGVLIFLSTAVSAD
KU365780        LGGVLIFLSTAVSAD
Sao             LGGVLIFLSTAVSAD
                ***************
```

ZIKA VIRAL ANTIGEN CONSTRUCTS

FIELD OF THE INVENTION

This invention is in the field of treating and preventing viral infections. In particular, the present invention relates to nucleic acid-based vaccine constructs encoding Zika viral antigens and the use of Zika viral antigens for treating and preventing Zika infections.

BACKGROUND TO THE INVENTION

Zika virus was first identified in Uganda in 1947 in rhesus monkeys through a monitoring network of sylvatic yellow fever. It was subsequently identified in humans in 1952 in Uganda and the United Republic of Tanzania. Outbreaks of Zika virus disease have been recorded in Africa, the Americas, Asia and the Pacific. Zika virus belongs to the genus flavivirus. Its reservoir is unknown.

Zika virus is a plus-strand RNA virus belonging to the family Flaviviridae. Zika virus disease is caused by a virus transmitted primarily by *Aedes* mosquitoes. People with Zika virus disease can have symptoms that can include mild fever, skin rash, conjunctivitis, muscle and joint pain, malaise or headache. These symptoms normally last for 2-7 days.

The Zika virus is known to circulate in Africa, the Americas, Asia and the Pacific. Transmitted by *Aedes* mosquitos, the virus has been known to cause either asymptomatic infection (in the majority of people infected) or a self-limiting illness with descending rash, conjunctivitis and low grade fever. However, during the ongoing Zika virus outbreak in the Americas an alarming increase in the number of babies born with microcephaly, as well as an increase in the incidence of Guillain-Barré syndrome has been reported. In addition to microcephaly, other fetal malformations and neurological disorders have been described.

Dowd et al. (Science, Vol. 354 Issue 6309, pp. 237-40 (2016) recently reported that DNA vaccines expressing the premembrane and envelope proteins of Zika virus were immunogenic in mice and nonhuman primates when administered by electroporation or needle-free injection; and that protection against viremia after Zika virus challenge correlated with serum neutralizing activity.

Chahal et al. (Scientific Reports, 7:252, pp. 1-9 (2017)) describe an alphavirus RNA vector encoding Zika virus structural antigens. When formulated with a modified dendrimer nanomaterial and administered to mice intramuscularly, the vaccine was found to be immunogenic.

Richner et al. (Cell, 168, pp. 1-12, (2017) describe a modified mRNA vaccine encoding wild-type or mutant Zika structural proteins. When encapsulated in lipid nanoparticles and administered intramuscularly to mice, the mRNA vaccine elicited high neutralizing antibody titers and protection from viral challenge.

Given the concerning disease burden and the potential for rapid dissemination, there is an urgent need for the development of components for use in a Zika virus immunogenic or vaccine composition.

SUMMARY OF THE INVENTION

The present inventors provide constructs useful as components of immunogenic compositions for the induction of an immune response in a subject against Zika viral infection, methods for their use in treatment, and processes for their manufacture.

In some embodiments, a nucleic acid-based vaccine construct encoding a polypeptide comprising a full-length Zika virus pre-M-E antigen (prME), or an immunogenic fragment thereof is provided.

In some embodiments, a vector comprising the construct as described is provided.

In some embodiments, a self-replicating RNA molecule (also referred to herein as a self-amplifying mRNA, or SAM molecule) comprising the construct as described is provided.

In some embodiments, a composition comprising an immunologically effective amount of one or more of the constructs, vectors, or self-replicating RNA molecules as described above is provided.

In some embodiments, a composition as described above is provided wherein the composition comprises an RNA-based vaccine.

In some embodiments, a composition as described above is provided wherein the composition comprises one or more constructs, vectors, or self-replicating RNA molecules as described above complexed with a particle of a cationic oil-in-water emulsion.

In some embodiments, a composition as described above for use in inducing an immune response against a Zika virus infection in a subject in need thereof is provided.

In some embodiments is provided a construct, a vector, a self-replicating RNA and/or molecule as described herein for use in therapy or medicine. In some embodiments, the compositions disclosed herein are for use in therapy or medicine. In preferred embodiment, the therapy is a vaccine therapy. Preferably the therapy is a vaccine to prevent Zika virus infection.

In some embodiments is provided a construct, a vector, a self-replicating RNA and/or molecule as described herein for use in preventing or treating Zika virus infection in a subject in need thereof.

In some embodiments, the compositions disclosed herein are for use in preventing or treating Zika virus infection in a subject in need thereof.

In some embodiments, a method is provided for inducing an immune response against a Zika virus infection in a subject in need thereof, which comprises administering to said subject an immunologically effective amount of a composition comprising one or more of the constructs, vectors, or self-replicating RNA molecules as described above.

In some embodiments, a method is provided for inducing an immune response sufficient to prevent or treat a Zika virus infection in a subject, which comprises administering to said subject a composition comprising one or more of the constructs, vectors, or self-replicating RNA molecules as described above in an amount sufficient to prevent or treat Zika virus infection.

In some embodiments, a method as described above is provided wherein the composition comprises one or more constructs, vectors, or self-replicating RNA molecules as described above complexed with a particle of a cationic oil-in-water emulsion.

In some embodiments, a process is provided for producing an RNA-based vaccine comprising a step of transcribing a vector or DNA molecule encoding a self-replicating RNA molecule described above to produce an RNA comprising a coding region for the antigen.

In some embodiments, a method of preparing a composition as described above is provided wherein the method comprises 1) preparing a cationic oil-in-water emulsion; 2) preparing one or more constructs, vectors, or self-replicating RNA molecules as described above; and 3) adding the one or more constructs, vectors, or self-replicating RNA molecules to the cationic oil-in-water emulsion so that the construct, vector, or self-replicating RNA molecule complexes with the emulsion.

In some embodiments, a composition produced by the process described above is provided.

In some embodiments, a use of the construct, vector, self-replicating RNA molecule, or composition described above for inducing an immune response against a Zika virus infection in a subject is provided.

In some embodiments, a use of the construct, vector, self-replicating RNA molecule, or composition described above in the manufacture of a medicament that induces an immune response against a Zika virus infection in a subject is provided.

DESCRIPTION OF DRAWINGS/FIGURES

FIG. 1: The organization of the Flavivirus genome, showing the polyprotein that is cleaved into structural and non-structural proteins by a combination of viral and cellular proteases.

Figure 2:
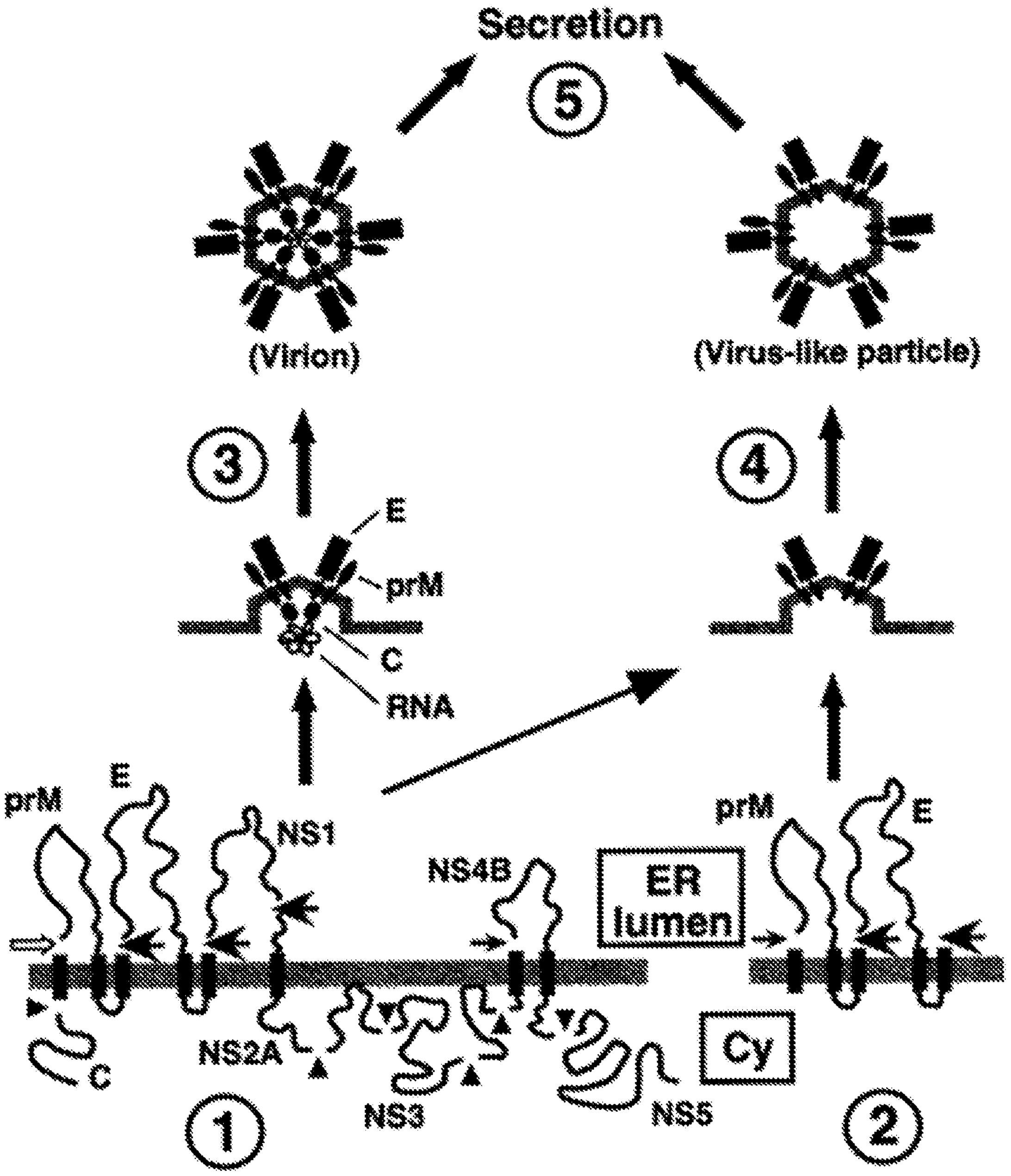

FIG. 2: Formation of Flavivirus virions and subviral particles. (1) In natural infections, flavivirus proteins are produced by the processing of a polyprotein translated from the viral genomic RNA and inserted co-translationally into the endoplasmic reticulum (ER) membrane. Horizontal arrows indicate polyprotein cleavages by signal peptidase and arrow heads indicate cleavage by the viral NS2B-3 protease. The open arrow indicates a signalase cleavage which is inefficient unless cytoplasmic capsid (C) cleavage has occurred. (2) The minimal requirement for production of subviral particles is the precursor membrane (prM) and envelope (E) proteins. (3) Flavivirus particles are formed by budding on the ER membrane driven by the prM and E proteins independent of the C protein or preformed nucleocapsids. Virus infection results predominantly in the formation of virions. (4) Nucleocapsid-free virus-like particles are efficiently produced by recombinant expression of the prM and E proteins and are a by-product of flavivirus infection. (5) Virions and virus-like particles follow the exocytic pathway for secretion from infected/transfected cells. 'Cy' denotes the cytoplasmic side of the ER membrane.

FIG. 3A-D: CLUSTAL O(1.2.1) multiple sequence alignment of CprME proteins of Zika virus. See Sequences herein and SEQ ID NO:2 and SEQ ID NOS: 15-23.

TABLE 1

Zika virus strains, year, and Genbank reference.

| STRAIN | YEAR | GENBANK NUMBER |
|---|---|---|
| Uganda | | NC_012532 |
| Micronesia | 2007 | EU545988.1 |
| Natal (Brazil) | 2016 | KU527068 |
| Salvador (Brazil) | 2016 | KU707826.1 |
| Sao Paulo (Brazil) | 2016 | KU321639 |
| French Polynesia | 2013 | KJ776791 |

FIG. 4A-C: CLUSTAL O(1.2.1) multiple sequence alignment of CprME proteins from Brazilian strains of Zika virus: Natal (SEQ ID NO:2); Salvador (SEQ ID NO:15); Genbank Accession No. KU365777 (SEQ ID NO:20); Genbank Accession No. KU365778 (SEQ ID NO:21); Genbank Accession No. KU365779 (SEQ ID NO:22); Genbank Accession No. KU365780 (SEQ ID NO:23); and Sao Paolo ("Sao") (SEQ ID NO:16). See Table 1 for Zika virus strains, year, and Genbank reference.

Figure 5:
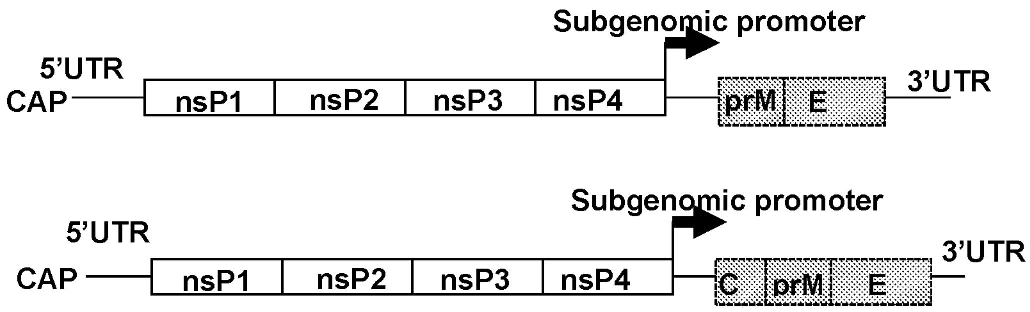

FIG. 5: A SAM-Zika construct. The self-amplifying mRNA (SAM) background consists of VEE TC-83 replicon encoding the viral nonstructural proteins 1-4 (nsP1-4), followed by the subgenomic promoter, and either Zika prME or Zika CprME. The empty vector is shown in SEQ ID NO:24; the insert starts immediately after nucleotide 7561.

Figure 6:
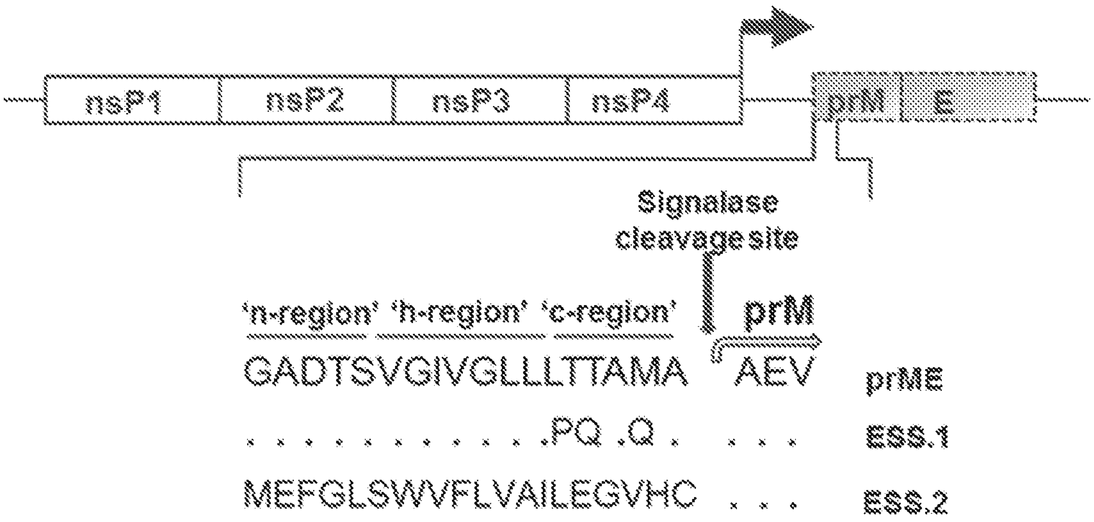

FIG. 6. Design of a Zika-SAM construct encoding the viral prME proteins. The schematic shows the prM signal sequence region of the prM gene, which contains basic residues in the NH2-terminal region (n-region), a hydrophobic core uninterrupted by charged or polar residues (h-region), and a −3, −1 amino acid motif in the COOH-terminal cleavage region (c-region) suitable for signalase recognition. The first construct is wild-type prME that has been codon-optimized for expression in mammalian cells. An uncharacteristic feature of the prM signal peptide of flaviviruses is the lack of polar residues in the c-region. Previously it has been shown that replacement of Gly, Phe, and Ala at positions −5, −4, and −2 with Pro, Gin, and Gin, respectively (PQAQA mutation), dramatically increases the extent of signalase cleavage of prM in vitro without requirement of prior cleavage of C. Stocks, et al. 1998. Signal peptidase cleavage at the flavivirus C-prM junction: dependence on the viral NS2B-3 protease for efficient processing requires determinants in C, the signal peptide, and prM. *J. Virol.* 72:2141-2149.

The second construct—ESS.1, has the PQAQA mutation. The third construct—ESS.2, has the native prM signal sequence replaced by the IgG signal peptide, which has been used previously for expression and secretion of IgG and Fab proteins from mammalian cells. Ciferri et al. (2015) "Antigenic Characterization of the HCMV gH/gL/gO and Pentamer Cell Entry Complexes Reveals Binding Sites for Potently Neutralizing Human Antibodies," *PLoS Pathog.* October 20; 11(10):e1005230.

Figure 7:
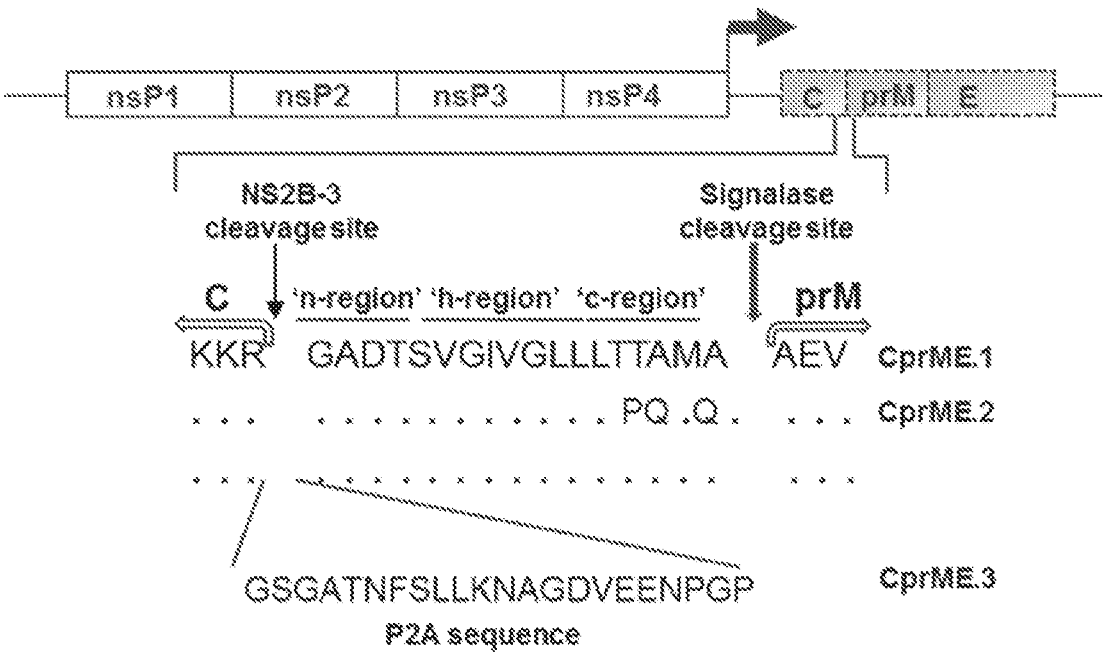

FIG. 7. Design of Zika-SAM constructs encoding the viral capsid and prME proteins. Zika capsid (C) protein is incorporated in constructs to test whether the presence of a cleavable capsid protein increases the efficiency of SVP generation. CprME.1 is a codon optimized nucleic acid sequence encoding the native Zika capsid, prM and E proteins, with the native NS2B-3 and signalase cleavage sites. CprME.2 is identical to CprME.1, but contains the -PQ-Q- mutation in the signal peptide C region. Finally, CprME.3 is identical to CprME.1, except that a P2A sequence is inserted at the NS2B-3 cleavage site.

Figure 8:
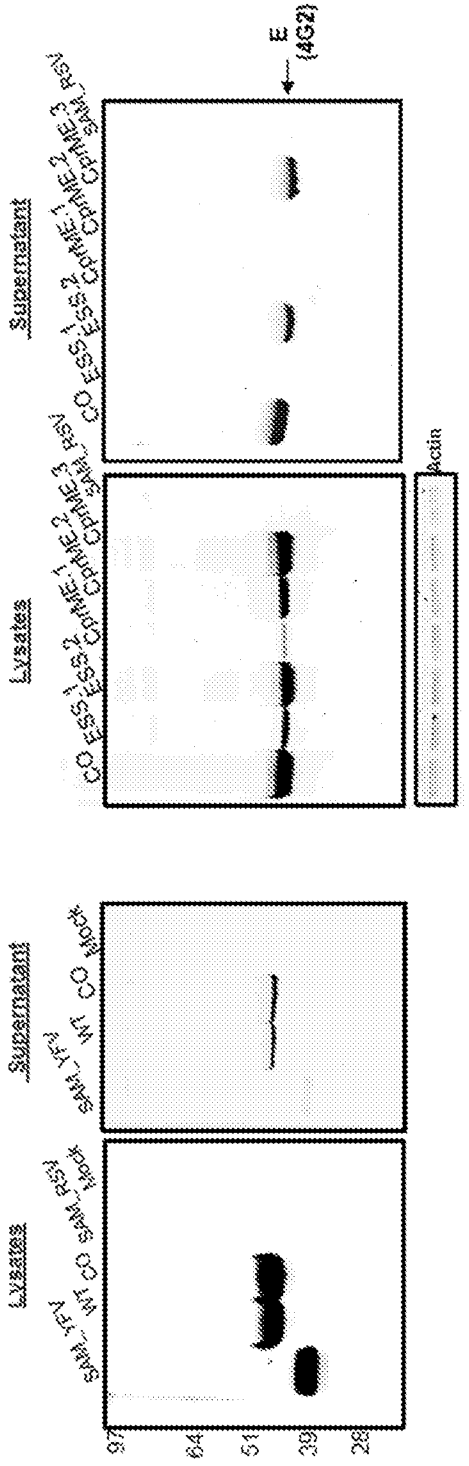

FIG. 8. Analysis of expression and secretion of E protein from Zika-SAM constructs. Expression of E protein was detected by immunoblot in cell lysates for all Zika-SAM constructs tested (see Table 2): wild type prME ("WT"; construct #1), codon optimized prME ("CO", construct #2), enhanced -PQ-Q- signal sequence ("ESS.1", construct #3), IgG signal sequence ("ESS.2", construct #4), and the three capsid constructs: CprME.1 (construct #5), CprME.2 (construct #6) and CprME.3 (construct #7). As positive control, a SAM construct which expresses E protein of another flavivirus, Yellow Fever virus, was included ("SAM-YFV"). Negative controls included a SAM-Respiratory Syncytial Virus ("SAM-RSV") construct and mock transfection ("Mock").

Secretion of E protein into cell supernatants was also detected by immunoblot for at least construct #1 ("VVT"), construct #2 ("CO"), construct #4 (ESS.2), and construct #7 (CprME.3).

Figure 9:
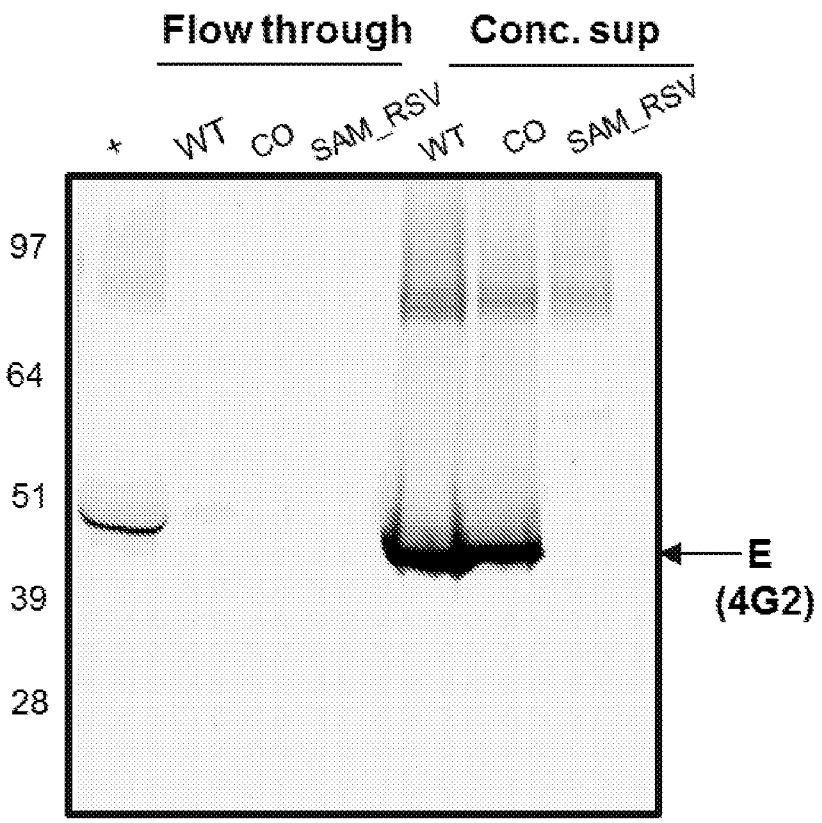

FIG. 9. Immunoblots of wild type ("VVT") and codon optimized ("CO") cell culture supernatants after 100 kDa cutoff concentration shows that secreted Zika E protein is present in a high molecular weight form that is retained in the column but not in the flow through. This result suggests that the secreted E protein forms higher order complexes than monomers or dimers, which is consistent with the hypothesis of SVPs.

Figure 10:
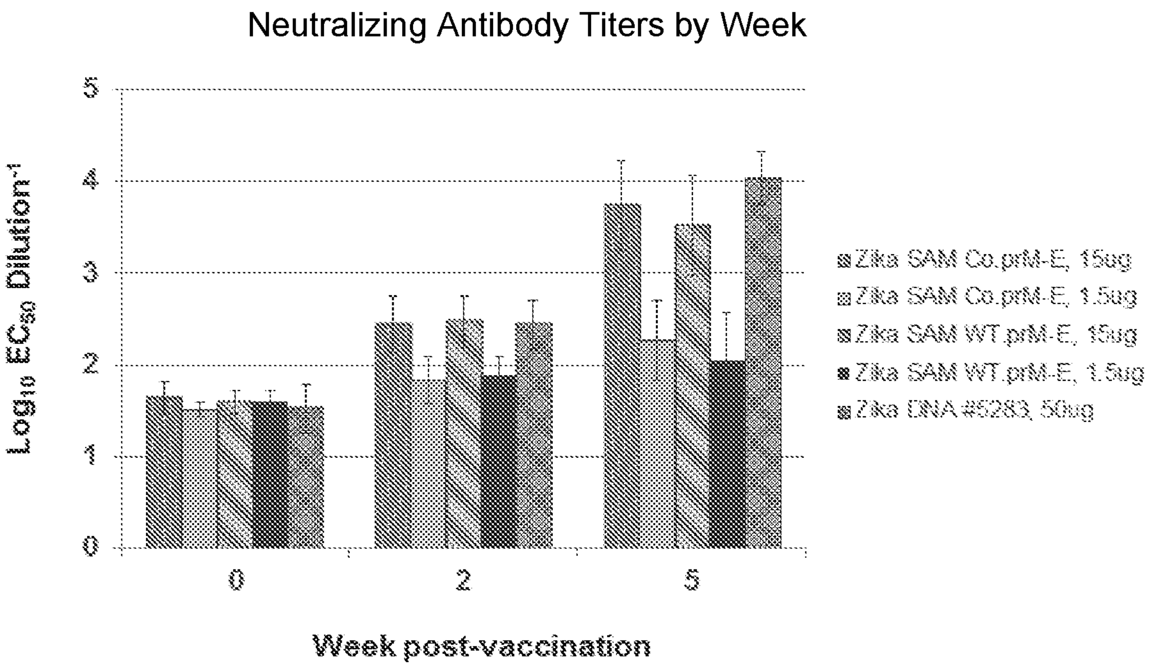

FIG. 10: Neutralizing Antibody Responses. Mice were found to have significant neutralizing Zika antibodies two weeks after a single vaccination with Zika-SAM constructs #1 or #2 (Co.prM-E and VVT.prM-E, respectively)), or with positive control Zika DNA construct #5283, as measured by reporter virus particle (RVP) neutralization assay. Neutralizing antibody titers were further increased two weeks after a second vaccination with the same Zika-SAM construct or the positive control. A dose-response effect was observed for SAM constructs #1 and #2, with 15 ug of RNA eliciting more neutralizing antibodies than 1.5 ug RNA.

Figure 11:
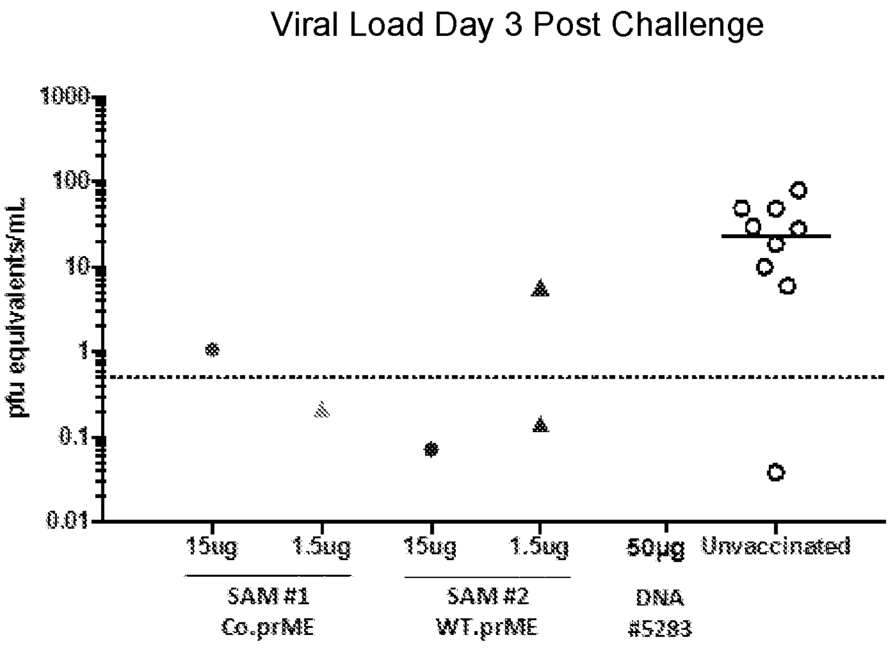

FIG. 11: Protection from Zika Challenge: Mice vaccinated on days 0 and 21 were challenged with live Zika virus on day 49. Viral load was measured 3 days post-challenge. Vaccination with SAM constructs #1 and #2 (at 1.5 μg and 15 μg doses), as well as the positive control (Zika DNA #5283) were protective against Zika viremia, as compared to unvaccinated mice. Dotted line indicates the limit of quantification (LOQ) of the assay.

DETAILED DESCRIPTION OF THE INVENTION

Antigens; Variants; Fragments; and Constructs

The present inventors provide constructs useful as components of immunogenic compositions for the induction of an immune response in a subject against Zika viral infection constructs useful for the expression of antigens, methods for their use in treatment, and processes for their manufacture. By "construct" is intended a nucleic acid that encodes polypeptide sequences described herein, and may comprise DNA, RNA, or non-naturally occurring nucleic acid monomers. The nucleic acid components of constructs are described more fully in the Nucleic Acids section herein.

In some embodiments, the constructs disclosed herein encode wild-type polypeptide sequences of a Zika virus, or a variant, or a fragment thereof. The constructs may further encode a polypeptide sequence heterologous to the polypeptide sequences of a Zika virus. In some embodiments, the constructs encode wild-type polypeptide sequences of a Brazilian strain Zika virus, or a variant, or a fragment thereof. By "Brazilian strain Zika virus" is intended any strain of Zika virus denoted as "Brazilian" in Table 1. Unless indicated otherwise, descriptions of the wild-type prME antigen are made by reference to the Natal strain (Brazil), GenBank number KU527068.1, as depicted in the SEQ ID NO:1 (nucleic acid) and SEQ ID NO:2 (polypeptide), and as depicted in FIG. 3A-D, and FIG. 4A-C.

A "variant" of a polypeptide sequence includes amino acid sequences having one or more amino acid substitutions, insertions and/or deletions when compared to the reference sequence. The variant may comprise an amino acid sequence which is at least 70%, at least 75%, at least 80%, at least 85%, at least 90%, at least 95%, at least 96%, at least 97%, at least 98%, or at least 99% identical to a full-length wild-type polypeptide, for example, to a polypeptide according to SEQ ID NO:2.

Alternatively, or in addition, a fragment of a polypeptide may comprise an immunogenic fragment (i.e. an epitope-containing fragment) of the full-length polypeptide which may comprise a contiguous amino acid sequence of at least 8, at least 9, at least 10, at least 11, at least 12, at least 13, at least 14, at least 15, at least 16, at least 17, at least 18, at least 19, or more amino acids which is identical to a contiguous amino acid sequence of the full-length polypeptide.

A fragment of a polypeptide may comprise N- and/or C-terminal deletions when compared to a full-length polypeptide, for example SEQ ID NO:2, wherein the fragment comprises a deletion of up to 1, 2, 3, 4, 5, 6, 7, 8, 9, 10, 15 or 20 amino acids from the N-terminus, the C-terminus, or both the N-terminus and C-terminus of the full-length sequence. It may be specified that the deletions are of consecutive amino acids.

As used herein, the term "antigen" refers to a molecule containing one or more epitopes (e.g., linear, conformational or both) that will stimulate a host's immune system to make a humoral and/or cellular antigen-specific immunological response (i.e. an immune response which specifically recognizes an antigen polypeptide). An "epitope" is that portion of an antigen that determines its immunological specificity.

T- and B-cell epitopes can be identified empirically (e.g. using PEPSCAN or similar methods). See the following references: Geysen et al. (1984) *PNAS USA* 81:3998-4002; Carter (1994) *Methods Mol Biol* 36:207-23. They can be predicted (e.g. using the Jameson-Wolf antigenic index (see Jameson et al. (1988) *CABIOS* 4(1): 181-186), matrix-based approaches (see Raddrizzani & Hammer (2000) *Brief Bioinform* 1(2): 179-89), TEPITOPE (see De Lalla et al. (1999) *J. Immunol.* 163: 1725-29), neural networks (see Brusic et al. (1998) *Bioinformatics* 14(2): 121-30), OptiMer & EpiMer (see Meister et al. (1995) *Vaccine* 13(6):581-91; see Roberts et al. (1996) *AIDS Res Hum Retroviruses* 12(7): 593-610), ADEPT (see Maksyutov & Zagrebelnaya (1993) *Comput Appl Biosci* 9(3):291-7), Tsites (see Feller & de la Cruz (1991) *Nature* 349(6311):720-1), hydrophilicity (see Hopp (1993) *Peptide Research* 6:183-190), antigenic index (see Welling et al. (1985) *FEBS Lett.* 188:215-218) or the methods disclosed in reference Davenport et al. (1995) *Immunogenetics* 42:392-297, etc.).

In some embodiments, the constructs herein encode a Zika virus prME antigen. By "Zika virus prME antigen" is intended the amino acid sequence, or a nucleotide sequence encoding the amino acid sequence, of a wild-type Zika virus structural protein prME, a variant, or a fragment thereof. FIG. 3 and FIG. 4 identify the amino acid sequence of several full-length wild-type Zika virus prME structural protein variants. The sequence identifier numbers for each are set forth in the Sequences section and Sequence Listing herein. See SEQ ID NOS:2 and 15-23.

Thus, where a Zika virus prME antigen is a variant of a wild-type prME polypeptide, the variant may comprise an amino acid sequence which is at least 70%, at least 75%, at least 80%, at least 85%, at least 90%, at least 95%, at least 96%, at least 97%, at least 98%, or at least 99% identical to a full-length wild-type polypeptide, for example, to a polypeptide according to SEQ ID NOS:2 and 15-23. Alternatively, or in addition, a fragment of a polypeptide may comprise an immunogenic fragment (i.e. an epitope-containing fragment) of the full-length polypeptide which may comprise a contiguous amino acid sequence of at least 8, at least 9, at least 10, at least 11, at least 12, at least 13, at least 14, at least 15, at least 16, at least 17, at least 18, at least 19, or more amino acids which is identical to a contiguous amino acid sequence of the full-length polypeptide.

A fragment of a Zika virus prME polypeptide may comprise N- and/or C-terminal deletions when compared to a full-length polypeptide, for example SEQ ID NOS:2 and 15-23, wherein the fragment comprises a deletion of up to 1, 2, 3, 4, 5, 6, 7, 8, 9, 10, or 20 amino acids from the N-terminus, the C-terminus, or both the N-terminus and C-terminus of the full-length sequence. It may be specified that the deletions are of consecutive amino acids. In some embodiments, the Zika virus prME polypeptide comprises a fragment selected from the group consisting of amino acids 1 to 692 of SEQ ID NO:2 and amino acids 21 to 692 of SEQ ID NO:2.

In some embodiments, an immunogenic fragment of a prME antigen comprises the full-length of the Zika virus M antigen. By "Zika virus M antigen" is intended the amino acid sequence, or a nucleotide sequence encoding the amino acid sequence, of SEQ ID NO:28. Where a Zika virus M antigen is a variant of a wild-type M polypeptide, the variant may comprise an amino acid sequence which is at least 70%, at least 75%, at least 80%, at least 85%, at least 90%, at least 95%, at least 96%, at least 97%, at least 98%, or at least 99% identical to a full-length wild-type polypeptide, for example, to a polypeptide according to SEQ ID NO:28.

A fragment of a Zika virus M antigen may comprise N- and/or C-terminal deletions when compared to a full-length polypeptide, for example SEQ ID NO:28, wherein the fragment comprises a deletion of up to 1, 2, 3, 4, 5, 6, 7, 8, 9, 10, 15 or 20 amino acids from the N-terminus, the C-terminus, or both the N-terminus and C-terminus of the full-length sequence. It may be specified that the deletions are of consecutive amino acids.

In some embodiments, an immunogenic fragment of a prME antigen comprises the full-length of the Zika virus E antigen. By "Zika virus E antigen" is intended the amino acid sequence, or a nucleotide sequence encoding the amino acid sequence, of SEQ ID NO:29. Where a Zika virus E antigen is a variant of a wild-type E polypeptide, the variant may comprise an amino acid sequence which is at least 70%, at least 75%, at least 80%, at least 85%, at least 90%, at least 95%, at least 96%, at least 97%, at least 98%, or at least 99% identical to a full-length wild-type polypeptide, for example, to a polypeptide according to SEQ ID NO:29.

A fragment of a Zika virus E antigen may comprise N- and/or C-terminal deletions when compared to a full-length polypeptide, for example SEQ ID NO:29, wherein the fragment comprises a deletion of up to 1, 2, 3, 4, 5, 6, 7, 8, 9, 10, 15 or 20 amino acids from the N-terminus, the C-terminus, or both the N-terminus and C-terminus of the full-length sequence. In one embodiment, a Zika virus E antigen comprises amino acids 1 to 520 of SEQ ID NO:29. It may be specified that the deletions are of consecutive amino acids.

As noted elsewhere herein, the Zika virus RNA is translated as a polyprotein comprising a prM signal sequence. The prM signal sequence is located N-terminal to the prM antigen sequence. Cleavage occurs in the ER lumen by a cellular signal peptidase and generates the N terminus of prM. Where the polyprotein comprises a wild-type amino acid sequence, the polyprotein comprises a native prM signal sequence, SEQ ID NO:5. By "native prM signal sequence" is intended the amino acid sequence, or a nucleotide sequence encoding the amino acid sequence, of a signal sequence of a wild-type viral prME, SEQ ID NO:5. FIG. 3A-B and FIG. 4A identify the amino acid sequence of several full-length native prM signal sequence variants from various Zika virus strains.

In some embodiments, the constructs encode a native prM signal sequence. Where the prM signal sequence is a variant of a native prM signal sequence, the variant may comprise an amino acid sequence which is at least 70%, at least 75%, at least 80%, at least 85%, at least 90%, at least 95%, at least 96%, at least 97%, at least 98%, or at least 99% identical to the full-length polypeptide according to SEQ ID NO:5. Alternatively, or in addition, a fragment of a polypeptide may comprise a functional fragment (i.e., containing the sequence recognized and cleaved by the protease) of the full-length polypeptide which may comprise a contiguous amino acid sequence of at least 9, at least 10, at least 11, at least 12, at least 13, at least 14, at least 15, at least 16, at least 17 amino acids of SEQ ID NO: 5 which is identical to a contiguous amino acid sequence of full-length polypeptide.

In some embodiments, the construct encodes a mutated prM signal sequence for enhanced prM cleavage. By "mutated prM signal sequence for enhanced prM cleavage" is intended a prM signal sequence in which the native amino acid sequence is modified such that residues are added, replaced or deleted to increase the extent of signalase cleavage. In one embodiment, the amino acid sequence of the native prM signal sequence is altered by the replacement of Gly, Phe, and Ala at positions −5, −4, and −2 from the signalase cleavage site with Pro, Gin, and Gin, respectively. See FIG. 6. The signalase cleavage site is located at the junction of the prM signal sequence and prME antigen. This is depicted in FIG. 3A and FIG. 4A for several Zika virus strains. In some embodiments, the mutated prM signal sequence for enhanced prM cleavage has the amino acid sequence set forth in FIG. 6 (ESS.1) (SEQ ID NO:8), or may be a variant or fragment thereof. A variant may comprise an amino acid sequence which is at least 70%, at least 75%, at least 80%, at least 85%, at least 90%, at least 95%, at least 96%, at least 97%, at least 98%, or at least 99% identical to a full-length wild-type polypeptide, for example, to a polypeptide according to SEQ ID NO:8. Alternatively, or in addition, a fragment of a polypeptide may comprise a functional fragment (i.e., containing the sequence recognized and cleaved by the protease) of the full-length polypeptide which may comprise a contiguous amino acid sequence of at least 9, at least 10, at least 11, at least 12, at least 13, at least 14, at least 15, at least 16, at least 17, which is identical to a contiguous amino acid sequence of the full-length polypeptide.

In some embodiments, the construct encodes a heterologous, non-Zika signal sequence. In some embodiments, the construct encodes an IgG signal sequence, variant, or fragment thereof, in place of the Zika prM signal sequence. By "lgG signal sequence" is intended the amino acid sequence as set forth in FIG. 6 (ESS.2) (SEQ ID NO:10). A variant may comprise an amino acid sequence which is at least 70%, at least 75%, at least 80%, at least 85%, at least 90%, at least 95%, at least 96%, at least 97%, at least 98%, or at least 99% identical to a full-length wild-type polypeptide, for example, to a polypeptide according to SEQ ID NO:10. Alternatively, or in addition, a fragment of a polypeptide may comprise a functional fragment (i.e., containing the sequence recognized and cleaved by the protease) of the full-length polypeptide which may comprise a contiguous amino acid sequence of at least 9, at least 10, at least 11, at least 12, at least 13, at least 14, at least 15, at least 16, at least 17, which is identical to a contiguous amino acid sequence of the full-length polypeptide.

In some embodiments, the construct encodes a polypeptide comprising a cleavable capsid protein. By "capsid sequence" is intended any of the amino acid sequences designated "capsid (C)" as set forth in FIG. 3 (for example, amino acids 1 to 104 of SEQ ID NO:12). A capsid sequence may further comprise the native C and prM cleavage sites (corresponding to the NS2B-3 and signalase cleavage sites depicted in FIG. 7). Where the capsid sequence is a variant of a wild-type capsid sequence, the variant may comprise an amino acid sequence which is at least 70%, at least 75%, at least 80%, at least 85%, at least 90%, at least 95%, at least 96%, at least 97%, at least 98%, or at least 99% identical to a full-length wild-type capsid polypeptide, for example, to amino acids 1 to 104 of SEQ ID NO:12. Alternatively, or in addition, a fragment of a polypeptide may comprise a functional fragment (i.e., containing the sequence recognized and cleaved by the protease) of the full-length polypeptide which may comprise a contiguous amino acid sequence of at least 8, at least 9, at least 10, at least 11, at least 12, at least 13, at least 14, at least 15, at least 16, at least 17, at least 18, at least 19, at least 25, at least 50 and at least 75 amino acids which is identical to a contiguous amino acid sequence of the full-length capsid polypeptide.

A fragment of a Zika virus capsid protein may comprise N- and/or C-terminal deletions when compared to a full-length polypeptide, for example amino acids 1 to 104 of SEQ ID NO:12, wherein the fragment comprises a deletion of up to 1, 2, 3, 4, 5, 6, 7, 8, 9, 10, 15 or 20 amino acids from the N-terminus, the C-terminus, or both the N-terminus and C-terminus of the full-length sequence.

In some embodiments, the construct encodes a polypeptide comprising a porcine teschovirus-1 2A cleavage sequence. By "porcine teschovirus-1 2A cleavage sequence" is intended the amino acid sequence as set forth in FIG. 7 (P2A sequence) (SEQ ID NO:14).

In some embodiments, the construct encodes a polypeptide comprising from the C-terminal portion to the N-terminal portion: a prME antigen, variant, or immunogenic fragment thereof; one or more components selected from the group consisting of a prM signal sequence, variant, or fragment thereof; a mutated prM signal sequence for enhanced prM cleavage, variant, or fragment thereof; an IgG signal sequence, variant, or fragment thereof; a porcine teschovirus-1 2A cleavage sequence variant, or fragment thereof; and a capsid sequence, variant, or fragment thereof.

In some embodiments, a construct encodes each component of the polypeptide, if present, juxtaposed immediately next to the adjacent component, i.e., without any intervening amino acids. In some embodiments, a linker group of 1, 2, 3, 4, or 5 amino acids is present between one or more of the components.

In some embodiments, the construct encodes a polypeptide having a sequence selected from the group consisting of SEQ ID NO:26, SEQ ID NO:31, SEQ ID NO:36, SEQ ID NO:41, SEQ ID NO:46, SEQ ID NO:52, and SEQ ID NO:58. In some embodiments, the construct encodes a polypeptide which is at least 70%, at least 75%, at least 80%, at least 85%, at least 90%, at least 95%, at least 96%, at least 97%, at least 98%, or at least 99% identical to a sequence selected from the group consisting of SEQ ID NO:26, SEQ ID NO:31, SEQ ID NO:36, SEQ ID NO:41, SEQ ID NO:46, SEQ ID NO:52, and SEQ ID NO:58. In some embodiments, the construct encodes a polypeptide which comprises a fragment of a full-length sequence selected from the group consisting of SEQ ID NO:26, SEQ ID NO:31, SEQ ID NO:36, SEQ ID NO:41, SEQ ID NO:46, SEQ ID NO:52, and SEQ ID NO:58, wherein the fragment comprises a contiguous stretch of the amino acid sequence of the full-length sequence up to 1, 2, 3, 4, 5, 6, 7, 8, 9, or 10 amino acids shorter than the full-length sequence.

In some embodiments, the construct comprises a DNA sequence selected from the group consisting of SEQ ID NO:25, SEQ ID NO:30, SEQ ID NO:35, SEQ ID NO:40, SEQ ID NO:45, SEQ ID NO:51, and SEQ ID NO:57. In some embodiments, the construct comprises a DNA sequence which is at least 70%, at least 75%, at least 80%, at least 85%, at least 90%, at least 95%, at least 96%, at least 97%, at least 98%, or at least 99% identical to a sequence selected from the group consisting of SEQ ID NO:25, SEQ ID NO:30, SEQ ID NO:35, SEQ ID NO:40, SEQ ID NO:45, SEQ ID NO:51, and SEQ ID NO:57. In some embodiments, the construct comprises a DNA sequence which comprises a fragment of a full-length sequence selected from the group consisting of SEQ ID NO:25, SEQ ID NO:30, SEQ ID NO:35, SEQ ID NO:40, SEQ ID NO:45, SEQ ID NO:51, and SEQ ID NO:57 wherein the fragment comprises a contiguous stretch of the DNA sequence of the full-length sequence up to 1, 2, 3, 4, 5, 6, 7, 8, 9, 10, 15, 20, 25, or 30 nucleic acids shorter than the full-length sequence.

In some embodiments, the construct comprises a fragment of a full-length DNA sequence selected from the group consisting of SEQ ID NO:25, SEQ ID NO:30, SEQ ID NO:35, SEQ ID NO:40, SEQ ID NO:45, SEQ ID NO:51, and SEQ ID NO:57, wherein the fragment comprises a deletion of up to 1, 2, 3, 4, 5, 6, 7, 8, 9, 10, 15, 20, 25, or 30 nucleic acids from the 5' end, the 3' end, or both the 5' and 3' ends of the full-length sequence. In some embodiments, the construct comprises nucleic acids 1 to 2076 of a sequence selected from the group consisting of SEQ ID NO:25, SEQ ID NO:30, SEQ ID NO:35, SEQ ID NO:40, SEQ ID NO:45, SEQ ID NO:51, and SEQ ID NO:57.

In some embodiments, the construct comprises an RNA sequence selected from the group consisting of SEQ ID NO:77, SEQ ID NO:78, SEQ ID NO:79, SEQ ID NO:80, SEQ ID NO:81, SEQ ID NO:82, and SEQ ID NO:83. In some embodiments, the construct comprises an RNA sequence which is at least 70%, at least 75%, at least 80%, at least 85%, at least 90%, at least 95%, at least 96%, at least 97%, at least 98%, or at least 99% identical to a sequence selected from the group consisting of SEQ ID NO:77, SEQ ID NO:78, SEQ ID NO:79, SEQ ID NO:80, SEQ ID NO:81, SEQ ID NO:82, and SEQ ID NO:83. In some embodiments, the construct comprises an RNA sequence which comprises a fragment of a full-length sequence selected from the group consisting of SEQ ID NO:77, SEQ ID NO:78, SEQ ID NO:79, SEQ ID NO:80, SEQ ID NO:81, SEQ ID NO:82, and SEQ ID NO:83 wherein the fragment comprises a contiguous stretch of the RNA sequence of the full-length sequence up to 1, 2, 3, 4, 5, 6, 7, 8, 9, 10, 15, 20, 25, or 30 nucleic acids shorter than the full-length sequence.

In some embodiments, the construct comprises a fragment of a full-length RNA sequence selected from the group consisting of SEQ ID NO:77, SEQ ID NO:78, SEQ ID NO:79, SEQ ID NO:80, SEQ ID NO:81, SEQ ID NO:82, or SEQ ID NO:83, wherein the fragment comprises a deletion of up to 1, 2, 3, 4, 5, 6, 7, 8, 9, 10, 15, 20, 25, or 30 nucleic acids from the 5' end, the 3' end, or both the 5' and 3' ends of the full-length sequence. In some embodiments, the construct comprises nucleic acids 1 to 2076 of a sequence selected from the group consisting of SEQ ID NO:77, SEQ ID NO:78, SEQ ID NO:79, SEQ ID NO:80, SEQ ID NO:81, SEQ ID NO:82, or SEQ ID NO:83.

Polypeptides

In some embodiments, a polypeptide herein is in a non-naturally occurring form (e.g. a recombinant or modified form).

For example, polypeptides (e.g. antigens) disclosed herein can be prepared by chemical synthesis (in whole or in part), by digesting longer polypeptides using proteases, by translation from RNA, by purification from cell culture (e.g. from recombinant expression), from the organism itself, etc. An exemplary method for production of peptides <40 amino acids long involves in vitro chemical synthesis, see the following references: Bodanszky (1993) Principles of Peptide Synthesis (ISBN: 0387564314); and Fields et al. (1997) Meth Enzymol 289: Solid-Phase Peptide Synthesis. ISBN: 0121821900. Solid-phase peptide synthesis techniques, such as methods based on tBoc or Fmoc chemistry, are known in the art, see the following reference: Chan & White (2000) Fmoc Solid Phase Peptide Synthesis. ISBN: 0199637245. Enzymatic synthesis may also be used in part or in full, see the following reference: Kullmann (1987) Enzymatic Peptide Synthesis. ISBN: 0849368413. As an alternative to chemical synthesis, biological synthesis may be used e.g. the polypeptides may be produced by translation. This may be carried out in vitro or in vivo. Biological methods are in general restricted to the production of polypeptides based on L-amino acids, but manipulation of translation machinery (e.g. of aminoacyl tRNA molecules) can be used to allow the introduction of D-amino acids (or of other non-natural amino acids, such as iodotyrosine or methylphenylalanine, azidohomoalanine, etc.), see the following reference: Kullmann (1987) Enzymatic Peptide Synthesis. ISBN: 0849368413. Where D-amino acids are included, however, it is preferred to use chemical synthesis. Polypeptides of the disclosure may have covalent modifications at the C-terminus and/or N-terminus. They can also take various forms (e.g. native, fusions, glycosylated, non-glycosylated, lipidated, non-lipidated, phosphorylated, non-phosphorylated, myristoylated, non-myristoylated, monomeric, multimeric, particulate, denatured, etc.). The polypeptides can be naturally or non-naturally glycosylated (i.e. the polypeptide may have a glycosylation pattern that differs from the glycosylation pattern found in the corresponding naturally occurring polypeptide).

Non-naturally occurring forms of polypeptides herein may comprise one or more heterologous amino acid sequences (e.g. another antigen sequence, another signal sequence, a detectable tag, or the like) in addition to a Zika virus prME antigen sequence. For example, a polypeptide herein may be a fusion protein. Alternatively, or in addition, the amino acid sequence or chemical structure of the polypeptide may be modified (e.g. with one or more non-natural amino acids, by covalent modification, and/or or by having a different glycosylation pattern, for example, by the removal or addition of one or more glycosyl groups) compared to a naturally-occurring polypeptide sequence.

Polypeptides (e.g. antigens) disclosed herein are preferably provided in purified or substantially purified form i.e. substantially free from other polypeptides (e.g. free from naturally-occurring polypeptides), particularly from other Zika virus or host cell polypeptides; for example, at least about 50% pure (by weight), at least about 60% pure (by weight), at least about 70% pure (by weight), at least about 80% pure (by weight), or at least about 90% pure, etc. Alternatively, less than about 50%, less than about 40%, less than about 30%, less than about 20%, less than about 10%, or less than about 5% of a composition is made up of other expressed polypeptides.

Nucleic Acids

The present inventors disclose herein nucleic acid molecules comprising a sequence which encodes a Zika virus prME antigen. Nucleic acids as disclosed herein can take various forms (e.g. single-stranded, double-stranded, vectors etc.). Nucleic acids may be circular or branched, but will generally be linear.

The nucleic acids used herein are preferably provided in purified or substantially purified form i.e. substantially free from other nucleic acids (e.g. free from naturally-occurring nucleic acids), particularly from other Zika virus or host cell nucleic acids, generally being at least about 50% pure (by weight), at least about 60% pure (by weight), at least about 70% pure (by weight), at least about 80% pure (by weight), and usually at least about 90% pure.

Nucleic acids may be prepared in many ways e.g. by chemical synthesis (e.g. phosphoramidite synthesis of DNA) in whole or in part, by digesting longer nucleic acids using nucleases (e.g. restriction enzymes), by joining shorter nucleic acids or nucleotides (e.g. using ligases or polymerases), from genomic or cDNA libraries, etc.

The term "nucleic acid" in general means a polymeric form of nucleotides of any length, which contain deoxyribonucleotides, ribonucleotides, and/or their analogs. It includes DNA, RNA, DNA/RNA hybrids. It also includes DNA or RNA analogs, such as those containing modified backbones (e.g. peptide nucleic acids (PNAs) or phosphorothioates) or modified bases. Thus the nucleic acid of the disclosure includes mRNA, DNA, cDNA, recombinant nucleic acids, branched nucleic acids, plasmids, vectors, etc. Where the nucleic acid takes the form of RNA, it may or may not have a 5' cap.

The nucleic acids herein comprise a sequence which encodes at least one Zika virus prME antigen. Typically, the nucleic acids of the invention will be in recombinant form, i.e. a form which does not occur in nature. For example, the nucleic acid may comprise one or more heterologous nucleic acid sequences (e.g. a sequence encoding another antigen and/or a control sequence such as a promoter or an internal ribosome entry site) in addition to the sequence encoding at least one Zika virus prME antigen. The nucleic acid may be part of a vector i.e. part of a nucleic acid construct designed for transduction/transfection of one or more cell types. Vectors may be, for example, "expression vectors" which are designed for expression of a nucleotide sequence in a host cell, or "viral vectors" which are designed to result in the production of a recombinant virus or virus-like particle.

Alternatively, or in addition, the sequence or chemical structure of the nucleic acid may be modified compared to a naturally-occurring sequence which encodes a Zika virus prME antigen. The sequence of the nucleic acid molecule may be modified, e.g. to increase the efficacy of expression or replication of the nucleic acid, or to provide additional stability or resistance to degradation.

The nucleic acid encoding the polypeptides described above may be codon optimized. By "codon optimized" is intended modification with respect to codon usage that may increase translation efficacy and/or half-life of the nucleic acid. A poly A tail (e.g., of about 30 adenosine residues or more) may be attached to the 3' end of the RNA to increase its half-life. The 5' end of the RNA may be capped with a modified ribonucleotide with the structure m7G (5') ppp (5') N (cap 0 structure) or a derivative thereof, which can be incorporated during RNA synthesis or can be enzymatically engineered after RNA transcription (e.g., by using Vaccinia Virus Capping Enzyme (VCE) consisting of mRNA triphosphatase, guanylyl-transferase and guanine-7-methytransferase, which catalyzes the construction of N7-monomethylated cap 0 structures). Cap 0 structure plays an important role in maintaining the stability and translational efficacy of the RNA molecule. The 5' cap of the RNA molecule may be further modified by a 2'-O-Methyltransferase which results in the generation of a cap 1 structure (m7Gppp [m2'-O] N), which may further increases translation efficacy.

The nucleic acids may comprise one or more nucleotide analogs or modified nucleotides. As used herein, "nucleotide analog" or "modified nucleotide" refers to a nucleotide that contains one or more chemical modifications (e.g., substitutions) in or on the nitrogenous base of the nucleoside (e.g., cytosine (C), thymine (T) or uracil (U)), adenine (A) or guanine (G)). A nucleotide analog can contain further chemical modifications in or on the sugar moiety of the nucleoside (e.g., ribose, deoxyribose, modified ribose, modified deoxyribose, six-membered sugar analog, or open-chain sugar analog), or the phosphate. The preparation of nucleotides and modified nucleotides and nucleosides are well-known in the art, see the following references: U.S. Pat. Nos. 4,373,071, 4,458,066, 4,500,707, 4,668,777, 4,973,679, 5,047,524, 5,132,418, 5,153,319, 5,262,530, 5,700,642. Many modified nucleosides and modified nucleotides are commercially available.

Modified nucleobases which can be incorporated into modified nucleosides and nucleotides and be present in the RNA molecules include: m5C (5-methylcytidine), m5U (5-methyluridine), m6A (N6-methyladenosine), s2U (2-thiouridine), Um (2'-0-methyluridine), mlA (1-methyladenosine); m2A (2-methyladenosine); Am (2-1-O-methyladenosine); ms2m6A (2-methylthio-N6-methyladenosine); i6A (N6-isopentenyladenosine); ms2i6A (2-methylthio-N6-isopentenyladenosine); io6A (N6-(cis-hydroxyisopentenyl) adenosine); ms2io6A (2-methylthio-N6-(cis-hydroxyisopentenyl) adenosine); g6A (N6-glycinylcarbamoyladenosine); t6A (N6-threonyl carbamoyladenosine); ms2t6A (2-methylthio-N6-threonyl carbamoyladenosine); m6t6A (N6-methyl-N6-threonylcarbamoyladenosine); hn6A(N6-hydroxynorvalylcarbamoyl adenosine); ms2hn6A (2-methylthio-N6-hydroxynorvalyl carbamoyladenosine); Ar(p) (2'-0-ribosyladenosine (phosphate)); I (inosine); mil (1-methylinosine); m'lm (I,2'-0-dimethylinosine); m3C (3-methylcytidine); Cm (2T-0-methylcytidine); s2C (2-thiocytidine); ac4C (N4-acetylcytidine); 5FC (5-fonnylcytidine); m5Cm (5,2-O-dimethylcytidine); ac4Cm (N4acetyl2TOmethylcytidine); k2C (lysidine); mlG (1-methylguanosine); m2G (N2-methylguanosine); m7G (7-methylguanosine); Gm (2'-0-methylguanosine); m22G (N2,N2-dimethylguanosine); m2Gm (N2,2'-0-dimethylguanosine); m22Gm (N2,N2,2'-0-trimethylguanosine); Gr(p) (2'-0-ribosylguanosine (phosphate)); yW (wybutosine); o2yW (peroxywybutosine); OHyW (hydroxywybutosine); OHyW* (undermodified hydroxywybutosine); imG (wyosine); mimG (methylguanosine); Q (queuosine); oQ (epoxyqueuosine); galQ (galtactosyl-queuosine); manQ (mannosyl-queuosine); preQo (7-cyano-7-deazaguanosine); preQi (7-aminomethyl-7-deazaguanosine); G* (archaeosine); D (dihydrouridine); m5Um (5,2'-0-dimethyluridine); s4U (4-thiouridine); m5s2U (5-methyl-2-thiouridine); s2Um (2-thio-2'-0-methyluridine); acp3U (3-(3-amino-3-carboxypropyl)uridine); hoSU (5-hydroxyuridine); moSU (5-methoxyuridine); cmo5U (uridine 5-oxyacetic acid); mcmo5U (uridine 5-oxyacetic acid methyl ester); chm5U (5-(carboxyhydroxymethyl)uridine)); mchm5U (5-(carboxyhydroxymethyl)uridine methyl ester); mcm5U (5-methoxycarbonyl methyluridine); mcm5Um (S-methoxycarbonylmethyl-2-O-methyluridine); mcm5s2U (5-methoxycarbonylmethyl-2-thiouridine); nm5s2U (5-aminomethyl-2-thiouridine); mnm5U (5-methylaminomethyluridine); mnm5s2U (5-methylaminomethyl-2-thiouridine); mnm5se2U (5-methylaminomethyl-2-selenouridine); ncm5U (5-carbamoylmethyl uridine); ncm5Um (5-carbamoylmethyl-2'-0-methyluridine); cmnm5U (5-carboxymethylaminomethyluridine); cnmm5Um (5-carboxymethy 1 aminomethyl-2-L-Omethyl uridine); cmnm5s2U (5-carboxymethylaminomethyl-2-thiouridine); m62A (N6,N6-dimethyladenosine); Tm (2'-0-methylinosine); m4C (N4-methylcytidine); m4Cm (N4,2-0-dimethylcytidine); hm5C (5-hydroxymethylcytidine); m3U (3-methyluridine); cm5U (5-carboxymethyluridine); m6Am (N6,T-0-dimethyladenosine); rn62Am (N6,N6,0-2-trimethyladenosine); m2'7G (N2,7-dimethylguanosine); m2'2'7G (N2,N2,7-trimethylguanosine); m3Um (3,2T-0-dimethyluridine); m5D (5-methyldihydrouridine); £5Cm (5-formyl-2'-0-methylcytidine); mlGm (I,2'-0-dimethylguanosine); m'Am (1,2-O-dimethyl adenosine) irinomethyluridine); tm5s2U (S-taurinomethyl-2-thiouridine)); iniG-14 (4-demethyl guanosine); imG2 (isoguanosine); ac6A (N6-acetyladenosine), hypoxanthine, inosine, 8-oxo-adenine, 7-substituted derivatives thereof, dihydrouracil, pseudouracil, 2-thiouracil, 4-thiouracil, 5-aminouracil, 5-(Ci-Ce)-alkyluracil, 5-methyluracil, 5-(C2-C6)-alkenyluracil, 5-(C2-Ce)-alkynyluracil, 5-(hydroxymethyl)uracil, 5-chlorouracil, 5-fluorouracil, 5-bromouracil, 5-hydroxycytosine, 5-(Ci-C6)-alkylcytosine, 5-methylcytosine, 5-(C2-C6)-alkenylcytosine, 5-(C2-C6)-alkynylcytosine, 5-chlorocytosine, 5-fluorocytosine, 5-bromocytosine, N2-dimethylguanine, 7-deazaguanine, 8-azaguanine, 7-deaza-7-substituted guanine, 7-deaza-7-(C2-C6)alkynylguanine, 7-deaza-8-substituted guanine, 8-hydroxyguanine, 6-thioguanine, 8-oxoguanine, 2-aminopurine, 2-amino-6-chloropurine, 2,4-diaminopurine, 2,6-diaminopurine, 8-azapurine, substituted 7-deazapurine, 7-deaza-7-substituted purine, 7-deaza-8-substituted purine, hydrogen (abasic residue), m5C, m5U, m6A, s2U, W, or 2'-0-methyl-U. Many of these modified nucleobases and their corresponding ribonucleosides are available from commercial suppliers.

Nucleic Acid-Based Vaccines

The present inventors disclose compositions comprising a nucleic acid sequence which encodes a polypeptide comprising a Zika virus antigen, variant or fragment thereof. Such compositions may be a nucleic acid-based vaccine. A further composition comprising a nucleic acid sequence which encodes one or more additional (e.g., a second, third, fourth, fifth or sixth) Zika virus antigens may also be provided as a nucleic acid-based vaccine. In some embodiments, a composition comprises a nucleic acid sequence encoding a Zika virus prME antigen from a first Zika virus strain and an additional nucleic acid sequence encoding an additional Zika virus prME antigen from one or more other strains of Zika virus. In some embodiments, a composition comprises a nucleic acid sequence encoding a Zika virus prME antigen and one or more additional (e.g., a second, third, fourth, fifth or sixth) Zika virus antigens. Alternatively, one or more additional non-Zika virus antigens may be encoded.

The nucleic acid may, for example, be RNA (i.e. an RNA-based vaccine) or DNA (i.e. a DNA-based vaccine, such as a plasmid DNA vaccine). In certain embodiments, the nucleic acid-based vaccine is an RNA-based vaccine. In certain embodiments, the RNA-based vaccine comprises a self-replicating RNA molecule, also referred to herein as a self-amplifying mRNA (SAM) molecule. The self-replicating RNA molecule may be an alphavirus-derived RNA replicon.

Self-replicating RNA molecules are well known in the art and can be produced by using replication elements derived from, e.g., alphaviruses, and substituting the structural viral proteins with a nucleotide sequence encoding a protein of interest. A self-replicating RNA molecule is typically a +-strand molecule which can be directly translated after delivery to a cell, and this translation provides a RNA-dependent RNA polymerase which then produces both antisense and sense transcripts from the delivered RNA. Thus the delivered RNA leads to the production of multiple daughter RNAs. These daughter RNAs, as well as collinear subgenomic transcripts, may be translated themselves to provide in situ expression of an encoded antigen (i.e. a Zika virus prM-F antigen), or may be transcribed to provide further transcripts with the same sense as the delivered RNA which are translated to provide in situ expression of the antigen. The overall result of this sequence of transcriptions is a huge amplification in the number of the introduced replicon RNAs and so the encoded antigen becomes a major polypeptide product of the cells.

One suitable system for achieving self-replication in this manner is to use an alphavirus-based replicon. These replicons are +-stranded (positive sense-stranded) RNAs which lead to translation of a replicase (or replicase-transcriptase) after delivery to a cell. The replicase is translated as a polyprotein which auto-cleaves to provide a replication complex which creates genomic-strand copies of the +-strand delivered RNA. These negative sense (−-strand) transcripts can themselves be transcribed to give further copies of the +-stranded parent RNA and also to give a subgenomic transcript which encodes the antigen. Translation of the subgenomic transcript thus leads to in situ expression of the antigen by the infected cell. Suitable alphavirus replicons can use a replicase from a Sindbis virus, a Semliki forest virus, an eastern equine encephalitis virus, a Venezuelan equine encephalitis virus, etc. Mutant or wild-type virus sequences can be used e.g. the attenuated TC83 mutant of VEEV has been used in replicons, see the following reference: WO2005/113782, the context of which is incorporated by reference.

In certain embodiments, the self-replicating RNA molecule described herein encodes (i) a RNA-dependent RNA polymerase which can transcribe RNA from the self-replicating RNA molecule and (ii) a Zika virus prME antigen. The polymerase can be an alphavirus replicase e.g. comprising one or more of alphavirus proteins nsPI, nsP2, nsP3 and nsP4.

Whereas natural alphavirus genomes encode structural virion proteins in addition to the non-structural replicase polyprotein, in certain embodiments, the self-replicating RNA molecules do not encode alphavirus structural proteins. Thus, the self-replicating RNA can lead to the production of genomic RNA copies of itself in a cell, but not to the production of RNA-containing virions. The inability to produce these virions means that, unlike a wild-type alphavirus, the self-replicating RNA molecule cannot perpetuate itself in infectious form. The alphavirus structural proteins which are necessary for perpetuation in wild-type viruses are absent from self-replicating RNAs of the present disclosure and their place is taken by gene(s) encoding the immunogen of interest, such that the subgenomic transcript encodes the immunogen rather than the structural alphavirus virion proteins.

Thus a self-replicating RNA molecule useful with the invention may have two open reading frames. The first (5') open reading frame encodes a replicase; the second (3') open reading frame encodes an antigen. In some embodiments the RNA may have additional (e.g. downstream) open reading frames e.g. to encode further antigens or to encode accessory polypeptides.

In certain embodiments, the self-replicating RNA molecule disclosed herein has a 5' cap (e.g. a 7-methylguanosine). This cap can enhance in vivo translation of the RNA. In some embodiments the 5' sequence of the self-replicating RNA molecule must be selected to ensure compatibility with the encoded replicase.

A self-replicating RNA molecule may have a 3' poly-A tail. It may also include a poly-A polymerase recognition sequence (e.g. AAUAAA) near its 3' end.

Self-replicating RNA molecules can have various lengths but they are typically 5000-25000 nucleotides long. Self-replicating RNA molecules will typically be single-stranded. Single-stranded RNAs can generally initiate an adjuvant effect by binding to TLR7, TLR8, RNA helicases and/or PKR. RNA delivered in double-stranded form (dsRNA) can bind to TLR3, and this receptor can also be triggered by dsRNA which is formed either during replication of a single-stranded RNA or within the secondary structure of a single-stranded RNA.

The self-replicating RNA can conveniently be prepared by in vitro transcription (IVT). IVT can use a (cDNA) template created and propagated in plasmid form in bacteria, or created synthetically (for example by gene synthesis and/or polymerase chain-reaction (PCR) engineering methods). For instance, a DNA-dependent RNA polymerase (such as the bacteriophage T7, T3 or SP6 RNA polymerases) can be used to transcribe the self-replicating RNA from a DNA template. Appropriate capping and poly-A addition reactions can be used as required (although the replicon's poly-A is usually encoded within the DNA template). These RNA polymerases can have stringent requirements for the transcribed 5' nucleotide(s) and in some embodiments these requirements must be matched with the requirements of the encoded replicase, to ensure that the IVT-transcribed RNA can function efficiently as a substrate for its self-encoded replicase.

A self-replicating RNA can include (in addition to any 5' cap structure) one or more nucleotides having a modified nucleobase. A RNA used with the invention ideally includes only phosphodiester linkages between nucleosides, but in some embodiments it can contain phosphoramidate, phosphorothioate, and/or methylphosphonate linkages.

The self-replicating RNA molecule may encode a single heterologous polypeptide antigen (i.e. a Zika virus prME antigen) or, optionally, two or more heterologous polypeptide antigens linked together in a way that each of the sequences retains its identity (e.g., linked in series) when expressed as an amino acid sequence. The heterologous polypeptides generated from the self-replicating RNA may then be produced as a fusion polypeptide or engineered in such a manner to result in separate polypeptide or peptide sequences.

The self-replicating RNA molecules described herein may be engineered to express multiple nucleotide sequences, from two or more open reading frames, thereby allowing co-expression of proteins, such as one, two or more Zika virus antigens (e.g. one, two or more Zika virus prME antigens) together with cytokines or other immunomodulators, which can enhance the generation of an immune response. Such a self-replicating RNA molecule might be particularly useful, for example, in the production of various gene products (e.g., proteins) at the same time, for example, as a bivalent or multivalent vaccine.

If desired, the self-replicating RNA molecules can be screened or analyzed to confirm their therapeutic and prophylactic properties using various in vitro or in vivo testing methods that are known to those of skill in the art. For example, vaccines comprising self-replicating RNA molecule can be tested for their effect on induction of proliferation or effector function of the particular lymphocyte type of interest, e.g., B cells, T cells, T cell lines, and T cell clones. For example, spleen cells from immunized mice can be isolated and the capacity of cytotoxic T lymphocytes to lyse autologous target cells that contain a self-replicating RNA molecule that encodes a Zika virus prME antigen. In addition, T helper cell differentiation can be analyzed by measuring proliferation or production of TH1 (IL-2 and IFN-γ) and/or TH2 (IL-4 and IL-5) cytokines by ELISA or directly in CD4+ T cells by cytoplasmic cytokine staining and flow cytometry.

Self-replicating RNA molecules that encode a Zika virus prME antigen can also be tested for ability to induce humoral immune responses, as evidenced, for example, by induction of B cell production of antibodies specific for a Zika virus prME antigen of interest. These assays can be conducted using, for example, peripheral B lymphocytes from immunized individuals. Such assay methods are known to those of skill in the art. Other assays that can be used to characterize the self-replicating RNA molecules can involve detecting expression of the encoded Zika virus prME antigen by the target cells. For example, FACS can be used to detect antigen expression on the cell surface or intracellularly. Another advantage of FACS selection is that one can sort for different levels of expression; sometimes-lower expression may be desired. Other suitable method for identifying cells which express a particular antigen involve panning using monoclonal antibodies on a plate or capture using magnetic beads coated with monoclonal antibodies.

In some embodiments, the self-replicating RNA molecules comprise a sequence selected from the group consisting of SEQ ID NO:70, SEQ ID NO:71, SEQ ID NO:72, SEQ ID NO:73, SEQ ID NO:74, SEQ ID NO:75, and SEQ ID NO:76. In some embodiments, the self-replicating RNA molecules comprise a sequence which is at least 70%, at least 75%, at least 80%, at least 85%, at least 90%, at least 95%, at least 96%, at least 97%, at least 98%, or at least 99% identical to a sequence selected from the group consisting of SEQ ID NO:70, SEQ ID NO:71, SEQ ID NO:72, SEQ ID NO:73, SEQ ID NO:74, SEQ ID NO:75, and SEQ ID NO:76. In some embodiments, the self-replicating RNA molecule comprises a fragment of a full-length sequence selected from the group consisting of SEQ ID NO:70, SEQ ID NO:71, SEQ ID NO:72, SEQ ID NO:73, SEQ ID NO:74, SEQ ID NO:75, and SEQ ID NO:76 wherein the fragment comprises a contiguous stretch of the nucleic acid sequence of the full-length sequence up to 1, 2, 3, 4, 5, 6, 7, 8, 9, 10, 15, 20, 25, or 30 nucleic acids shorter than full-length sequence.

In some embodiments, a DNA sequence encoding a self-replicating RNA molecule is provided, said DNA sequence selected from the group consisting of SEQ ID NO:63, SEQ ID NO:64, SEQ ID NO:65, SEQ ID NO:66, SEQ ID NO:67, SEQ ID NO:68, and SEQ ID NO:69. In some embodiments, DNA sequence encoding a self-replicating RNA molecule comprises a sequence which is at least 70%, at least 75%, at least 80%, at least 85%, at least 90%, at least 95%, at least 96%, at least 97%, at least 98%, or at least 99% identical to a sequence selected from the group consisting of SEQ ID NO:63, SEQ ID NO:64, SEQ ID NO:65, SEQ ID NO:66, SEQ ID NO:67, SEQ ID NO:68, and SEQ ID NO:69. In some embodiments, the DNA sequence encoding a self-replicating RNA molecule comprises a fragment of a full-length sequence selected from the group consisting of SEQ ID NO:63, SEQ ID NO:64, SEQ ID NO:65, SEQ ID NO:66, SEQ ID NO:67, SEQ ID NO:68, and SEQ ID NO:69 wherein the fragment comprises a contiguous stretch of the nucleic acid sequence of the full-length sequence up to 1, 2, 3, 4, 5, 6, 7, 8, 9, 10, 15, 20, 25, or 30 nucleic acids shorter than full-length sequence.

The nucleic acid-based vaccine may comprise a viral or a non-viral delivery system. The delivery system (also referred to herein as a delivery vehicle) may have adjuvant effects which enhance the immunogenicity of the encoded Zika virus prME antigen. For example, the nucleic acid molecule may be encapsulated in liposomes, non-toxic biodegradable polymeric microparticles or viral replicon particles (VRPs), or complexed with particles of a cationic oil-in-water emulsion. In some embodiments, the nucleic acid-based vaccine comprises a cationic nano-emulsion (CNE) delivery system or a lipid nanoparticle (LNP) delivery system. In some embodiments, the nucleic acid-based vaccine comprises a non-viral delivery system, i.e., the nucleic acid-based vaccine is substantially free of viral capsid. Alternatively, the nucleic acid-based vaccine may comprise viral replicon particles. In other embodiments, the nucleic acid-based vaccine may comprise a naked nucleic acid, such as naked RNA (e.g. mRNA), but delivery via CNEs or LNPs is preferred.

In certain embodiments, the nucleic acid-based vaccine comprises a cationic nano-emulsion (CNE) delivery system. CNE delivery systems and methods for their preparation are described in the following reference: WO2012/006380. In a CNE delivery system, the nucleic acid molecule (e.g. RNA) which encodes the antigen is complexed with a particle of a cationic oil-in-water emulsion. Cationic oil-in-water emulsions can be used to deliver negatively charged molecules, such as an RNA molecule to cells. The emulsion particles comprise an oil core and a cationic lipid. The cationic lipid can interact with the negatively charged molecule thereby anchoring the molecule to the emulsion particles. Further details of useful CNEs can be found in the following references: WO2012/006380; WO2013/006834; and WO2013/006837 (the contents of each of which are incorporated herein in their entirety).

Thus, in a nucleic acid-based vaccine of the invention, an RNA molecule encoding a Zika virus prME antigen may be complexed with a particle of a cationic oil-in-water emulsion. The particles typically comprise an oil core (e.g. a plant oil or squalene) that is in liquid phase at 25° C., a cationic lipid (e.g. phospholipid) and, optionally, a surfactant (e.g. sorbitan trioleate, polysorbate 80); polyethylene glycol can also be included. In some embodiments, the CNE comprises squalene and a cationic lipid, such as 1,2-dioleoyloxy-3-(trimethylammonio)propane (DOTAP). In some preferred embodiments, the delivery system is a non-viral delivery system, such as CNE, and the nucleic acid-based vaccine comprises a self-replicating RNA (mRNA). This may be particularly effective in eliciting humoral and cellular immune responses. Advantages also include the absence of a limiting anti-vector immune response and a lack of risk of genomic integration.

In some embodiments, an RNA molecule encoding a Zika virus prME antigen may be complexed with a submicron cationic oil-in-water emulsion. In some embodiments the cationic oil-in-water emulsion is characterized by an average particle size of from about 80 nm to 180 nm in diameter (or alternatively from about 80 to about 150 nm; from about 80 to 130 nm; or from about 100 nm). In some embodiments, the concentration of DOTAP in said emulsion, before RNA complexation, is at least about 2.5 mM, or from about 2.5 mM to about 8 mM. In a particular embodiment, the concentration of DOTAP in said emulsion is about 4 mg/ml (5.73 mM). The oil can be squalene or squalane.

In some embodiments, an RNA molecule encoding a Zika virus prME antigen is complexed to a cationic oil-in-water emulsion comprising DOTAP, squalene, sorbitan trioleate and polysorbate 80 in citrate buffer. Cationic oil-in-water emulsions suitable for delivery of an RNA molecule encoding a Zika virus prME antigen may contain about 2 mg/ml to 7 mg/ml DOTAP; about 3 mg/ml to 6 mg/ml Span 85; about 3 mg/ml to 6 mg/ml Tween 80; and about 30 mg/ml to 50 mg/ml squalene. In certain embodiments, the cationic oil-in-water emulsion, before complexing with RNA, contains about 4.3% w/v squalene, 0.5% Tween 80, 0.5% SPAN85, and 4 mg/mL DOTAP.

Also provided is a method of preparing a composition comprising an RNA molecule encoding a Zika virus prME antigen complexed to a cationic oil-in-water emulsion, the method comprising: (i) providing an oil-in-water emulsion as described herein; (ii) providing an aqueous solution comprising the RNA molecule; and (iii) combining the aqueous solution of (ii) and the oil-in-water emulsion of (i), thereby preparing the composition. If desired, the aqueous solution comprising the RNA molecule may be a buffer. The buffer may comprise one or more salt, buffer, saccharide, or polymer. In an preferred embodiment, the buffer comprises 560 mM sucrose, 20 mM NaCl, and 10 mM citrate, which can be mixed with a cationic oil in water emulsion described herein to produce a final aqueous phase that comprises 280 mM sucrose, 10 mM NaCl and 10 mM citrate.

LNP delivery systems and non-toxic biodegradable polymeric microparticles, and methods for their preparation are described in the following references: WO2012/006376 (LNP and microparticle delivery systems); Geall et al. (2012) PNAS USA. September 4; 109(36): 14604-9 (LNP delivery system); and WO2012/006359 (microparticle delivery systems). LNPs are non-virion liposome particles in which a nucleic acid molecule (e.g. RNA) can be encapsulated. The particles can include some external RNA (e.g. on the surface of the particles), but at least half of the RNA (and ideally all of it) is encapsulated. Liposomal particles can, for example, be formed of a mixture of zwitterionic, cationic and anionic lipids which can be saturated or unsaturated, for example; DSPC (zwitterionic, saturated), DlinDMA (cationic, unsaturated), and/or DMG (anionic, saturated). Preferred LNPs for use with the invention include an amphiphilic lipid which can form liposomes, optionally in combination with at least one cationic lipid (such as DOTAP, DSDMA, DODMA, DLinDMA, DLenDMA, etc.). A mixture of DSPC, DlinDMA, PEG-DMG and cholesterol is particularly effective. Other useful LNPs are described in the following references: WO2012/006376; WO2012/030901; WO2012/031046; WO2012/031043; WO2012/006378; WO2011/076807; WO2013/033563; WO2013/006825; WO2014/136086; WO2015/095340; WO2015/095346; WO2016/037053. In some embodiments, the LNPs are RV01 liposomes, see the following references: WO2012/006376 and Geall et al. (2012) PNAS USA. September 4; 109(36): 14604-9.

Pharmaceutical Compositions; Immunogenic Compositions

The disclosure provides compositions comprising a nucleic acid comprising a sequence which encodes a Zika virus polypeptide, for example a Zika virus prME antigen. The composition may be a pharmaceutical composition, e.g., an immunogenic composition or a vaccine composition. Accordingly, the composition may also comprise a pharmaceutically acceptable carrier. In some embodiments, the Zika virus is a Brazilian strain Zika virus.

A "pharmaceutically acceptable carrier" includes any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, sucrose, trehalose, lactose, and lipid aggregates (such as oil droplets or liposomes). Such carriers are well known to those of ordinary skill in the art. The compositions may also contain a pharmaceutically acceptable diluent, such as water, saline, glycerol, etc. Additionally, auxiliary substances, such as wetting or emulsifying agents, pH buffering substances, and the like, may be present. Sterile pyrogen-free, phosphate-buffered physiologic saline is a typical carrier.

Pharmaceutical compositions may include the constructs, nucleic acid sequences, and/or polypeptide sequences described elsewhere herein in plain water (e.g. "w.f.i.") or in a buffer e.g. a phosphate buffer, a Tris buffer, a borate buffer, a succinate buffer, a histidine buffer, or a citrate buffer. Buffer salts will typically be included in the 5-20 mM range. Pharmaceutical compositions may have a pH between 5.0 and 9.5 e.g. between 6.0 and 8.0. Compositions may include sodium salts (e.g. sodium chloride) to give tonicity. A concentration of 10±2 mg/mL NaCl is typical, e.g. about 9 mg/mL. Compositions may include metal ion chelators. These can prolong RNA stability by removing ions which can accelerate phosphodiester hydrolysis. Thus a composition may include one or more of EDTA, EGTA, BAPTA, pentetic acid, etc. Such chelators are typically present at between 10-500 μM e.g. 0.1 mM. A citrate salt, such as sodium citrate, can also act as a chelator, while advantageously also providing buffering activity. Pharmaceutical compositions may have an osmolality of between 200 mOsm/kg and 400 mOsm/kg, e.g. between 240-360 mOsm/kg, or between 290-310 mOsm/kg. Pharmaceutical compositions may include one or more preservatives, such as thiomersal or 2-phenoxyethanol. Mercury-free compositions are preferred, and preservative-free vaccines can be prepared. Pharmaceutical compositions may be aseptic or sterile. Pharmaceutical compositions may be non-pyrogenic e.g. containing <1 EU (endotoxin unit, a standard measure) per dose, and preferably <0.1 EU per dose. Pharmaceutical compositions may be gluten free. Pharmaceutical compositions may be prepared in unit dose form. In some embodiments a unit dose may have a volume of between 0.1-1.0 mL e.g. about 0.5 mL.

In some embodiments, the compositions disclosed herein are immunogenic composition that, when administered to a subject, induce a humoral and/or cellular antigen-specific immune response (i.e. an immune response which specifically recognizes a naturally occurring Zika virus polypeptide). For example, an immunogenic composition may induce a memory T and/or B cell population relative to an untreated subject following Zika virus infection, particularly in those embodiments where the composition comprises a nucleic acid comprising a sequence which encodes a Zika virus prME antigen or comprises a Zika virus antigen. In some embodiments, the subject is a vertebrate, such as a mammal e.g. a human or a veterinary mammal.

The compositions of the invention can be formulated as vaccine compositions. The vaccine will comprise an immunologically effective amount of antigen. By "an immunologically effective amount" is intended that the administration of that amount to a subject, either in a single dose or as part of a series, is effective for inducing a measurable immune response against Zika virus in the subject. This amount varies depending upon the health and physical condition of the individual to be treated, age, the taxonomic group of individual to be treated (e.g. human, non-human primate, etc.), the capacity of the individual's immune system to synthesize antibodies, the degree of protection desired, the formulation of the composition or vaccine, the treating doctor's assessment of the medical situation, the severity of the disease, the potency of the compound administered, the mode of administration, and other relevant factors. It is expected that the amount will fall in a relatively broad range that can be determined through routine trials. In one embodiment, an immunologically effective amount of a Zika virus antigen is an amount sufficient to prevent or treat Zika virus infection. Vaccines as disclosed herein may either be prophylactic (i.e. to prevent infection) or therapeutic (i.e. to treat infection), but will typically be prophylactic. In some embodiments, the vaccine compositions disclosed herein may induce an effective immune response against a Zika virus infection, i.e., a response sufficient for treatment or prevention of a Zika virus infection.

In some embodiments, the composition further comprises an additional antigen. In some embodiments, the composition is administered to a subject in combination with a further composition which comprises an additional antigen.

A composition of the present disclosure may also comprise, or be administered in conjunction with, one or more adjuvants (e.g. vaccine adjuvants), in particular where the composition comprises an immunologically effective amount of a nucleic acid encoding a Zika virus prME antigen or a Zika virus prME antigen. By "adjuvant" is intended that is capable of increasing an immune response against an antigen compared to administration of said antigen alone. In some aspects, adjuvant compositions as disclosed herein further comprise one or more immunostimulants, for example, a saponin such as QS21.

Adjuvants which may be used in compositions of the invention include, but are not limited to: (A) Mineral-containing compositions, for example aluminum and calcium salts, such as aluminum phosphates. (B) Oil emulsions, for example squalene-in-water emulsions, such as MF59 or AS03. Complete Freund's adjuvant (CFA) and incomplete Freund's adjuvant (IF A) may also be used. (C) Saponin formulations. (D) Virosomes and virus-like particles (VLPs). (E) Bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof. (F) Human immunomodulators, for example cytokines, such as interleukins, interferons, macrophage colony stimulating factor, and tumor necrosis factor. (G) Bioadhesives and mucoadhesives, such as esterified hyaluronic acid microspheres, cross-linked derivatives of poly(acrylic acid), polyvinyl alcohol, polyvinyl pyrollidone, polysaccharides and carboxymethylcellulose. (H) Microparticles, for example particles of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(a-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB). (I) Liposomes. (J) Polyoxyethylene ether and polyoxyethylene ester formulations. (K) Polyphosphazene (PCPP). (L) Muramyl peptides. (M) Imidazoquinolone compounds, for example Imiquamod and its homologues.

Combinations of one or more of the adjuvants identified above may also be used with the invention.

Methods of Use/Uses

In some embodiments are provided methods for inducing an immune response against a Zika virus infection in a subject in need thereof comprising a step of administering an immunologically effective amount of a construct or composition as disclosed herein. In some embodiments are provided the use of the constructs or compositions disclosed herein for inducing an immune response to a Zika virus prME antigen in a subject in need thereof. In some embodiments are provided the use of the constructs or compositions disclosed herein for inducing an immune response against a Zika virus infection in a subject. In some embodiments are provided use of the construct or composition as disclosed herein in the manufacture of a medicament that induces an immune response to a Zika virus infection in a subject. By "subject" is intended a vertebrate, such as a mammal e.g. a human or a veterinary mammal. In some embodiments the subject is human. By "immune response" is intended a humoral and/or cellular antigen-specific immunological response (i.e. an immune response which specifically recognizes an antigen polypeptide) that can be demonstrated to neutralize Zika virus in vitro or control/reduce/eliminate Zika virus infection in vivo.

In some embodiments, the immune response is characterized by immunological memory against the Zika virus and/or an effective Zika virus-responsive memory T cell population.

In some embodiments the composition comprises an RNA molecule encoding a polypeptide selected from the group consisting of SEQ ID NO:26, SEQ ID NO:31, SEQ ID NO:36, SEQ ID NO:41, SEQ ID NO:46, SEQ ID NO:52, SEQ ID NO:58. In some embodiments, the composition comprises an RNA molecule encoding a polypeptide which is at least 70%, at least 75%, at least 80%, at least 85%, at least 90%, at least 95%, at least 96%, at least 97%, at least 98%, or at least 99% identical to a sequence selected from the group consisting of SEQ ID NO:26, SEQ ID NO:31, SEQ ID NO:36, SEQ ID NO:41, SEQ ID NO:46, SEQ ID NO:52, SEQ ID NO:58. In some embodiments, the composition comprises an RNA molecule encoding a polypeptide which comprises a fragment of a full-length sequence selected from the group consisting of SEQ ID NO:26, SEQ ID NO:31, SEQ ID NO:36, SEQ ID NO:41, SEQ ID NO:46, SEQ ID NO:52, SEQ ID NO:58, wherein the fragment comprises a contiguous stretch of the amino acid sequence of the full-length sequence up to 1, 2, 3, 4, 5, 6, 7, 8, 9, or 10 amino acids shorter than full-length sequence.

In some embodiments is provided a construct, a vector, a self-replicating RNA and/or molecule as described herein for use in therapy or medicine. In some embodiments, the compositions disclosed herein are for use in therapy or medicine. In preferred embodiment, the therapy is a vaccine therapy. Preferably the therapy is a vaccine to prevent Zika virus infection.

In some embodiments is provided a construct, a vector, a self-replicating RNA and/or molecule as described herein for use in preventing or treating Zika virus infection in a subject in need thereof.

In some embodiments, the compositions disclosed herein are for use in preventing or treating Zika virus infection in a subject in need thereof.

In some embodiments, the compositions disclosed herein are for use in inducing an immune response against a Zika virus infection in a subject in need thereof.

In some embodiments is provided a construct, a vector, a self-replicating RNA molecule, and/or a composition as described herein for use in a method of inducing an immune response to a Zika virus infection in a subject in need thereof.

In some embodiments, methods are provided for preventing or shortening Zika virus infection and/or reducing or preventing the clinical symptoms upon Zika virus infection in a subject in need thereof, which comprises administering to said subject an immunologically effective amount of an immunogenic composition as provided herein.

In some embodiments is provided use of a construct or composition disclosed herein in the manufacture of an immunogenic composition for preventing or shortening Zika virus infection in a subject and/or reducing or prevent the clinical symptoms upon Zika virus infection in a subject.

In some embodiments, methods are provided for preventing or reducing transmission of a Zika virus infection from one subject to another. In specific embodiments, methods are provided for preventing or reducing transmission of a Zika virus infection to a fetus across the placental barrier. In some embodiments, a composition as described herein is administered to a woman in an amount effective to prevent transmission of a Zika virus infection across the placental barrier.

In some embodiments, methods are provided for inducing an immune response sufficient to prevent or treat a Zika virus infection in a subject, which comprises administering to said subject a composition comprising one or more of the constructs, vectors, or self-replicating RNA molecules as described above in an amount sufficient to prevent or treat Zika virus infection. In some embodiments is provided use of a construct or composition disclosed herein in the manufacture of an immunogenic composition for preventing or reducing transmission of a Zika virus infection to a fetus across the placental barrier.

In some embodiments is provided a construct, a vector, a self-replicating RNA molecule, and/or a composition as described herein for use in a method of preventing or reducing transmission of a Zika virus infection to a fetus across the placental barrier.

In some embodiments, the subject is a human subject. In specific embodiments, the human subject has been exposed, or is at risk of being exposed, to a Zika virus infection.

Routes of Administration/Dosages

Compositions disclosed herein will generally be administered directly to a subject. Direct delivery may be accomplished by parenteral injection (e.g. subcutaneously, intraperitoneally, intravenously, intramuscularly, intradermally, or to the interstitial space of a tissue). Alternative delivery routes include rectal, oral (e.g. tablet, spray), buccal, sublingual, vaginal, topical, transdermal or transcutaneous, intranasal, ocular, aural, pulmonary or other mucosal administration. Intradermal and intramuscular administration are two preferred routes. Injection may be via a needle (e.g. a hypodermic needle), but needle-free injection may alternatively be used. A typical human intramuscular dose volume is 0.5 ml.

A dose of a nucleic acid (e.g. a nucleic acid-based vaccine, such as a Zika SAM vaccine) may have about 50 μg to about 100 μg nucleic acid. In one embodiment, a Zika SAM vaccine dose contains 50, 55, 60, 65, 70, 75, 80, 85, 90, 95 or 100 μg RNA. In other embodiments, a dose of a Zika SAM vaccine may have <10 μg nucleic acid; e.g. from 1-10 μg, such as about 1 μg, 2.5 μg, 5 μg, 7.5 μg or 10 μg, but expression can be seen at much lower levels; e.g. using <1 μg/dose, <100 ng/dose, <10 ng/dose, <1 ng/dose, etc. Similarly, a dose of a protein antigen may have <10 μg protein; e.g. from 1-10 μg, such as about 1 μg, 2.5 μg, 5 μg, 7.5 μg or 10 μg.

In preferred embodiments, a Zika SAM vaccine or vaccine composition is administered to a subject at an effective dose, meaning a dose sufficient to achieve a desired immune response, such as induction of neutralizing antibodies to Zika virus and/or protection against Zika virus infection.

In some embodiments, a Zika SAM vaccine described herein has an effective dose that is less than or equal to 50%, 40%, 30%, 20% or 10% of the effective dose of a DNA vaccine or vaccine composition encoding the same antigen. In some embodiments, a Zika SAM vaccine described herein has an effective dose that is one third or less of the effective dose of a DNA vaccine or vaccine composition encoding the same antigen.

Processes of Manufacture/Formulation

Processes for the manufacture of self-replicating RNA are provided herein. In some embodiments, the process of manufacturing a self-replicating RNA comprises a step of in vitro transcription (IVT) as described elsewhere herein. In some embodiments, the process of manufacturing a self-replicating RNA comprises a step of IVT to produce a RNA, and further comprises a step of combining the RNA with a non-viral delivery system as described elsewhere herein. In some embodiments, the process of manufacturing a self-replicating RNA comprises a step of IVT to produce a RNA, and further comprises a step of combining the RNA with a CNE delivery system as described elsewhere herein.

Sequence Identity

Identity or homology with respect to an amino acid sequence is defined herein as the percentage of amino acid residues in the candidate sequence that are identical with the reference amino acid sequence after aligning the sequences and introducing gaps, if necessary, to achieve the maximum percent sequence identity, and not considering any conservative substitutions as part of the sequence identity. Identity or homology with respect to a nucleic acid sequence is defined herein as the percentage of nucleotides in the candidate sequence that are identical with the reference nucleic acid sequence after aligning the sequences and introducing gaps, if necessary, to achieve the maximum percent sequence identity.

Sequence identity can be determined by standard methods that are commonly used to compare the similarity in position of the amino acids of two polypeptides. Using a computer program such as BLAST, two polypeptides are aligned for optimal matching of their respective amino acids (either along the full length of one or both sequences or along a pre-determined portion of one or both sequences). The programs provide a default opening penalty and a default gap penalty, and a scoring matrix such as PAM 250 [a standard scoring matrix; see Dayhoff et al., in *Atlas of Protein Sequence and Structure*, vol. 5, supp. 3 (1978)] can be used in conjunction with the computer program. For example, the percent identity can then be calculated as: the total number of identical matches multiplied by 100 and then divided by the sum of the length of the longer sequence within the matched span and the number of gaps introduced into the shorter sequences in order to align the two sequences. The same methods used to compare polypeptides can also be used to calculate the percent identity of two polynucleotide sequences.

Where the present disclosure refers to a sequence by reference to a UniProt or Genbank accession code, the sequence referred to is the current version at the filing date of the present application.

General

Unless otherwise explained, all technical and scientific terms used herein have the same meaning as commonly understood by one of ordinary skill in the art to which this disclosure belongs. The singular terms "a," "an," and "the"

include plural referents unless context clearly indicates otherwise. Similarly, the word "or" is intended to include "and" unless the context clearly indicates otherwise. The term "plurality" refers to two or more. Additionally, numerical limitations given with respect to concentrations or levels of a substance, such as solution component concentrations or ratios thereof, and reaction conditions such as temperatures, pressures and cycle times are intended to be approximate. The term "about" used herein is intended to mean the amount +10%.

The term "comprises" means "includes." Thus, unless the context requires otherwise, the word "comprises," and variations such as "comprise" and "comprising" will be understood to imply the inclusion of a stated compound or composition (e.g., nucleic acid, polypeptide, antigen) or step, or group of compounds or steps, but not to the exclusion of any other compounds, composition, steps, or groups thereof. Embodiments described as comprising certain components are intended to include embodiments consisting of the indicated components.

The abbreviation, "e.g." is derived from the Latin exempli gratia, and is used herein to indicate a non-limiting example. Thus, the abbreviation "e.g." is synonymous with the term "for example."

The invention will be further described by reference to the following, non-limiting, figures and examples.

EXAMPLES

Example 1. Project Summary

The present inventors initiated work on a Zika vaccine using the SAM platform—synthetic, self-amplifying mRNA (SAM) derived from the alphavirus genome, expressing antigens of interest. The SAM constructs are evaluated for robust antigen production and antigenicity and further tested for their immunogenicity and efficacy using in vivo models.

Methods

The SAM vector VEE TC-83 was used as the background construct for cloning in the Examples. See SEQ ID NO:24.

Example 2. Selection of Antigen

The Flavivirus genome consists of capped single-stranded RNA of positive polarity of approximately 11.3 kb in length (FIG. 1). The 5' proximal quarter of the genome encodes the structural proteins capsid (C), pre-membrane (prM), and envelope (E). The nonstructural proteins NS1, NS2A, NS2B, NS3, NS4A, NS4B, and NS5 are involved in viral RNA replication. The coding region is flanked by 5' and 3' untranslated regions (5' and 3' UTRs) of approximately 100 and 600 nucleotides in length, respectively. Translation of the viral genome yields a single polypeptide that is processed into the individual proteins by a combination of cellular proteases and a viral protease consisting of a catalytic subunit, NS3, and its cofactor, NS2B.

The structural proteins prM and E are cotranslationally inserted into the endoplasmic reticulum (ER) membrane and processed by signal peptidases, producing proteins that encapsidate C together with the viral RNA, by budding into the ER lumen (FIG. 2). At a later step in viral maturation, prM on these particles is cleaved into mature M protein by a cellular furin protease prior to release from the cell. This prM cleavage is required for infectivity of the released virions. In addition to infectious virions, flavivirus-infected cells release sub-viral particles (SVPs) (FIG. 2). These particles are smaller than virions, but contain the antigenically important E protein and the prM/M protein, which is essential for correct folding and incorporation of the E protein into SVPs and viral particles. However, unlike virions, SVPs do not contain either the C protein or the viral genome, and are thus non-infectious. SVPs can be produced in a variety of systems by co-expression of the prM and E proteins, and SVPs share properties with wild-type viruses, such as fusogenic activity and induction of a neutralizing immune response and have repeatedly been shown to stimulate protective immune responses against a number of flavivirus diseases. The present inventors selected the structural proteins of Zika virus, namely-prM and E, and in some cases, C, for further experimentation.

Example 3. Strain Selection

The amino acid sequences of the C-prME proteins from Zika virus strains (available from NCBI/Genbank) from Zika outbreaks around the world from 2007 onwards were aligned to look for similarities and differences (FIG. 3). These included the original African lineage strain from Uganda, Micronesia (2007), *French Polynesia* (2013), and the Brazilian strains from 2016 (FIG. 3). In addition seven strains of Zika virus from various regions in Brazil, were also compared for amino acid differences in the C-prME region (FIG. 4). A high conservation was observed across the strains from different outbreaks, with the Brazilian strains almost identical in the CprME region. The Natal, Bahia strain (KU527068) was chosen as the representative strain. KU527068 was one of the first strains to be isolated from the brain of a fetus showing microcephaly.

Example 4. Design of Constructs

The design of Zika-SAM constructs of FIG. 5 includes cloning the sequence encoding the Zika virus (Natal, Brazil strain) structural pre-membrane (prM) and envelope (E) proteins [with or without the Capsid (C)], under the subgenomic promoter in a SAM vector. A series of modifications to the SAM-prME constructs were made (Table 1, FIG. 6 and FIG. 7). These include:

i. Codon optimization of the coding sequence for the antigen (CO-prME or CO-CprME).

ii. Genetic modifications in the native prM signal peptide (FIG. 6). In addition to proteolytic processing by signal peptidases, the viral NS3/NS2B protease is also involved in maturation of the structural proteins. The junction of the C and prM region undergoes two proteolytic cleavage events during maturation. One cleavage liberates C from its transmembrane anchor sequence and is dependent on NS2B/NS3 activity. A second cleavage occurs at the end of the C-anchor sequence in the ER lumen by a cellular signal peptidase and generates the N terminus of prM. Previous studies conclude that processing by the viral protease, regardless of the presence of the signal peptidase cleavage site, is required for efficient secretion of viral particles. However, in some flaviviruses, when this obligatory sequence of cleavages was uncoupled in a mutant virus, there is greatly reduced incorporation of virions into budding membranes and augmented release of subviral particles (Lobigs et al (2004) "Inefficient signalase cleavage promotes efficient nucleocapsid incorporation into budding flavivirus membranes," *J Virol.* 2004 January; 78(1):178-86).

iii. Replacement of the native prM signal peptide with a heterogeneous signal peptide to enhance SVP generation. The present inventors used the signal peptide of IgG1 used previously for cleavage and secretion of IgG or Fab proteins (Ciferri et al. (2015) "Antigenic Characterization of the HCMV gH/gL/gO and Pentamer Cell Entry Complexes Reveals Binding Sites for Potently Neutralizing Human Antibodies," *PLoS Pathog*. October 20; 11(10):e1005230.).

iv. Zika capsid (C) protein is incorporated in other constructs to test whether the presence of a cleavable capsid protein increases the efficiency of SVP generation. (FIG. 7). This includes the porcine teschovirus-1 2A (P2A)-mediated cleavage of C protein in the absence of the viral protease.

TABLE 2

SAM Zika constructs.

| No. | SAM insert | Description |
|---|---|---|
| 1 | WT-prME | Wildtype prM & E sequences |
| 2 | CO-prME | Codon optimized prM & E sequences |
| 3 | CO-prME-ESS.1 | Same as CO-prME but with an enhanced signal sequence (ESS) - PQAQA mutation in prM signal peptide c region to promote VLP |
| 4 | CO-prME-ESS.2 | Same as CO-prME but with an ESS - prM signal peptide sequence is replaced with the IgG signal peptide sequence to promote VLP |
| 5 | CO-CprME.1 | Same as CO-prME but also expressing Zika capsid protein with the native C and prM cleavage sites |
| 6 | CO-CprME.2 | Same as CO-prME but also expressing Zika capsid protein with the signal peptide c region mutation PQAQA |
| 7 | CO-CprME.3 | Same as CO-prME but also expressing Zika capsid protein with a P2A site inserted after the native NS2B-3 cleavage site |

Key:
WT—wild-type;
CO—Codon-optimized.
Constructs are in the SAM vector described elsewhere. Zika sequences are derived from the Natal strain (Brazil) - KU527068.1, unless noted otherwise.

Evaluation/Study Design

The constructs are evaluated in mammalian cells following electroporation of Zika-SAM RNA into BHK cells using the following methods:

a. SAM RNA replication-potency of the SAM-Zika constructs is tested by using antibodies against dsRNA and FACS.

b. Antigen expression is determined by immunoblots and immunofluorescence assays, to investigate cleaved prM and E protein in cell lysates and cell supernatant.

c. The production of SVPs is tested in mammalian cells by using established procedures for SVP isolation from cell supernatant.

Following identification of the most efficient candidate constructs formulation into LNP/CNE based-delivery systems is carried out and testing for antigenicity and immunogenicity is carried out in vivo.

Example 5. Expression and Secretion of Zika-SAM Constructs

The ability of cells to express and secrete Zika E protein from the Zika-SAM constructs described above was evaluated according to the following methods.

On Day 0, BHK cells were plated at $8\times10^6$ in T225 flasks in Growth Media. For trypsinization, media was removed and cells were washed with 5 mls of PBS. The PBS wash was removed, and 5 mls of pre-warmed trypsin was added and spread thoroughly across the plate. Trypsin was removed and plates were kept at 37 deg C. for 1-2 mins. Cells were then resuspended in 10 mls of growth media (5% FBS). Cells were counted and plated at required concentration into a new flask. The cells were then incubated at 37 deg C., 5% $CO_2$ for about 20 hours.

On Day 1, plates were prepared by adding 2 ml DMEM+ 1% FBS+P/S (outgrowth media) to each well of a 6-well plate (one well per electroporation). Plates were kept warm in a 37 deg C. incubator. The electroporator was prepared to deliver 120V, 25 ms pulse, 0.0 pulse interval, 1 pulse for a 2 mm cuvette. Cuvettes were labeled and kept on ice. Cells in growth phase were harvested as normal into BHK media (growth) and counted using a hemocytometer. Cells were trypsinized following the same trypsinization protocol as above. Standards and negative control electroporations were also prepared.

Cells were centrifuged at 1500 rpm (462×g) for 5 mins. Media was aspirated, and cells were washed once with 20 ml cold Opti-MEM media. Cells were again centrifuged at 1500 rpm (462×g) for 5 mins. Media was aspirated, and the cells were resuspended in Opti-MEM media to 0.25 ml per electroporation.

For each sample, 4000 ng of RNA was mixed with 250 ul cells, and the mixture was pipetted gently 4-5 times. The cells and RNA mixture were transferred to 2 mm cuvettes and subjected to one pulse of electroporation using the parameters described above. Cells were allowed to rest at room temperature for 10 mins. Cells from one cuvette were added to one well of a pre-warmed 6-well plate, and the plate was tipped front and back and then side to side at a 45° angle to distribute cells evenly.

On Day 2 (30 h post-electroporation), the supernatant was collected. An aliquot of 75 ul was removed for Western blot, 25 ul 4× NuPAGE buffer was added to the aliquot (no reducing agent), and the aliquot was stored at −20 deg C. The rest of the supernatant was stored at −80 deg C.

Cells were washed once with ice cold PBS, and then scraped into 200 ul of RIPA buffer containing protease inhibitor cocktail (1 tablet in 10 ml) while keeping the plate on ice. The buffer containing cells was collected in micro-centrifuge tubes, and subjected to two rounds of freeze thawing on dry ice. Samples were vortexed briefly, and pelleted at 8000 rpm for 5 min. Pellets were discarded and the supernatants were retained. 25 ul 4× NuPAGE buffer was added to a 75 ul aliquot of the lysates for Western blotting. Aliquots were stored at −20 deg C. The rest of the lysates were stored at −80 deg C.

Concentration and Filtration of Zika E Protein Species from Cell Supernatant

Cell supernatant from single transfections (1 million cells, 4000 ng RNA, 30 h post-electroporation) were loaded, 500 μl each, into the upper chamber of the Amicon Ultra-0.5 Centrifugal Filter Devices, 100K (100,000 NMWL). The Centrifugal Filter Devices were centrifuged at 14000×g for 10 minutes each. After each spin, the flow through was collected in a separate tube. After centrifugation, the samples remaining in the upper chamber were further washed by mixing with 500 μl of buffer HEPES 20 mM, pH=7.4, and centrifuging again at 14000×g for 10 minutes each.

The final samples remaining in the upper chamber, about 35-40 μl, were centrifuged into a fresh Eppendorf tube according to the manufacturer's instructions. Five μl of this sample was mixed with 5 μl of 4× NuPAGE buffer for immunoblotting, and the remaining samples were stored at −80 deg C. Also, 75 μl of the flowthrough was mixed with 25 μl of the 4× NuPAGE buffer for immunoblotting, and the remaining flow through was saved at −80 deg C.

Immunoblotting

15 μl of the cell culture supernatants and 15 μl of the cell lysates (or 10 μl of the concentrated supernatants and 15 μl flow through) were run on a 4-12% SDS PAGE gel (Bis-Tris) in 1×MOPS running buffer. The separated samples were transferred onto nitrocellulose membranes. Membranes were blocked for 2-3 hours in PBS-Tween 20+5% milk. The flavivirus 4G2 primary antibody was added at 1:120 dilution in PBS-T-Milk and membranes were incubated overnight at 4 deg C. Membranes were then washed 3 times for 10 minutes each in PBS-T. Anti-mouse secondary (Odyssey® anti-Mouse 800CW-green (LI-COR, Inc., Lincoln, Nebr.) at 1:5000) in LI-COR blocking buffer was then added, and the membranes were incubated for 1 hour. Membranes were washed three times for 2 minutes each, and then scanned on LI-COR Odyssey® imager (LI-COR, Inc., Lincoln, Nebr.) at 800 channel, medium intensity.

Results

Zika E protein expression was detectable by immunoblot in all lysates from cells electroporated with Zika-SAM constructs or with positive control SAM-YFV (FIG. 8). Expression of Zika E protein was not detected in the SAM-RSV or Mock negative controls. However, Zika E protein secretion was detectable by immunoblot only in the supernatants of Construct #1 (wild type, WT), Construct #2 (codon optimized, CO), Construct #4 (codon optimized with IgG signal peptide, CO-prME-ESS.2), and Construct #7 (codon optimized with Zika capsid protein and P2A site, CO-CprME.3).

The filtration of supernatant through 100 kD cutoff filters and immunoblotting showed that almost all of the E protein was retained in the filter and there was no detectable E in the flow through (FIG. 9). This indicated that the E protein detected in the supernatant may be a part of a higher molecular weight structure, presumably SVPs.

Example 6: Cationic Oil-in-Water Emulsions

Cationic nanoemulsions (CNEs) were prepared essentially according to the methods described in Brito et al., Molecular Therapy, Vol. 22, No. 12, pp. 2118-29 (2014) and International Patent Publication WO2013006834.

Briefly, squalene (Sigma, St. Louis, Mo.) was heated to 37° C., and DOTAP (Lipoid, Ludwigshafen Germany) was dissolved directly in squalene in the presence of sorbitan trioleate (SPAN 85; Sigma, St. Louis, Mo.). The resulting oil phase was then combined with the aqueous phase (Tween 80; Sigma, St. Louis, Mo., in citrate buffer) and immediately homogenized for 2 min using an T25 homogenizer (IKA, Wilmington, N.C.) at 24K RPM to produce a primary emulsion. The primary emulsions were passed three to five times through a M-110S Microfluidizer or a M-110P Microfluidizer (Microfluidics, Newton, Mass.) with an ice bath cooling coil at a homogenization pressure of approximately 15K-20K PSI. The batch samples were removed from the unit and stored at 4° C. The CNE formulation used in the present examples contains 4 mg/ml DOTAP; 4.7 mg/ml Span 85; 4.7 mg/ml Tween 80; and 39 mg/ml squalene.

Example 7. Preparation of RNA-CNE Complexes

1. RNA Synthesis

Zika SAM constructs contain a bacteriophage T7 promoter located upstream of the alphavirus cDNA to facilitate the synthesis of the replicon RNA in vitro. SAM-Zika RNA for construct #1 (encoding wild type Zika prM & E sequences (WT-prME)) and construct #2 (encoding codon-optimized prM & E sequences (CO-prME)), were synthesized using standard molecular biology techniques. Briefly, plasmid DNA encoding Zika-SAM constructs were linearized by endonuclease digestion a unique site located at the 3' end of the replicon sequence. The linearized DNA was then transcribed into RNA by in vitro synthesis using a T7 RNA polymerase in the presence of the template DNA and nucleoside triphosphates (ATP, CTP, GTP and UTP). Following transcription, DNA template was digested with DNase, and the RNA transcripts were purified by LiCl precipitation and reconstituted in nuclease-free water. RNA was then capped using the Vaccinia Capping System (New England BioLabs, Ipswich, Mass.) and purified by LiCl precipitation. RNA concentration in each reaction was determined by spectrophotometry. Prior to RNA complexation, RNA was diluted to a concentration of 300 μg/ml in citrate buffer (10 mM citrate pH 6.2, 20 mM NaCl, 560 mM sucrose).

2. RNA Complexation

Zika SAM RNA was complexed with cationic nanoemulsion (CNE) particles essentially as described in Brito et al., Molecular Therapy, Vol. 22, No. 12, pp. 2118-29 (2014). Briefly, Zika SAM RNA (300 μg/ml in citrate buffer) was added to an equal volume of the CNE produced in Example 6, mixed, and allowed to complex on ice for 30 minutes to 2 hours. The final concentration of CNE-complexed RNA was 150 μg/ml.

The ratio of RNA to cationic lipid can be expressed as an N/P ratio, defined as the amount (moles) of protonatable nitrogen (N) atoms in the cationic lipid divided by the amount (moles) of phosphates (P) on the RNA. DOTAP for example has one nitrogen that can be protonated per molecule. The RNA concentration was used to calculate the amount of phosphate in solution using an estimate of 3 nmols of phosphate per microgram of RNA. The CNE formulations described above have an N/P ratio of 6.3:1.

Example 8. In Vivo Immunogenicity and Protection of Zika SAM CNE Formulations Female BALB/c mice (6-12 weeks old; The Jackson Laboratory), were housed and bred in the animal facility of the Vaccine Research Center, NIAID, NIH, Bethesda, Md. All animal experiments were reviewed and approved by the Animal Care and Use Committee of the VRC, NIAID, NIH. All animals were housed and cared for in accordance with local, state, federal, and institutional policies in an American Association for Accreditation of Laboratory Animal Care-accredited facility at the NIH.

Mice were immunized twice according to the study design shown in Table 2. Briefly, groups of 10 mice each were administered CNE formulations containing the Zika SAM RNA constructs #1 or #2. As a positive control, another group of mice received 50 μg of a Zika DNA vaccine (construct #5283, as described in Dowd et al., Science, Vol. 354 Issue 6309, pp. 237-40 (2016)) by intramuscular electroporation. All mice were challenged by intraperitoneal (i.p.) injection of live Zika virus on day 49.

TABLE 2

| Mouse study design | | | | | | |
|---|---|---|---|---|---|---|
| Group | n | Delivery | Construct | Immunization Day 0 | Immunization Day 21 | Challenge Day 49 |
| 1 | 10 | CNE56/RNA | CO•prME | 15 μg | 15 μg | 100 PFU, IP |
| 2 | 10 | CNE56/RNA | CO•prME | 1.5 μg | 1.5 μg | 100 PFU, IP |
| 3 | 10 | CNE56/RNA | WT•prME | 15 μg | 15 μg | 100 PFU, IP |
| 4 | 10 | CNE56/RNA | WT•prME | 1.5 μg | 1.5 μg | 100 PFU, IP |
| 5 | 10 | Electroporation/ DNA | 5283 | 50 μg | 50 μg | 100 PFU, IP |

Blood sera were collected on day 0, as well as 2 weeks after the first immunization, 2 weeks after the second immunization, and three days after the Zika virus challenge.

Zika neutralizing antibody titers were measured by reporter virus particle (RVP) neutralization assay according to methods described in Dowd, K A et al. *Cell Rep.* 16(6): 1485-9 (2016). Results are shown in FIG. 10. Two weeks after the first immunization with Zika SAM constructs #1 or #2, or the positive control Zika DNA construct, there were significant levels of Zika neutralizing antibodies detected in the sera of immunized mice. Zika neutralizing antibody levels were even higher two weeks after the second immunization with the same Zika-SAM construct or the positive control.

A dose-dependent effect was observed, with the 15 μg dose of Zika SAM constructs #1 and #2 producing higher levels of neutralizing antibodies than the 1.5 μg dose. Notably, the 15 μg dose of Zika SAM constructs #1 and #2 produced a neutralizing antibody response that was comparable to the 50 μg dose of the Zika DNA vaccine construct (DNA #5283). These results indicate that Zika SAM constructs #1 and #2 are capable of inducing a significant neutralizing antibody response to Zika virus.

On day 49 of the study, mice were challenged with intraperitoneal injections of live Zika virus (strain PRV-ABC57) at a dose of 100 plaque forming units (PFU). Serum samples were taken three days after challenge, and viral loads were determined by real time quantitative PCR (qPCR) of the Zika virus capsid gene.

As shown in FIG. 11, mice vaccinated with Zika SAM constructs #1 or #2 (1.5 or 15 μg doses) or the positive control construct (DNA #5283) showed markedly reduced Zika virus detected in the serum as compared to unvaccinated animals. These results indicate that Zika SAM constructs #1 and #2 are capable of generating a protective immune response against Zika virus infection.

We claim:

1. A method of inducing an immune response against a Zika virus infection in a subject in need thereof, which comprises administering to said subject a composition comprising an immunologically effective amount of a self-replicating RNA molecule comprising a construct encoding a polypeptide at least 90% identical to an amino acid sequence selected from the group consisting of SEQ ID NO:26; SEQ ID NO:31; SEQ ID NO:36; SEQ ID NO:41; SEQ ID NO:46; SEQ ID NO:52; and SEQ ID NO:58.

2. The method of claim 1, wherein the composition comprises a non-viral delivery system selected from the group consisting of a submicron cationic oil-in-water emulsion; a liposome; and a biodegradable polymeric microparticle.

3. The method of claim 2, wherein the submicron cationic oil-in-water emulsion comprises an oil core, a cationic lipid, and a surfactant.

4. The method of claim 1, wherein the construct is codon optimized.

5. A method of inducing an immune response against a Zika virus infection in a subject in need thereof, which comprises administering to said subject a composition comprising an immunologically effective amount of a self-replicating RNA molecule comprising a nucleic acid sequence selected from the group consisting of SEQ ID NO:70, SEQ ID NO:71, SEQ ID NO:72, SEQ ID NO:73, SEQ ID NO:74, SEQ ID NO:75, and SEQ ID NO:76.

6. The method of claim 2, wherein the non-viral delivery system comprises a liposome.

7. The method of claim 2, wherein the non-viral delivery system comprises a submicron cationic oil-in-water emulsion further comprising an oil core, a cationic lipid, and a surfactant.

8. The method of claim 1, wherein the composition further comprises one or more additional antigens.

9. The method of claim 1, wherein the composition comprises one or more adjuvants.

10. The method of claim 1, wherein said construct encodes a polypeptide having a sequence at least 90% identical to SEQ ID NO:26.

11. The method of claim 1, wherein said construct encodes a polypeptide having a sequence at least 90% identical to SEQ ID NO:31.

12. A method of inducing an immune response against a Zika virus infection in a subject in need thereof, which comprises administering to said subject a composition comprising an immunologically effective amount of a self-replicating RNA molecule comprising a construct encoding a polypeptide selected from the group consisting of SEQ ID NO:26; SEQ ID NO:31; SEQ ID NO:36; SEQ ID NO:41; SEQ ID NO:46; SEQ ID NO:52; and SEQ ID NO:58.

13. The method of claim 12, wherein said construct encodes a polypeptide comprising SEQ ID NO:26.

14. The method of claim 12, wherein said construct encodes a polypeptide comprising SEQ ID NO:31.

15. The method of claim 12, wherein said construct encodes a polypeptide comprising SEQ ID NO:36.

16. The method of claim 12, wherein said construct encodes a polypeptide comprising SEQ ID NO:41.

17. The method of claim 12, wherein said construct encodes a polypeptide comprising SEQ ID NO:46.

18. The method of claim 12, wherein said construct encodes a polypeptide comprising SEQ ID NO:52.

19. The method of claim 12, wherein said construct encodes a polypeptide comprising SEQ ID NO:58.

20. The method of claim 1, wherein said polypeptide at least 95% identical to an amino acid sequence selected from the group consisting of SEQ ID NO:26; SEQ ID NO:31; SEQ ID NO:36; SEQ ID NO:41; SEQ ID NO:46; SEQ ID NO:52; and SEQ ID NO:58.

21. The method of claim 1, wherein said polypeptide at least 97% identical to an amino acid sequence selected from the group consisting of SEQ ID NO:26; SEQ ID NO:31; SEQ ID NO:36; SEQ ID NO:41; SEQ ID NO:46; SEQ ID NO:52; and SEQ ID NO:58.

22. The method of claim 1, wherein said polypeptide at least 98% identical to an amino acid sequence selected from the group consisting of SEQ ID NO:26; SEQ ID NO:31; SEQ ID NO:36; SEQ ID NO:41; SEQ ID NO:46; SEQ ID NO:52; and SEQ ID NO:58.

23. The method of claim 1, wherein said polypeptide at least 99% identical to an amino acid sequence selected from the group consisting of SEQ ID NO:26; SEQ ID NO:31; SEQ ID NO:36; SEQ ID NO:41; SEQ ID NO:46; SEQ ID NO:52; and SEQ ID NO:58.

* * * * *

SEQUENCE LISTING

```
<160> NUMBER OF SEQ ID NOS: 83

<210> SEQ ID NO 1
<211> LENGTH: 2079
<212> TYPE: DNA
<213> ORGANISM: Zika virus

<400> SEQUENCE: 1

atgcgaggcg cagatactag tgtcggaatt gttggcctcc tgctgaccac agctatggca      60

gcggaggtca ctagacgtgg gagtgcatac tatatgtact tggacagaaa cgatgctggg     120

gaggccatat cttttccaac cacattgggg atgaataagt gttatataca gatcatggat     180

cttggacaca tgtgtgatgc caccatgagc tatgaatgcc ctatgctgga tgagggggtg     240

gaaccagatg acgtcgattg ttggtgcaac acgacgtcaa cttgggttgt gtacggaacc     300

tgccatcaca aaaaaggtga agcacggaga tctaggagag ctgtgacgct cccctcccat     360

tccactagga agctgcaaac gcggtcgcaa acctggttgg aatcaagaga atacacaaag     420

cacttgatta gagtcgaaaa ttggatattc aggaaccctg gcttcgcgtt agcagcagct     480

gccatcgctt ggcttttggg aagctcaacg agccaaaaag tcatatactt ggtcatgata     540

ctgctgattg ccccggcata cagcatcagg tgcataggag tcagcaatag ggactttgtg     600

gaaggtatgt caggtgggac ttgggttgat gttgtcttgg aacatggagg ttgtgtcacc     660

gtaatggcac aggacaaacc gactgtcgac atagagctgg ttacaacaac agtcagcaac     720

atggcggagg taagatccta ctgctatgag gcatcaatat cagacatggc ttcggacagc     780

cgctgcccaa cacaaggtga agcctacctt gacaagcaat cagacactca atatgtctgc     840

aaaagaacgt tagtggacag aggctgggga aatggatgtg gactttttgg caaagggagc     900
```

-continued

```
ctggtgacat gcgctaagtt tgcatgctcc aagaaaatga ccgggaaaag catccagcca    960

gagaatctgg agtaccggat aatgctgtca gttcatggct cccagcacag tgggatgatc   1020

gttaatgaca caggacatga aactgatgag aatagagcga aggttgagat aacgcccaat   1080

tcaccaagag ccgaagccac cctgggggt tttggaagcc taggacttga ttgtgaaccg   1140

aggacaggcc ttgacttttc agatttgtat tacttgacta tgaataacaa gcactggttg   1200

gtccacaagg agtggttcca cgacattcca ttaccttggc acgctggggc agacaccgga   1260

actccacact ggaacaacaa agaagcactg gtagagttca aggacgcaca tgccaaaagg   1320

caaactgtcg tggttctagg gagtcaagaa ggagcagttc acacggccct tgctggagct   1380

ctggaggctg agatggatgg tgcaaaggga aggctgtcct ctggccactt gaaatgtcgc   1440

ctgaaaatgg ataaacttag attgaagggc gtgtcatact ccttgtgtac cgcagcgttc   1500

acattcacca agatcccggc tgaaacactg cacgggacag tcacagtgga ggtacagtac   1560

gcagggacag atggaccttg caaggttcca gctcagatgg cggtggacat gcaaactctg   1620

accccagttg ggaggttgat aaccgctaac cccgtaatca ctgaaagcac tgagaactct   1680

aagatgatgc tggaacttga tccaccattt ggggactctt acattgtcat aggagtcggg   1740

gagaagaaga tcacccacca ctggcacagg agtggcagca ccattggaaa agcatttgaa   1800

gccactgtga gaggtgccaa gagaatggca gtcttgggag acacagcctg ggactttgga   1860

tcagttggag gcgctctcaa ctcattgggc aagggcatcc atcaaatttt tggagcagct   1920

ttcaaatcat tgtttggagg aatgtcctgg ttctcacaaa tcctcattgg aacgttgctg   1980

atgtggttgg gtctgaacac aaagaatgga tctatttccc ttatgtgctt ggccttaggg   2040

ggagtgttga tcttcttatc cacagccgtc tctgctgat                          2079
```

<210> SEQ ID NO 2
<211> LENGTH: 693
<212> TYPE: PRT
<213> ORGANISM: Zika virus

<400> SEQUENCE: 2

```
Met Arg Gly Ala Asp Thr Ser Val Gly Ile Val Gly Leu Leu Leu Thr
1               5                   10                  15

Thr Ala Met Ala Ala Glu Val Thr Arg Arg Gly Ser Ala Tyr Tyr Met
            20                  25                  30

Tyr Leu Asp Arg Asn Asp Ala Gly Glu Ala Ile Ser Phe Pro Thr Thr
        35                  40                  45

Leu Gly Met Asn Lys Cys Tyr Ile Gln Ile Met Asp Leu Gly His Met
    50                  55                  60

Cys Asp Ala Thr Met Ser Tyr Glu Cys Pro Met Leu Asp Glu Gly Val
65                  70                  75                  80

Glu Pro Asp Asp Val Asp Cys Trp Cys Asn Thr Thr Ser Thr Trp Val
                85                  90                  95

Val Tyr Gly Thr Cys His His Lys Lys Gly Glu Ala Arg Arg Ser Arg
            100                 105                 110

Arg Ala Val Thr Leu Pro Ser His Ser Thr Arg Lys Leu Gln Thr Arg
        115                 120                 125

Ser Gln Thr Trp Leu Glu Ser Arg Glu Tyr Thr Lys His Leu Ile Arg
    130                 135                 140

Val Glu Asn Trp Ile Phe Arg Asn Pro Gly Phe Ala Leu Ala Ala Ala
145                 150                 155                 160
```

-continued

```
Ala Ile Ala Trp Leu Leu Gly Ser Ser Thr Ser Gln Lys Val Ile Tyr
                165                 170                 175

Leu Val Met Ile Leu Leu Ile Ala Pro Ala Tyr Ser Ile Arg Cys Ile
            180                 185                 190

Gly Val Ser Asn Arg Asp Phe Val Glu Gly Met Ser Gly Gly Thr Trp
        195                 200                 205

Val Asp Val Val Leu Glu His Gly Gly Cys Val Thr Val Met Ala Gln
    210                 215                 220

Asp Lys Pro Thr Val Asp Ile Glu Leu Val Thr Thr Thr Val Ser Asn
225                 230                 235                 240

Met Ala Glu Val Arg Ser Tyr Cys Tyr Glu Ala Ser Ile Ser Asp Met
                245                 250                 255

Ala Ser Asp Ser Arg Cys Pro Thr Gln Gly Glu Ala Tyr Leu Asp Lys
            260                 265                 270

Gln Ser Asp Thr Gln Tyr Val Cys Lys Arg Thr Leu Val Asp Arg Gly
        275                 280                 285

Trp Gly Asn Gly Cys Gly Leu Phe Gly Lys Gly Ser Leu Val Thr Cys
    290                 295                 300

Ala Lys Phe Ala Cys Ser Lys Lys Met Thr Gly Lys Ser Ile Gln Pro
305                 310                 315                 320

Glu Asn Leu Glu Tyr Arg Ile Met Leu Ser Val His Gly Ser Gln His
                325                 330                 335

Ser Gly Met Ile Val Asn Asp Thr Gly His Glu Thr Asp Glu Asn Arg
            340                 345                 350

Ala Lys Val Glu Ile Thr Pro Asn Ser Pro Arg Ala Glu Ala Thr Leu
        355                 360                 365

Gly Gly Phe Gly Ser Leu Gly Leu Asp Cys Glu Pro Arg Thr Gly Leu
    370                 375                 380

Asp Phe Ser Asp Leu Tyr Tyr Leu Thr Met Asn Asn Lys His Trp Leu
385                 390                 395                 400

Val His Lys Glu Trp Phe His Asp Ile Pro Leu Pro Trp His Ala Gly
                405                 410                 415

Ala Asp Thr Gly Thr Pro His Trp Asn Asn Lys Glu Ala Leu Val Glu
            420                 425                 430

Phe Lys Asp Ala His Ala Lys Arg Gln Thr Val Val Val Leu Gly Ser
        435                 440                 445

Gln Glu Gly Ala Val His Thr Ala Leu Ala Gly Ala Leu Glu Ala Glu
    450                 455                 460

Met Asp Gly Ala Lys Gly Arg Leu Ser Ser Gly His Leu Lys Cys Arg
465                 470                 475                 480

Leu Lys Met Asp Lys Leu Arg Leu Lys Gly Val Ser Tyr Ser Leu Cys
                485                 490                 495

Thr Ala Ala Phe Thr Phe Thr Lys Ile Pro Ala Glu Thr Leu His Gly
            500                 505                 510

Thr Val Thr Val Glu Val Gln Tyr Ala Gly Thr Asp Gly Pro Cys Lys
        515                 520                 525

Val Pro Ala Gln Met Ala Val Asp Met Gln Thr Leu Thr Pro Val Gly
    530                 535                 540

Arg Leu Ile Thr Ala Asn Pro Val Ile Thr Glu Ser Thr Glu Asn Ser
545                 550                 555                 560

Lys Met Met Leu Glu Leu Asp Pro Pro Phe Gly Asp Ser Tyr Ile Val
                565                 570                 575

Ile Gly Val Gly Glu Lys Lys Ile Thr His His Trp His Arg Ser Gly
```

-continued

```
            580                 585                 590

Ser Thr Ile Gly Lys Ala Phe Glu Ala Thr Val Arg Gly Ala Lys Arg
        595                 600                 605

Met Ala Val Leu Gly Asp Thr Ala Trp Asp Phe Gly Ser Val Gly Gly
    610                 615                 620

Ala Leu Asn Ser Leu Gly Lys Gly Ile His Gln Ile Phe Gly Ala Ala
625                 630                 635                 640

Phe Lys Ser Leu Phe Gly Gly Met Ser Trp Phe Ser Gln Ile Leu Ile
                645                 650                 655

Gly Thr Leu Leu Met Trp Leu Gly Leu Asn Thr Lys Asn Gly Ser Ile
            660                 665                 670

Ser Leu Met Cys Leu Ala Leu Gly Gly Val Leu Ile Phe Leu Ser Thr
        675                 680                 685

Ala Val Ser Ala Asp
    690


<210> SEQ ID NO 3
<211> LENGTH: 2079
<212> TYPE: DNA
<213> ORGANISM: Zika virus

<400> SEQUENCE: 3

atgagaggag ctgacaccag cgtgggcatt gtgggcctcc tgctgacaac cgccatggcc     60

gctgaggtca ccagaagagg cagcgcctac tacatgtacc tggacagaaa cgacgctggc    120

gaggctatta gcttccccac cacactcggc atgaacaagt gttacatcca gatcatggac    180

ctgggccaca tgtgcgatgc caccatgagc tacgaatgtc ctatgctgga cgaaggcgtg    240

gagcccgacg acgtggactg ttggtgcaac acaaccagca cctgggtggt gtacggcacc    300

tgccatcata agaagggaga agccaggaga agcaggaggg ctgtcacact cccctcccac    360

tccacaagaa agctgcaaac caggagccag acctggctgg aaagcaggga gtacaccaag    420

cacctgatca gggtcgagaa ctggatcttc aggaaccctg gattcgccct cgccgctgct    480

gctattgcct ggctcctggg ctcctccacc agccaaaagg tgatctacct ggtgatgatc    540

ctcctgatcg cccccgccta cagcatcagg tgcatcggcg tgtccaatag ggactttgtc    600

gaaggaatgt ccggcggcac atgggtggac gtcgtgctgg agcatggcgg ctgtgtgaca    660

gtcatggccc aggacaaacc caccgtggat atcgagctgg tgacaaccac agtgtccaac    720

atggccgagg tgaggagcta ctgctacgag gctagcatca gcgacatggc ttccgacagc    780

agatgcccca cacagggcga ggcctacctc gacaaacagt ccgacaccca gtacgtgtgc    840

aaaaggaccc tggtcgacag aggatggggc aacggctgcg gcctgttcgg aaaaggaagc    900

ctggtcacct gtgctaagtt cgcctgctcc aagaagatga ccggcaagag catccagccc    960

gagaacctcg agtacaggat catgctctcc gtccatggca gccagcacag cggaatgatc   1020

gtgaacgaca ccggccacga gaccgatgag aacagggcca aggtggaaat cacccccaac   1080

agccctaggg ctgaagctac cctcggcgga tttggatccc tgggcctgga ttgtgaaccc   1140

aggaccggac tcgacttcag cgatctgtac tacctgacca tgaacaacaa gcactggctg   1200

gtgcataagg agtggttcca tgatatcccc ctgccctggc atgctggagc cgatacaggc   1260

acccctcact ggaacaacaa ggaagccctg gtggagttca aagatgccca cgccaagaga   1320

cagacagtcg tcgtcctggg cagccaagag ggcgctgtgc atacagccct ggctggagcc   1380

ctggaggccg aaatggacgg cgccaaggga aggctgtcca gcggacatct gaagtgcagg   1440
```

```
ctgaagatgg acaagctgag gctcaagggc gtcagctact ccctgtgcac cgccgccttt   1500

acctttacaa aaatccccgc cgagaccctc cacggcacag tcacagtcga ggtgcagtac   1560

gctggaaccg acggaccttg taaggtgccc gcccaaatgg ccgtggacat gcagacactg   1620

acccctgtgg gcagactcat cacagccaac cctgtgatca cagagtccac cgagaacagc   1680

aagatgatgc tcgagctgga tcctcctttc ggcgacagct acatcgtgat cggagtgggc   1740

gagaagaaaa tcacccacca ctggcacagg tccggcagca ccattggcaa agcctttgaa   1800

gccaccgtca gaggagctaa aaggatggct gtgctgggcg acaccgcttg ggacttcggc   1860

tccgtgggag gagccctcaa ctccctgggc aagggcattc accagatttt cggcgccgct   1920

ttcaagagcc tctttggcgg catgtcctgg tttagccaga ttctcatcgg cacactgctg   1980

atgtggctgg gcctgaatac caagaacggc agcatcagcc tgatgtgtct ggccctggga   2040

ggcgtgctga tctttctgtc caccgctgtc agcgccgac                          2079


<210> SEQ ID NO 4
<211> LENGTH: 693
<212> TYPE: PRT
<213> ORGANISM: Zika virus

<400> SEQUENCE: 4

Met Arg Gly Ala Asp Thr Ser Val Gly Ile Val Gly Leu Leu Leu Thr
1               5                   10                  15

Thr Ala Met Ala Ala Glu Val Thr Arg Arg Gly Ser Ala Tyr Tyr Met
            20                  25                  30

Tyr Leu Asp Arg Asn Asp Ala Gly Glu Ala Ile Ser Phe Pro Thr Thr
        35                  40                  45

Leu Gly Met Asn Lys Cys Tyr Ile Gln Ile Met Asp Leu Gly His Met
    50                  55                  60

Cys Asp Ala Thr Met Ser Tyr Glu Cys Pro Met Leu Asp Glu Gly Val
65                  70                  75                  80

Glu Pro Asp Asp Val Asp Cys Trp Cys Asn Thr Thr Ser Thr Trp Val
                85                  90                  95

Val Tyr Gly Thr Cys His His Lys Lys Gly Glu Ala Arg Arg Ser Arg
            100                 105                 110

Arg Ala Val Thr Leu Pro Ser His Ser Thr Arg Lys Leu Gln Thr Arg
        115                 120                 125

Ser Gln Thr Trp Leu Glu Ser Arg Glu Tyr Thr Lys His Leu Ile Arg
    130                 135                 140

Val Glu Asn Trp Ile Phe Arg Asn Pro Gly Phe Ala Leu Ala Ala Ala
145                 150                 155                 160

Ala Ile Ala Trp Leu Leu Gly Ser Ser Thr Ser Gln Lys Val Ile Tyr
                165                 170                 175

Leu Val Met Ile Leu Leu Ile Ala Pro Ala Tyr Ser Ile Arg Cys Ile
            180                 185                 190

Gly Val Ser Asn Arg Asp Phe Val Glu Gly Met Ser Gly Gly Thr Trp
        195                 200                 205

Val Asp Val Val Leu Glu His Gly Gly Cys Val Thr Val Met Ala Gln
    210                 215                 220

Asp Lys Pro Thr Val Asp Ile Glu Leu Val Thr Thr Thr Val Ser Asn
225                 230                 235                 240

Met Ala Glu Val Arg Ser Tyr Cys Tyr Glu Ala Ser Ile Ser Asp Met
                245                 250                 255

Ala Ser Asp Ser Arg Cys Pro Thr Gln Gly Glu Ala Tyr Leu Asp Lys
```

-continued

```
            260                 265                 270

Gln Ser Asp Thr Gln Tyr Val Cys Lys Arg Thr Leu Val Asp Arg Gly
        275                 280                 285

Trp Gly Asn Gly Cys Gly Leu Phe Gly Lys Gly Ser Leu Val Thr Cys
    290                 295                 300

Ala Lys Phe Ala Cys Ser Lys Lys Met Thr Gly Lys Ser Ile Gln Pro
305                 310                 315                 320

Glu Asn Leu Glu Tyr Arg Ile Met Leu Ser Val His Gly Ser Gln His
                325                 330                 335

Ser Gly Met Ile Val Asn Asp Thr Gly His Glu Thr Asp Glu Asn Arg
            340                 345                 350

Ala Lys Val Glu Ile Thr Pro Asn Ser Pro Arg Ala Glu Ala Thr Leu
        355                 360                 365

Gly Gly Phe Gly Ser Leu Gly Leu Asp Cys Glu Pro Arg Thr Gly Leu
    370                 375                 380

Asp Phe Ser Asp Leu Tyr Tyr Leu Thr Met Asn Asn Lys His Trp Leu
385                 390                 395                 400

Val His Lys Glu Trp Phe His Asp Ile Pro Leu Pro Trp His Ala Gly
                405                 410                 415

Ala Asp Thr Gly Thr Pro His Trp Asn Asn Lys Glu Ala Leu Val Glu
            420                 425                 430

Phe Lys Asp Ala His Ala Lys Arg Gln Thr Val Val Val Leu Gly Ser
        435                 440                 445

Gln Glu Gly Ala Val His Thr Ala Leu Ala Gly Ala Leu Glu Ala Glu
    450                 455                 460

Met Asp Gly Ala Lys Gly Arg Leu Ser Ser Gly His Leu Lys Cys Arg
465                 470                 475                 480

Leu Lys Met Asp Lys Leu Arg Leu Lys Gly Val Ser Tyr Ser Leu Cys
                485                 490                 495

Thr Ala Ala Phe Thr Phe Thr Lys Ile Pro Ala Glu Thr Leu His Gly
            500                 505                 510

Thr Val Thr Val Glu Val Gln Tyr Ala Gly Thr Asp Gly Pro Cys Lys
        515                 520                 525

Val Pro Ala Gln Met Ala Val Asp Met Gln Thr Leu Thr Pro Val Gly
    530                 535                 540

Arg Leu Ile Thr Ala Asn Pro Val Ile Thr Glu Ser Thr Glu Asn Ser
545                 550                 555                 560

Lys Met Met Leu Glu Leu Asp Pro Pro Phe Gly Asp Ser Tyr Ile Val
                565                 570                 575

Ile Gly Val Gly Glu Lys Lys Ile Thr His His Trp His Arg Ser Gly
            580                 585                 590

Ser Thr Ile Gly Lys Ala Phe Glu Ala Thr Val Arg Gly Ala Lys Arg
        595                 600                 605

Met Ala Val Leu Gly Asp Thr Ala Trp Asp Phe Gly Ser Val Gly Gly
    610                 615                 620

Ala Leu Asn Ser Leu Gly Lys Gly Ile His Gln Ile Phe Gly Ala Ala
625                 630                 635                 640

Phe Lys Ser Leu Phe Gly Gly Met Ser Trp Phe Ser Gln Ile Leu Ile
                645                 650                 655

Gly Thr Leu Leu Met Trp Leu Gly Leu Asn Thr Lys Asn Gly Ser Ile
            660                 665                 670

Ser Leu Met Cys Leu Ala Leu Gly Gly Val Leu Ile Phe Leu Ser Thr
        675                 680                 685
```

```
Ala Val Ser Ala Asp
    690


<210> SEQ ID NO 5
<211> LENGTH: 18
<212> TYPE: PRT
<213> ORGANISM: Zika virus

<400> SEQUENCE: 5

Gly Ala Asp Thr Ser Val Gly Ile Val Gly Leu Leu Leu Thr Thr Ala
1               5                   10                  15

Met Ala


<210> SEQ ID NO 6
<211> LENGTH: 54
<212> TYPE: DNA
<213> ORGANISM: Zika virus

<400> SEQUENCE: 6

ggagctgaca ccagcgtggg cattgtgggc ctcctgctgc cccaggccca ggcc           54


<210> SEQ ID NO 7
<211> LENGTH: 54
<212> TYPE: DNA
<213> ORGANISM: Zika virus

<400> SEQUENCE: 7

ggcgctgaca caagcgtggg aatcgtggga ctgctgctcc cccaggccca ggct           54


<210> SEQ ID NO 8
<211> LENGTH: 18
<212> TYPE: PRT
<213> ORGANISM: Zika virus

<400> SEQUENCE: 8

Gly Ala Asp Thr Ser Val Gly Ile Val Gly Leu Leu Leu Pro Gln Ala
1               5                   10                  15

Gln Ala


<210> SEQ ID NO 9
<211> LENGTH: 54
<212> TYPE: DNA
<213> ORGANISM: Zika virus

<400> SEQUENCE: 9

gagttcggcc tgagctgggt gttcctggtg gccatcctgg agggcgtgca ttgc           54


<210> SEQ ID NO 10
<211> LENGTH: 18
<212> TYPE: PRT
<213> ORGANISM: Zika virus

<400> SEQUENCE: 10

Glu Phe Gly Leu Ser Trp Val Phe Leu Val Ala Ile Leu Glu Gly Val
1               5                   10                  15

His Cys


<210> SEQ ID NO 11
<211> LENGTH: 2391
<212> TYPE: DNA
<213> ORGANISM: Zika virus
```

<400> SEQUENCE: 11
atgaagaatc ctaagaaaaa gtccggcgga ttcaggatcg tgaatatgct gaagaggggc 60
gtggccaggg tctccccttt tggaggcctg aaaaggctgc ctgctggact gctgctggga 120
cacggcccca tcaggatggt cctggccatc ctcgccttcc tcagattcac cgccatcaag 180
ccctccctcg gcctgattaa caggtggggc agcgtcggca agaaagaagc catggaaatc 240
attaagaagt tcaaaaaaga cctggccgcc atgctgagga tcatcaatgc caggaaggag 300
aagaagagga ggggagctga tacctccgtg ggcatcgtgg gactgctgct caccacagcc 360
atggccgccg aggtcaccag aagaggcagc gcttattaca tgtacctgga cagaaatgac 420
gccggcgaag ctatcagctt ccctaccacc ctgggcatga acaagtgcta catccagatc 480
atggacctgg gccacatgtg cgatgccacc atgtcctacg agtgccccat gctcgacgaa 540
ggagtggagc ctgacgacgt ggattgttgg tgcaacacca cctccacatg ggtggtctat 600
ggcacctgcc atcacaagaa aggcgaagcc aggaggtcca ggagggctgt gaccctgccc 660
agccactcca ccaggaagct gcaaacaaga tcccagacct ggctggaatc cagggagtac 720
accaagcacc tgatcagggt ggagaactgg attttcagga atcccggctt cgccctggcc 780
gctgccgcca tcgcttggct gctcggcagc agcacctccc agaaagtgat ttacctggtg 840
atgatcctgc tcatcgcccc cgcctacagc atcagatgca tcggagtgag caacagggat 900
ttcgtggagg gcatgtccgg aggaacatgg gtggatgtgg tgctggaaca tggcggctgc 960
gtgacagtga tggcccagga caagcccaca gtggacatcg agctggtgac caccacagtg 1020
tccaatatgg ccgaggtcag gagctattgc tacgaggcta gcatctccga catggcttcc 1080
gacagcaggt gtcccacaca gggcgaggct tatctggaca agcagtccga tacccagtac 1140
gtgtgcaaaa ggaccctggt ggatagagga tggggaaacg gctgtggcct gttcggcaag 1200
ggctccctgg tgacctgtgc taaatttgcc tgctccaaga agatgaccgg caagtccatc 1260
caacctgaga acctggagta caggatcatg ctgtccgtgc acggcagcca acatagcggc 1320
atgatcgtga atgacaccgg acacgaaacc gacgaaaaca gggccaaggt ggagattacc 1380
cccaatagcc ccagagctga ggccacactg ggcggctttg gatccctcgg cctggattgt 1440
gagcccagga ccggcctcga cttctccgat ctgtattacc tgaccatgaa caacaagcat 1500
tggctcgtgc acaaagagtg gtttcacgac attcccctgc cttggcacgc tggcgccgat 1560
acaggaaccc cccactggaa caacaaggag gctctggtcg aatttaaaga cgcccatgcc 1620
aaaagacaga cagtcgtggt gctgggctcc caagagggag ccgtgcatac agccctggcc 1680
ggagccctcg aggctgaaat ggacggagct aaaggcaggc tgtccagcgg acacctgaag 1740
tgcaggctca agatggacaa gctcagactc aagggagtga gctatagcct gtgtacagcc 1800
gccttcacat tcaccaaaat ccccgccgaa accctgcacg gcacagtgac cgtggaggtc 1860
cagtacgccg gcacagacgg cccttgcaaa gtgcccgccc agatggctgt cgacatgcag 1920
acactgaccc ctgtgggcag gctgattacc gctaaccccg tgattaccga gagcacagag 1980
aacagcaaga tgatgctgga gctggaccct cctttcggcg attcctacat cgtgatcgga 2040
gtgggcgaga aaaagatcac ccaccattgg cacaggtccg gctccacaat tggcaaggcc 2100
tttgaggcca ccgtgagggg agctaagagg atggccgtgc tcggcgacac agcctgggat 2160
ttcggaagcg tgggaggcgc cctgaattcc ctcggcaagg gcatccatca gatcttcggc 2220
gctgccttca agtccctctt cggaggcatg agctggttca gccagatcct gatcggaacc 2280
ctcctgatgt ggctgggcct gaacaccaag aacggatcca ttagcctgat gtgtctcgcc 2340
ctgggcggcg tgctgatctt cctgtccacc gccgtgtccg ccgattgata a 2391

<210> SEQ ID NO 12
<211> LENGTH: 795
<212> TYPE: PRT
<213> ORGANISM: Zika virus

<400> SEQUENCE: 12

Met Lys Asn Pro Lys Lys Lys Ser Gly Gly Phe Arg Ile Val Asn Met
1 5 10 15

Leu Lys Arg Gly Val Ala Arg Val Ser Pro Phe Gly Gly Leu Lys Arg
20 25 30

Leu Pro Ala Gly Leu Leu Leu Gly His Gly Pro Ile Arg Met Val Leu
35 40 45

Ala Ile Leu Ala Phe Leu Arg Phe Thr Ala Ile Lys Pro Ser Leu Gly
50 55 60

Leu Ile Asn Arg Trp Gly Ser Val Gly Lys Lys Glu Ala Met Glu Ile
65 70 75 80

Ile Lys Lys Phe Lys Lys Asp Leu Ala Ala Met Leu Arg Ile Ile Asn
85 90 95

Ala Arg Lys Glu Lys Lys Arg Arg Gly Ala Asp Thr Ser Val Gly Ile
100 105 110

Val Gly Leu Leu Leu Thr Thr Ala Met Ala Ala Glu Val Thr Arg Arg
115 120 125

Gly Ser Ala Tyr Tyr Met Tyr Leu Asp Arg Asn Asp Ala Gly Glu Ala
130 135 140

Ile Ser Phe Pro Thr Thr Leu Gly Met Asn Lys Cys Tyr Ile Gln Ile
145 150 155 160

Met Asp Leu Gly His Met Cys Asp Ala Thr Met Ser Tyr Glu Cys Pro
165 170 175

Met Leu Asp Glu Gly Val Glu Pro Asp Asp Val Asp Cys Trp Cys Asn
180 185 190

Thr Thr Ser Thr Trp Val Val Tyr Gly Thr Cys His His Lys Lys Gly
195 200 205

Glu Ala Arg Arg Ser Arg Arg Ala Val Thr Leu Pro Ser His Ser Thr
210 215 220

Arg Lys Leu Gln Thr Arg Ser Gln Thr Trp Leu Glu Ser Arg Glu Tyr
225 230 235 240

Thr Lys His Leu Ile Arg Val Glu Asn Trp Ile Phe Arg Asn Pro Gly
245 250 255

Phe Ala Leu Ala Ala Ala Ala Ile Ala Trp Leu Leu Gly Ser Ser Thr
260 265 270

Ser Gln Lys Val Ile Tyr Leu Val Met Ile Leu Leu Ile Ala Pro Ala
275 280 285

Tyr Ser Ile Arg Cys Ile Gly Val Ser Asn Arg Asp Phe Val Glu Gly
290 295 300

Met Ser Gly Gly Thr Trp Val Asp Val Val Leu Glu His Gly Gly Cys
305 310 315 320

Val Thr Val Met Ala Gln Asp Lys Pro Thr Val Asp Ile Glu Leu Val
325 330 335

Thr Thr Thr Val Ser Asn Met Ala Glu Val Arg Ser Tyr Cys Tyr Glu
340 345 350

Ala Ser Ile Ser Asp Met Ala Ser Asp Ser Arg Cys Pro Thr Gln Gly
355 360 365

-continued

```
Glu Ala Tyr Leu Asp Lys Gln Ser Asp Thr Gln Tyr Val Cys Lys Arg
    370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Ala Cys Ser Lys Lys Met Thr
                405                 410                 415

Gly Lys Ser Ile Gln Pro Glu Asn Leu Glu Tyr Arg Ile Met Leu Ser
            420                 425                 430

Val His Gly Ser Gln His Ser Gly Met Ile Val Asn Asp Thr Gly His
        435                 440                 445

Glu Thr Asp Glu Asn Arg Ala Lys Val Glu Ile Thr Pro Asn Ser Pro
    450                 455                 460

Arg Ala Glu Ala Thr Leu Gly Gly Phe Gly Ser Leu Gly Leu Asp Cys
465                 470                 475                 480

Glu Pro Arg Thr Gly Leu Asp Phe Ser Asp Leu Tyr Tyr Leu Thr Met
                485                 490                 495

Asn Asn Lys His Trp Leu Val His Lys Glu Trp Phe His Asp Ile Pro
            500                 505                 510

Leu Pro Trp His Ala Gly Ala Asp Thr Gly Thr Pro His Trp Asn Asn
        515                 520                 525

Lys Glu Ala Leu Val Glu Phe Lys Asp Ala His Ala Lys Arg Gln Thr
    530                 535                 540

Val Val Val Leu Gly Ser Gln Glu Gly Ala Val His Thr Ala Leu Ala
545                 550                 555                 560

Gly Ala Leu Glu Ala Glu Met Asp Gly Ala Lys Gly Arg Leu Ser Ser
                565                 570                 575

Gly His Leu Lys Cys Arg Leu Lys Met Asp Lys Leu Arg Leu Lys Gly
            580                 585                 590

Val Ser Tyr Ser Leu Cys Thr Ala Ala Phe Thr Phe Thr Lys Ile Pro
        595                 600                 605

Ala Glu Thr Leu His Gly Thr Val Thr Val Glu Val Gln Tyr Ala Gly
    610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
                645                 650                 655

Glu Ser Thr Glu Asn Ser Lys Met Met Leu Glu Leu Asp Pro Pro Phe
            660                 665                 670

Gly Asp Ser Tyr Ile Val Ile Gly Val Gly Glu Lys Lys Ile Thr His
        675                 680                 685

His Trp His Arg Ser Gly Ser Thr Ile Gly Lys Ala Phe Glu Ala Thr
    690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
                725                 730                 735

Gln Ile Phe Gly Ala Ala Phe Lys Ser Leu Phe Gly Gly Met Ser Trp
            740                 745                 750

Phe Ser Gln Ile Leu Ile Gly Thr Leu Leu Met Trp Leu Gly Leu Asn
        755                 760                 765

Thr Lys Asn Gly Ser Ile Ser Leu Met Cys Leu Ala Leu Gly Gly Val
    770                 775                 780
```

-continued

```
Leu Ile Phe Leu Ser Thr Ala Val Ser Ala Asp
785                 790                 795


<210> SEQ ID NO 13
<211> LENGTH: 66
<212> TYPE: DNA
<213> ORGANISM: porcine teschovirus

<400> SEQUENCE: 13

ggctccggag ccacaaactt cagcctgctg aaacaagccg gcgacgtcga agaaaatccc      60

ggcccc                                                                 66


<210> SEQ ID NO 14
<211> LENGTH: 22
<212> TYPE: PRT
<213> ORGANISM: porcine teschovirus

<400> SEQUENCE: 14

Gly Ser Gly Ala Thr Asn Phe Ser Leu Leu Lys Gln Ala Gly Asp Val
1               5                   10                  15

Glu Glu Asn Pro Gly Pro
            20


<210> SEQ ID NO 15
<211> LENGTH: 795
<212> TYPE: PRT
<213> ORGANISM: Zika virus

<400> SEQUENCE: 15

Met Lys Asn Pro Lys Lys Lys Ser Gly Gly Phe Arg Ile Val Asn Met
1               5                   10                  15

Leu Lys Arg Gly Val Ala Arg Val Ser Pro Phe Gly Gly Leu Lys Arg
            20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Ile
65                  70                  75                  80

Ile Lys Lys Phe Lys Lys Asp Leu Ala Ala Met Leu Arg Ile Ile Asn
                85                  90                  95

Ala Arg Lys Glu Lys Lys Arg Arg Gly Ala Asp Thr Ser Val Gly Ile
            100                 105                 110

Val Gly Leu Leu Leu Thr Thr Ala Met Ala Ala Glu Val Thr Arg Arg
        115                 120                 125

Gly Ser Ala Tyr Tyr Met Tyr Leu Asp Arg Asn Asp Ala Gly Glu Ala
    130                 135                 140

Ile Ser Phe Pro Thr Thr Leu Gly Met Asn Lys Cys Tyr Ile Gln Ile
145                 150                 155                 160

Met Asp Leu Gly His Met Cys Asp Ala Thr Met Ser Tyr Glu Cys Pro
                165                 170                 175

Met Leu Asp Glu Gly Val Glu Pro Asp Asp Val Asp Cys Trp Cys Asn
            180                 185                 190

Thr Thr Ser Thr Trp Val Val Tyr Gly Thr Cys His His Lys Lys Gly
        195                 200                 205

Glu Ala Arg Arg Ser Arg Arg Ala Val Thr Leu Pro Ser His Ser Thr
    210                 215                 220
```

-continued

```
Arg Lys Leu Gln Thr Arg Ser Gln Thr Trp Leu Glu Ser Arg Glu Tyr
225                 230                 235                 240

Thr Lys His Leu Ile Arg Val Glu Asn Trp Ile Phe Arg Asn Pro Gly
                245                 250                 255

Phe Ala Leu Ala Ala Ala Ala Ile Ala Trp Leu Leu Gly Ser Ser Thr
            260                 265                 270

Ser Gln Lys Val Ile Tyr Leu Val Met Ile Leu Leu Ile Ala Pro Ala
        275                 280                 285

Tyr Ser Ile Arg Cys Ile Gly Val Ser Asn Arg Asp Phe Val Glu Gly
    290                 295                 300

Met Ser Gly Gly Thr Trp Val Asp Val Val Leu Glu His Gly Gly Cys
305                 310                 315                 320

Val Thr Val Met Ala Gln Asp Lys Pro Thr Val Asp Ile Glu Leu Val
                325                 330                 335

Thr Thr Thr Val Ser Asn Met Ala Glu Val Arg Ser Tyr Cys Tyr Glu
            340                 345                 350

Ala Ser Ile Ser Asp Met Ala Ser Asp Ser Arg Cys Pro Thr Gln Gly
        355                 360                 365

Glu Ala Tyr Leu Asp Lys Gln Ser Asp Thr Gln Tyr Val Cys Lys Arg
    370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Ala Cys Ser Lys Lys Met Thr
                405                 410                 415

Gly Lys Ser Ile Gln Pro Glu Asn Leu Glu Tyr Arg Ile Met Leu Ser
            420                 425                 430

Val His Gly Ser Gln His Ser Gly Met Ile Val Asn Asp Thr Gly His
        435                 440                 445

Glu Thr Asp Glu Asn Arg Ala Lys Val Glu Ile Thr Pro Asn Ser Pro
    450                 455                 460

Arg Ala Glu Ala Thr Leu Gly Gly Phe Gly Ser Leu Gly Leu Asp Cys
465                 470                 475                 480

Glu Pro Arg Thr Gly Leu Asp Phe Ser Asp Leu Tyr Tyr Leu Thr Met
                485                 490                 495

Asn Asn Lys His Trp Leu Val His Lys Glu Trp Phe His Asp Ile Pro
            500                 505                 510

Leu Pro Trp His Ala Gly Ala Asp Thr Gly Thr Pro His Trp Asn Asn
        515                 520                 525

Lys Glu Ala Leu Val Glu Phe Lys Asp Ala His Ala Lys Arg Gln Thr
    530                 535                 540

Val Val Val Leu Gly Ser Gln Glu Gly Ala Val His Thr Ala Leu Ala
545                 550                 555                 560

Gly Ala Leu Glu Ala Glu Met Asp Gly Ala Lys Gly Arg Leu Ser Ser
                565                 570                 575

Gly His Leu Lys Cys Arg Leu Lys Met Asp Lys Leu Arg Leu Lys Gly
            580                 585                 590

Val Ser Tyr Ser Leu Cys Thr Ala Ala Phe Thr Phe Thr Lys Ile Pro
        595                 600                 605

Ala Glu Thr Leu His Gly Thr Val Thr Val Glu Val Gln Tyr Ala Gly
    610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
```

```
                645                 650                 655

Glu Ser Thr Glu Asn Ser Lys Met Met Leu Glu Leu Asp Pro Pro Phe
            660                 665                 670

Gly Asp Ser Tyr Ile Val Ile Gly Val Gly Glu Lys Lys Ile Thr His
        675                 680                 685

His Trp His Arg Ser Gly Ser Thr Ile Gly Lys Ala Phe Glu Ala Thr
    690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
                725                 730                 735

Gln Ile Phe Gly Ala Ala Phe Lys Ser Leu Phe Gly Gly Met Ser Trp
            740                 745                 750

Phe Ser Gln Ile Leu Ile Gly Thr Leu Leu Met Trp Leu Gly Leu Asn
        755                 760                 765

Thr Lys Asn Gly Ser Ile Ser Leu Met Cys Leu Ala Leu Gly Gly Val
    770                 775                 780

Leu Ile Phe Leu Ser Thr Ala Val Ser Ala Asp
785                 790                 795


<210> SEQ ID NO 16
<211> LENGTH: 795
<212> TYPE: PRT
<213> ORGANISM: Zika virus

<400> SEQUENCE: 16

Met Lys Asn Pro Lys Lys Lys Ser Gly Gly Phe Arg Ile Val Asn Met
1               5                   10                  15

Leu Lys Arg Gly Val Ala Arg Val Ser Pro Phe Gly Gly Leu Lys Arg
            20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Ile
65                  70                  75                  80

Ile Lys Lys Phe Lys Lys Asp Leu Ala Ala Met Leu Arg Ile Ile Asn
                85                  90                  95

Ala Arg Lys Glu Lys Lys Arg Arg Gly Ala Asp Thr Ser Val Gly Ile
            100                 105                 110

Val Gly Leu Leu Leu Thr Thr Ala Met Ala Ala Glu Val Thr Arg Arg
        115                 120                 125

Gly Ser Ala Tyr Tyr Met Tyr Leu Asp Arg Asn Asp Ala Gly Glu Ala
    130                 135                 140

Ile Ser Phe Pro Thr Thr Leu Gly Met Asn Lys Cys Tyr Ile Gln Ile
145                 150                 155                 160

Met Asp Leu Gly His Met Cys Asp Ala Thr Met Ser Tyr Glu Cys Pro
                165                 170                 175

Met Leu Asp Glu Gly Val Glu Pro Asp Asp Val Asp Cys Trp Cys Asn
            180                 185                 190

Thr Thr Ser Thr Trp Val Val Tyr Gly Thr Cys His His Lys Lys Gly
        195                 200                 205

Glu Ala Arg Arg Ser Arg Arg Ala Val Thr Leu Pro Ser His Ser Thr
    210                 215                 220
```

-continued

```
Arg Lys Leu Gln Thr Arg Ser Gln Thr Trp Leu Glu Ser Arg Glu Tyr
225                 230                 235                 240

Thr Lys His Leu Ile Arg Val Glu Asn Trp Ile Phe Arg Asn Pro Gly
                245                 250                 255

Phe Ala Leu Ala Ala Ala Ala Ile Ala Trp Leu Leu Gly Ser Ser Thr
            260                 265                 270

Ser Gln Lys Val Ile Tyr Leu Val Met Ile Leu Leu Ile Ala Pro Ala
        275                 280                 285

Tyr Ser Ile Arg Cys Ile Gly Val Ser Asn Arg Asp Phe Val Glu Gly
    290                 295                 300

Met Ser Gly Gly Thr Trp Val Asp Ile Val Leu Glu His Gly Gly Cys
305                 310                 315                 320

Val Thr Val Met Ala Gln Asp Lys Pro Thr Val Asp Ile Glu Leu Val
                325                 330                 335

Thr Thr Thr Val Ser Asn Met Ala Glu Val Arg Ser Tyr Cys Tyr Glu
            340                 345                 350

Ala Ser Ile Ser Asp Met Ala Ser Asp Ser Arg Cys Pro Thr Gln Gly
        355                 360                 365

Glu Ala Tyr Leu Asp Lys Gln Ser Asp Thr Gln Tyr Val Cys Lys Arg
    370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Ala Cys Ser Lys Lys Met Thr
                405                 410                 415

Gly Lys Ser Ile Gln Pro Glu Asn Leu Glu Tyr Arg Ile Met Leu Ser
            420                 425                 430

Val His Gly Ser Gln His Ser Gly Met Ile Val Asn Asp Thr Gly His
        435                 440                 445

Glu Thr Asp Glu Asn Arg Ala Lys Val Glu Ile Thr Pro Asn Ser Pro
    450                 455                 460

Arg Ala Glu Ala Thr Leu Gly Gly Phe Gly Ser Leu Gly Leu Asp Cys
465                 470                 475                 480

Glu Pro Arg Thr Gly Leu Asp Phe Ser Asp Leu Tyr Tyr Leu Thr Met
                485                 490                 495

Asn Asn Lys His Trp Leu Val His Lys Glu Trp Phe His Asp Ile Pro
            500                 505                 510

Leu Pro Trp His Ala Gly Ala Asp Thr Gly Thr Pro His Trp Asn Asn
        515                 520                 525

Lys Glu Ala Leu Val Glu Phe Lys Asp Ala His Ala Lys Arg Gln Thr
    530                 535                 540

Val Val Val Leu Gly Ser Gln Glu Gly Ala Val His Thr Ala Leu Ala
545                 550                 555                 560

Gly Ala Leu Glu Ala Glu Met Asp Gly Ala Lys Gly Arg Leu Ser Ser
                565                 570                 575

Gly His Leu Lys Cys Arg Leu Lys Met Asp Lys Leu Arg Leu Lys Gly
            580                 585                 590

Val Ser Tyr Ser Leu Cys Thr Ala Ala Phe Thr Phe Thr Lys Ile Pro
        595                 600                 605

Ala Glu Thr Leu His Gly Thr Val Thr Val Glu Val Gln Tyr Ala Gly
    610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
```

```
                645                 650                 655

Glu Ser Thr Glu Asn Ser Lys Met Met Leu Glu Leu Asp Pro Pro Phe
            660                 665                 670

Gly Asp Ser Tyr Ile Val Ile Gly Val Gly Glu Lys Lys Ile Thr His
        675                 680                 685

His Trp His Arg Ser Gly Ser Thr Ile Gly Lys Ala Phe Glu Ala Thr
    690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
                725                 730                 735

Gln Ile Phe Gly Ala Ala Phe Lys Ser Leu Phe Gly Gly Met Ser Trp
            740                 745                 750

Phe Ser Gln Ile Leu Ile Gly Thr Leu Leu Met Trp Leu Gly Leu Asn
        755                 760                 765

Thr Lys Asn Gly Ser Ile Ser Leu Met Cys Leu Ala Leu Gly Gly Val
    770                 775                 780

Leu Ile Phe Leu Ser Thr Ala Val Ser Ala Asp
785                 790                 795


<210> SEQ ID NO 17
<211> LENGTH: 791
<212> TYPE: PRT
<213> ORGANISM: Zika virus

<400> SEQUENCE: 17

Met Lys Asn Pro Lys Glu Glu Ile Arg Arg Ile Arg Ile Val Asn Met
1               5                   10                  15

Leu Lys Arg Gly Val Ala Arg Val Asn Pro Leu Gly Gly Leu Lys Arg
            20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Ile
65                  70                  75                  80

Ile Lys Lys Phe Lys Lys Asp Leu Ala Ala Met Leu Arg Ile Ile Asn
                85                  90                  95

Ala Arg Lys Glu Arg Lys Arg Arg Gly Ala Asp Thr Ser Ile Gly Ile
            100                 105                 110

Ile Gly Leu Leu Leu Thr Thr Ala Met Ala Ala Glu Ile Thr Arg Arg
        115                 120                 125

Gly Ser Ala Tyr Tyr Met Tyr Leu Asp Arg Ser Asp Ala Gly Lys Ala
    130                 135                 140

Ile Ser Phe Ala Thr Thr Leu Gly Val Asn Lys Cys His Val Gln Ile
145                 150                 155                 160

Met Asp Leu Gly His Met Cys Asp Ala Thr Met Ser Tyr Glu Cys Pro
                165                 170                 175

Met Leu Asp Glu Gly Val Glu Pro Asp Asp Val Asp Cys Trp Cys Asn
            180                 185                 190

Thr Thr Ser Thr Trp Val Val Tyr Gly Thr Cys His His Lys Lys Gly
        195                 200                 205

Glu Ala Arg Arg Ser Arg Arg Ala Val Thr Leu Pro Ser His Ser Thr
    210                 215                 220
```

```
Arg Lys Leu Gln Thr Arg Ser Gln Thr Trp Leu Glu Ser Arg Glu Tyr
225                 230                 235                 240

Thr Lys His Leu Ile Lys Val Glu Asn Trp Ile Phe Arg Asn Pro Gly
                245                 250                 255

Phe Ala Leu Val Ala Val Ala Ile Ala Trp Leu Leu Gly Ser Ser Thr
            260                 265                 270

Ser Gln Lys Val Ile Tyr Leu Val Met Ile Leu Leu Ile Ala Pro Ala
        275                 280                 285

Tyr Ser Ile Arg Cys Ile Gly Val Ser Asn Arg Asp Phe Val Glu Gly
    290                 295                 300

Met Ser Gly Gly Thr Trp Val Asp Val Val Leu Glu His Gly Gly Cys
305                 310                 315                 320

Val Thr Val Met Ala Gln Asp Lys Pro Thr Val Asp Ile Glu Leu Val
                325                 330                 335

Thr Thr Thr Val Ser Asn Met Ala Glu Val Arg Ser Tyr Cys Tyr Glu
            340                 345                 350

Ala Ser Ile Ser Asp Met Ala Ser Asp Ser Arg Cys Pro Thr Gln Gly
        355                 360                 365

Glu Ala Tyr Leu Asp Lys Gln Ser Asp Thr Gln Tyr Val Cys Lys Arg
    370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Thr Cys Ser Lys Lys Met Thr
                405                 410                 415

Gly Lys Ser Ile Gln Pro Glu Asn Leu Glu Tyr Arg Ile Met Leu Ser
            420                 425                 430

Val His Gly Ser Gln His Ser Gly Met Ile Gly Tyr Glu Thr Asp Glu
        435                 440                 445

Asp Arg Ala Lys Val Glu Val Thr Pro Asn Ser Pro Arg Ala Glu Ala
    450                 455                 460

Thr Leu Gly Gly Phe Gly Ser Leu Gly Leu Asp Cys Glu Pro Arg Thr
465                 470                 475                 480

Gly Leu Asp Phe Ser Asp Leu Tyr Tyr Leu Thr Met Asn Asn Lys His
                485                 490                 495

Trp Leu Val His Lys Glu Trp Phe His Asp Ile Pro Leu Pro Trp His
            500                 505                 510

Ala Gly Ala Asp Thr Gly Thr Pro His Trp Asn Asn Lys Glu Ala Leu
        515                 520                 525

Val Glu Phe Lys Asp Ala His Ala Lys Arg Gln Thr Val Val Val Leu
    530                 535                 540

Gly Ser Gln Glu Gly Ala Val His Thr Ala Leu Ala Gly Ala Leu Glu
545                 550                 555                 560

Ala Glu Met Asp Gly Ala Lys Gly Arg Leu Phe Ser Gly His Leu Lys
                565                 570                 575

Cys Arg Leu Lys Met Asp Lys Leu Arg Leu Lys Gly Val Ser Tyr Ser
            580                 585                 590

Leu Cys Thr Ala Ala Phe Thr Phe Thr Lys Val Pro Ala Glu Thr Leu
        595                 600                 605

His Gly Thr Val Thr Val Glu Val Gln Tyr Ala Gly Thr Asp Gly Pro
    610                 615                 620

Cys Lys Ile Pro Val Gln Met Ala Val Asp Met Gln Thr Leu Thr Pro
625                 630                 635                 640

Val Gly Arg Leu Ile Thr Ala Asn Pro Val Ile Thr Glu Ser Thr Glu
```

-continued

```
                645                 650                 655

Asn Ser Lys Met Met Leu Glu Leu Asp Pro Pro Phe Gly Asp Ser Tyr
            660                 665                 670

Ile Val Ile Gly Val Gly Asp Lys Lys Ile Thr His His Trp His Arg
        675                 680                 685

Ser Gly Ser Thr Ile Gly Lys Ala Phe Glu Ala Thr Val Arg Gly Ala
    690                 695                 700

Lys Arg Met Ala Val Leu Gly Asp Thr Ala Trp Asp Phe Gly Ser Val
705                 710                 715                 720

Gly Gly Val Phe Asn Ser Leu Gly Lys Gly Ile His Gln Ile Phe Gly
                725                 730                 735

Ala Ala Phe Lys Ser Leu Phe Gly Gly Met Ser Trp Phe Ser Gln Ile
            740                 745                 750

Leu Ile Gly Thr Leu Leu Val Trp Leu Gly Leu Asn Thr Lys Asn Gly
        755                 760                 765

Ser Ile Ser Leu Thr Cys Leu Ala Leu Gly Gly Val Met Ile Phe Leu
    770                 775                 780

Ser Thr Ala Val Ser Ala Asp
785                 790


<210> SEQ ID NO 18
<211> LENGTH: 795
<212> TYPE: PRT
<213> ORGANISM: Zika virus

<400> SEQUENCE: 18

Met Lys Asn Pro Lys Glu Glu Ile Arg Arg Ile Arg Ile Val Asn Met
1               5                   10                  15

Leu Lys Arg Gly Val Ala Arg Val Ser Pro Phe Gly Gly Leu Lys Arg
            20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Ile
65                  70                  75                  80

Ile Lys Lys Phe Lys Lys Asp Leu Ala Ala Met Leu Arg Ile Ile Asn
                85                  90                  95

Ala Arg Lys Glu Lys Lys Arg Arg Gly Thr Asp Thr Ser Val Gly Ile
            100                 105                 110

Val Gly Leu Leu Leu Thr Thr Ala Met Ala Val Glu Val Thr Arg Arg
        115                 120                 125

Gly Ser Ala Tyr Tyr Met Tyr Leu Asp Arg Ser Asp Ala Gly Glu Ala
    130                 135                 140

Ile Ser Phe Pro Thr Thr Leu Gly Met Asn Lys Cys Tyr Ile Gln Ile
145                 150                 155                 160

Met Asp Leu Gly His Met Cys Asp Ala Thr Met Ser Tyr Glu Cys Pro
                165                 170                 175

Met Leu Asp Glu Gly Val Glu Pro Asp Asp Val Asp Cys Trp Cys Asn
            180                 185                 190

Thr Thr Ser Thr Trp Val Val Tyr Gly Thr Cys His His Lys Lys Gly
        195                 200                 205

Glu Ala Arg Arg Ser Arg Arg Ala Val Thr Leu Pro Ser His Ser Thr
    210                 215                 220
```

-continued

```
Arg Lys Leu Gln Thr Arg Ser Gln Thr Trp Leu Glu Ser Arg Glu Tyr
225                 230                 235                 240

Thr Lys His Leu Ile Arg Val Glu Asn Trp Ile Phe Arg Asn Pro Gly
                245                 250                 255

Phe Ala Leu Ala Ala Ala Ala Ile Ala Trp Leu Leu Gly Ser Ser Thr
            260                 265                 270

Ser Gln Lys Val Ile Tyr Leu Val Met Ile Leu Leu Ile Ala Pro Ala
        275                 280                 285

Tyr Ser Ile Arg Cys Ile Gly Val Ser Asn Arg Asp Phe Val Glu Gly
    290                 295                 300

Met Ser Gly Gly Thr Trp Val Asp Val Val Leu Glu His Gly Gly Cys
305                 310                 315                 320

Val Thr Val Met Ala Gln Asp Lys Pro Ala Val Asp Ile Glu Leu Val
                325                 330                 335

Thr Thr Thr Val Ser Asn Met Ala Glu Val Arg Ser Tyr Cys Tyr Glu
            340                 345                 350

Ala Ser Ile Ser Asp Met Ala Ser Asp Ser Arg Cys Pro Thr Gln Gly
        355                 360                 365

Glu Ala Tyr Leu Asp Lys Gln Ser Asp Thr Gln Tyr Val Cys Lys Arg
    370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Ala Cys Ser Lys Lys Met Thr
                405                 410                 415

Gly Lys Ser Ile Gln Pro Glu Asn Leu Glu Tyr Arg Ile Met Leu Ser
            420                 425                 430

Val His Gly Ser Gln His Ser Gly Met Ile Val Asn Asp Thr Gly His
        435                 440                 445

Glu Thr Asp Glu Asn Arg Ala Lys Val Glu Ile Thr Pro Asn Ser Pro
    450                 455                 460

Arg Ala Glu Ala Thr Leu Gly Gly Phe Gly Ser Leu Gly Leu Asp Cys
465                 470                 475                 480

Glu Pro Arg Thr Gly Leu Asp Phe Ser Asp Leu Tyr Tyr Leu Thr Met
                485                 490                 495

Asn Asn Lys His Trp Leu Val His Lys Glu Trp Phe His Asp Ile Pro
            500                 505                 510

Leu Pro Trp His Ala Gly Ala Asp Thr Gly Thr Pro His Trp Asn Asn
        515                 520                 525

Lys Glu Ala Leu Val Glu Phe Lys Asp Ala His Ala Lys Arg Gln Thr
    530                 535                 540

Val Val Val Leu Gly Ser Gln Glu Gly Ala Val His Thr Ala Leu Ala
545                 550                 555                 560

Gly Ala Leu Glu Ala Glu Met Asp Gly Ala Lys Gly Arg Leu Ser Ser
                565                 570                 575

Gly His Leu Lys Cys Arg Leu Lys Met Asp Lys Leu Arg Leu Lys Gly
            580                 585                 590

Val Ser Tyr Ser Leu Cys Thr Ala Ala Phe Thr Phe Thr Lys Ile Pro
        595                 600                 605

Ala Glu Thr Leu His Gly Thr Val Thr Val Glu Val Gln Tyr Ala Gly
    610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
```

```
                645                 650                 655

Glu Ser Thr Glu Asn Ser Lys Met Met Leu Glu Leu Asp Pro Pro Phe
            660                 665                 670

Gly Asp Ser Tyr Ile Val Ile Gly Val Gly Glu Lys Lys Ile Thr His
        675                 680                 685

His Trp His Arg Ser Gly Ser Thr Ile Gly Lys Ala Phe Glu Ala Thr
    690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
                725                 730                 735

Gln Ile Phe Gly Ala Ala Phe Lys Ser Leu Phe Gly Gly Met Ser Trp
            740                 745                 750

Phe Ser Gln Ile Leu Ile Gly Thr Leu Leu Val Trp Leu Gly Leu Asn
        755                 760                 765

Thr Lys Asn Gly Ser Ile Ser Leu Thr Cys Leu Ala Leu Gly Gly Val
    770                 775                 780

Leu Ile Phe Leu Ser Thr Ala Val Ser Ala Asp
785                 790                 795


<210> SEQ ID NO 19
<211> LENGTH: 795
<212> TYPE: PRT
<213> ORGANISM: Zika virus

<400> SEQUENCE: 19

Met Lys Asn Pro Lys Lys Lys Ser Gly Gly Phe Arg Ile Val Asn Met
1               5                   10                  15

Leu Lys Arg Gly Val Ala Arg Val Ser Pro Phe Gly Gly Leu Lys Arg
            20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Ile
65                  70                  75                  80

Ile Lys Lys Phe Lys Lys Asp Leu Ala Ala Met Leu Arg Ile Ile Asn
                85                  90                  95

Ala Arg Lys Glu Lys Lys Arg Arg Gly Ala Asp Thr Ser Val Gly Ile
            100                 105                 110

Val Gly Leu Leu Leu Thr Thr Ala Met Ala Ala Glu Val Thr Arg Arg
        115                 120                 125

Gly Ser Ala Tyr Tyr Met Tyr Leu Asp Arg Asn Asp Ala Gly Glu Ala
    130                 135                 140

Ile Ser Phe Pro Thr Thr Leu Gly Met Asn Lys Cys Tyr Ile Gln Ile
145                 150                 155                 160

Met Asp Leu Gly His Met Cys Asp Ala Thr Met Ser Tyr Glu Cys Pro
                165                 170                 175

Met Leu Asp Glu Gly Val Glu Pro Asp Asp Val Asp Cys Trp Cys Asn
            180                 185                 190

Thr Thr Ser Thr Trp Val Val Tyr Gly Thr Cys His His Lys Lys Gly
        195                 200                 205

Glu Ala Arg Arg Ser Arg Arg Ala Val Thr Leu Pro Ser His Ser Thr
    210                 215                 220
```

-continued

```
Arg Lys Leu Gln Thr Arg Ser Gln Thr Trp Leu Glu Ser Arg Glu Tyr
225                 230                 235                 240

Thr Lys His Leu Ile Arg Val Glu Asn Trp Ile Phe Arg Asn Pro Gly
                245                 250                 255

Phe Ala Leu Ala Ala Ala Ala Ile Ala Trp Leu Leu Gly Ser Ser Thr
            260                 265                 270

Ser Gln Lys Val Ile Tyr Leu Val Met Ile Leu Leu Ile Ala Pro Ala
        275                 280                 285

Tyr Ser Ile Arg Cys Ile Gly Val Ser Asn Arg Asp Phe Val Glu Gly
    290                 295                 300

Met Ser Gly Gly Thr Trp Val Asp Val Val Leu Glu His Gly Gly Cys
305                 310                 315                 320

Val Thr Val Met Ala Gln Asp Lys Pro Thr Val Asp Ile Glu Leu Val
                325                 330                 335

Thr Thr Thr Val Ser Asn Met Ala Glu Val Arg Ser Tyr Cys Tyr Glu
            340                 345                 350

Ala Ser Ile Ser Asp Met Ala Ser Asp Ser Arg Cys Pro Thr Gln Gly
        355                 360                 365

Glu Ala Tyr Leu Asp Lys Gln Ser Asp Thr Gln Tyr Val Cys Lys Arg
    370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Ala Cys Ser Lys Lys Met Thr
                405                 410                 415

Gly Lys Ser Ile Gln Pro Glu Asn Leu Glu Tyr Arg Ile Met Leu Ser
            420                 425                 430

Val His Gly Ser Gln His Ser Gly Met Ile Val Asn Asp Thr Gly His
        435                 440                 445

Glu Thr Asp Glu Asn Arg Ala Lys Val Glu Ile Thr Pro Asn Ser Pro
    450                 455                 460

Arg Ala Glu Ala Thr Leu Gly Gly Phe Gly Ser Leu Gly Leu Asp Cys
465                 470                 475                 480

Glu Pro Arg Thr Gly Leu Asp Phe Ser Asp Leu Tyr Tyr Leu Thr Met
                485                 490                 495

Asn Asn Lys His Trp Leu Val His Lys Glu Trp Phe His Asp Ile Pro
            500                 505                 510

Leu Pro Trp His Ala Gly Ala Asp Thr Gly Thr Pro His Trp Asn Asn
        515                 520                 525

Lys Glu Ala Leu Val Glu Phe Lys Asp Ala His Ala Lys Arg Gln Thr
    530                 535                 540

Val Val Val Leu Gly Ser Gln Glu Gly Ala Val His Thr Ala Leu Ala
545                 550                 555                 560

Gly Ala Leu Glu Ala Glu Met Asp Gly Ala Lys Gly Arg Leu Ser Ser
                565                 570                 575

Gly His Leu Lys Cys Arg Leu Lys Met Asp Lys Leu Arg Leu Lys Gly
            580                 585                 590

Val Ser Tyr Ser Leu Cys Thr Ala Ala Phe Thr Phe Thr Lys Ile Pro
        595                 600                 605

Ala Glu Thr Leu His Gly Thr Val Thr Val Glu Val Gln Tyr Ala Gly
    610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
```

-continued

```
                645                 650                 655

Glu Ser Thr Glu Asn Ser Lys Met Met Leu Glu Leu Asp Pro Pro Phe
            660                 665                 670

Gly Asp Ser Tyr Ile Val Ile Gly Val Gly Glu Lys Lys Ile Thr His
        675                 680                 685

His Trp His Arg Ser Gly Ser Thr Ile Gly Lys Ala Phe Glu Ala Thr
    690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
                725                 730                 735

Gln Ile Phe Gly Ala Ala Phe Lys Ser Leu Phe Gly Gly Met Ser Trp
            740                 745                 750

Phe Ser Gln Ile Leu Ile Gly Thr Leu Leu Met Trp Leu Gly Leu Asn
        755                 760                 765

Thr Lys Asn Gly Ser Ile Ser Leu Met Cys Leu Ala Leu Gly Gly Val
    770                 775                 780

Leu Ile Phe Leu Ser Thr Ala Val Ser Ala Asp
785                 790                 795


<210> SEQ ID NO 20
<211> LENGTH: 795
<212> TYPE: PRT
<213> ORGANISM: Zika virus

<400> SEQUENCE: 20

Met Lys Asn Pro Lys Lys Lys Ser Gly Gly Phe Arg Ile Val Asn Met
1               5                   10                  15

Leu Lys Arg Gly Val Ala Arg Val Ser Pro Phe Gly Gly Leu Lys Arg
            20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Ile
65                  70                  75                  80

Ile Lys Lys Phe Lys Lys Asp Leu Ala Ala Met Leu Arg Ile Ile Asn
                85                  90                  95

Ala Arg Lys Glu Lys Lys Arg Arg Gly Ala Asp Thr Ser Val Gly Ile
            100                 105                 110

Val Gly Leu Leu Leu Thr Thr Ala Met Ala Ala Glu Val Thr Arg Arg
        115                 120                 125

Gly Ser Ala Tyr Tyr Met Tyr Leu Asp Arg Asn Asp Ala Gly Glu Ala
    130                 135                 140

Ile Ser Phe Pro Thr Thr Leu Gly Met Asn Lys Cys Tyr Ile Gln Ile
145                 150                 155                 160

Met Asp Leu Gly His Met Cys Asp Ala Thr Met Ser Tyr Glu Cys Pro
                165                 170                 175

Met Leu Asp Glu Gly Val Glu Pro Asp Asp Val Asp Cys Trp Cys Asn
            180                 185                 190

Thr Thr Ser Thr Trp Val Val Tyr Gly Thr Cys His His Lys Lys Gly
        195                 200                 205

Glu Ala Arg Arg Ser Arg Arg Ala Val Thr Leu Pro Ser His Ser Thr
    210                 215                 220
```

-continued

```
Arg Lys Leu Gln Thr Arg Ser Gln Thr Trp Leu Glu Ser Arg Glu Tyr
225                 230                 235                 240

Thr Lys His Leu Ile Arg Val Glu Asn Trp Ile Phe Arg Asn Pro Gly
                245                 250                 255

Phe Ala Leu Ala Ala Ala Ala Ile Ala Trp Leu Leu Gly Ser Ser Thr
            260                 265                 270

Ser Gln Lys Val Ile Tyr Leu Val Met Ile Leu Leu Ile Ala Pro Ala
        275                 280                 285

Tyr Ser Ile Arg Cys Ile Gly Val Ser Asn Arg Asp Phe Val Glu Gly
    290                 295                 300

Met Ser Gly Gly Thr Trp Val Asp Val Val Leu Glu His Gly Gly Cys
305                 310                 315                 320

Val Thr Val Met Ala Gln Asp Lys Pro Thr Val Asp Ile Glu Leu Val
                325                 330                 335

Thr Thr Thr Val Ser Asn Met Ala Glu Val Arg Ser Tyr Cys Tyr Glu
            340                 345                 350

Ala Ser Ile Ser Asp Met Ala Ser Asp Ser Arg Cys Pro Thr Gln Gly
        355                 360                 365

Glu Ala Tyr Leu Asp Lys Gln Ser Asp Thr Gln Tyr Val Cys Lys Arg
    370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Ala Cys Ser Lys Lys Met Thr
                405                 410                 415

Gly Lys Ser Ile Gln Pro Glu Asn Leu Glu Tyr Arg Ile Met Leu Ser
            420                 425                 430

Val His Gly Ser Gln His Ser Gly Met Ile Val Asn Asp Thr Gly His
        435                 440                 445

Glu Thr Asp Glu Asn Arg Ala Lys Val Glu Ile Thr Pro Asn Ser Pro
    450                 455                 460

Arg Ala Glu Ala Thr Leu Gly Gly Phe Gly Ser Leu Gly Leu Asp Cys
465                 470                 475                 480

Glu Pro Arg Thr Gly Leu Asp Phe Ser Asp Leu Tyr Tyr Leu Thr Met
                485                 490                 495

Asn Asn Lys His Trp Leu Val His Lys Glu Trp Phe His Asp Ile Pro
            500                 505                 510

Leu Pro Trp His Ala Gly Ala Asp Thr Gly Thr Pro His Trp Asn Asn
        515                 520                 525

Lys Glu Ala Leu Val Glu Phe Lys Asp Ala His Ala Lys Arg Gln Thr
    530                 535                 540

Val Val Val Leu Gly Ser Gln Glu Gly Ala Val His Thr Ala Leu Ala
545                 550                 555                 560

Gly Ala Leu Glu Ala Glu Met Asp Gly Ala Lys Gly Arg Leu Ser Ser
                565                 570                 575

Gly His Leu Lys Cys Arg Leu Lys Met Asp Lys Leu Arg Leu Lys Gly
            580                 585                 590

Val Ser Tyr Ser Leu Cys Thr Ala Ala Phe Thr Phe Thr Lys Ile Pro
        595                 600                 605

Ala Glu Thr Leu His Gly Thr Val Thr Val Glu Val Gln Tyr Ala Gly
    610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
```

```
                645                 650                 655

Glu Ser Thr Glu Asn Ser Lys Met Met Leu Glu Leu Asp Pro Pro Phe
            660                 665                 670

Gly Asp Ser Tyr Ile Val Ile Gly Val Gly Glu Lys Lys Ile Thr His
        675                 680                 685

His Trp His Arg Ser Gly Ser Thr Ile Gly Lys Ala Phe Glu Ala Thr
    690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
                725                 730                 735

Gln Ile Phe Gly Ala Ala Phe Lys Ser Leu Phe Gly Gly Met Ser Trp
            740                 745                 750

Phe Ser Gln Ile Leu Ile Gly Thr Leu Leu Met Trp Leu Gly Leu Asn
        755                 760                 765

Thr Lys Asn Gly Ser Ile Ser Leu Met Cys Leu Ala Leu Gly Gly Val
    770                 775                 780

Leu Ile Phe Leu Ser Thr Ala Val Ser Ala Asp
785                 790                 795


<210> SEQ ID NO 21
<211> LENGTH: 795
<212> TYPE: PRT
<213> ORGANISM: Zika virus

<400> SEQUENCE: 21

Met Lys Asn Pro Lys Lys Lys Ser Gly Gly Phe Arg Ile Val Asn Met
1               5                   10                  15

Leu Lys Arg Gly Val Ala Arg Val Ser Pro Phe Gly Gly Leu Lys Arg
            20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Ile
65                  70                  75                  80

Ile Lys Lys Phe Lys Lys Asp Leu Ala Ala Met Leu Arg Ile Ile Asn
                85                  90                  95

Ala Arg Lys Glu Lys Lys Arg Arg Gly Ala Asp Thr Ser Val Gly Ile
            100                 105                 110

Val Gly Leu Leu Leu Thr Thr Ala Met Ala Ala Glu Val Thr Arg Arg
        115                 120                 125

Gly Ser Ala Tyr Tyr Met Tyr Leu Asp Arg Asn Asp Ala Gly Glu Ala
    130                 135                 140

Ile Ser Phe Pro Thr Thr Leu Gly Met Asn Lys Cys Tyr Ile Gln Ile
145                 150                 155                 160

Met Asp Leu Gly His Met Cys Asp Ala Thr Met Ser Tyr Glu Cys Pro
                165                 170                 175

Met Leu Asp Glu Gly Val Glu Pro Asp Asp Val Asp Cys Trp Cys Asn
            180                 185                 190

Thr Thr Ser Thr Trp Val Val Tyr Gly Thr Cys His His Lys Lys Gly
        195                 200                 205

Glu Ala Arg Arg Ser Arg Arg Ala Val Thr Leu Pro Ser His Ser Thr
    210                 215                 220
```

-continued

```
Arg Lys Leu Gln Thr Arg Ser Gln Thr Trp Leu Glu Ser Arg Glu Tyr
225                 230                 235                 240

Thr Lys His Leu Ile Arg Val Glu Asn Trp Ile Phe Arg Asn Pro Gly
                245                 250                 255

Phe Ala Leu Ala Ala Ala Ala Ile Ala Trp Leu Leu Gly Ser Ser Thr
            260                 265                 270

Ser Gln Lys Val Ile Tyr Leu Val Met Ile Leu Leu Ile Ala Pro Ala
        275                 280                 285

Tyr Ser Ile Arg Cys Ile Gly Val Ser Asn Arg Asp Phe Val Glu Gly
    290                 295                 300

Met Ser Gly Gly Thr Trp Val Asp Val Val Leu Glu His Gly Gly Cys
305                 310                 315                 320

Val Thr Val Met Ala Gln Asp Lys Pro Thr Val Asp Ile Glu Leu Val
                325                 330                 335

Thr Thr Thr Val Ser Asn Met Ala Glu Val Arg Ser Tyr Cys Tyr Glu
            340                 345                 350

Ala Ser Ile Ser Asp Met Ala Ser Asp Ser Arg Cys Pro Thr Gln Gly
        355                 360                 365

Glu Ala Tyr Leu Asp Lys Gln Ser Asp Thr Gln Tyr Val Cys Lys Arg
    370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Ala Cys Ser Lys Lys Met Thr
                405                 410                 415

Gly Lys Ser Ile Gln Pro Glu Asn Leu Glu Tyr Arg Ile Met Leu Ser
            420                 425                 430

Val His Gly Ser Gln His Ser Gly Met Ile Val Asn Asp Thr Gly His
        435                 440                 445

Glu Thr Asp Glu Asn Arg Ala Lys Val Glu Ile Thr Pro Asn Ser Pro
    450                 455                 460

Arg Ala Glu Ala Thr Leu Gly Gly Phe Gly Ser Leu Gly Leu Asp Cys
465                 470                 475                 480

Glu Pro Arg Thr Gly Leu Asp Phe Ser Asp Leu Tyr Tyr Leu Thr Met
                485                 490                 495

Asn Asn Lys His Trp Leu Val His Lys Glu Trp Phe His Asp Ile Pro
            500                 505                 510

Leu Pro Trp His Ala Gly Ala Asp Thr Gly Thr Pro His Trp Asn Asn
        515                 520                 525

Lys Glu Ala Leu Val Glu Phe Lys Asp Ala His Ala Lys Arg Gln Thr
    530                 535                 540

Val Val Val Leu Gly Ser Gln Glu Gly Ala Val His Thr Ala Leu Ala
545                 550                 555                 560

Gly Ala Leu Glu Ala Glu Met Asp Gly Ala Lys Gly Arg Leu Ser Ser
                565                 570                 575

Gly His Leu Lys Cys Arg Leu Lys Met Asp Lys Leu Arg Leu Lys Gly
            580                 585                 590

Val Ser Tyr Ser Leu Cys Thr Ala Ala Phe Thr Phe Thr Lys Ile Pro
        595                 600                 605

Ala Glu Thr Leu His Gly Thr Val Thr Val Glu Val Gln Tyr Ala Gly
    610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
```

```
                645                 650                 655

Glu Ser Thr Glu Asn Ser Lys Met Met Leu Glu Leu Asp Pro Pro Phe
            660                 665                 670

Gly Asp Ser Tyr Ile Val Ile Gly Val Gly Glu Lys Lys Ile Thr His
        675                 680                 685

His Trp His Arg Ser Gly Ser Thr Ile Gly Lys Ala Phe Glu Ala Thr
    690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
                725                 730                 735

Gln Ile Phe Gly Ala Ala Phe Lys Ser Leu Phe Gly Gly Met Ser Trp
            740                 745                 750

Phe Ser Gln Ile Leu Ile Gly Thr Leu Leu Met Trp Leu Gly Leu Asn
        755                 760                 765

Thr Lys Asn Gly Ser Ile Ser Leu Met Cys Leu Ala Leu Gly Gly Val
    770                 775                 780

Leu Ile Phe Leu Ser Thr Ala Val Ser Ala Asp
785                 790                 795


<210> SEQ ID NO 22
<211> LENGTH: 795
<212> TYPE: PRT
<213> ORGANISM: Zika virus

<400> SEQUENCE: 22

Met Lys Asn Pro Lys Lys Lys Ser Gly Gly Phe Arg Ile Val Asn Met
1               5                   10                  15

Leu Lys Arg Gly Val Ala Arg Val Ser Pro Phe Gly Gly Leu Lys Arg
            20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Ile
65                  70                  75                  80

Ile Lys Lys Phe Lys Lys Asp Leu Ala Ala Met Leu Arg Ile Ile Asn
                85                  90                  95

Ala Arg Lys Glu Lys Lys Arg Arg Gly Ala Asp Thr Ser Val Gly Ile
            100                 105                 110

Val Gly Leu Leu Leu Thr Thr Ala Met Ala Ala Glu Val Thr Arg Arg
        115                 120                 125

Gly Ser Ala Tyr Tyr Met Tyr Leu Asp Arg Asn Asp Ala Gly Glu Ala
    130                 135                 140

Ile Ser Phe Pro Thr Thr Leu Gly Met Asn Lys Cys Tyr Ile Gln Ile
145                 150                 155                 160

Met Asp Leu Gly His Met Cys Asp Ala Thr Met Ser Tyr Glu Cys Pro
                165                 170                 175

Met Leu Asp Glu Gly Val Glu Pro Asp Asp Val Asp Cys Trp Cys Asn
            180                 185                 190

Thr Thr Ser Thr Trp Val Val Tyr Gly Thr Cys His His Lys Lys Gly
        195                 200                 205

Glu Ala Arg Arg Ser Arg Arg Ala Val Thr Leu Pro Ser His Ser Thr
    210                 215                 220
```

-continued

```
Arg Lys Leu Gln Thr Arg Ser Gln Thr Trp Leu Glu Ser Arg Glu Tyr
225                 230                 235                 240

Thr Lys His Leu Ile Arg Val Glu Asn Trp Ile Phe Arg Asn Pro Gly
                245                 250                 255

Phe Ala Leu Ala Ala Ala Ala Ile Ala Trp Leu Leu Gly Ser Ser Thr
            260                 265                 270

Ser Gln Lys Val Ile Tyr Leu Val Met Ile Leu Leu Ile Ala Pro Ala
        275                 280                 285

Tyr Ser Ile Arg Cys Ile Gly Val Ser Asn Arg Asp Phe Val Glu Gly
    290                 295                 300

Met Ser Gly Gly Thr Trp Val Asp Val Val Leu Glu His Gly Gly Cys
305                 310                 315                 320

Val Thr Val Met Ala Gln Asp Lys Pro Thr Val Asp Ile Glu Leu Val
                325                 330                 335

Thr Thr Thr Val Ser Asn Met Ala Glu Val Arg Ser Tyr Cys Tyr Glu
            340                 345                 350

Ala Ser Ile Ser Asp Met Ala Ser Asp Ser Arg Cys Pro Thr Gln Gly
        355                 360                 365

Glu Ala Tyr Leu Asp Lys Gln Ser Asp Thr Gln Tyr Val Cys Lys Arg
    370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Ala Cys Ser Lys Lys Met Thr
                405                 410                 415

Gly Lys Ser Ile Gln Pro Glu Asn Leu Glu Tyr Arg Ile Met Leu Ser
            420                 425                 430

Val His Gly Ser Gln His Ser Gly Met Ile Val Asn Asp Thr Gly His
        435                 440                 445

Glu Thr Asp Glu Asn Arg Ala Lys Val Glu Ile Thr Pro Asn Ser Pro
    450                 455                 460

Arg Ala Glu Ala Thr Leu Gly Gly Phe Gly Ser Leu Gly Leu Asp Cys
465                 470                 475                 480

Glu Pro Arg Thr Gly Leu Asp Phe Ser Asp Leu Tyr Tyr Leu Thr Met
                485                 490                 495

Asn Asn Lys His Trp Leu Val His Lys Glu Trp Phe His Asp Ile Pro
            500                 505                 510

Leu Pro Trp His Ala Gly Ala Asp Thr Gly Thr Pro His Trp Asn Asn
        515                 520                 525

Lys Glu Ala Leu Val Glu Phe Lys Asp Ala His Ala Lys Arg Gln Thr
    530                 535                 540

Val Val Val Leu Gly Ser Gln Glu Gly Ala Val His Thr Ala Leu Ala
545                 550                 555                 560

Gly Ala Leu Glu Ala Glu Met Asp Gly Ala Lys Gly Arg Leu Ser Ser
                565                 570                 575

Gly His Leu Lys Cys Arg Leu Lys Met Asp Lys Leu Arg Leu Lys Gly
            580                 585                 590

Val Ser Tyr Ser Leu Cys Thr Ala Ala Phe Thr Phe Thr Lys Ile Pro
        595                 600                 605

Ala Glu Thr Leu His Gly Thr Val Thr Val Glu Val Gln Tyr Ala Gly
    610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
```

```
                645                 650                 655

Glu Ser Thr Glu Asn Ser Lys Met Met Leu Glu Leu Asp Pro Pro Phe
            660                 665                 670

Gly Asp Ser Tyr Ile Val Ile Gly Val Gly Glu Lys Lys Ile Thr His
        675                 680                 685

His Trp His Arg Ser Gly Ser Thr Ile Gly Lys Ala Phe Glu Ala Thr
    690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
                725                 730                 735

Gln Ile Phe Gly Ala Ala Phe Lys Ser Leu Phe Gly Gly Met Ser Trp
            740                 745                 750

Phe Ser Gln Ile Leu Ile Gly Thr Leu Leu Met Trp Leu Gly Leu Asn
        755                 760                 765

Thr Lys Asn Gly Ser Ile Ser Leu Met Cys Leu Ala Leu Gly Gly Val
    770                 775                 780

Leu Ile Phe Leu Ser Thr Ala Val Ser Ala Asp
785                 790                 795


<210> SEQ ID NO 23
<211> LENGTH: 795
<212> TYPE: PRT
<213> ORGANISM: Zika virus

<400> SEQUENCE: 23

Met Lys Asn Pro Lys Lys Lys Ser Gly Gly Phe Arg Ile Val Asn Met
1               5                   10                  15

Leu Lys Arg Gly Val Ala Arg Val Ser Pro Phe Gly Gly Leu Lys Arg
            20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Ile
65                  70                  75                  80

Ile Lys Lys Phe Lys Lys Asp Leu Ala Ala Met Leu Arg Ile Ile Asn
                85                  90                  95

Ala Arg Lys Glu Lys Lys Arg Arg Gly Ala Asp Thr Ser Val Gly Ile
            100                 105                 110

Val Gly Leu Leu Leu Thr Thr Ala Met Ala Ala Glu Val Thr Arg Arg
        115                 120                 125

Gly Ser Ala Tyr Tyr Met Tyr Leu Asp Arg Asn Asp Ala Gly Glu Ala
    130                 135                 140

Ile Ser Phe Pro Thr Thr Leu Gly Met Asn Lys Cys Tyr Ile Gln Ile
145                 150                 155                 160

Met Asp Leu Gly His Met Cys Asp Ala Thr Met Ser Tyr Glu Cys Pro
                165                 170                 175

Met Leu Asp Glu Gly Val Glu Pro Asp Asp Val Asp Cys Trp Cys Asn
            180                 185                 190

Thr Thr Ser Thr Trp Val Val Tyr Gly Thr Cys His His Lys Lys Gly
        195                 200                 205

Glu Ala Arg Arg Ser Arg Arg Ala Val Thr Leu Pro Ser His Ser Thr
    210                 215                 220
```

-continued

```
Arg Lys Leu Gln Thr Arg Ser Gln Thr Trp Leu Glu Ser Arg Glu Tyr
225                 230                 235                 240

Thr Lys His Leu Ile Arg Val Glu Asn Trp Ile Phe Arg Asn Pro Gly
                245                 250                 255

Phe Ala Leu Ala Ala Ala Ala Ile Ala Trp Leu Leu Gly Ser Ser Thr
            260                 265                 270

Ser Gln Lys Val Ile Tyr Leu Val Met Ile Leu Leu Ile Ala Pro Ala
        275                 280                 285

Tyr Ser Ile Arg Cys Ile Gly Val Ser Asn Arg Asp Phe Val Glu Gly
    290                 295                 300

Met Ser Gly Gly Thr Trp Val Asp Val Val Leu Glu His Gly Gly Cys
305                 310                 315                 320

Val Thr Val Met Ala Gln Asp Lys Pro Thr Val Asp Ile Glu Leu Val
                325                 330                 335

Thr Thr Thr Val Ser Asn Met Ala Glu Val Arg Ser Tyr Cys Tyr Glu
            340                 345                 350

Ala Ser Ile Ser Asp Met Ala Ser Asp Ser Arg Cys Pro Thr Gln Gly
        355                 360                 365

Glu Ala Tyr Leu Asp Lys Gln Ser Asp Thr Gln Tyr Val Cys Lys Arg
    370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Ala Cys Ser Lys Lys Met Thr
                405                 410                 415

Gly Lys Ser Ile Gln Pro Glu Asn Leu Glu Tyr Arg Ile Met Leu Ser
            420                 425                 430

Val His Gly Ser Gln His Ser Gly Met Ile Val Asn Asp Thr Gly His
        435                 440                 445

Glu Thr Asp Glu Asn Arg Ala Lys Val Glu Ile Thr Pro Asn Ser Pro
    450                 455                 460

Arg Ala Glu Ala Thr Leu Gly Gly Phe Gly Ser Leu Gly Leu Asp Cys
465                 470                 475                 480

Glu Pro Arg Thr Gly Leu Asp Phe Ser Asp Leu Tyr Tyr Leu Thr Met
                485                 490                 495

Asn Asn Lys His Trp Leu Val His Lys Glu Trp Phe His Asp Ile Pro
            500                 505                 510

Leu Pro Trp His Ala Gly Ala Asp Thr Gly Thr Pro His Trp Asn Asn
        515                 520                 525

Lys Glu Ala Leu Val Glu Phe Lys Asp Ala His Ala Lys Arg Gln Thr
    530                 535                 540

Val Val Val Leu Gly Ser Gln Glu Gly Ala Val His Thr Ala Leu Ala
545                 550                 555                 560

Gly Ala Leu Glu Ala Glu Met Asp Gly Ala Lys Gly Arg Leu Ser Ser
                565                 570                 575

Gly His Leu Lys Cys Arg Leu Lys Met Asp Lys Leu Arg Leu Lys Gly
            580                 585                 590

Val Ser Tyr Ser Leu Cys Thr Ala Ala Phe Thr Phe Thr Lys Ile Pro
        595                 600                 605

Ala Glu Thr Leu His Gly Thr Val Thr Val Glu Val Gln Tyr Ala Gly
    610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
```

```
                645                 650                 655

Glu Ser Thr Glu Asn Ser Lys Met Met Leu Glu Leu Asp Pro Pro Phe
            660                 665                 670

Gly Asp Ser Tyr Ile Val Ile Gly Val Gly Glu Lys Lys Ile Thr His
        675                 680                 685

His Trp His Arg Ser Gly Ser Thr Ile Gly Lys Ala Phe Glu Ala Thr
    690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
                725                 730                 735

Gln Ile Phe Gly Ala Ala Phe Lys Ser Leu Phe Gly Gly Met Ser Trp
            740                 745                 750

Phe Ser Gln Ile Leu Ile Gly Thr Leu Leu Met Trp Leu Gly Leu Asn
        755                 760                 765

Thr Lys Asn Gly Ser Ile Ser Leu Met Cys Leu Ala Leu Gly Gly Val
    770                 775                 780

Leu Ile Phe Leu Ser Thr Ala Val Ser Ala Asp
785                 790                 795


<210> SEQ ID NO 24
<211> LENGTH: 9999
<212> TYPE: DNA
<213> ORGANISM: Artificial
<220> FEATURE:
<223> OTHER INFORMATION: SAM Vector
<220> FEATURE:
<221> NAME/KEY: misc_feature
<222> LOCATION: (7562)..(7563)
<220> FEATURE:
<221> NAME/KEY: misc_feature
<222> LOCATION: (7562)..(7563)
<223> OTHER INFORMATION: Insert starts after nucleotide 7562

<400> SEQUENCE: 24

ataggcggcg catgagagaa gcccagacca attacctacc caaaatggag aaagttcacg     60

ttgacatcga ggaagacagc ccattcctca gagctttgca gcggagcttc ccgcagtttg    120

aggtagaagc caagcaggtc actgataatg accatgctaa tgccagagcg ttttcgcatc    180

tggcttcaaa actgatcgaa acggaggtgg acccatccga cacgatcctt gacattggaa    240

gtgcgcccgc ccgcagaatg tattctaagc acaagtatca ttgtatctgt ccgatgagat    300

gtgcggaaga tccggacaga ttgtataagt atgcaactaa gctgaagaaa aactgtaagg    360

aaataactga taaggaattg gacaagaaaa tgaaggagct cgccgccgtc atgagcgacc    420

ctgacctgga aactgagact atgtgcctcc acgacgacga gtcgtgtcgc tacgaagggc    480

aagtcgctgt ttaccaggat gtatacgcgg ttgacggacc gacaagtctc tatcaccaag    540

ccaataaggg agttagagtc gcctactgga taggctttga caccacccct tttatgttta    600

agaacttggc tggagcatat ccatcatact ctaccaactg ggccgacgaa accgtgttaa    660

cggctcgtaa cataggccta tgcagctctg acgttatgga gcggtcacgt agagggatgt    720

ccattcttag aaagaagtat ttgaaaccat ccaacaatgt tctattctct gttggctcga    780

ccatctacca cgagaagagg gacttactga ggagctggca cctgccgtct gtatttcact    840

tacgtggcaa gcaaaattac acatgtcggt gtgagactat agttagttgc gacgggtacg    900

tcgttaaaag aatagctatc agtccaggcc tgtatgggaa gccttcaggc tatgctgcta    960

cgatgcaccg cgagggattc ttgtgctgca aagtgacaga cacattgaac ggggagaggg   1020
```

tctcttttcc cgtgtgcacg tatgtgccag ctacattgtg tgaccaaatg actggcatac 1080
tggcaacaga tgtcagtgcg gacgacgcgc aaaaactgct ggttgggctc aaccagcgta 1140
tagtcgtcaa cggtcgcacc cagagaaaca ccaataccat gaaaaattac cttttgcccg 1200
tagtggccca ggcatttgct aggtgggcaa aggaatataa ggaagatcaa gaagatgaaa 1260
ggccactagg actacgagat agacagttag tcatggggtg ttgttgggct tttagaaggc 1320
acaagataac atctatttat aagcgcccgg atacccaaac catcatcaaa gtgaacagcg 1380
atttccactc attcgtgctg cccaggatag gcagtaacac attggagatc gggctgagaa 1440
caagaatcag gaaaatgtta gaggagcaca aggagccgtc acctctcatt accgccgagg 1500
acgtacaaga agctaagtgc gcagccgatg aggctaagga ggtgcgtgaa gccgaggagt 1560
tgcgcgcagc tctaccacct ttggcagctg atgttgagga gcccactctg gaagccgatg 1620
tcgacttgat gttacaagag gctggggccg gctcagtgga gacacctcgt ggcttgataa 1680
aggttaccag ctacgatggc gaggacaaga tcggctctta cgctgtgctt tctccgcagg 1740
ctgtactcaa gagtgaaaaa ttatcttgca tccaccctct cgctgaacaa gtcatagtga 1800
taacacactc tggccgaaaa gggcgttatg ccgtggaacc ataccatggt aaagtagtgg 1860
tgccagaggg acatgcaata cccgtccagg actttcaagc tctgagtgaa agtgccacca 1920
ttgtgtacaa cgaacgtgag ttcgtaaaca ggtacctgca ccatattgcc acacatggag 1980
gagcgctgaa cactgatgaa gaatattaca aaactgtcaa gcccagcgag cacgacggcg 2040
aatacctgta cgacatcgac aggaaacagt gcgtcaagaa agaactagtc actgggctag 2100
ggctcacagg cgagctggtg gatcctccct tccatgaatt cgcctacgag agtctgagaa 2160
cacgaccagc cgctccttac caagtaccaa ccataggggt gtatggcgtg ccaggatcag 2220
gcaagtctgg catcattaaa agcgcagtca ccaaaaaaga tctagtggtg agcgccaaga 2280
aagaaaactg tgcagaaatt ataagggacg tcaagaaaat gaaagggctg gacgtcaatg 2340
ccagaactgt ggactcagtg ctcttgaatg gatgcaaaca ccccgtagag accctgtata 2400
ttgacgaagc ttttgcttgt catgcaggta ctctcagagc gctcatagcc attataagac 2460
ctaaaaaggc agtgctctgc ggggatccca aacagtgcgg ttttttaac atgatgtgcc 2520
tgaaagtgca ttttaaccac gagatttgca cacaagtctt ccacaaaagc atctctcgcc 2580
gttgcactaa atctgtgact tcggtcgtct caaccttgtt ttacgacaaa aaaatgagaa 2640
cgacgaatcc gaaagagact aagattgtga ttgacactac cggcagtacc aaacctaagc 2700
aggacgatct cattctcact tgtttcagag ggtgggtgaa gcagttgcaa atagattaca 2760
aaggcaacga aataatgacg gcagctgcct ctcaagggct gacccgtaaa ggtgtgtatg 2820
ccgttcggta caaggtgaat gaaaatcctc tgtacgcacc cacctcagaa catgtgaacg 2880
tcctactgac ccgcacggag gaccgcatcg tgtggaaaac actagccggc gacccatgga 2940
taaaaacact gactgccaag taccctggga atttcactgc cacgatagag gagtggcaag 3000
cagagcatga tgccatcatg aggcacatct tggagagacc ggaccctacc gacgtcttcc 3060
agaataaggc aaacgtgtgt tgggccaagg ctttagtgcc ggtgctgaag accgctggca 3120
tagacatgac cactgaacaa tggaacactg tggattattt tgaaacggac aaagctcact 3180
cagcagagat agtattgaac caactatgcg tgaggttctt tggactcgat ctggactccg 3240
gtctattttc tgcacccact gttccgttat ccattaggaa taatcactgg gataactccc 3300
cgtcgcctaa catgtacggg ctgaataaag aagtggtccg tcagctctct cgcaggtacc 3360

-continued

```
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggagggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
```

-continued cggtgctatc cgaagtggtg ttggagagga ccgaattgga gatttcgtat gccccgcgcc 5820
tcgaccaaga aaaagaagaa ttactacgca agaaattaca gttaaatccc acacctgcta 5880
acagaagcag ataccagtcc aggaaggtgg agaacatgaa agccataaca gctagacgta 5940
ttctgcaagg cctagggcat tatttgaagg cagaaggaaa agtggagtgc taccgaaccc 6000
tgcatcctgt tcctttgtat tcatctagtg tgaaccgtgc cttttcaagc cccaaggtcg 6060
cagtggaagc ctgtaacgcc atgttgaaag agaactttcc gactgtggct tcttactgta 6120
ttattccaga gtacgatgcc tatttggaca tggttgacgg agcttcatgc tgcttagaca 6180
ctgccagttt ttgccctgca aagctgcgca gctttccaaa gaaacactcc tatttggaac 6240
ccacaatacg atcggcagtg ccttcagcga tccagaacac gctccagaac gtcctggcag 6300
ctgccacaaa aagaaattgc aatgtcacgc aaatgagaga attgcccgta ttggattcgg 6360
cggcctttaa tgtggaatgc ttcaagaaat atgcgtgtaa taatgaatat tgggaaacgt 6420
ttaaagaaaa ccccatcagg cttactgaag aaaacgtggt aaattacatt accaaattaa 6480
aaggaccaaa agctgctgct ctttttgcga agacacataa tttgaatatg ttgcaggaca 6540
taccaatgga caggtttgta atggacttaa agagagacgt gaaagtgact ccaggaacaa 6600
aacatactga agaacggccc aaggtacagg tgatccaggc tgccgatccg ctagcaacag 6660
cgtatctgtg cggaatccac cgagagctgg ttaggagatt aaatgcggtc ctgcttccga 6720
acattcatac actgtttgat atgtcggctg aagactttga cgctattata gccgagcact 6780
tccagcctgg ggattgtgtt ctggaaactg acatcgcgtc gtttgataaa agtgaggacg 6840
acgccatggc tctgaccgcg ttaatgattc tggaagactt aggtgtggac gcagagctgt 6900
tgacgctgat tgaggcggct ttcggcgaaa tttcatcaat acatttgccc actaaaacta 6960
aatttaaatt cggagccatg atgaaatctg gaatgttcct cacactgttt gtgaacacag 7020
tcattaacat tgtaatcgca agcagagtgt tgagagaacg gctaaccgga tcaccatgtg 7080
cagcattcat tggagatgac aatatcgtga aaggagtcaa atcggacaaa ttaatggcag 7140
acaggtgcgc cacctggttg aatatggaag tcaagattat agatgctgtg gtgggcgaga 7200
aagcgcctta tttctgtgga gggtttattt tgtgtgactc cgtgaccggc acagcgtgcc 7260
gtgtggcaga ccccctaaaa aggctgttta agcttggcaa acctctggca gcagacgatg 7320
aacatgatga tgacaggaga agggcattgc atgaagagtc aacacgctgg aaccgagtgg 7380
gtattctttc agagctgtgc aaggcagtag aatcaaggta tgaaaccgta ggaacttcca 7440
tcatagttat ggccatgact actctagcta gcagtgttaa atcattcagc tacctgagag 7500
gggcccctat aactctctac ggctaacctg aatggactac gacatagtct agtccgccaa 7560
gtgataaggc gcgcccaccc agcggccgca tacagcagca attggcaagc tgcttacata 7620
gaactcgcgg cgattggcat gccgccttaa aatttttatt ttattttttct tttcttttcc 7680
gaatcggatt ttgtttttaa tatttcaaaa aaaaaaaaaa aaaaaaaaaa aaaaaaaaaa 7740
aaaaaagaag agcgtttaaa cacgtgatat ctggcctcat gggccttcct ttcactgccc 7800
gctttccagt cgggaaacct gtcgtgccag ctgcattaac atggtcatag ctgtttcctt 7860
gcgtattggg cgctctccgc ttcctcgctc actgactcgc tgcgctcggt cgttcgggta 7920
aagcctgggg tgcctaatga gcaaaaggcc agcaaaaggc caggaaccgt aaaaaggccg 7980
cgttgctggc gtttttccat aggctccgcc cccctgacga gcatcacaaa aatcgacgct 8040
caagtcagag gtggcgaaac ccgacaggac tataaagata ccaggcgttt ccccctggaa 8100
gctccctcgt gcgctctcct gttccgaccc tgccgcttac cggatacctg tccgcctttc 8160
tcccttcggg aagcgtggcg ctttctcata gctcacgctg taggtatctc agttcggtgt 8220
aggtcgttcg ctccaagctg ggctgtgtgc acgaaccccc cgttcagccc gaccgctgcg 8280
ccttatccgg taactatcgt cttgagtcca acccggtaag acacgactta tcgccactgg 8340
cagcagccac tggtaacagg attagcagag cgaggtatgt aggcggtgct acagagttct 8400
tgaagtggtg gcctaactac ggctacacta gaagaacagt atttggtatc tgcgctctgc 8460
tgaagccagt taccttcgga aaaagagttg gtagctcttg atccggcaaa caaaccaccg 8520
ctggtagcgg tggttttttt gtttgcaagc agcagattac gcgcagaaaa aaaggatctc 8580
aagaagatcc tttgatcttt tctacggggt ctgacgctca gtggaacgaa aactcacgtt 8640
aagggatttt ggtcatgaat acacggtgcc tgactgcgtt agcaatttaa ctgtgataaa 8700
ctaccgcatt aaagcttatc gatgataagc tgtcaaacat gagaattctt agaaaaactc 8760
atcgagcatc aaatgaaact gcaatttatt catatcagga ttatcaatac catatttttg 8820
aaaaagccgt ttctgtaatg aaggagaaaa ctcaccgagg cagttccata ggatggcaag 8880
atcctggtat cggtctgcga ttccgactcg tccaacatca atacaaccta ttaatttccc 8940
ctcgtcaaaa ataaggttat caagtgagaa atcaccatga gtgacgactg aatccggtga 9000
gaatggcaaa agcttatgca tttctttcca gacttgttca acaggccagc cattacgctc 9060
gtcatcaaaa tcactcgcat caaccaaacc gttattcatt cgtgattgcg cctgagcgag 9120
acgaaatacg cgatcgctgt taaaaggaca attacaaaca ggaatcgaat gcaaccggcg 9180
caggaacact gccagcgcat caacaatatt ttcacctgaa tcaggatatt cttctaatac 9240
ctggaatgct gttttcccgg ggatcgcagt ggtgagtaac catgcatcat caggagtacg 9300
gataaaatgc ttgatggtcg gaagaggcat aaattccgtc agccagttta gtctgaccat 9360
ctcatctgta acatcattgg caacgctacc tttgccatgt ttcagaaaca actctggcgc 9420
atcgggcttc ccatacaatc gatagattgt cgcacctgat tgcccgacat tatcgcgagc 9480
ccatttatac ccatataaat cagcatccat gttggaattt aatcgcggcc tcgagcaaga 9540
cgtttcccgt tgaatatggc tcataacacc ccttgtatta ctgtttatgt aagcagacag 9600
ttttattgtt catgagcgga tacatatttg aatgtattta gaaaaataaa caaatagggg 9660
ttccgcgcac atttccccga aaagtgccac ctaaattgta agcgttaata ttttgttaaa 9720
attcgcgtta aatttttgtt aaatcagctc attttttaac caataggccg aaatcggcaa 9780
aatcccttat aaatcaaaag aatagaccga gatagggttg agtggccgct acagggcgct 9840
cccattcgcc attcaggctg cgcaactgtt gggaagggcg tttcggtgcg ggcctcttcg 9900
ctattacgcc agctggcgaa agggggatgt gctgcaaggc gattaagttg ggtaacgcca 9960
gggttttccc agtcacacgc gtaatacgac tcactatag 9999

<210> SEQ ID NO 25
<211> LENGTH: 2079
<212> TYPE: DNA
<213> ORGANISM: Ziika virus

<400> SEQUENCE: 25
atgcgaggcg cagatactag tgtcggaatt gttggcctcc tgctgaccac agctatggca 60
gcggaggtca ctagacgtgg gagtgcatac tatatgtact tggacagaaa cgatgctggg 120
gaggccatat cttttccaac cacattgggg atgaataagt gttatataca gatcatggat 180
cttggacaca tgtgtgatgc caccatgagc tatgaatgcc ctatgctgga tgagggggtg 240

-continued

```
gaaccagatg acgtcgattg ttggtgcaac acgacgtcaa cttgggttgt gtacggaacc    300
tgccatcaca aaaaaggtga agcacggaga tctaggagag ctgtgacgct cccctcccat    360
tccactagga agctgcaaac gcggtcgcaa acctggttgg aatcaagaga atacacaaag    420
cacttgatta gagtcgaaaa ttggatattc aggaaccctg gcttcgcgtt agcagcagct    480
gccatcgctt ggcttttggg aagctcaacg agccaaaaag tcatatactt ggtcatgata    540
ctgctgattg ccccggcata cagcatcagg tgcataggag tcagcaatag ggactttgtg    600
gaaggtatgt caggtgggac ttgggttgat gttgtcttgg aacatggagg ttgtgtcacc    660
gtaatggcac aggacaaacc gactgtcgac atagagctgg ttacaacaac agtcagcaac    720
atggcggagg taagatccta ctgctatgag gcatcaatat cagacatggc ttcggacagc    780
cgctgcccaa cacaaggtga agcctacctt gacaagcaat cagacactca atatgtctgc    840
aaaagaacgt tagtggacag aggctgggga aatggatgtg gactttttgg caaagggagc    900
ctggtgacat gcgctaagtt tgcatgctcc aagaaaatga ccgggaaaag catccagcca    960
gagaatctgg agtaccggat aatgctgtca gttcatggct cccagcacag tgggatgatc   1020
gttaatgaca caggacatga aactgatgag aatagagcga aggttgagat aacgcccaat   1080
tcaccaagag ccgaagccac cctgggggg tttggaagcc taggacttga ttgtgaaccg   1140
aggacaggcc ttgacttttc agatttgtat tacttgacta tgaataacaa gcactggttg   1200
gtccacaagg agtggttcca cgacattcca ttaccttggc acgctggggc agacaccgga   1260
actccacact ggaacaacaa agaagcactg gtagagttca aggacgcaca tgccaaaagg   1320
caaactgtcg tggttctagg gagtcaagaa ggagcagttc acacggccct tgctggagct   1380
ctggaggctg agatggatgg tgcaaaggga aggctgtcct ctggccactt gaaatgtcgc   1440
ctgaaaatgg ataaacttag attgaagggc gtgtcatact ccttgtgtac cgcagcgttc   1500
acattcacca agatcccggc tgaaacactg cacgggacag tcacagtgga ggtacagtac   1560
gcagggacag atggaccttg caaggttcca gctcagatgg cggtggacat gcaaactctg   1620
accccagttg ggaggttgat aaccgctaac cccgtaatca ctgaaagcac tgagaactct   1680
aagatgatgc tggaacttga tccaccattt ggggactctt acattgtcat aggagtcggg   1740
gagaagaaga tcacccacca ctggcacagg agtggcagca ccattggaaa agcatttgaa   1800
gccactgtga gaggtgccaa gagaatggca gtcttgggag acacagcctg ggactttgga   1860
tcagttggag gcgctctcaa ctcattgggc aagggcatcc atcaaatttt tggagcagct   1920
ttcaaatcat tgtttggagg aatgtcctgg ttctcacaaa tcctcattgg aacgttgctg   1980
atgtggttgg gtctgaacac aaagaatgga tctatttccc ttatgtgctt ggccttaggg   2040
ggagtgttga tcttcttatc cacagccgtc tctgctgat                         2079
```

<210> SEQ ID NO 26
<211> LENGTH: 693
<212> TYPE: PRT
<213> ORGANISM: Zika virus

<400> SEQUENCE: 26

```
Met Arg Gly Ala Asp Thr Ser Val Gly Ile Val Gly Leu Leu Leu Thr
1               5                   10                  15

Thr Ala Met Ala Ala Glu Val Thr Arg Arg Gly Ser Ala Tyr Tyr Met
            20                  25                  30

Tyr Leu Asp Arg Asn Asp Ala Gly Glu Ala Ile Ser Phe Pro Thr Thr
        35                  40                  45
```

```
Leu Gly Met Asn Lys Cys Tyr Ile Gln Ile Met Asp Leu Gly His Met
    50                  55                  60

Cys Asp Ala Thr Met Ser Tyr Glu Cys Pro Met Leu Asp Glu Gly Val
65                  70                  75                  80

Glu Pro Asp Asp Val Asp Cys Trp Cys Asn Thr Thr Ser Thr Trp Val
                85                  90                  95

Val Tyr Gly Thr Cys His His Lys Lys Gly Glu Ala Arg Arg Ser Arg
            100                 105                 110

Arg Ala Val Thr Leu Pro Ser His Ser Thr Arg Lys Leu Gln Thr Arg
        115                 120                 125

Ser Gln Thr Trp Leu Glu Ser Arg Glu Tyr Thr Lys His Leu Ile Arg
    130                 135                 140

Val Glu Asn Trp Ile Phe Arg Asn Pro Gly Phe Ala Leu Ala Ala Ala
145                 150                 155                 160

Ala Ile Ala Trp Leu Leu Gly Ser Ser Thr Ser Gln Lys Val Ile Tyr
                165                 170                 175

Leu Val Met Ile Leu Leu Ile Ala Pro Ala Tyr Ser Ile Arg Cys Ile
            180                 185                 190

Gly Val Ser Asn Arg Asp Phe Val Glu Gly Met Ser Gly Gly Thr Trp
        195                 200                 205

Val Asp Val Val Leu Glu His Gly Gly Cys Val Thr Val Met Ala Gln
    210                 215                 220

Asp Lys Pro Thr Val Asp Ile Glu Leu Val Thr Thr Thr Val Ser Asn
225                 230                 235                 240

Met Ala Glu Val Arg Ser Tyr Cys Tyr Glu Ala Ser Ile Ser Asp Met
                245                 250                 255

Ala Ser Asp Ser Arg Cys Pro Thr Gln Gly Glu Ala Tyr Leu Asp Lys
            260                 265                 270

Gln Ser Asp Thr Gln Tyr Val Cys Lys Arg Thr Leu Val Asp Arg Gly
        275                 280                 285

Trp Gly Asn Gly Cys Gly Leu Phe Gly Lys Gly Ser Leu Val Thr Cys
    290                 295                 300

Ala Lys Phe Ala Cys Ser Lys Lys Met Thr Gly Lys Ser Ile Gln Pro
305                 310                 315                 320

Glu Asn Leu Glu Tyr Arg Ile Met Leu Ser Val His Gly Ser Gln His
                325                 330                 335

Ser Gly Met Ile Val Asn Asp Thr Gly His Glu Thr Asp Glu Asn Arg
            340                 345                 350

Ala Lys Val Glu Ile Thr Pro Asn Ser Pro Arg Ala Glu Ala Thr Leu
        355                 360                 365

Gly Gly Phe Gly Ser Leu Gly Leu Asp Cys Glu Pro Arg Thr Gly Leu
    370                 375                 380

Asp Phe Ser Asp Leu Tyr Tyr Leu Thr Met Asn Asn Lys His Trp Leu
385                 390                 395                 400

Val His Lys Glu Trp Phe His Asp Ile Pro Leu Pro Trp His Ala Gly
                405                 410                 415

Ala Asp Thr Gly Thr Pro His Trp Asn Asn Lys Glu Ala Leu Val Glu
            420                 425                 430

Phe Lys Asp Ala His Ala Lys Arg Gln Thr Val Val Val Leu Gly Ser
        435                 440                 445

Gln Glu Gly Ala Val His Thr Ala Leu Ala Gly Ala Leu Glu Ala Glu
    450                 455                 460
```

```
Met Asp Gly Ala Lys Gly Arg Leu Ser Ser Gly His Leu Lys Cys Arg
465                 470                 475                 480

Leu Lys Met Asp Lys Leu Arg Leu Lys Gly Val Ser Tyr Ser Leu Cys
                485                 490                 495

Thr Ala Ala Phe Thr Phe Thr Lys Ile Pro Ala Glu Thr Leu His Gly
            500                 505                 510

Thr Val Thr Val Glu Val Gln Tyr Ala Gly Thr Asp Gly Pro Cys Lys
        515                 520                 525

Val Pro Ala Gln Met Ala Val Asp Met Gln Thr Leu Thr Pro Val Gly
    530                 535                 540

Arg Leu Ile Thr Ala Asn Pro Val Ile Thr Glu Ser Thr Glu Asn Ser
545                 550                 555                 560

Lys Met Met Leu Glu Leu Asp Pro Pro Phe Gly Asp Ser Tyr Ile Val
                565                 570                 575

Ile Gly Val Gly Glu Lys Lys Ile Thr His His Trp His Arg Ser Gly
            580                 585                 590

Ser Thr Ile Gly Lys Ala Phe Glu Ala Thr Val Arg Gly Ala Lys Arg
        595                 600                 605

Met Ala Val Leu Gly Asp Thr Ala Trp Asp Phe Gly Ser Val Gly Gly
    610                 615                 620

Ala Leu Asn Ser Leu Gly Lys Gly Ile His Gln Ile Phe Gly Ala Ala
625                 630                 635                 640

Phe Lys Ser Leu Phe Gly Gly Met Ser Trp Phe Ser Gln Ile Leu Ile
                645                 650                 655

Gly Thr Leu Leu Met Trp Leu Gly Leu Asn Thr Lys Asn Gly Ser Ile
            660                 665                 670

Ser Leu Met Cys Leu Ala Leu Gly Gly Val Leu Ile Phe Leu Ser Thr
        675                 680                 685

Ala Val Ser Ala Asp
    690


<210> SEQ ID NO 27
<211> LENGTH: 92
<212> TYPE: PRT
<213> ORGANISM: Zika virus

<400> SEQUENCE: 27

Ala Glu Val Thr Arg Arg Gly Ser Ala Tyr Tyr Met Tyr Leu Asp Arg
1               5                   10                  15

Asn Asp Ala Gly Glu Ala Ile Ser Phe Pro Thr Thr Leu Gly Met Asn
            20                  25                  30

Lys Cys Tyr Ile Gln Ile Met Asp Leu Gly His Met Cys Asp Ala Thr
        35                  40                  45

Met Ser Tyr Glu Cys Pro Met Leu Asp Glu Gly Val Glu Pro Asp Asp
    50                  55                  60

Val Asp Cys Trp Cys Asn Thr Thr Ser Thr Trp Val Val Tyr Gly Thr
65                  70                  75                  80

Cys His His Lys Lys Gly Glu Ala Arg Arg Ser Arg
                85                  90


<210> SEQ ID NO 28
<211> LENGTH: 60
<212> TYPE: PRT
<213> ORGANISM: Zika virus

<400> SEQUENCE: 28
```

-continued

```
Arg Ala Val Thr Leu Pro Ser His Ser Thr Arg Lys Leu Gln Thr Arg
1               5                   10                  15

Ser Gln Thr Trp Leu Glu Ser Arg Glu Tyr Thr Lys His Leu Ile Arg
            20                  25                  30

Val Glu Asn Trp Ile Phe Arg Asn Pro Gly Phe Ala Leu Ala Ala Ala
        35                  40                  45

Ala Ile Ala Trp Leu Leu Gly Ser Ser Thr Ser Gln
    50                  55                  60


<210> SEQ ID NO 29
<211> LENGTH: 521
<212> TYPE: PRT
<213> ORGANISM: Zika virus

<400> SEQUENCE: 29

Lys Val Ile Tyr Leu Val Met Ile Leu Leu Ile Ala Pro Ala Tyr Ser
1               5                   10                  15

Ile Arg Cys Ile Gly Val Ser Asn Arg Asp Phe Val Glu Gly Met Ser
            20                  25                  30

Gly Gly Thr Trp Val Asp Val Val Leu Glu His Gly Gly Cys Val Thr
        35                  40                  45

Val Met Ala Gln Asp Lys Pro Thr Val Asp Ile Glu Leu Val Thr Thr
    50                  55                  60

Thr Val Ser Asn Met Ala Glu Val Arg Ser Tyr Cys Tyr Glu Ala Ser
65                  70                  75                  80

Ile Ser Asp Met Ala Ser Asp Ser Arg Cys Pro Thr Gln Gly Glu Ala
                85                  90                  95

Tyr Leu Asp Lys Gln Ser Asp Thr Gln Tyr Val Cys Lys Arg Thr Leu
            100                 105                 110

Val Asp Arg Gly Trp Gly Asn Gly Cys Gly Leu Phe Gly Lys Gly Ser
        115                 120                 125

Leu Val Thr Cys Ala Lys Phe Ala Cys Ser Lys Lys Met Thr Gly Lys
    130                 135                 140

Ser Ile Gln Pro Glu Asn Leu Glu Tyr Arg Ile Met Leu Ser Val His
145                 150                 155                 160

Gly Ser Gln His Ser Gly Met Ile Val Asn Asp Thr Gly His Glu Thr
                165                 170                 175

Asp Glu Asn Arg Ala Lys Val Glu Ile Thr Pro Asn Ser Pro Arg Ala
            180                 185                 190

Glu Ala Thr Leu Gly Gly Phe Gly Ser Leu Gly Leu Asp Cys Glu Pro
        195                 200                 205

Arg Thr Gly Leu Asp Phe Ser Asp Leu Tyr Tyr Leu Thr Met Asn Asn
    210                 215                 220

Lys His Trp Leu Val His Lys Glu Trp Phe His Asp Ile Pro Leu Pro
225                 230                 235                 240

Trp His Ala Gly Ala Asp Thr Gly Thr Pro His Trp Asn Asn Lys Glu
                245                 250                 255

Ala Leu Val Glu Phe Lys Asp Ala His Ala Lys Arg Gln Thr Val Val
            260                 265                 270

Val Leu Gly Ser Gln Glu Gly Ala Val His Thr Ala Leu Ala Gly Ala
        275                 280                 285

Leu Glu Ala Glu Met Asp Gly Ala Lys Gly Arg Leu Ser Ser Gly His
    290                 295                 300

Leu Lys Cys Arg Leu Lys Met Asp Lys Leu Arg Leu Lys Gly Val Ser
305                 310                 315                 320
```

Tyr Ser Leu Cys Thr Ala Ala Phe Thr Phe Thr Lys Ile Pro Ala Glu
325 330 335

Thr Leu His Gly Thr Val Thr Val Glu Val Gln Tyr Ala Gly Thr Asp
340 345 350

Gly Pro Cys Lys Val Pro Ala Gln Met Ala Val Asp Met Gln Thr Leu
355 360 365

Thr Pro Val Gly Arg Leu Ile Thr Ala Asn Pro Val Ile Thr Glu Ser
370 375 380

Thr Glu Asn Ser Lys Met Met Leu Glu Leu Asp Pro Pro Phe Gly Asp
385 390 395 400

Ser Tyr Ile Val Ile Gly Val Gly Glu Lys Lys Ile Thr His His Trp
405 410 415

His Arg Ser Gly Ser Thr Ile Gly Lys Ala Phe Glu Ala Thr Val Arg
420 425 430

Gly Ala Lys Arg Met Ala Val Leu Gly Asp Thr Ala Trp Asp Phe Gly
435 440 445

Ser Val Gly Gly Ala Leu Asn Ser Leu Gly Lys Gly Ile His Gln Ile
450 455 460

Phe Gly Ala Ala Phe Lys Ser Leu Phe Gly Gly Met Ser Trp Phe Ser
465 470 475 480

Gln Ile Leu Ile Gly Thr Leu Leu Met Trp Leu Gly Leu Asn Thr Lys
485 490 495

Asn Gly Ser Ile Ser Leu Met Cys Leu Ala Leu Gly Gly Val Leu Ile
500 505 510

Phe Leu Ser Thr Ala Val Ser Ala Asp
515 520

<210> SEQ ID NO 30
<211> LENGTH: 2079
<212> TYPE: DNA
<213> ORGANISM: Zika virus

<400> SEQUENCE: 30
atgagaggag ctgacaccag cgtgggcatt gtgggcctcc tgctgacaac cgccatggcc 60
gctgaggtca ccagaagagg cagcgcctac tacatgtacc tggacagaaa cgacgctggc 120
gaggctatta gcttccccac cacactcggc atgaacaagt gttacatcca gatcatggac 180
ctgggccaca tgtgcgatgc caccatgagc tacgaatgtc ctatgctgga cgaaggcgtg 240
gagcccgacg acgtggactg ttggtgcaac acaaccagca cctgggtggt gtacggcacc 300
tgccatcata agaagggaga agccaggaga agcaggaggg ctgtcacact cccctcccac 360
tccacaagaa agctgcaaac caggagccag acctggctgg aaagcaggga gtacaccaag 420
cacctgatca gggtcgagaa ctggatcttc aggaaccctg gattcgccct cgccgctgct 480
gctattgcct ggctcctggg ctcctccacc agccaaaagg tgatctacct ggtgatgatc 540
ctcctgatcg cccccgccta cagcatcagg tgcatcggcg tgtccaatag ggactttgtc 600
gaaggaatgt ccggcggcac atgggtggac gtcgtgctgg agcatggcgg ctgtgtgaca 660
gtcatggccc aggacaaacc caccgtggat atcgagctgg tgacaaccac agtgtccaac 720
atggccgagg tgaggagcta ctgctacgag gctagcatca gcgacatggc ttccgacagc 780
agatgcccca cacagggcga ggcctacctc gacaaacagt ccgacaccca gtacgtgtgc 840
aaaaggaccc tggtcgacag aggatggggc aacggctgcg gcctgttcgg aaaaggaagc 900
ctggtcacct gtgctaagtt cgcctgctcc aagaagatga ccggcaagag catccagccc 960
gagaacctcg agtacaggat catgctctcc gtccatggca gccagcacag cggaatgatc 1020
gtgaacgaca ccggccacga gaccgatgag aacagggcca aggtggaaat cacccccaac 1080
agccctaggg ctgaagctac cctcggcgga tttggatccc tgggcctgga ttgtgaaccc 1140
aggaccggac tcgacttcag cgatctgtac tacctgacca tgaacaacaa gcactggctg 1200
gtgcataagg agtggttcca tgatatcccc ctgccctggc atgctggagc cgatacaggc 1260
acccctcact ggaacaacaa ggaagccctg gtggagttca aagatgccca cgccaagaga 1320
cagacagtcg tcgtcctggg cagccaagag ggcgctgtgc atacagccct ggctggagcc 1380
ctggaggccg aaatggacgg cgccaaggga aggctgtcca gcggacatct gaagtgcagg 1440
ctgaagatgg acaagctgag gctcaagggc gtcagctact ccctgtgcac cgccgccttt 1500
acctttacaa aaatccccgc cgagaccctc cacggcacag tcacagtcga ggtgcagtac 1560
gctggaaccg acggaccttg taaggtgccc gcccaaatgg ccgtggacat gcagacactg 1620
acccctgtgg gcagactcat cacagccaac cctgtgatca cagagtccac cgagaacagc 1680
aagatgatgc tcgagctgga tcctcctttc ggcgacagct acatcgtgat cggagtgggc 1740
gagaagaaaa tcacccacca ctggcacagg tccggcagca ccattggcaa agcctttgaa 1800
gccaccgtca gaggagctaa aaggatggct gtgctgggcg acaccgcttg ggacttcggc 1860
tccgtgggag gagccctcaa ctccctgggc aagggcattc accagatttt cggcgccgct 1920
ttcaagagcc tctttggcgg catgtcctgg tttagccaga ttctcatcgg cacactgctg 1980
atgtggctgg gcctgaatac caagaacggc agcatcagcc tgatgtgtct ggccctggga 2040
ggcgtgctga tctttctgtc caccgctgtc agcgccgac 2079

<210> SEQ ID NO 31
<211> LENGTH: 693
<212> TYPE: PRT
<213> ORGANISM: Zika virus

<400> SEQUENCE: 31

Met Arg Gly Ala Asp Thr Ser Val Gly Ile Val Gly Leu Leu Leu Thr
1 5 10 15

Thr Ala Met Ala Ala Glu Val Thr Arg Arg Gly Ser Ala Tyr Tyr Met
20 25 30

Tyr Leu Asp Arg Asn Asp Ala Gly Glu Ala Ile Ser Phe Pro Thr Thr
35 40 45

Leu Gly Met Asn Lys Cys Tyr Ile Gln Ile Met Asp Leu Gly His Met
50 55 60

Cys Asp Ala Thr Met Ser Tyr Glu Cys Pro Met Leu Asp Glu Gly Val
65 70 75 80

Glu Pro Asp Asp Val Asp Cys Trp Cys Asn Thr Thr Ser Thr Trp Val
85 90 95

Val Tyr Gly Thr Cys His His Lys Lys Gly Glu Ala Arg Arg Ser Arg
100 105 110

Arg Ala Val Thr Leu Pro Ser His Ser Thr Arg Lys Leu Gln Thr Arg
115 120 125

Ser Gln Thr Trp Leu Glu Ser Arg Glu Tyr Thr Lys His Leu Ile Arg
130 135 140

Val Glu Asn Trp Ile Phe Arg Asn Pro Gly Phe Ala Leu Ala Ala Ala
145 150 155 160

Ala Ile Ala Trp Leu Leu Gly Ser Ser Thr Ser Gln Lys Val Ile Tyr
165 170 175

```
Leu Val Met Ile Leu Leu Ile Ala Pro Ala Tyr Ser Ile Arg Cys Ile
            180                 185                 190

Gly Val Ser Asn Arg Asp Phe Val Glu Gly Met Ser Gly Gly Thr Trp
        195                 200                 205

Val Asp Val Val Leu Glu His Gly Gly Cys Val Thr Val Met Ala Gln
    210                 215                 220

Asp Lys Pro Thr Val Asp Ile Glu Leu Val Thr Thr Thr Val Ser Asn
225                 230                 235                 240

Met Ala Glu Val Arg Ser Tyr Cys Tyr Glu Ala Ser Ile Ser Asp Met
                245                 250                 255

Ala Ser Asp Ser Arg Cys Pro Thr Gln Gly Glu Ala Tyr Leu Asp Lys
            260                 265                 270

Gln Ser Asp Thr Gln Tyr Val Cys Lys Arg Thr Leu Val Asp Arg Gly
        275                 280                 285

Trp Gly Asn Gly Cys Gly Leu Phe Gly Lys Gly Ser Leu Val Thr Cys
    290                 295                 300

Ala Lys Phe Ala Cys Ser Lys Lys Met Thr Gly Lys Ser Ile Gln Pro
305                 310                 315                 320

Glu Asn Leu Glu Tyr Arg Ile Met Leu Ser Val His Gly Ser Gln His
                325                 330                 335

Ser Gly Met Ile Val Asn Asp Thr Gly His Glu Thr Asp Glu Asn Arg
            340                 345                 350

Ala Lys Val Glu Ile Thr Pro Asn Ser Pro Arg Ala Glu Ala Thr Leu
        355                 360                 365

Gly Gly Phe Gly Ser Leu Gly Leu Asp Cys Glu Pro Arg Thr Gly Leu
    370                 375                 380

Asp Phe Ser Asp Leu Tyr Tyr Leu Thr Met Asn Asn Lys His Trp Leu
385                 390                 395                 400

Val His Lys Glu Trp Phe His Asp Ile Pro Leu Pro Trp His Ala Gly
                405                 410                 415

Ala Asp Thr Gly Thr Pro His Trp Asn Asn Lys Glu Ala Leu Val Glu
            420                 425                 430

Phe Lys Asp Ala His Ala Lys Arg Gln Thr Val Val Val Leu Gly Ser
        435                 440                 445

Gln Glu Gly Ala Val His Thr Ala Leu Ala Gly Ala Leu Glu Ala Glu
    450                 455                 460

Met Asp Gly Ala Lys Gly Arg Leu Ser Ser Gly His Leu Lys Cys Arg
465                 470                 475                 480

Leu Lys Met Asp Lys Leu Arg Leu Lys Gly Val Ser Tyr Ser Leu Cys
                485                 490                 495

Thr Ala Ala Phe Thr Phe Thr Lys Ile Pro Ala Glu Thr Leu His Gly
            500                 505                 510

Thr Val Thr Val Glu Val Gln Tyr Ala Gly Thr Asp Gly Pro Cys Lys
        515                 520                 525

Val Pro Ala Gln Met Ala Val Asp Met Gln Thr Leu Thr Pro Val Gly
    530                 535                 540

Arg Leu Ile Thr Ala Asn Pro Val Ile Thr Glu Ser Thr Glu Asn Ser
545                 550                 555                 560

Lys Met Met Leu Glu Leu Asp Pro Pro Phe Gly Asp Ser Tyr Ile Val
                565                 570                 575

Ile Gly Val Gly Glu Lys Lys Ile Thr His His Trp His Arg Ser Gly
            580                 585                 590
```

```
Ser Thr Ile Gly Lys Ala Phe Glu Ala Thr Val Arg Gly Ala Lys Arg
        595                 600                 605

Met Ala Val Leu Gly Asp Thr Ala Trp Asp Phe Gly Ser Val Gly Gly
    610                 615                 620

Ala Leu Asn Ser Leu Gly Lys Gly Ile His Gln Ile Phe Gly Ala Ala
625                 630                 635                 640

Phe Lys Ser Leu Phe Gly Gly Met Ser Trp Phe Ser Gln Ile Leu Ile
                645                 650                 655

Gly Thr Leu Leu Met Trp Leu Gly Leu Asn Thr Lys Asn Gly Ser Ile
            660                 665                 670

Ser Leu Met Cys Leu Ala Leu Gly Gly Val Leu Ile Phe Leu Ser Thr
        675                 680                 685

Ala Val Ser Ala Asp
    690


<210> SEQ ID NO 32
<211> LENGTH: 92
<212> TYPE: PRT
<213> ORGANISM: Zika virus

<400> SEQUENCE: 32

Ala Glu Val Thr Arg Arg Gly Ser Ala Tyr Tyr Met Tyr Leu Asp Arg
1               5                   10                  15

Asn Asp Ala Gly Glu Ala Ile Ser Phe Pro Thr Thr Leu Gly Met Asn
            20                  25                  30

Lys Cys Tyr Ile Gln Ile Met Asp Leu Gly His Met Cys Asp Ala Thr
        35                  40                  45

Met Ser Tyr Glu Cys Pro Met Leu Asp Glu Gly Val Glu Pro Asp Asp
    50                  55                  60

Val Asp Cys Trp Cys Asn Thr Thr Ser Thr Trp Val Val Tyr Gly Thr
65                  70                  75                  80

Cys His His Lys Lys Gly Glu Ala Arg Arg Ser Arg
                85                  90


<210> SEQ ID NO 33
<211> LENGTH: 60
<212> TYPE: PRT
<213> ORGANISM: Zika virus

<400> SEQUENCE: 33

Arg Ala Val Thr Leu Pro Ser His Ser Thr Arg Lys Leu Gln Thr Arg
1               5                   10                  15

Ser Gln Thr Trp Leu Glu Ser Arg Glu Tyr Thr Lys His Leu Ile Arg
            20                  25                  30

Val Glu Asn Trp Ile Phe Arg Asn Pro Gly Phe Ala Leu Ala Ala Ala
        35                  40                  45

Ala Ile Ala Trp Leu Leu Gly Ser Ser Thr Ser Gln
    50                  55                  60


<210> SEQ ID NO 34
<211> LENGTH: 521
<212> TYPE: PRT
<213> ORGANISM: Zika virus

<400> SEQUENCE: 34

Lys Val Ile Tyr Leu Val Met Ile Leu Leu Ile Ala Pro Ala Tyr Ser
1               5                   10                  15

Ile Arg Cys Ile Gly Val Ser Asn Arg Asp Phe Val Glu Gly Met Ser
```

-continued

```
            20                  25                  30

Gly Gly Thr Trp Val Asp Val Val Leu Glu His Gly Gly Cys Val Thr
        35                  40                  45

Val Met Ala Gln Asp Lys Pro Thr Val Asp Ile Glu Leu Val Thr Thr
    50                  55                  60

Thr Val Ser Asn Met Ala Glu Val Arg Ser Tyr Cys Tyr Glu Ala Ser
65                  70                  75                  80

Ile Ser Asp Met Ala Ser Asp Ser Arg Cys Pro Thr Gln Gly Glu Ala
                85                  90                  95

Tyr Leu Asp Lys Gln Ser Asp Thr Gln Tyr Val Cys Lys Arg Thr Leu
            100                 105                 110

Val Asp Arg Gly Trp Gly Asn Gly Cys Gly Leu Phe Gly Lys Gly Ser
        115                 120                 125

Leu Val Thr Cys Ala Lys Phe Ala Cys Ser Lys Lys Met Thr Gly Lys
    130                 135                 140

Ser Ile Gln Pro Glu Asn Leu Glu Tyr Arg Ile Met Leu Ser Val His
145                 150                 155                 160

Gly Ser Gln His Ser Gly Met Ile Val Asn Asp Thr Gly His Glu Thr
                165                 170                 175

Asp Glu Asn Arg Ala Lys Val Glu Ile Thr Pro Asn Ser Pro Arg Ala
            180                 185                 190

Glu Ala Thr Leu Gly Gly Phe Gly Ser Leu Gly Leu Asp Cys Glu Pro
        195                 200                 205

Arg Thr Gly Leu Asp Phe Ser Asp Leu Tyr Tyr Leu Thr Met Asn Asn
    210                 215                 220

Lys His Trp Leu Val His Lys Glu Trp Phe His Asp Ile Pro Leu Pro
225                 230                 235                 240

Trp His Ala Gly Ala Asp Thr Gly Thr Pro His Trp Asn Asn Lys Glu
                245                 250                 255

Ala Leu Val Glu Phe Lys Asp Ala His Ala Lys Arg Gln Thr Val Val
            260                 265                 270

Val Leu Gly Ser Gln Glu Gly Ala Val His Thr Ala Leu Ala Gly Ala
        275                 280                 285

Leu Glu Ala Glu Met Asp Gly Ala Lys Gly Arg Leu Ser Ser Gly His
    290                 295                 300

Leu Lys Cys Arg Leu Lys Met Asp Lys Leu Arg Leu Lys Gly Val Ser
305                 310                 315                 320

Tyr Ser Leu Cys Thr Ala Ala Phe Thr Phe Thr Lys Ile Pro Ala Glu
                325                 330                 335

Thr Leu His Gly Thr Val Thr Val Glu Val Gln Tyr Ala Gly Thr Asp
            340                 345                 350

Gly Pro Cys Lys Val Pro Ala Gln Met Ala Val Asp Met Gln Thr Leu
        355                 360                 365

Thr Pro Val Gly Arg Leu Ile Thr Ala Asn Pro Val Ile Thr Glu Ser
    370                 375                 380

Thr Glu Asn Ser Lys Met Met Leu Glu Leu Asp Pro Pro Phe Gly Asp
385                 390                 395                 400

Ser Tyr Ile Val Ile Gly Val Gly Glu Lys Lys Ile Thr His His Trp
                405                 410                 415

His Arg Ser Gly Ser Thr Ile Gly Lys Ala Phe Glu Ala Thr Val Arg
            420                 425                 430

Gly Ala Lys Arg Met Ala Val Leu Gly Asp Thr Ala Trp Asp Phe Gly
        435                 440                 445
```

-continued

```
Ser Val Gly Gly Ala Leu Asn Ser Leu Gly Lys Gly Ile His Gln Ile
    450                 455                 460

Phe Gly Ala Ala Phe Lys Ser Leu Phe Gly Gly Met Ser Trp Phe Ser
465                 470                 475                 480

Gln Ile Leu Ile Gly Thr Leu Leu Met Trp Leu Gly Leu Asn Thr Lys
                485                 490                 495

Asn Gly Ser Ile Ser Leu Met Cys Leu Ala Leu Gly Gly Val Leu Ile
            500                 505                 510

Phe Leu Ser Thr Ala Val Ser Ala Asp
        515                 520
```

<210> SEQ ID NO 35
<211> LENGTH: 2079
<212> TYPE: DNA
<213> ORGANISM: Zika virus

<400> SEQUENCE: 35

```
atgagaggag ctgacaccag cgtgggcatt gtgggcctcc tgctgcccca ggcccaggcc      60

gctgaggtca ccagaagagg cagcgcctac tacatgtacc tggacagaaa cgacgctggc     120

gaggctatta gcttccccac cacactcggc atgaacaagt gttacatcca gatcatggac     180

ctgggccaca tgtgcgatgc caccatgagc tacgaatgtc ctatgctgga cgaaggcgtg     240

gagcccgacg acgtggactg ttggtgcaac acaaccagca cctgggtggt gtacggcacc     300

tgccatcata agaagggaga agccaggaga agcaggaggg ctgtcacact cccctcccac     360

tccacaagaa agctgcaaac caggagccag acctggctgg aaagcaggga gtacaccaag     420

cacctgatca gggtcgagaa ctggatcttc aggaaccctg gattcgccct cgccgctgct     480

gctattgcct ggctcctggg ctcctccacc agccaaaagg tgatctacct ggtgatgatc     540

ctcctgatcg cccccgccta cagcatcagg tgcatcggcg tgtccaatag ggactttgtc     600

gaaggaatgt ccggcggcac atgggtggac gtcgtgctgg agcatggcgg ctgtgtgaca     660

gtcatggccc aggacaaacc caccgtggat atcgagctgg tgacaaccac agtgtccaac     720

atggccgagg tgaggagcta ctgctacgag gctagcatca gcgacatggc ttccgacagc     780

agatgcccca cacagggcga ggcctacctc gacaaacagt ccgacaccca gtacgtgtgc     840

aaaaggaccc tggtcgacag aggatggggc aacggctgcg gcctgttcgg aaaaggaagc     900

ctggtcacct gtgctaagtt cgcctgctcc aagaagatga ccggcaagag catccagccc     960

gagaacctcg agtacaggat catgctctcc gtccatggca gccagcacag cggaatgatc    1020

gtgaacgaca ccggccacga gaccgatgag aacagggcca aggtggaaat cacccccaac    1080

agccctaggg ctgaagctac cctcggcgga tttggatccc tgggcctgga ttgtgaaccc    1140

aggaccggac tcgacttcag cgatctgtac tacctgacca tgaacaacaa gcactggctg    1200

gtgcataagg agtggttcca tgatatcccc ctgccctggc atgctggagc cgatacaggc    1260

acccctcact ggaacaacaa ggaagccctg gtggagttca aagatgccca cgccaagaga    1320

cagacagtcg tcgtcctggg cagccaagag ggcgctgtgc atacagccct ggctggagcc    1380

ctggaggccg aaatggacgg cgccaaggga aggctgtcca gcggacatct gaagtgcagg    1440

ctgaagatgg acaagctgag gctcaagggc gtcagctact ccctgtgcac cgccgccttt    1500

acctttacaa aaatccccgc cgagaccctc cacggcacag tcacagtcga ggtgcagtac    1560

gctggaaccg acggaccttg taaggtgccc gcccaaatgg ccgtggacat gcagacactg    1620

acccctgtgg gcagactcat cacagccaac cctgtgatca cagagtccac cgagaacagc    1680
```

```
aagatgatgc tcgagctgga tcctcctttc ggcgacagct acatcgtgat cggagtgggc   1740

gagaagaaaa tcacccacca ctggcacagg tccggcagca ccattggcaa agcctttgaa   1800

gccaccgtca gaggagctaa aaggatggct gtgctgggcg acaccgcttg ggacttcggc   1860

tccgtgggag gagccctcaa ctccctgggc aagggcattc accagatttt cggcgccgct   1920

ttcaagagcc tctttggcgg catgtcctgg tttagccaga ttctcatcgg cacactgctg   1980

atgtggctgg gcctgaatac caagaacggc agcatcagcc tgatgtgtct ggccctggga   2040

ggcgtgctga tctttctgtc caccgctgtc agcgccgac                          2079


<210> SEQ ID NO 36
<211> LENGTH: 693
<212> TYPE: PRT
<213> ORGANISM: Zika virus

<400> SEQUENCE: 36

Met Arg Gly Ala Asp Thr Ser Val Gly Ile Val Gly Leu Leu Leu Pro
1               5                   10                  15

Gln Ala Gln Ala Ala Glu Val Thr Arg Arg Gly Ser Ala Tyr Tyr Met
            20                  25                  30

Tyr Leu Asp Arg Asn Asp Ala Gly Glu Ala Ile Ser Phe Pro Thr Thr
        35                  40                  45

Leu Gly Met Asn Lys Cys Tyr Ile Gln Ile Met Asp Leu Gly His Met
    50                  55                  60

Cys Asp Ala Thr Met Ser Tyr Glu Cys Pro Met Leu Asp Glu Gly Val
65                  70                  75                  80

Glu Pro Asp Asp Val Asp Cys Trp Cys Asn Thr Thr Ser Thr Trp Val
                85                  90                  95

Val Tyr Gly Thr Cys His His Lys Lys Gly Glu Ala Arg Arg Ser Arg
            100                 105                 110

Arg Ala Val Thr Leu Pro Ser His Ser Thr Arg Lys Leu Gln Thr Arg
        115                 120                 125

Ser Gln Thr Trp Leu Glu Ser Arg Glu Tyr Thr Lys His Leu Ile Arg
    130                 135                 140

Val Glu Asn Trp Ile Phe Arg Asn Pro Gly Phe Ala Leu Ala Ala Ala
145                 150                 155                 160

Ala Ile Ala Trp Leu Leu Gly Ser Ser Thr Ser Gln Lys Val Ile Tyr
                165                 170                 175

Leu Val Met Ile Leu Leu Ile Ala Pro Ala Tyr Ser Ile Arg Cys Ile
            180                 185                 190

Gly Val Ser Asn Arg Asp Phe Val Glu Gly Met Ser Gly Gly Thr Trp
        195                 200                 205

Val Asp Val Val Leu Glu His Gly Gly Cys Val Thr Val Met Ala Gln
    210                 215                 220

Asp Lys Pro Thr Val Asp Ile Glu Leu Val Thr Thr Thr Val Ser Asn
225                 230                 235                 240

Met Ala Glu Val Arg Ser Tyr Cys Tyr Glu Ala Ser Ile Ser Asp Met
                245                 250                 255

Ala Ser Asp Ser Arg Cys Pro Thr Gln Gly Glu Ala Tyr Leu Asp Lys
            260                 265                 270

Gln Ser Asp Thr Gln Tyr Val Cys Lys Arg Thr Leu Val Asp Arg Gly
        275                 280                 285

Trp Gly Asn Gly Cys Gly Leu Phe Gly Lys Gly Ser Leu Val Thr Cys
    290                 295                 300
```

-continued

Ala Lys Phe Ala Cys Ser Lys Lys Met Thr Gly Lys Ser Ile Gln Pro
305 310 315 320

Glu Asn Leu Glu Tyr Arg Ile Met Leu Ser Val His Gly Ser Gln His
325 330 335

Ser Gly Met Ile Val Asn Asp Thr Gly His Glu Thr Asp Glu Asn Arg
340 345 350

Ala Lys Val Glu Ile Thr Pro Asn Ser Pro Arg Ala Glu Ala Thr Leu
355 360 365

Gly Gly Phe Gly Ser Leu Gly Leu Asp Cys Glu Pro Arg Thr Gly Leu
370 375 380

Asp Phe Ser Asp Leu Tyr Tyr Leu Thr Met Asn Asn Lys His Trp Leu
385 390 395 400

Val His Lys Glu Trp Phe His Asp Ile Pro Leu Pro Trp His Ala Gly
405 410 415

Ala Asp Thr Gly Thr Pro His Trp Asn Asn Lys Glu Ala Leu Val Glu
420 425 430

Phe Lys Asp Ala His Ala Lys Arg Gln Thr Val Val Val Leu Gly Ser
435 440 445

Gln Glu Gly Ala Val His Thr Ala Leu Ala Gly Ala Leu Glu Ala Glu
450 455 460

Met Asp Gly Ala Lys Gly Arg Leu Ser Ser Gly His Leu Lys Cys Arg
465 470 475 480

Leu Lys Met Asp Lys Leu Arg Leu Lys Gly Val Ser Tyr Ser Leu Cys
485 490 495

Thr Ala Ala Phe Thr Phe Thr Lys Ile Pro Ala Glu Thr Leu His Gly
500 505 510

Thr Val Thr Val Glu Val Gln Tyr Ala Gly Thr Asp Gly Pro Cys Lys
515 520 525

Val Pro Ala Gln Met Ala Val Asp Met Gln Thr Leu Thr Pro Val Gly
530 535 540

Arg Leu Ile Thr Ala Asn Pro Val Ile Thr Glu Ser Thr Glu Asn Ser
545 550 555 560

Lys Met Met Leu Glu Leu Asp Pro Pro Phe Gly Asp Ser Tyr Ile Val
565 570 575

Ile Gly Val Gly Glu Lys Lys Ile Thr His His Trp His Arg Ser Gly
580 585 590

Ser Thr Ile Gly Lys Ala Phe Glu Ala Thr Val Arg Gly Ala Lys Arg
595 600 605

Met Ala Val Leu Gly Asp Thr Ala Trp Asp Phe Gly Ser Val Gly Gly
610 615 620

Ala Leu Asn Ser Leu Gly Lys Gly Ile His Gln Ile Phe Gly Ala Ala
625 630 635 640

Phe Lys Ser Leu Phe Gly Gly Met Ser Trp Phe Ser Gln Ile Leu Ile
645 650 655

Gly Thr Leu Leu Met Trp Leu Gly Leu Asn Thr Lys Asn Gly Ser Ile
660 665 670

Ser Leu Met Cys Leu Ala Leu Gly Gly Val Leu Ile Phe Leu Ser Thr
675 680 685

Ala Val Ser Ala Asp
690

<210> SEQ ID NO 37
<211> LENGTH: 92

-continued

<212> TYPE: PRT
<213> ORGANISM: Zika virus

<400> SEQUENCE: 37

```
Ala Glu Val Thr Arg Arg Gly Ser Ala Tyr Tyr Met Tyr Leu Asp Arg
1               5                   10                  15

Asn Asp Ala Gly Glu Ala Ile Ser Phe Pro Thr Thr Leu Gly Met Asn
            20                  25                  30

Lys Cys Tyr Ile Gln Ile Met Asp Leu Gly His Met Cys Asp Ala Thr
        35                  40                  45

Met Ser Tyr Glu Cys Pro Met Leu Asp Glu Gly Val Glu Pro Asp Asp
    50                  55                  60

Val Asp Cys Trp Cys Asn Thr Thr Ser Thr Trp Val Val Tyr Gly Thr
65                  70                  75                  80

Cys His His Lys Lys Gly Glu Ala Arg Arg Ser Arg
                85                  90
```

<210> SEQ ID NO 38
<211> LENGTH: 60
<212> TYPE: PRT
<213> ORGANISM: Zika virus

<400> SEQUENCE: 38

```
Arg Ala Val Thr Leu Pro Ser His Ser Thr Arg Lys Leu Gln Thr Arg
1               5                   10                  15

Ser Gln Thr Trp Leu Glu Ser Arg Glu Tyr Thr Lys His Leu Ile Arg
            20                  25                  30

Val Glu Asn Trp Ile Phe Arg Asn Pro Gly Phe Ala Leu Ala Ala Ala
        35                  40                  45

Ala Ile Ala Trp Leu Leu Gly Ser Ser Thr Ser Gln
    50                  55                  60
```

<210> SEQ ID NO 39
<211> LENGTH: 521
<212> TYPE: PRT
<213> ORGANISM: Zika virus

<400> SEQUENCE: 39

```
Lys Val Ile Tyr Leu Val Met Ile Leu Leu Ile Ala Pro Ala Tyr Ser
1               5                   10                  15

Ile Arg Cys Ile Gly Val Ser Asn Arg Asp Phe Val Glu Gly Met Ser
            20                  25                  30

Gly Gly Thr Trp Val Asp Val Val Leu Glu His Gly Gly Cys Val Thr
        35                  40                  45

Val Met Ala Gln Asp Lys Pro Thr Val Asp Ile Glu Leu Val Thr Thr
    50                  55                  60

Thr Val Ser Asn Met Ala Glu Val Arg Ser Tyr Cys Tyr Glu Ala Ser
65                  70                  75                  80

Ile Ser Asp Met Ala Ser Asp Ser Arg Cys Pro Thr Gln Gly Glu Ala
                85                  90                  95

Tyr Leu Asp Lys Gln Ser Asp Thr Gln Tyr Val Cys Lys Arg Thr Leu
            100                 105                 110

Val Asp Arg Gly Trp Gly Asn Gly Cys Gly Leu Phe Gly Lys Gly Ser
        115                 120                 125

Leu Val Thr Cys Ala Lys Phe Ala Cys Ser Lys Lys Met Thr Gly Lys
    130                 135                 140

Ser Ile Gln Pro Glu Asn Leu Glu Tyr Arg Ile Met Leu Ser Val His
```

```
145                 150                 155                 160

Gly Ser Gln His Ser Gly Met Ile Val Asn Asp Thr Gly His Glu Thr
                165                 170                 175

Asp Glu Asn Arg Ala Lys Val Glu Ile Thr Pro Asn Ser Pro Arg Ala
            180                 185                 190

Glu Ala Thr Leu Gly Gly Phe Gly Ser Leu Gly Leu Asp Cys Glu Pro
        195                 200                 205

Arg Thr Gly Leu Asp Phe Ser Asp Leu Tyr Tyr Leu Thr Met Asn Asn
    210                 215                 220

Lys His Trp Leu Val His Lys Glu Trp Phe His Asp Ile Pro Leu Pro
225                 230                 235                 240

Trp His Ala Gly Ala Asp Thr Gly Thr Pro His Trp Asn Asn Lys Glu
                245                 250                 255

Ala Leu Val Glu Phe Lys Asp Ala His Ala Lys Arg Gln Thr Val Val
            260                 265                 270

Val Leu Gly Ser Gln Glu Gly Ala Val His Thr Ala Leu Ala Gly Ala
        275                 280                 285

Leu Glu Ala Glu Met Asp Gly Ala Lys Gly Arg Leu Ser Ser Gly His
    290                 295                 300

Leu Lys Cys Arg Leu Lys Met Asp Lys Leu Arg Leu Lys Gly Val Ser
305                 310                 315                 320

Tyr Ser Leu Cys Thr Ala Ala Phe Thr Phe Thr Lys Ile Pro Ala Glu
                325                 330                 335

Thr Leu His Gly Thr Val Thr Val Glu Val Gln Tyr Ala Gly Thr Asp
            340                 345                 350

Gly Pro Cys Lys Val Pro Ala Gln Met Ala Val Asp Met Gln Thr Leu
        355                 360                 365

Thr Pro Val Gly Arg Leu Ile Thr Ala Asn Pro Val Ile Thr Glu Ser
    370                 375                 380

Thr Glu Asn Ser Lys Met Met Leu Glu Leu Asp Pro Pro Phe Gly Asp
385                 390                 395                 400

Ser Tyr Ile Val Ile Gly Val Gly Glu Lys Lys Ile Thr His His Trp
                405                 410                 415

His Arg Ser Gly Ser Thr Ile Gly Lys Ala Phe Glu Ala Thr Val Arg
            420                 425                 430

Gly Ala Lys Arg Met Ala Val Leu Gly Asp Thr Ala Trp Asp Phe Gly
        435                 440                 445

Ser Val Gly Gly Ala Leu Asn Ser Leu Gly Lys Gly Ile His Gln Ile
    450                 455                 460

Phe Gly Ala Ala Phe Lys Ser Leu Phe Gly Gly Met Ser Trp Phe Ser
465                 470                 475                 480

Gln Ile Leu Ile Gly Thr Leu Leu Met Trp Leu Gly Leu Asn Thr Lys
                485                 490                 495

Asn Gly Ser Ile Ser Leu Met Cys Leu Ala Leu Gly Gly Val Leu Ile
            500                 505                 510

Phe Leu Ser Thr Ala Val Ser Ala Asp
        515                 520
```

<210> SEQ ID NO 40
<211> LENGTH: 2076
<212> TYPE: DNA
<213> ORGANISM: Zika virus

<400> SEQUENCE: 40

-continued

```
atggagttcg gcctgagctg ggtgttcctg gtggccatcc tggagggcgt gcattgcgct     60
gaggtcacca gaagaggcag cgcctactac atgtacctgg acagaaacga cgctggcgag    120
gctattagct tccccaccac actcggcatg aacaagtgtt acatccagat catggacctg    180
ggccacatgt gcgatgccac catgagctac gaatgtccta tgctggacga aggcgtggag    240
cccgacgacg tggactgttg gtgcaacaca accagcacct gggtggtgta cggcacctgc    300
catcataaga agggagaagc caggagaagc aggagggctg tcacactccc ctcccactcc    360
acaagaaagc tgcaaaccag gagccagacc tggctggaaa gcagggagta caccaagcac    420
ctgatcaggg tcgagaactg gatcttcagg aaccctggat tcgccctcgc cgctgctgct    480
attgcctggc tcctgggctc ctccaccagc caaaaggtga tctacctggt gatgatcctc    540
ctgatcgccc ccgcctacag catcaggtgc atcggcgtgt ccaataggga ctttgtcgaa    600
ggaatgtccg gcggcacatg ggtggacgtc gtgctggagc atggcggctg tgtgacagtc    660
atggcccagg acaaacccac cgtggatatc gagctggtga caaccacagt gtccaacatg    720
gccgaggtga ggagctactg ctacgaggct agcatcagcg acatggcttc cgacagcaga    780
tgccccacac agggcgaggc ctacctcgac aaacagtccg acacccagta cgtgtgcaaa    840
aggaccctgg tcgacagagg atggggcaac ggctgcggcc tgttcggaaa aggaagcctg    900
gtcacctgtg ctaagttcgc ctgctccaag aagatgaccg gcaagagcat ccagcccgag    960
aacctcgagt acaggatcat gctctccgtc catggcagcc agcacagcgg aatgatcgtg   1020
aacgacaccg gccacgagac cgatgagaac agggccaagg tggaaatcac ccccaacagc   1080
cctagggctg aagctaccct cggcggattt ggatccctgg gcctggattg tgaacccagg   1140
accggactcg acttcagcga tctgtactac ctgaccatga acaacaagca ctggctggtg   1200
cataaggagt ggttccatga tatccccctg ccctggcatg ctggagccga tacaggcacc   1260
cctcactgga acaacaagga agccctggtg gagttcaaag atgcccacgc caagagacag   1320
acagtcgtcg tcctgggcag ccaagagggc gctgtgcata cagccctggc tggagccctg   1380
gaggccgaaa tggacggcgc caagggaagg ctgtccagcg gacatctgaa gtgcaggctg   1440
aagatggaca agctgaggct caagggcgtc agctactccc tgtgcaccgc cgcctttacc   1500
tttacaaaaa tccccgccga gaccctccac ggcacagtca cagtcgaggt gcagtacgct   1560
ggaaccgacg gaccttgtaa ggtgcccgcc caaatggccg tggacatgca gacactgacc   1620
cctgtgggca gactcatcac agccaaccct gtgatcacag agtccaccga gaacagcaag   1680
atgatgctcg agctggatcc tcctttcggc gacagctaca tcgtgatcgg agtgggcgag   1740
aagaaaatca cccaccactg gcacaggtcc ggcagcacca ttggcaaagc ctttgaagcc   1800
accgtcagag gagctaaaag gatggctgtg ctgggcgaca ccgcttggga cttcggctcc   1860
gtgggaggag ccctcaactc cctgggcaag ggcattcacc agattttcgg cgccgctttc   1920
aagagcctct ttggcggcat gtcctggttt agccagattc tcatcggcac actgctgatg   1980
tggctgggcc tgaataccaa gaacggcagc atcagcctga tgtgtctggc cctgggaggc   2040
gtgctgatct ttctgtccac cgctgtcagc gccgac                             2076
```

<210> SEQ ID NO 41
<211> LENGTH: 692
<212> TYPE: PRT
<213> ORGANISM: Zika virus

<400> SEQUENCE: 41

Met Glu Phe Gly Leu Ser Trp Val Phe Leu Val Ala Ile Leu Glu Gly

-continued

```
1               5                   10                  15

Val His Cys Ala Glu Val Thr Arg Arg Gly Ser Ala Tyr Tyr Met Tyr
            20                  25                  30

Leu Asp Arg Asn Asp Ala Gly Glu Ala Ile Ser Phe Pro Thr Thr Leu
        35                  40                  45

Gly Met Asn Lys Cys Tyr Ile Gln Ile Met Asp Leu Gly His Met Cys
    50                  55                  60

Asp Ala Thr Met Ser Tyr Glu Cys Pro Met Leu Asp Glu Gly Val Glu
65                  70                  75                  80

Pro Asp Asp Val Asp Cys Trp Cys Asn Thr Thr Ser Thr Trp Val Val
                85                  90                  95

Tyr Gly Thr Cys His His Lys Lys Gly Glu Ala Arg Arg Ser Arg Arg
            100                 105                 110

Ala Val Thr Leu Pro Ser His Ser Thr Arg Lys Leu Gln Thr Arg Ser
        115                 120                 125

Gln Thr Trp Leu Glu Ser Arg Glu Tyr Thr Lys His Leu Ile Arg Val
    130                 135                 140

Glu Asn Trp Ile Phe Arg Asn Pro Gly Phe Ala Leu Ala Ala Ala Ala
145                 150                 155                 160

Ile Ala Trp Leu Leu Gly Ser Ser Thr Ser Gln Lys Val Ile Tyr Leu
                165                 170                 175

Val Met Ile Leu Leu Ile Ala Pro Ala Tyr Ser Ile Arg Cys Ile Gly
            180                 185                 190

Val Ser Asn Arg Asp Phe Val Glu Gly Met Ser Gly Gly Thr Trp Val
        195                 200                 205

Asp Val Val Leu Glu His Gly Gly Cys Val Thr Val Met Ala Gln Asp
    210                 215                 220

Lys Pro Thr Val Asp Ile Glu Leu Val Thr Thr Thr Val Ser Asn Met
225                 230                 235                 240

Ala Glu Val Arg Ser Tyr Cys Tyr Glu Ala Ser Ile Ser Asp Met Ala
                245                 250                 255

Ser Asp Ser Arg Cys Pro Thr Gln Gly Glu Ala Tyr Leu Asp Lys Gln
            260                 265                 270

Ser Asp Thr Gln Tyr Val Cys Lys Arg Thr Leu Val Asp Arg Gly Trp
        275                 280                 285

Gly Asn Gly Cys Gly Leu Phe Gly Lys Gly Ser Leu Val Thr Cys Ala
    290                 295                 300

Lys Phe Ala Cys Ser Lys Lys Met Thr Gly Lys Ser Ile Gln Pro Glu
305                 310                 315                 320

Asn Leu Glu Tyr Arg Ile Met Leu Ser Val His Gly Ser Gln His Ser
                325                 330                 335

Gly Met Ile Val Asn Asp Thr Gly His Glu Thr Asp Glu Asn Arg Ala
            340                 345                 350

Lys Val Glu Ile Thr Pro Asn Ser Pro Arg Ala Glu Ala Thr Leu Gly
        355                 360                 365

Gly Phe Gly Ser Leu Gly Leu Asp Cys Glu Pro Arg Thr Gly Leu Asp
    370                 375                 380

Phe Ser Asp Leu Tyr Tyr Leu Thr Met Asn Asn Lys His Trp Leu Val
385                 390                 395                 400

His Lys Glu Trp Phe His Asp Ile Pro Leu Pro Trp His Ala Gly Ala
                405                 410                 415

Asp Thr Gly Thr Pro His Trp Asn Asn Lys Glu Ala Leu Val Glu Phe
            420                 425                 430
```

```
Lys Asp Ala His Ala Lys Arg Gln Thr Val Val Val Leu Gly Ser Gln
        435                 440                 445

Glu Gly Ala Val His Thr Ala Leu Ala Gly Ala Leu Glu Ala Glu Met
    450                 455                 460

Asp Gly Ala Lys Gly Arg Leu Ser Ser Gly His Leu Lys Cys Arg Leu
465                 470                 475                 480

Lys Met Asp Lys Leu Arg Leu Lys Gly Val Ser Tyr Ser Leu Cys Thr
                485                 490                 495

Ala Ala Phe Thr Phe Thr Lys Ile Pro Ala Glu Thr Leu His Gly Thr
            500                 505                 510

Val Thr Val Glu Val Gln Tyr Ala Gly Thr Asp Gly Pro Cys Lys Val
        515                 520                 525

Pro Ala Gln Met Ala Val Asp Met Gln Thr Leu Thr Pro Val Gly Arg
    530                 535                 540

Leu Ile Thr Ala Asn Pro Val Ile Thr Glu Ser Thr Glu Asn Ser Lys
545                 550                 555                 560

Met Met Leu Glu Leu Asp Pro Pro Phe Gly Asp Ser Tyr Ile Val Ile
                565                 570                 575

Gly Val Gly Glu Lys Lys Ile Thr His His Trp His Arg Ser Gly Ser
            580                 585                 590

Thr Ile Gly Lys Ala Phe Glu Ala Thr Val Arg Gly Ala Lys Arg Met
        595                 600                 605

Ala Val Leu Gly Asp Thr Ala Trp Asp Phe Gly Ser Val Gly Gly Ala
    610                 615                 620

Leu Asn Ser Leu Gly Lys Gly Ile His Gln Ile Phe Gly Ala Ala Phe
625                 630                 635                 640

Lys Ser Leu Phe Gly Gly Met Ser Trp Phe Ser Gln Ile Leu Ile Gly
                645                 650                 655

Thr Leu Leu Met Trp Leu Gly Leu Asn Thr Lys Asn Gly Ser Ile Ser
            660                 665                 670

Leu Met Cys Leu Ala Leu Gly Gly Val Leu Ile Phe Leu Ser Thr Ala
        675                 680                 685

Val Ser Ala Asp
    690


<210> SEQ ID NO 42
<211> LENGTH: 92
<212> TYPE: PRT
<213> ORGANISM: Zika virus

<400> SEQUENCE: 42

Ala Glu Val Thr Arg Arg Gly Ser Ala Tyr Tyr Met Tyr Leu Asp Arg
1               5                   10                  15

Asn Asp Ala Gly Glu Ala Ile Ser Phe Pro Thr Thr Leu Gly Met Asn
            20                  25                  30

Lys Cys Tyr Ile Gln Ile Met Asp Leu Gly His Met Cys Asp Ala Thr
        35                  40                  45

Met Ser Tyr Glu Cys Pro Met Leu Asp Glu Gly Val Glu Pro Asp Asp
    50                  55                  60

Val Asp Cys Trp Cys Asn Thr Thr Ser Thr Trp Val Val Tyr Gly Thr
65                  70                  75                  80

Cys His His Lys Lys Gly Glu Ala Arg Arg Ser Arg
                85                  90
```

<210> SEQ ID NO 43
<211> LENGTH: 60
<212> TYPE: PRT
<213> ORGANISM: Zika virus

<400> SEQUENCE: 43

```
Arg Ala Val Thr Leu Pro Ser His Ser Thr Arg Lys Leu Gln Thr Arg
1               5                   10                  15

Ser Gln Thr Trp Leu Glu Ser Arg Glu Tyr Thr Lys His Leu Ile Arg
            20                  25                  30

Val Glu Asn Trp Ile Phe Arg Asn Pro Gly Phe Ala Leu Ala Ala Ala
        35                  40                  45

Ala Ile Ala Trp Leu Leu Gly Ser Ser Thr Ser Gln
    50                  55                  60
```

<210> SEQ ID NO 44
<211> LENGTH: 521
<212> TYPE: PRT
<213> ORGANISM: Zika virus

<400> SEQUENCE: 44

```
Lys Val Ile Tyr Leu Val Met Ile Leu Leu Ile Ala Pro Ala Tyr Ser
1               5                   10                  15

Ile Arg Cys Ile Gly Val Ser Asn Arg Asp Phe Val Glu Gly Met Ser
            20                  25                  30

Gly Gly Thr Trp Val Asp Val Val Leu Glu His Gly Gly Cys Val Thr
        35                  40                  45

Val Met Ala Gln Asp Lys Pro Thr Val Asp Ile Glu Leu Val Thr Thr
    50                  55                  60

Thr Val Ser Asn Met Ala Glu Val Arg Ser Tyr Cys Tyr Glu Ala Ser
65                  70                  75                  80

Ile Ser Asp Met Ala Ser Asp Ser Arg Cys Pro Thr Gln Gly Glu Ala
                85                  90                  95

Tyr Leu Asp Lys Gln Ser Asp Thr Gln Tyr Val Cys Lys Arg Thr Leu
            100                 105                 110

Val Asp Arg Gly Trp Gly Asn Gly Cys Gly Leu Phe Gly Lys Gly Ser
        115                 120                 125

Leu Val Thr Cys Ala Lys Phe Ala Cys Ser Lys Lys Met Thr Gly Lys
    130                 135                 140

Ser Ile Gln Pro Glu Asn Leu Glu Tyr Arg Ile Met Leu Ser Val His
145                 150                 155                 160

Gly Ser Gln His Ser Gly Met Ile Val Asn Asp Thr Gly His Glu Thr
                165                 170                 175

Asp Glu Asn Arg Ala Lys Val Glu Ile Thr Pro Asn Ser Pro Arg Ala
            180                 185                 190

Glu Ala Thr Leu Gly Gly Phe Gly Ser Leu Gly Leu Asp Cys Glu Pro
        195                 200                 205

Arg Thr Gly Leu Asp Phe Ser Asp Leu Tyr Tyr Leu Thr Met Asn Asn
    210                 215                 220

Lys His Trp Leu Val His Lys Glu Trp Phe His Asp Ile Pro Leu Pro
225                 230                 235                 240

Trp His Ala Gly Ala Asp Thr Gly Thr Pro His Trp Asn Asn Lys Glu
                245                 250                 255

Ala Leu Val Glu Phe Lys Asp Ala His Ala Lys Arg Gln Thr Val Val
            260                 265                 270

Val Leu Gly Ser Gln Glu Gly Ala Val His Thr Ala Leu Ala Gly Ala
```

-continued

```
        275                 280                 285

Leu Glu Ala Glu Met Asp Gly Ala Lys Gly Arg Leu Ser Ser Gly His
    290                 295                 300

Leu Lys Cys Arg Leu Lys Met Asp Lys Leu Arg Leu Lys Gly Val Ser
305                 310                 315                 320

Tyr Ser Leu Cys Thr Ala Ala Phe Thr Phe Thr Lys Ile Pro Ala Glu
                325                 330                 335

Thr Leu His Gly Thr Val Thr Val Glu Val Gln Tyr Ala Gly Thr Asp
            340                 345                 350

Gly Pro Cys Lys Val Pro Ala Gln Met Ala Val Asp Met Gln Thr Leu
        355                 360                 365

Thr Pro Val Gly Arg Leu Ile Thr Ala Asn Pro Val Ile Thr Glu Ser
    370                 375                 380

Thr Glu Asn Ser Lys Met Met Leu Glu Leu Asp Pro Pro Phe Gly Asp
385                 390                 395                 400

Ser Tyr Ile Val Ile Gly Val Gly Glu Lys Lys Ile Thr His His Trp
                405                 410                 415

His Arg Ser Gly Ser Thr Ile Gly Lys Ala Phe Glu Ala Thr Val Arg
            420                 425                 430

Gly Ala Lys Arg Met Ala Val Leu Gly Asp Thr Ala Trp Asp Phe Gly
        435                 440                 445

Ser Val Gly Gly Ala Leu Asn Ser Leu Gly Lys Gly Ile His Gln Ile
    450                 455                 460

Phe Gly Ala Ala Phe Lys Ser Leu Phe Gly Gly Met Ser Trp Phe Ser
465                 470                 475                 480

Gln Ile Leu Ile Gly Thr Leu Leu Met Trp Leu Gly Leu Asn Thr Lys
                485                 490                 495

Asn Gly Ser Ile Ser Leu Met Cys Leu Ala Leu Gly Gly Val Leu Ile
            500                 505                 510

Phe Leu Ser Thr Ala Val Ser Ala Asp
        515                 520


<210> SEQ ID NO 45
<211> LENGTH: 2391
<212> TYPE: DNA
<213> ORGANISM: Zika virus

<400> SEQUENCE: 45

atgaagaatc ctaagaaaaa gtccggcgga ttcaggatcg tgaatatgct gaagaggggc      60

gtggccaggg tctccccttt tggaggcctg aaaaggctgc ctgctggact gctgctggga     120

cacggcccca tcaggatggt cctggccatc ctcgccttcc tcagattcac cgccatcaag     180

ccctccctcg gcctgattaa caggtggggc agcgtcggca agaaagaagc catggaaatc     240

attaagaagt tcaaaaaaga cctggccgcc atgctgagga tcatcaatgc caggaaggag     300

aagaagagga ggggagctga tacctccgtg ggcatcgtgg gactgctgct caccacagcc     360

atggccgccg aggtcaccag aagaggcagc gcttattaca tgtacctgga cagaaatgac     420

gccggcgaag ctatcagctt ccctaccacc ctgggcatga acaagtgcta catccagatc     480

atggacctgg gccacatgtg cgatgccacc atgtcctacg agtgccccat gctcgacgaa     540

ggagtggagc ctgacgacgt ggattgttgg tgcaacacca cctccacatg ggtggtctat     600

ggcacctgcc atcacaagaa aggcgaagcc aggaggtcca ggagggctgt gaccctgccc     660

agccactcca ccaggaagct gcaaacaaga tcccagacct ggctggaatc cagggagtac     720
```

-continued

```
accaagcacc tgatcagggt ggagaactgg attttcagga atcccggctt cgccctggcc    780

gctgccgcca tcgcttggct gctcggcagc agcacctccc agaaagtgat ttacctggtg    840

atgatcctgc tcatcgcccc cgcctacagc atcagatgca tcggagtgag caacagggat    900

ttcgtggagg gcatgtccgg aggaacatgg gtggatgtgg tgctggaaca tggcggctgc    960

gtgacagtga tggcccagga caagcccaca gtggacatcg agctggtgac caccacagtg   1020

tccaatatgg ccgaggtcag gagctattgc tacgaggcta gcatctccga catggcttcc   1080

gacagcaggt gtcccacaca gggcgaggct tatctggaca agcagtccga tacccagtac   1140

gtgtgcaaaa ggaccctggt ggatagagga tggggaaacg gctgtggcct gttcggcaag   1200

ggctccctgg tgacctgtgc taaatttgcc tgctccaaga agatgaccgg caagtccatc   1260

caacctgaga acctggagta caggatcatg ctgtccgtgc acggcagcca acatagcggc   1320

atgatcgtga atgacaccgg acacgaaacc gacgaaaaca gggccaaggt ggagattacc   1380

cccaatagcc ccagagctga ggccacactg ggcggctttg gatccctcgg cctggattgt   1440

gagcccagga ccggcctcga cttctccgat ctgtattacc tgaccatgaa caacaagcat   1500

tggctcgtgc acaaagagtg gtttcacgac attcccctgc cttggcacgc tggcgccgat   1560

acaggaaccc cccactggaa caacaaggag gctctggtcg aatttaaaga cgcccatgcc   1620

aaaagacaga cagtcgtggt gctgggctcc caagagggag ccgtgcatac agccctggcc   1680

ggagccctcg aggctgaaat ggacggagct aaaggcaggc tgtccagcgg acacctgaag   1740

tgcaggctca agatggacaa gctcagactc aagggagtga gctatagcct gtgtacagcc   1800

gccttcacat tcaccaaaat ccccgccgaa accctgcacg gcacagtgac cgtggaggtc   1860

cagtacgccg gcacagacgg cccttgcaaa gtgcccgccc agatggctgt cgacatgcag   1920

acactgaccc ctgtgggcag gctgattacc gctaaccccg tgattaccga gagcacagag   1980

aacagcaaga tgatgctgga gctggaccct cctttcggcg attcctacat cgtgatcgga   2040

gtgggcgaga aaaagatcac ccaccattgg cacaggtccg gctccacaat tggcaaggcc   2100

tttgaggcca ccgtgagggg agctaagagg atggccgtgc tcggcgacac agcctgggat   2160

ttcggaagcg tgggaggcgc cctgaattcc ctcggcaagg gcatccatca gatcttcggc   2220

gctgccttca agtccctctt cggaggcatg agctggttca gccagatcct gatcggaacc   2280

ctcctgatgt ggctgggcct gaacaccaag aacggatcca ttagcctgat gtgtctcgcc   2340

ctgggcggcg tgctgatctt cctgtccacc gccgtgtccg ccgattgata a            2391
```

```
<210> SEQ ID NO 46
<211> LENGTH: 795
<212> TYPE: PRT
<213> ORGANISM: Zika virus

<400> SEQUENCE: 46

Met Lys Asn Pro Lys Lys Lys Ser Gly Gly Phe Arg Ile Val Asn Met
1               5                   10                  15

Leu Lys Arg Gly Val Ala Arg Val Ser Pro Phe Gly Gly Leu Lys Arg
            20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Ile
65                  70                  75                  80
```

-continued

```
Ile Lys Lys Phe Lys Lys Asp Leu Ala Ala Met Leu Arg Ile Ile Asn
                85                  90                  95

Ala Arg Lys Glu Lys Lys Arg Arg Gly Ala Asp Thr Ser Val Gly Ile
            100                 105                 110

Val Gly Leu Leu Leu Thr Thr Ala Met Ala Ala Glu Val Thr Arg Arg
        115                 120                 125

Gly Ser Ala Tyr Tyr Met Tyr Leu Asp Arg Asn Asp Ala Gly Glu Ala
    130                 135                 140

Ile Ser Phe Pro Thr Thr Leu Gly Met Asn Lys Cys Tyr Ile Gln Ile
145                 150                 155                 160

Met Asp Leu Gly His Met Cys Asp Ala Thr Met Ser Tyr Glu Cys Pro
                165                 170                 175

Met Leu Asp Glu Gly Val Glu Pro Asp Asp Val Asp Cys Trp Cys Asn
            180                 185                 190

Thr Thr Ser Thr Trp Val Val Tyr Gly Thr Cys His His Lys Lys Gly
        195                 200                 205

Glu Ala Arg Arg Ser Arg Arg Ala Val Thr Leu Pro Ser His Ser Thr
    210                 215                 220

Arg Lys Leu Gln Thr Arg Ser Gln Thr Trp Leu Glu Ser Arg Glu Tyr
225                 230                 235                 240

Thr Lys His Leu Ile Arg Val Glu Asn Trp Ile Phe Arg Asn Pro Gly
                245                 250                 255

Phe Ala Leu Ala Ala Ala Ala Ile Ala Trp Leu Leu Gly Ser Ser Thr
            260                 265                 270

Ser Gln Lys Val Ile Tyr Leu Val Met Ile Leu Leu Ile Ala Pro Ala
        275                 280                 285

Tyr Ser Ile Arg Cys Ile Gly Val Ser Asn Arg Asp Phe Val Glu Gly
    290                 295                 300

Met Ser Gly Gly Thr Trp Val Asp Val Val Leu Glu His Gly Gly Cys
305                 310                 315                 320

Val Thr Val Met Ala Gln Asp Lys Pro Thr Val Asp Ile Glu Leu Val
                325                 330                 335

Thr Thr Thr Val Ser Asn Met Ala Glu Val Arg Ser Tyr Cys Tyr Glu
            340                 345                 350

Ala Ser Ile Ser Asp Met Ala Ser Asp Ser Arg Cys Pro Thr Gln Gly
        355                 360                 365

Glu Ala Tyr Leu Asp Lys Gln Ser Asp Thr Gln Tyr Val Cys Lys Arg
    370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Ala Cys Ser Lys Lys Met Thr
                405                 410                 415

Gly Lys Ser Ile Gln Pro Glu Asn Leu Glu Tyr Arg Ile Met Leu Ser
            420                 425                 430

Val His Gly Ser Gln His Ser Gly Met Ile Val Asn Asp Thr Gly His
        435                 440                 445

Glu Thr Asp Glu Asn Arg Ala Lys Val Glu Ile Thr Pro Asn Ser Pro
    450                 455                 460

Arg Ala Glu Ala Thr Leu Gly Gly Phe Gly Ser Leu Gly Leu Asp Cys
465                 470                 475                 480

Glu Pro Arg Thr Gly Leu Asp Phe Ser Asp Leu Tyr Tyr Leu Thr Met
                485                 490                 495

Asn Asn Lys His Trp Leu Val His Lys Glu Trp Phe His Asp Ile Pro
```

```
            500                 505                 510

Leu Pro Trp His Ala Gly Ala Asp Thr Gly Thr Pro His Trp Asn Asn
        515                 520                 525

Lys Glu Ala Leu Val Glu Phe Lys Asp Ala His Ala Lys Arg Gln Thr
    530                 535                 540

Val Val Val Leu Gly Ser Gln Glu Gly Ala Val His Thr Ala Leu Ala
545                 550                 555                 560

Gly Ala Leu Glu Ala Glu Met Asp Gly Ala Lys Gly Arg Leu Ser Ser
                565                 570                 575

Gly His Leu Lys Cys Arg Leu Lys Met Asp Lys Leu Arg Leu Lys Gly
            580                 585                 590

Val Ser Tyr Ser Leu Cys Thr Ala Ala Phe Thr Phe Thr Lys Ile Pro
        595                 600                 605

Ala Glu Thr Leu His Gly Thr Val Thr Val Glu Val Gln Tyr Ala Gly
    610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
                645                 650                 655

Glu Ser Thr Glu Asn Ser Lys Met Met Leu Glu Leu Asp Pro Pro Phe
            660                 665                 670

Gly Asp Ser Tyr Ile Val Ile Gly Val Gly Glu Lys Lys Ile Thr His
        675                 680                 685

His Trp His Arg Ser Gly Ser Thr Ile Gly Lys Ala Phe Glu Ala Thr
    690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
                725                 730                 735

Gln Ile Phe Gly Ala Ala Phe Lys Ser Leu Phe Gly Gly Met Ser Trp
            740                 745                 750

Phe Ser Gln Ile Leu Ile Gly Thr Leu Leu Met Trp Leu Gly Leu Asn
        755                 760                 765

Thr Lys Asn Gly Ser Ile Ser Leu Met Cys Leu Ala Leu Gly Gly Val
    770                 775                 780

Leu Ile Phe Leu Ser Thr Ala Val Ser Ala Asp
785                 790                 795


<210> SEQ ID NO 47
<211> LENGTH: 122
<212> TYPE: PRT
<213> ORGANISM: Zika virus

<400> SEQUENCE: 47

Met Lys Asn Pro Lys Lys Lys Ser Gly Gly Phe Arg Ile Val Asn Met
1               5                   10                  15

Leu Lys Arg Gly Val Ala Arg Val Ser Pro Phe Gly Gly Leu Lys Arg
            20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Ile
65                  70                  75                  80
```

-continued

```
Ile Lys Lys Phe Lys Lys Asp Leu Ala Ala Met Leu Arg Ile Ile Asn
                85                  90                  95

Ala Arg Lys Glu Lys Lys Arg Arg Gly Ala Asp Thr Ser Val Gly Ile
            100                 105                 110

Val Gly Leu Leu Leu Thr Thr Ala Met Ala
        115                 120


<210> SEQ ID NO 48
<211> LENGTH: 92
<212> TYPE: PRT
<213> ORGANISM: Zika virus

<400> SEQUENCE: 48

Ala Glu Val Thr Arg Arg Gly Ser Ala Tyr Tyr Met Tyr Leu Asp Arg
1               5                   10                  15

Asn Asp Ala Gly Glu Ala Ile Ser Phe Pro Thr Thr Leu Gly Met Asn
            20                  25                  30

Lys Cys Tyr Ile Gln Ile Met Asp Leu Gly His Met Cys Asp Ala Thr
        35                  40                  45

Met Ser Tyr Glu Cys Pro Met Leu Asp Glu Gly Val Glu Pro Asp Asp
    50                  55                  60

Val Asp Cys Trp Cys Asn Thr Thr Ser Thr Trp Val Val Tyr Gly Thr
65                  70                  75                  80

Cys His His Lys Lys Gly Glu Ala Arg Arg Ser Arg
                85                  90


<210> SEQ ID NO 49
<211> LENGTH: 60
<212> TYPE: PRT
<213> ORGANISM: Zika virus

<400> SEQUENCE: 49

Arg Ala Val Thr Leu Pro Ser His Ser Thr Arg Lys Leu Gln Thr Arg
1               5                   10                  15

Ser Gln Thr Trp Leu Glu Ser Arg Glu Tyr Thr Lys His Leu Ile Arg
            20                  25                  30

Val Glu Asn Trp Ile Phe Arg Asn Pro Gly Phe Ala Leu Ala Ala Ala
        35                  40                  45

Ala Ile Ala Trp Leu Leu Gly Ser Ser Thr Ser Gln
    50                  55                  60


<210> SEQ ID NO 50
<211> LENGTH: 521
<212> TYPE: PRT
<213> ORGANISM: Zika virus

<400> SEQUENCE: 50

Lys Val Ile Tyr Leu Val Met Ile Leu Leu Ile Ala Pro Ala Tyr Ser
1               5                   10                  15

Ile Arg Cys Ile Gly Val Ser Asn Arg Asp Phe Val Glu Gly Met Ser
            20                  25                  30

Gly Gly Thr Trp Val Asp Val Val Leu Glu His Gly Gly Cys Val Thr
        35                  40                  45

Val Met Ala Gln Asp Lys Pro Thr Val Asp Ile Glu Leu Val Thr Thr
    50                  55                  60

Thr Val Ser Asn Met Ala Glu Val Arg Ser Tyr Cys Tyr Glu Ala Ser
65                  70                  75                  80

Ile Ser Asp Met Ala Ser Asp Ser Arg Cys Pro Thr Gln Gly Glu Ala
```

-continued

```
                85                  90                  95

Tyr Leu Asp Lys Gln Ser Asp Thr Gln Tyr Val Cys Lys Arg Thr Leu
            100                 105                 110

Val Asp Arg Gly Trp Gly Asn Gly Cys Gly Leu Phe Gly Lys Gly Ser
        115                 120                 125

Leu Val Thr Cys Ala Lys Phe Ala Cys Ser Lys Lys Met Thr Gly Lys
    130                 135                 140

Ser Ile Gln Pro Glu Asn Leu Glu Tyr Arg Ile Met Leu Ser Val His
145                 150                 155                 160

Gly Ser Gln His Ser Gly Met Ile Val Asn Asp Thr Gly His Glu Thr
                165                 170                 175

Asp Glu Asn Arg Ala Lys Val Glu Ile Thr Pro Asn Ser Pro Arg Ala
            180                 185                 190

Glu Ala Thr Leu Gly Gly Phe Gly Ser Leu Gly Leu Asp Cys Glu Pro
        195                 200                 205

Arg Thr Gly Leu Asp Phe Ser Asp Leu Tyr Tyr Leu Thr Met Asn Asn
    210                 215                 220

Lys His Trp Leu Val His Lys Glu Trp Phe His Asp Ile Pro Leu Pro
225                 230                 235                 240

Trp His Ala Gly Ala Asp Thr Gly Thr Pro His Trp Asn Asn Lys Glu
                245                 250                 255

Ala Leu Val Glu Phe Lys Asp Ala His Ala Lys Arg Gln Thr Val Val
            260                 265                 270

Val Leu Gly Ser Gln Glu Gly Ala Val His Thr Ala Leu Ala Gly Ala
        275                 280                 285

Leu Glu Ala Glu Met Asp Gly Ala Lys Gly Arg Leu Ser Ser Gly His
    290                 295                 300

Leu Lys Cys Arg Leu Lys Met Asp Lys Leu Arg Leu Lys Gly Val Ser
305                 310                 315                 320

Tyr Ser Leu Cys Thr Ala Ala Phe Thr Phe Thr Lys Ile Pro Ala Glu
                325                 330                 335

Thr Leu His Gly Thr Val Thr Val Glu Val Gln Tyr Ala Gly Thr Asp
            340                 345                 350

Gly Pro Cys Lys Val Pro Ala Gln Met Ala Val Asp Met Gln Thr Leu
        355                 360                 365

Thr Pro Val Gly Arg Leu Ile Thr Ala Asn Pro Val Ile Thr Glu Ser
    370                 375                 380

Thr Glu Asn Ser Lys Met Met Leu Glu Leu Asp Pro Pro Phe Gly Asp
385                 390                 395                 400

Ser Tyr Ile Val Ile Gly Val Gly Glu Lys Lys Ile Thr His His Trp
                405                 410                 415

His Arg Ser Gly Ser Thr Ile Gly Lys Ala Phe Glu Ala Thr Val Arg
            420                 425                 430

Gly Ala Lys Arg Met Ala Val Leu Gly Asp Thr Ala Trp Asp Phe Gly
        435                 440                 445

Ser Val Gly Gly Ala Leu Asn Ser Leu Gly Lys Gly Ile His Gln Ile
    450                 455                 460

Phe Gly Ala Ala Phe Lys Ser Leu Phe Gly Gly Met Ser Trp Phe Ser
465                 470                 475                 480

Gln Ile Leu Ile Gly Thr Leu Leu Met Trp Leu Gly Leu Asn Thr Lys
                485                 490                 495

Asn Gly Ser Ile Ser Leu Met Cys Leu Ala Leu Gly Gly Val Leu Ile
            500                 505                 510
```

Phe Leu Ser Thr Ala Val Ser Ala Asp
515 520

<210> SEQ ID NO 51
<211> LENGTH: 2391
<212> TYPE: DNA
<213> ORGANISM: Zika virus

<400> SEQUENCE: 51
atgaagaatc ccaagaaaaa gagcggcggc ttcagaatcg tgaacatgct gaagagggga 60
gtggccagag tgtccccctt tggcggcctg aaaagactcc ctgccggcct gctcctggga 120
catggcccta tcaggatggt cctggccatt ctggctttcc tgaggttcac agccatcaag 180
cctagcctgg gcctgattaa caggtggggc agcgtcggca agaaggaagc catggagatt 240
attaagaagt tcaagaaaga cctcgctgcc atgctgagga tcatcaatgc caggaaggag 300
aagaaaagga ggggcgctga cacaagcgtg ggaatcgtgg gactgctgct cccccaggcc 360
caggctgctg aagtgaccag aaggggctcc gcctactata tgtacctcga caggaacgac 420
gccggagagg ccatcagctt ccctaccacc ctgggaatga acaaatgcta catccagatc 480
atggacctcg gccacatgtg cgacgccacc atgagctacg aatgccccat gctggacgag 540
ggcgtggagc ctgacgatgt ggactgctgg tgcaacacaa ccagcacctg ggtggtctac 600
ggcacctgtc accacaagaa aggagaggcc agaaggtcca ggagggccgt caccctgcct 660
agccacagca ccagaaagct gcagaccagg agccagacct ggctggagag cagagagtac 720
accaaacacc tcatcagggt ggagaactgg atttttagga atcctggctt tgccctcgct 780
gccgccgcta tcgcttggct cctcggaagc agcaccagcc agaaggtcat ctatctcgtg 840
atgatcctgc tcatcgctcc cgcttactcc atcaggtgca tcggcgtgag caacagagac 900
ttcgtggagg gaatgtccgg cggaacctgg gtggatgtgg tgctcgagca cggcggatgc 960
gtcaccgtga tggcccaaga taagcctacc gtggacatcg aactggtgac aacaaccgtg 1020
tccaacatgg ccgaggtgag aagctactgt tacgaggcct ccatcagcga catggcctcc 1080
gactccaggt gccctaccca gggagaggct tacctggaca agcaatccga cacccagtac 1140
gtgtgtaaga ggaccctggt cgatagaggc tggggcaatg gctgtggact gttcggcaag 1200
ggaagcctgg tgacctgcgc taagttcgcc tgctccaaaa agatgaccgg caagagcatc 1260
cagcccgaga acctggagta cagaatcatg ctgtccgtgc acggcagcca gcacagcggc 1320
atgattgtga acgacaccgg acacgaaacc gacgagaaca gggccaaagt ggagatcacc 1380
cccaatagcc ccagggctga agctacactg ggaggatttg gcagcctggg cctggattgt 1440
gagcctagga ccggactgga tttcagcgat ctgtactatc tgaccatgaa taacaagcac 1500
tggctggtgc acaaggagtg gtttcacgac atccctctgc cctggcacgc tggagccgat 1560
acaggcaccc cccactggaa caataaggag gccctcgtgg aattcaagga cgcccacgcc 1620
aagagacaaa ccgtcgtggt gctgggaagc caggaaggcg ccgtgcatac cgccctcgcc 1680
ggcgctctcg aggctgagat ggacggagcc aagggcagac tgagcagcgg acatctcaag 1740
tgcaggctga agatggacaa gctcaggctg aaaggagtct cctacagcct gtgcaccgcc 1800
gccttcacat ttaccaaaat ccccgccgag accctccacg gaaccgtcac agtggaagtg 1860
caatacgccg gcacagatgg cccctgtaag gtgcccgccc agatggccgt ggatatgcag 1920
accctgaccc ctgtcggcag gctgattacc gccaaccctg tgatcaccga gtccaccgag 1980
aacagcaaaa tgatgctgga gctggatccc cccttcggcg actcctacat tgtgatcggc 2040

```
gtgggcgaga agaaaattac ccatcactgg catagaagcg gcagcacaat cggcaaggcc   2100

tttgaggcca cagtgagagg cgccaaaaga atggccgtgc tgggagatac agcttgggat   2160

tttggatccg tgggcggcgc cctgaactcc ctgggcaaag gaatccatca gatcttcggc   2220

gctgctttca agagcctctt tggcggcatg tcctggttct cccaaatcct gatcggcaca   2280

ctcctgatgt ggctgggcct caacacaaaa aacggcagca tcagcctgat gtgcctcgcc   2340

ctcggaggcg tgctgatctt cctgtccacc gctgtgagcg ctgattgata a            2391
```

<210> SEQ ID NO 52
<211> LENGTH: 795
<212> TYPE: PRT
<213> ORGANISM: Zika virus

<400> SEQUENCE: 52

```
Met Lys Asn Pro Lys Lys Lys Ser Gly Gly Phe Arg Ile Val Asn Met
1               5                   10                  15

Leu Lys Arg Gly Val Ala Arg Val Ser Pro Phe Gly Gly Leu Lys Arg
            20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Ile
65                  70                  75                  80

Ile Lys Lys Phe Lys Lys Asp Leu Ala Ala Met Leu Arg Ile Ile Asn
                85                  90                  95

Ala Arg Lys Glu Lys Lys Arg Arg Gly Ala Asp Thr Ser Val Gly Ile
            100                 105                 110

Val Gly Leu Leu Leu Pro Gln Ala Gln Ala Ala Glu Val Thr Arg Arg
        115                 120                 125

Gly Ser Ala Tyr Tyr Met Tyr Leu Asp Arg Asn Asp Ala Gly Glu Ala
    130                 135                 140

Ile Ser Phe Pro Thr Thr Leu Gly Met Asn Lys Cys Tyr Ile Gln Ile
145                 150                 155                 160

Met Asp Leu Gly His Met Cys Asp Ala Thr Met Ser Tyr Glu Cys Pro
                165                 170                 175

Met Leu Asp Glu Gly Val Glu Pro Asp Asp Val Asp Cys Trp Cys Asn
            180                 185                 190

Thr Thr Ser Thr Trp Val Val Tyr Gly Thr Cys His His Lys Lys Gly
        195                 200                 205

Glu Ala Arg Arg Ser Arg Arg Ala Val Thr Leu Pro Ser His Ser Thr
    210                 215                 220

Arg Lys Leu Gln Thr Arg Ser Gln Thr Trp Leu Glu Ser Arg Glu Tyr
225                 230                 235                 240

Thr Lys His Leu Ile Arg Val Glu Asn Trp Ile Phe Arg Asn Pro Gly
                245                 250                 255

Phe Ala Leu Ala Ala Ala Ala Ile Ala Trp Leu Leu Gly Ser Ser Thr
            260                 265                 270

Ser Gln Lys Val Ile Tyr Leu Val Met Ile Leu Leu Ile Ala Pro Ala
        275                 280                 285

Tyr Ser Ile Arg Cys Ile Gly Val Ser Asn Arg Asp Phe Val Glu Gly
    290                 295                 300

Met Ser Gly Gly Thr Trp Val Asp Val Val Leu Glu His Gly Gly Cys
```

-continued

```
305                 310                 315                 320

Val Thr Val Met Ala Gln Asp Lys Pro Thr Val Asp Ile Glu Leu Val
                325                 330                 335

Thr Thr Thr Val Ser Asn Met Ala Glu Val Arg Ser Tyr Cys Tyr Glu
            340                 345                 350

Ala Ser Ile Ser Asp Met Ala Ser Asp Ser Arg Cys Pro Thr Gln Gly
        355                 360                 365

Glu Ala Tyr Leu Asp Lys Gln Ser Asp Thr Gln Tyr Val Cys Lys Arg
    370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Ala Cys Ser Lys Lys Met Thr
                405                 410                 415

Gly Lys Ser Ile Gln Pro Glu Asn Leu Glu Tyr Arg Ile Met Leu Ser
            420                 425                 430

Val His Gly Ser Gln His Ser Gly Met Ile Val Asn Asp Thr Gly His
        435                 440                 445

Glu Thr Asp Glu Asn Arg Ala Lys Val Glu Ile Thr Pro Asn Ser Pro
    450                 455                 460

Arg Ala Glu Ala Thr Leu Gly Gly Phe Gly Ser Leu Gly Leu Asp Cys
465                 470                 475                 480

Glu Pro Arg Thr Gly Leu Asp Phe Ser Asp Leu Tyr Tyr Leu Thr Met
                485                 490                 495

Asn Asn Lys His Trp Leu Val His Lys Glu Trp Phe His Asp Ile Pro
            500                 505                 510

Leu Pro Trp His Ala Gly Ala Asp Thr Gly Thr Pro His Trp Asn Asn
        515                 520                 525

Lys Glu Ala Leu Val Glu Phe Lys Asp Ala His Ala Lys Arg Gln Thr
    530                 535                 540

Val Val Val Leu Gly Ser Gln Glu Gly Ala Val His Thr Ala Leu Ala
545                 550                 555                 560

Gly Ala Leu Glu Ala Glu Met Asp Gly Ala Lys Gly Arg Leu Ser Ser
                565                 570                 575

Gly His Leu Lys Cys Arg Leu Lys Met Asp Lys Leu Arg Leu Lys Gly
            580                 585                 590

Val Ser Tyr Ser Leu Cys Thr Ala Ala Phe Thr Phe Thr Lys Ile Pro
        595                 600                 605

Ala Glu Thr Leu His Gly Thr Val Thr Val Glu Val Gln Tyr Ala Gly
    610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
                645                 650                 655

Glu Ser Thr Glu Asn Ser Lys Met Met Leu Glu Leu Asp Pro Pro Phe
            660                 665                 670

Gly Asp Ser Tyr Ile Val Ile Gly Val Gly Glu Lys Lys Ile Thr His
        675                 680                 685

His Trp His Arg Ser Gly Ser Thr Ile Gly Lys Ala Phe Glu Ala Thr
    690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
                725                 730                 735
```

Gln Ile Phe Gly Ala Ala Phe Lys Ser Leu Phe Gly Gly Met Ser Trp
740 745 750

Phe Ser Gln Ile Leu Ile Gly Thr Leu Leu Met Trp Leu Gly Leu Asn
755 760 765

Thr Lys Asn Gly Ser Ile Ser Leu Met Cys Leu Ala Leu Gly Gly Val
770 775 780

Leu Ile Phe Leu Ser Thr Ala Val Ser Ala Asp
785 790 795

<210> SEQ ID NO 53
<211> LENGTH: 122
<212> TYPE: PRT
<213> ORGANISM: Zika virus

<400> SEQUENCE: 53

Met Lys Asn Pro Lys Lys Lys Ser Gly Gly Phe Arg Ile Val Asn Met
1 5 10 15

Leu Lys Arg Gly Val Ala Arg Val Ser Pro Phe Gly Gly Leu Lys Arg
20 25 30

Leu Pro Ala Gly Leu Leu Leu Gly His Gly Pro Ile Arg Met Val Leu
35 40 45

Ala Ile Leu Ala Phe Leu Arg Phe Thr Ala Ile Lys Pro Ser Leu Gly
50 55 60

Leu Ile Asn Arg Trp Gly Ser Val Gly Lys Lys Glu Ala Met Glu Ile
65 70 75 80

Ile Lys Lys Phe Lys Lys Asp Leu Ala Ala Met Leu Arg Ile Ile Asn
85 90 95

Ala Arg Lys Glu Lys Lys Arg Arg Gly Ala Asp Thr Ser Val Gly Ile
100 105 110

Val Gly Leu Leu Leu Pro Gln Ala Gln Ala
115 120

<210> SEQ ID NO 54
<211> LENGTH: 92
<212> TYPE: PRT
<213> ORGANISM: Zika virus

<400> SEQUENCE: 54

Ala Glu Val Thr Arg Arg Gly Ser Ala Tyr Tyr Met Tyr Leu Asp Arg
1 5 10 15

Asn Asp Ala Gly Glu Ala Ile Ser Phe Pro Thr Thr Leu Gly Met Asn
20 25 30

Lys Cys Tyr Ile Gln Ile Met Asp Leu Gly His Met Cys Asp Ala Thr
35 40 45

Met Ser Tyr Glu Cys Pro Met Leu Asp Glu Gly Val Glu Pro Asp Asp
50 55 60

Val Asp Cys Trp Cys Asn Thr Thr Ser Thr Trp Val Val Tyr Gly Thr
65 70 75 80

Cys His His Lys Lys Gly Glu Ala Arg Arg Ser Arg
85 90

<210> SEQ ID NO 55
<211> LENGTH: 60
<212> TYPE: PRT
<213> ORGANISM: Zika virus

<400> SEQUENCE: 55

-continued

Arg Ala Val Thr Leu Pro Ser His Ser Thr Arg Lys Leu Gln Thr Arg
1 5 10 15

Ser Gln Thr Trp Leu Glu Ser Arg Glu Tyr Thr Lys His Leu Ile Arg
20 25 30

Val Glu Asn Trp Ile Phe Arg Asn Pro Gly Phe Ala Leu Ala Ala Ala
35 40 45

Ala Ile Ala Trp Leu Leu Gly Ser Ser Thr Ser Gln
50 55 60

<210> SEQ ID NO 56
<211> LENGTH: 521
<212> TYPE: PRT
<213> ORGANISM: Zika virus

<400> SEQUENCE: 56

Lys Val Ile Tyr Leu Val Met Ile Leu Leu Ile Ala Pro Ala Tyr Ser
1 5 10 15

Ile Arg Cys Ile Gly Val Ser Asn Arg Asp Phe Val Glu Gly Met Ser
20 25 30

Gly Gly Thr Trp Val Asp Val Val Leu Glu His Gly Gly Cys Val Thr
35 40 45

Val Met Ala Gln Asp Lys Pro Thr Val Asp Ile Glu Leu Val Thr Thr
50 55 60

Thr Val Ser Asn Met Ala Glu Val Arg Ser Tyr Cys Tyr Glu Ala Ser
65 70 75 80

Ile Ser Asp Met Ala Ser Asp Ser Arg Cys Pro Thr Gln Gly Glu Ala
85 90 95

Tyr Leu Asp Lys Gln Ser Asp Thr Gln Tyr Val Cys Lys Arg Thr Leu
100 105 110

Val Asp Arg Gly Trp Gly Asn Gly Cys Gly Leu Phe Gly Lys Gly Ser
115 120 125

Leu Val Thr Cys Ala Lys Phe Ala Cys Ser Lys Lys Met Thr Gly Lys
130 135 140

Ser Ile Gln Pro Glu Asn Leu Glu Tyr Arg Ile Met Leu Ser Val His
145 150 155 160

Gly Ser Gln His Ser Gly Met Ile Val Asn Asp Thr Gly His Glu Thr
165 170 175

Asp Glu Asn Arg Ala Lys Val Glu Ile Thr Pro Asn Ser Pro Arg Ala
180 185 190

Glu Ala Thr Leu Gly Gly Phe Gly Ser Leu Gly Leu Asp Cys Glu Pro
195 200 205

Arg Thr Gly Leu Asp Phe Ser Asp Leu Tyr Tyr Leu Thr Met Asn Asn
210 215 220

Lys His Trp Leu Val His Lys Glu Trp Phe His Asp Ile Pro Leu Pro
225 230 235 240

Trp His Ala Gly Ala Asp Thr Gly Thr Pro His Trp Asn Asn Lys Glu
245 250 255

Ala Leu Val Glu Phe Lys Asp Ala His Ala Lys Arg Gln Thr Val Val
260 265 270

Val Leu Gly Ser Gln Glu Gly Ala Val His Thr Ala Leu Ala Gly Ala
275 280 285

Leu Glu Ala Glu Met Asp Gly Ala Lys Gly Arg Leu Ser Ser Gly His
290 295 300

Leu Lys Cys Arg Leu Lys Met Asp Lys Leu Arg Leu Lys Gly Val Ser
305 310 315 320

```
Tyr Ser Leu Cys Thr Ala Ala Phe Thr Phe Thr Lys Ile Pro Ala Glu
                325                 330                 335

Thr Leu His Gly Thr Val Thr Val Glu Val Gln Tyr Ala Gly Thr Asp
            340                 345                 350

Gly Pro Cys Lys Val Pro Ala Gln Met Ala Val Asp Met Gln Thr Leu
        355                 360                 365

Thr Pro Val Gly Arg Leu Ile Thr Ala Asn Pro Val Ile Thr Glu Ser
    370                 375                 380

Thr Glu Asn Ser Lys Met Met Leu Glu Leu Asp Pro Pro Phe Gly Asp
385                 390                 395                 400

Ser Tyr Ile Val Ile Gly Val Gly Glu Lys Lys Ile Thr His His Trp
                405                 410                 415

His Arg Ser Gly Ser Thr Ile Gly Lys Ala Phe Glu Ala Thr Val Arg
            420                 425                 430

Gly Ala Lys Arg Met Ala Val Leu Gly Asp Thr Ala Trp Asp Phe Gly
        435                 440                 445

Ser Val Gly Gly Ala Leu Asn Ser Leu Gly Lys Gly Ile His Gln Ile
    450                 455                 460

Phe Gly Ala Ala Phe Lys Ser Leu Phe Gly Gly Met Ser Trp Phe Ser
465                 470                 475                 480

Gln Ile Leu Ile Gly Thr Leu Leu Met Trp Leu Gly Leu Asn Thr Lys
                485                 490                 495

Asn Gly Ser Ile Ser Leu Met Cys Leu Ala Leu Gly Gly Val Leu Ile
            500                 505                 510

Phe Leu Ser Thr Ala Val Ser Ala Asp
        515                 520
```

<210> SEQ ID NO 57
<211> LENGTH: 2457
<212> TYPE: DNA
<213> ORGANISM: Zika virus

<400> SEQUENCE: 57

```
atgaagaacc ccaagaagaa aagcggcgga ttcaggattg tgaacatgct gaagaggggc     60

gtggccaggg tgtccccttt tggcggcctg aagagactgc ctgctggact gctcctgggc    120

cacggaccta tcaggatggt gctcgccatc ctggctttcc tcaggtttac agccatcaaa    180

cccagcctcg gcctgatcaa cagatgggga agcgtgggca agaaggaggc catggagatc    240

atcaagaagt ttaagaagga tctggccgcc atgctgagaa tcatcaacgc caggaaggag    300

aagaaaagaa ggggctccgg agccacaaac ttcagcctgc tgaaacaagc cggcgacgtc    360

gaagaaaatc ccggccccgg cgctgacacc tccgtcggaa tcgtgggcct gctgctgaca    420

accgctatgg ccgctgaggt gaccaggaga ggctccgcct actacatgta cctggataga    480

aatgacgccg gcgaggccat ctcctttccc accaccctcg gcatgaacaa gtgctacatc    540

caaatcatgg acctcggcca tatgtgcgac gctaccatga gctacgaatg ccctatgctg    600

gacgagggcg tggagcctga tgacgtggac tgttggtgca ataccaccag cacctgggtg    660

gtgtatggca catgccacca caagaaaggc gaggccagaa ggtccaggag ggccgtgaca    720

ctgcccagcc acagcaccag aaagctgcag acaagaagcc agacctggct cgagagcagg    780

gagtatacca agcacctgat tagagtcgag aactggatct tcagaaatcc cggcttcgct    840

ctggctgctg ccgccattgc ttggctgctg ggctccagca cctcccagaa ggtgatttac    900

ctggtcatga tcctgctgat cgcccctgcc tactccatta gatgcatcgg cgtctccaac    960
```

```
agagacttcg tggaaggaat gtccggcggc acatgggtcg atgtggtgct ggagcacggc   1020
ggctgcgtga cagtcatggc ccaggacaag cctaccgtgg acatcgagct ggtgacaacc   1080
accgtctcca acatggccga agtgaggtcc tactgctacg aggccagcat ttccgacatg   1140
gcttccgact ccaggtgccc tacccagggc gaggcctacc tcgacaagca gagcgacacc   1200
cagtacgtct gcaaaagaac cctggtggac aggggctggg gcaatggatg cggcctgttt   1260
ggcaagggct ccctcgtgac atgtgccaag ttcgcttgca gcaagaagat gaccggcaag   1320
tccatccagc ccgagaatct cgagtacagg atcatgctct ccgtgcacgg cagccagcac   1380
tccggcatga ttgtgaatga cacaggccat gagaccgatg aaaatagggc caaggtggag   1440
atcaccccta acagccctag ggccgaagct acactgggcg gattcggctc cctcggcctc   1500
gactgtgagc ccaggacagg cctcgacttc agcgacctgt actacctcac catgaataat   1560
aaacactggc tggtgcacaa agagtggttc cacgacatcc ccctgccctg gcatgccgga   1620
gccgataccg gaacacccca ctggaacaac aaggaagccc tggtcgagtt caaggacgcc   1680
cacgccaaga ggcaaaccgt ggtggtgctg ggatcccagg agggagccgt gcatacagct   1740
ctcgccggcg ctctggaggc cgaaatggac ggagccaaag gcaggctgtc cagcggccac   1800
ctgaaatgca ggctcaagat ggacaagctc agactgaagg gagtgtccta cagcctctgc   1860
accgccgcct ttacctttac caagatcccc gccgagaccc tccacggaac cgtgaccgtc   1920
gaagtccagt acgctggcac agacggcccc tgtaaggtgc ctgcccagat ggccgtggat   1980
atgcagaccc tgacacccgt gggcaggctg atcaccgcta accctgtgat caccgagagc   2040
accgagaatt ccaagatgat gctggagctg gaccctccct tcggcgacag ctatatcgtg   2100
atcggcgtcg gcgagaagaa aattacccac cactggcaca gaagcggcag caccattggc   2160
aaggcttttg aggccacagt gagaggcgct aagagaatgg ccgtgctggg cgataccgcc   2220
tgggactttg gcagcgtggg cggagccctg aacagcctgg gcaaaggcat ccaccagatc   2280
tttggcgccg cctttaagag cctcttcggc ggcatgtcct ggttcagcca gatcctgatc   2340
ggcacactgc tgatgtggct cggcctcaat accaaaaatg gcagcatcag cctgatgtgc   2400
ctcgctctcg gaggcgtgct gattttcctg tccacagccg tctccgctga ttgataa      2457
```

<210> SEQ ID NO 58
<211> LENGTH: 817
<212> TYPE: PRT
<213> ORGANISM: Zika virus

<400> SEQUENCE: 58

```
Met Lys Asn Pro Lys Lys Lys Ser Gly Gly Phe Arg Ile Val Asn Met
1               5                   10                  15

Leu Lys Arg Gly Val Ala Arg Val Ser Pro Phe Gly Gly Leu Lys Arg
            20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Ile
65                  70                  75                  80

Ile Lys Lys Phe Lys Lys Asp Leu Ala Ala Met Leu Arg Ile Ile Asn
                85                  90                  95

Ala Arg Lys Glu Lys Lys Arg Arg Gly Ser Gly Ala Thr Asn Phe Ser
            100                 105                 110
```

```
Leu Leu Lys Gln Ala Gly Asp Val Glu Glu Asn Pro Gly Pro Gly Ala
        115                 120                 125

Asp Thr Ser Val Gly Ile Val Gly Leu Leu Leu Thr Thr Ala Met Ala
    130                 135                 140

Ala Glu Val Thr Arg Arg Gly Ser Ala Tyr Tyr Met Tyr Leu Asp Arg
145                 150                 155                 160

Asn Asp Ala Gly Glu Ala Ile Ser Phe Pro Thr Thr Leu Gly Met Asn
                165                 170                 175

Lys Cys Tyr Ile Gln Ile Met Asp Leu Gly His Met Cys Asp Ala Thr
            180                 185                 190

Met Ser Tyr Glu Cys Pro Met Leu Asp Glu Gly Val Glu Pro Asp Asp
        195                 200                 205

Val Asp Cys Trp Cys Asn Thr Thr Ser Thr Trp Val Val Tyr Gly Thr
    210                 215                 220

Cys His His Lys Lys Gly Glu Ala Arg Arg Ser Arg Arg Ala Val Thr
225                 230                 235                 240

Leu Pro Ser His Ser Thr Arg Lys Leu Gln Thr Arg Ser Gln Thr Trp
                245                 250                 255

Leu Glu Ser Arg Glu Tyr Thr Lys His Leu Ile Arg Val Glu Asn Trp
            260                 265                 270

Ile Phe Arg Asn Pro Gly Phe Ala Leu Ala Ala Ala Ala Ile Ala Trp
        275                 280                 285

Leu Leu Gly Ser Ser Thr Ser Gln Lys Val Ile Tyr Leu Val Met Ile
    290                 295                 300

Leu Leu Ile Ala Pro Ala Tyr Ser Ile Arg Cys Ile Gly Val Ser Asn
305                 310                 315                 320

Arg Asp Phe Val Glu Gly Met Ser Gly Gly Thr Trp Val Asp Val Val
                325                 330                 335

Leu Glu His Gly Gly Cys Val Thr Val Met Ala Gln Asp Lys Pro Thr
            340                 345                 350

Val Asp Ile Glu Leu Val Thr Thr Thr Val Ser Asn Met Ala Glu Val
        355                 360                 365

Arg Ser Tyr Cys Tyr Glu Ala Ser Ile Ser Asp Met Ala Ser Asp Ser
    370                 375                 380

Arg Cys Pro Thr Gln Gly Glu Ala Tyr Leu Asp Lys Gln Ser Asp Thr
385                 390                 395                 400

Gln Tyr Val Cys Lys Arg Thr Leu Val Asp Arg Gly Trp Gly Asn Gly
                405                 410                 415

Cys Gly Leu Phe Gly Lys Gly Ser Leu Val Thr Cys Ala Lys Phe Ala
            420                 425                 430

Cys Ser Lys Lys Met Thr Gly Lys Ser Ile Gln Pro Glu Asn Leu Glu
        435                 440                 445

Tyr Arg Ile Met Leu Ser Val His Gly Ser Gln His Ser Gly Met Ile
    450                 455                 460

Val Asn Asp Thr Gly His Glu Thr Asp Glu Asn Arg Ala Lys Val Glu
465                 470                 475                 480

Ile Thr Pro Asn Ser Pro Arg Ala Glu Ala Thr Leu Gly Gly Phe Gly
                485                 490                 495

Ser Leu Gly Leu Asp Cys Glu Pro Arg Thr Gly Leu Asp Phe Ser Asp
            500                 505                 510

Leu Tyr Tyr Leu Thr Met Asn Asn Lys His Trp Leu Val His Lys Glu
        515                 520                 525
```

```
Trp Phe His Asp Ile Pro Leu Pro Trp His Ala Gly Ala Asp Thr Gly
    530                 535                 540

Thr Pro His Trp Asn Asn Lys Glu Ala Leu Val Glu Phe Lys Asp Ala
545                 550                 555                 560

His Ala Lys Arg Gln Thr Val Val Val Leu Gly Ser Gln Glu Gly Ala
                565                 570                 575

Val His Thr Ala Leu Ala Gly Ala Leu Glu Ala Glu Met Asp Gly Ala
            580                 585                 590

Lys Gly Arg Leu Ser Ser Gly His Leu Lys Cys Arg Leu Lys Met Asp
        595                 600                 605

Lys Leu Arg Leu Lys Gly Val Ser Tyr Ser Leu Cys Thr Ala Ala Phe
    610                 615                 620

Thr Phe Thr Lys Ile Pro Ala Glu Thr Leu His Gly Thr Val Thr Val
625                 630                 635                 640

Glu Val Gln Tyr Ala Gly Thr Asp Gly Pro Cys Lys Val Pro Ala Gln
                645                 650                 655

Met Ala Val Asp Met Gln Thr Leu Thr Pro Val Gly Arg Leu Ile Thr
            660                 665                 670

Ala Asn Pro Val Ile Thr Glu Ser Thr Glu Asn Ser Lys Met Met Leu
        675                 680                 685

Glu Leu Asp Pro Pro Phe Gly Asp Ser Tyr Ile Val Ile Gly Val Gly
    690                 695                 700

Glu Lys Lys Ile Thr His His Trp His Arg Ser Gly Ser Thr Ile Gly
705                 710                 715                 720

Lys Ala Phe Glu Ala Thr Val Arg Gly Ala Lys Arg Met Ala Val Leu
                725                 730                 735

Gly Asp Thr Ala Trp Asp Phe Gly Ser Val Gly Gly Ala Leu Asn Ser
            740                 745                 750

Leu Gly Lys Gly Ile His Gln Ile Phe Gly Ala Ala Phe Lys Ser Leu
        755                 760                 765

Phe Gly Gly Met Ser Trp Phe Ser Gln Ile Leu Ile Gly Thr Leu Leu
    770                 775                 780

Met Trp Leu Gly Leu Asn Thr Lys Asn Gly Ser Ile Ser Leu Met Cys
785                 790                 795                 800

Leu Ala Leu Gly Gly Val Leu Ile Phe Leu Ser Thr Ala Val Ser Ala
                805                 810                 815

Asp


<210> SEQ ID NO 59
<211> LENGTH: 125
<212> TYPE: PRT
<213> ORGANISM: Zika virus

<400> SEQUENCE: 59

Met Lys Asn Pro Lys Lys Lys Ser Gly Gly Phe Arg Ile Val Asn Met
1               5                   10                  15

Leu Lys Arg Gly Val Ala Arg Val Ser Pro Phe Gly Gly Leu Lys Arg
            20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Ile
65                  70                  75                  80
```

-continued

```
Ile Lys Lys Phe Lys Lys Asp Leu Ala Ala Met Leu Arg Ile Ile Asn
                85                  90                  95

Ala Arg Lys Glu Lys Lys Arg Arg Gly Ser Gly Ala Thr Asn Phe Ser
            100                 105                 110

Leu Leu Lys Gln Ala Gly Asp Val Glu Glu Asn Pro Gly
        115                 120                 125


<210> SEQ ID NO 60
<211> LENGTH: 111
<212> TYPE: PRT
<213> ORGANISM: Zika virus

<400> SEQUENCE: 60

Pro Gly Ala Asp Thr Ser Val Gly Ile Val Gly Leu Leu Leu Thr Thr
1               5                   10                  15

Ala Met Ala Ala Glu Val Thr Arg Arg Gly Ser Ala Tyr Tyr Met Tyr
            20                  25                  30

Leu Asp Arg Asn Asp Ala Gly Glu Ala Ile Ser Phe Pro Thr Thr Leu
        35                  40                  45

Gly Met Asn Lys Cys Tyr Ile Gln Ile Met Asp Leu Gly His Met Cys
    50                  55                  60

Asp Ala Thr Met Ser Tyr Glu Cys Pro Met Leu Asp Glu Gly Val Glu
65                  70                  75                  80

Pro Asp Asp Val Asp Cys Trp Cys Asn Thr Thr Ser Thr Trp Val Val
                85                  90                  95

Tyr Gly Thr Cys His His Lys Lys Gly Glu Ala Arg Arg Ser Arg
            100                 105                 110


<210> SEQ ID NO 61
<211> LENGTH: 76
<212> TYPE: PRT
<213> ORGANISM: Zika virus

<400> SEQUENCE: 61

Arg Ala Val Thr Leu Pro Ser His Ser Thr Arg Lys Leu Gln Thr Arg
1               5                   10                  15

Ser Gln Thr Trp Leu Glu Ser Arg Glu Tyr Thr Lys His Leu Ile Arg
            20                  25                  30

Val Glu Asn Trp Ile Phe Arg Asn Pro Gly Phe Ala Leu Ala Ala Ala
        35                  40                  45

Ala Ile Ala Trp Leu Leu Gly Ser Ser Thr Ser Gln Lys Val Ile Tyr
    50                  55                  60

Leu Val Met Ile Leu Leu Ile Ala Pro Ala Tyr Ser
65                  70                  75


<210> SEQ ID NO 62
<211> LENGTH: 505
<212> TYPE: PRT
<213> ORGANISM: Zika virus

<400> SEQUENCE: 62

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
```

```
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480
```

```
Asn Gly Ser Ile Ser Leu Met Cys Leu Ala Leu Gly Gly Val Leu Ile
                485                 490                 495

Phe Leu Ser Thr Ala Val Ser Ala Asp
            500                 505


<210> SEQ ID NO 63
<211> LENGTH: 12078
<212> TYPE: DNA
<213> ORGANISM: Zika virus

<400> SEQUENCE: 63

ataggcggcg catgagagaa gcccagacca attacctacc caaaatggag aaagttcacg     60

ttgacatcga ggaagacagc ccattcctca gagctttgca gcggagcttc ccgcagtttg    120

aggtagaagc caagcaggtc actgataatg accatgctaa tgccagagcg ttttcgcatc    180

tggcttcaaa actgatcgaa acggaggtgg acccatccga cacgatcctt gacattggaa    240

gtgcgcccgc ccgcagaatg tattctaagc acaagtatca ttgtatctgt ccgatgagat    300

gtgcggaaga tccggacaga ttgtataagt atgcaactaa gctgaagaaa aactgtaagg    360

aaataactga taaggaattg gacaagaaaa tgaaggagct cgccgccgtc atgagcgacc    420

ctgacctgga aactgagact atgtgcctcc acgacgacga gtcgtgtcgc tacgaagggc    480

aagtcgctgt ttaccaggat gtatacgcgg ttgacggacc gacaagtctc tatcaccaag    540

ccaataaggg agttagagtc gcctactgga taggctttga caccacccct tttatgttta    600

agaacttggc tggagcatat ccatcatact ctaccaactg ggccgacgaa accgtgttaa    660

cggctcgtaa cataggccta tgcagctctg acgttatgga gcggtcacgt agagggatgt    720

ccattcttag aaagaagtat ttgaaaccat ccaacaatgt tctattctct gttggctcga    780

ccatctacca cgagaagagg gacttactga ggagctggca cctgccgtct gtatttcact    840

tacgtggcaa gcaaaattac acatgtcggt gtgagactat agttagttgc gacgggtacg    900

tcgttaaaag aatagctatc agtccaggcc tgtatgggaa gccttcaggc tatgctgcta    960

cgatgcaccg cgagggattc ttgtgctgca aagtgacaga cacattgaac ggggagaggg   1020

tctcttttcc cgtgtgcacg tatgtgccag ctacattgtg tgaccaaatg actggcatac   1080

tggcaacaga tgtcagtgcg gacgacgcgc aaaaactgct ggttgggctc aaccagcgta   1140

tagtcgtcaa cggtcgcacc cagagaaaca ccaataccat gaaaaattac cttttgcccg   1200

tagtggccca ggcatttgct aggtgggcaa aggaatataa ggaagatcaa gaagatgaaa   1260

ggccactagg actacgagat agacagttag tcatggggtg ttgttgggct tttagaaggc   1320

acaagataac atctatttat aagcgcccgg atacccaaac catcatcaaa gtgaacagcg   1380

atttccactc attcgtgctg cccaggatag gcagtaacac attggagatc gggctgagaa   1440

caagaatcag gaaaatgtta gaggagcaca aggagccgtc acctctcatt accgccgagg   1500

acgtacaaga agctaagtgc gcagccgatg aggctaagga ggtgcgtgaa gccgaggagt   1560

tgcgcgcagc tctaccacct ttggcagctg atgttgagga gcccactctg gaagccgatg   1620

tcgacttgat gttacaagag gctggggccg gctcagtgga gacacctcgt ggcttgataa   1680

aggttaccag ctacgatggc gaggacaaga tcggctctta cgctgtgctt tctccgcagg   1740

ctgtactcaa gagtgaaaaa ttatcttgca tccaccctct cgctgaacaa gtcatagtga   1800

taacacactc tggccgaaaa gggcgttatg ccgtggaacc ataccatggt aaagtagtgg   1860

tgccagaggg acatgcaata cccgtccagg actttcaagc tctgagtgaa agtgccacca   1920
```

-continued ttgtgtacaa cgaacgtgag ttcgtaaaca ggtacctgca ccatattgcc acacatggag 1980
gagcgctgaa cactgatgaa gaatattaca aaactgtcaa gcccagcgag cacgacggcg 2040
aatacctgta cgacatcgac aggaaacagt gcgtcaagaa agaactagtc actgggctag 2100
ggctcacagg cgagctggtg gatcctccct tccatgaatt cgcctacgag agtctgagaa 2160
cacgaccagc cgctccttac caagtaccaa ccataggggt gtatggcgtg ccaggatcag 2220
gcaagtctgg catcattaaa agcgcagtca ccaaaaaaga tctagtggtg agcgccaaga 2280
aagaaaactg tgcagaaatt ataaggggacg tcaagaaaat gaaagggctg gacgtcaatg 2340
ccagaactgt ggactcagtg ctcttgaatg gatgcaaaca ccccgtagag accctgtata 2400
ttgacgaagc ttttgcttgt catgcaggta ctctcagagc gctcatagcc attataagac 2460
ctaaaaaggc agtgctctgc ggggatccca aacagtgcgg ttttttaac atgatgtgcc 2520
tgaaagtgca ttttaaccac gagatttgca cacaagtctt ccacaaaagc atctctcgcc 2580
gttgcactaa atctgtgact tcggtcgtct caaccttgtt ttacgacaaa aaaatgagaa 2640
cgacgaatcc gaaagagact aagattgtga ttgacactac cggcagtacc aaacctaagc 2700
aggacgatct cattctcact tgtttcagag ggtgggtgaa gcagttgcaa atagattaca 2760
aaggcaacga aataatgacg gcagctgcct ctcaagggct gacccgtaaa ggtgtgtatg 2820
ccgttcggta caaggtgaat gaaaatcctc tgtacgcacc cacctcagaa catgtgaacg 2880
tcctactgac ccgcacggag gaccgcatcg tgtggaaaac actagccggc gacccatgga 2940
taaaaacact gactgccaag taccctggga atttcactgc cacgatagag gagtggcaag 3000
cagagcatga tgccatcatg aggcacatct tggagagacc ggaccctacc gacgtcttcc 3060
agaataaggc aaacgtgtgt tgggccaagg ctttagtgcc ggtgctgaag accgctggca 3120
tagacatgac cactgaacaa tggaacactg tggattattt tgaaacggac aaagctcact 3180
cagcagagat agtattgaac caactatgcg tgaggttctt tggactcgat ctggactccg 3240
gtctattttc tgcacccact gttccgttat ccattaggaa taatcactgg gataactccc 3300
cgtcgcctaa catgtacggg ctgaataaag aagtggtccg tcagctctct cgcaggtacc 3360
cacaactgcc tcgggcagtt gccactggaa gagtctatga catgaacact ggtacactgc 3420
gcaattatga tccgcgcata aacctagtac ctgtaaacag aagactgcct catgctttag 3480
tcctccacca taatgaacac ccacagagtg actttttcttc attcgtcagc aaattgaagg 3540
gcagaactgt cctggtggtc ggggaaaagt tgtccgtccc aggcaaaatg gttgactggt 3600
tgtcagaccg gcctgaggct accttcagag ctcggctgga tttaggcatc ccaggtgatg 3660
tgcccaaata tgacataata tttgttaatg tgaggacccc atataaatac catcactatc 3720
agcagtgtga agaccatgcc attaagctta gcatgttgac caagaaagct tgtctgcatc 3780
tgaatcccgg cggaacctgt gtcagcatag gttatggtta cgctgacagg gccagcgaaa 3840
gcatcattgg tgctatagcg cggcagttca agttttcccg ggtatgcaaa ccgaaatcct 3900
cacttgaaga gacggaagtt ctgtttgtat tcattgggta cgatcgcaag gcccgtacgc 3960
acaatcctta caagctttca tcaaccttga ccaacattta tacaggttcc agactccacg 4020
aagccggatg tgcaccctca tatcatgtgg tgcgaggggga tattgccacg gccaccgaag 4080
gagtgattat aaatgctgct aacagcaaag gacaacctgg cggagggggtg tgcggagcgc 4140
tgtataagaa attcccggaa agcttcgatt tacagccgat cgaagtagga aaagcgcgac 4200
tggtcaaagg tgcagctaaa catatcattc atgccgtagg accaaacttc aacaaagttt 4260
cggaggttga aggtgacaaa cagttggcag aggcttatga gtccatcgct aagattgtca 4320

```
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
```

-continued

```
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gatgcgaggc gcagatacta gtgtcggaat tgttggcctc ctgctgacca cagctatggc   7620
agcggaggtc actagacgtg ggagtgcata ctatatgtac ttggacagaa acgatgctgg   7680
ggaggccata tcttttccaa ccacattggg gatgaataag tgttatatac agatcatgga   7740
tcttggacac atgtgtgatg ccaccatgag ctatgaatgc cctatgctgg atgagggggt   7800
ggaaccagat gacgtcgatt gttggtgcaa cacgacgtca acttgggttg tgtacggaac   7860
ctgccatcac aaaaaaggtg aagcacggag atctaggaga gctgtgacgc tccccctccca   7920
ttccactagg aagctgcaaa cgcggtcgca aacctggttg gaatcaagag aatacacaaa   7980
gcacttgatt agagtcgaaa attggatatt caggaaccct ggcttcgcgt tagcagcagc   8040
tgccatcgct tggcttttgg gaagctcaac gagccaaaaa gtcatatact tggtcatgat   8100
actgctgatt gccccggcat acagcatcag gtgcatagga gtcagcaata gggactttgt   8160
ggaaggtatg tcaggtggga cttgggttga tgttgtcttg gaacatggag gttgtgtcac   8220
cgtaatggca caggacaaac cgactgtcga catagagctg gttacaacaa cagtcagcaa   8280
catggcggag gtaagatcct actgctatga ggcatcaata tcagacatgg cttcggacag   8340
ccgctgccca acacaaggtg aagcctacct tgacaagcaa tcagacactc aatatgtctg   8400
caaaagaacg ttagtggaca gaggctgggg aaatggatgt ggactttttg gcaaagggag   8460
cctggtgaca tgcgctaagt ttgcatgctc caagaaaatg accgggaaaa gcatccagcc   8520
agagaatctg gagtaccgga taatgctgtc agttcatggc tcccagcaca gtgggatgat   8580
cgttaatgac acaggacatg aaactgatga gaatagagcg aaggttgaga taacgcccaa   8640
ttcaccaaga gccgaagcca ccctgggggg ttttggaagc ctaggacttg attgtgaacc   8700
gaggacaggc cttgactttt cagatttgta ttacttgact atgaataaca agcactggtt   8760
ggtccacaag gagtggttcc acgacattcc attaccttgg cacgctgggg cagacaccgg   8820
aactccacac tggaacaaca aagaagcact ggtagagttc aaggacgcac atgccaaaag   8880
gcaaactgtc gtggttctag ggagtcaaga aggagcagtt cacacggccc ttgctggagc   8940
tctggaggct gagatggatg gtgcaaaggg aaggctgtcc tctggccact tgaaatgtcg   9000
cctgaaaatg gataaactta gattgaaggg cgtgtcatac tccttgtgta ccgcagcgtt   9060
```

```
cacattcacc aagatcccgg ctgaaacact gcacgggaca gtcacagtgg aggtacagta   9120
cgcagggaca gatggacctt gcaaggttcc agctcagatg gcggtggaca tgcaaactct   9180
gaccccagtt gggaggttga taaccgctaa ccccgtaatc actgaaagca ctgagaactc   9240
taagatgatg ctggaacttg atccaccatt tggggactct tacattgtca taggagtcgg   9300
ggagaagaag atcacccacc actggcacag gagtggcagc accattggaa aagcatttga   9360
agccactgtg agaggtgcca agagaatggc agtcttggga gacacagcct gggactttgg   9420
atcagttgga ggcgctctca actcattggg caagggcatc catcaaattt ttggagcagc   9480
tttcaaatca ttgtttggag gaatgtcctg gttctcacaa atcctcattg gaacgttgct   9540
gatgtggttg ggtctgaaca caaagaatgg atctatttcc cttatgtgct tggccttagg   9600
gggagtgttg atcttcttat ccacagccgt ctctgctgat tgataaggcg cgcccaccca   9660
gcggccgcat acagcagcaa ttggcaagct gcttacatag aactcgcggc gattggcatg   9720
ccgccttaaa atttttattt tatttttctt ttcttttccg aatcggattt tgtttttaat   9780
atttcaaaaa aaaaaaaaaa aaaaaaaaaa aaaaaaaaaa aaaaagaaga gcgtttaaac   9840
acgtgatatc tggcctcatg ggccttcctt tcactgcccg ctttccagtc gggaaacctg   9900
tcgtgccagc tgcattaaca tggtcatagc tgtttccttg cgtattgggc gctctccgct   9960
tcctcgctca ctgactcgct gcgctcggtc gttcgggtaa agcctggggt gcctaatgag  10020
caaaaggcca gcaaaaggcc aggaaccgta aaaaggccgc gttgctggcg tttttccata  10080
ggctccgccc ccctgacgag catcacaaaa atcgacgctc aagtcagagg tggcgaaacc  10140
cgacaggact ataaagatac caggcgtttc cccctggaag ctccctcgtg cgctctcctg  10200
ttccgaccct gccgcttacc ggatacctgt ccgcctttct cccttcggga agcgtggcgc  10260
tttctcatag ctcacgctgt aggtatctca gttcggtgta ggtcgttcgc tccaagctgg  10320
gctgtgtgca cgaacccccc gttcagcccg accgctgcgc cttatccggt aactatcgtc  10380
ttgagtccaa cccggtaaga cacgacttat cgccactggc agcagccact ggtaacagga  10440
ttagcagagc gaggtatgta ggcggtgcta cagagttctt gaagtggtgg cctaactacg  10500
gctacactag aagaacagta tttggtatct gcgctctgct gaagccagtt accttcggaa  10560
aaagagttgg tagctcttga tccggcaaac aaaccaccgc tggtagcggt ggtttttttg  10620
tttgcaagca gcagattacg cgcagaaaaa aaggatctca agaagatcct ttgatctttt  10680
ctacggggtc tgacgctcag tggaacgaaa actcacgtta agggattttg gtcatgaata  10740
cacggtgcct gactgcgtta gcaatttaac tgtgataaac taccgcatta aagcttatcg  10800
atgataagct gtcaaacatg agaattctta gaaaaactca tcgagcatca aatgaaactg  10860
caatttattc atatcaggat tatcaatacc atatttttga aaaagccgtt tctgtaatga  10920
aggagaaaac tcaccgaggc agttccatag gatggcaaga tcctggtatc ggtctgcgat  10980
tccgactcgt ccaacatcaa tacaacctat taatttcccc tcgtcaaaaa taaggttatc  11040
aagtgagaaa tcaccatgag tgacgactga atccggtgag aatggcaaaa gcttatgcat  11100
ttctttccag acttgttcaa caggccagcc attacgctcg tcatcaaaat cactcgcatc  11160
aaccaaaccg ttattcattc gtgattgcgc ctgagcgaga cgaaatacgc gatcgctgtt  11220
aaaaggacaa ttacaaacag gaatcgaatg caaccggcgc aggaacactg ccagcgcatc  11280
aacaatattt tcacctgaat caggatattc ttctaatacc tggaatgctg ttttcccggg  11340
gatcgcagtg gtgagtaacc atgcatcatc aggagtacgg ataaaatgct tgatggtcgg  11400
```

aagaggcata aattccgtca gccagtttag tctgaccatc tcatctgtaa catcattggc 11460
aacgctacct ttgccatgtt tcagaaacaa ctctggcgca tcgggcttcc catacaatcg 11520
atagattgtc gcacctgatt gcccgacatt atcgcgagcc catttatacc catataaatc 11580
agcatccatg ttggaattta atcgcggcct cgagcaagac gtttcccgtt gaatatggct 11640
cataacaccc cttgtattac tgtttatgta agcagacagt tttattgttc atgagcggat 11700
acatatttga atgtatttag aaaaataaac aaataggggt tccgcgcaca tttccccgaa 11760
aagtgccacc taaattgtaa gcgttaatat tttgttaaaa ttcgcgttaa atttttgtta 11820
aatcagctca ttttttaacc aataggccga aatcggcaaa atcccttata aatcaaaaga 11880
atagaccgag atagggttga gtggccgcta cagggcgctc ccattcgcca ttcaggctgc 11940
gcaactgttg ggaagggcgt ttcggtgcgg gcctcttcgc tattacgcca gctggcgaaa 12000
gggggatgtg ctgcaaggcg attaagttgg gtaacgccag ggttttccca gtcacacgcg 12060
taatacgact cactatag 12078

<210> SEQ ID NO 64
<211> LENGTH: 12078
<212> TYPE: DNA
<213> ORGANISM: Zika virus

<400> SEQUENCE: 64
ataggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct cgccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540
ccaataaggg agttagagtc gcctactgga taggctttga caccacccct tttatgttta 600
agaacttggc tggagcatat ccatcatact ctaccaactg ggccgacgaa accgtgttaa 660
cggctcgtaa cataggccta tgcagctctg acgttatgga gcggtcacgt agagggatgt 720
ccattcttag aaagaagtat ttgaaaccat ccaacaatgt tctattctct gttggctcga 780
ccatctacca cgagaagagg gacttactga ggagctggca cctgccgtct gtatttcact 840
tacgtggcaa gcaaaattac acatgtcggt gtgagactat agttagttgc gacgggtacg 900
tcgttaaaag aatagctatc agtccaggcc tgtatgggaa gccttcaggc tatgctgcta 960
cgatgcaccg cgagggattc ttgtgctgca aagtgacaga cacattgaac ggggagaggg 1020
tctcttttcc cgtgtgcacg tatgtgccag ctacattgtg tgaccaaatg actggcatac 1080
tggcaacaga tgtcagtgcg gacgacgcgc aaaaactgct ggttgggctc aaccagcgta 1140
tagtcgtcaa cggtcgcacc cagagaaaca ccaataccat gaaaaattac cttttgcccg 1200
tagtggccca ggcatttgct aggtgggcaa aggaatataa ggaagatcaa gaagatgaaa 1260
ggccactagg actacgagat agacagttag tcatggggtg ttgttgggct tttagaaggc 1320
acaagataac atctatttat aagcgcccgg atacccaaac catcatcaaa gtgaacagcg 1380
atttccactc attcgtgctg cccaggatag gcagtaacac attggagatc gggctgagaa 1440

```
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccatagggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
```

-continued

```
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
```

-continued

```
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga cccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gatgagagga gctgacacca gcgtgggcat tgtgggcctc ctgctgacaa ccgccatggc   7620
cgctgaggtc accagaagag gcagcgccta ctacatgtac ctggacagaa acgacgctgg   7680
cgaggctatt agcttcccca ccacactcgg catgaacaag tgttacatcc agatcatgga   7740
cctgggccac atgtgcgatg ccaccatgag ctacgaatgt cctatgctgg acgaaggcgt   7800
ggagcccgac gacgtggact gttggtgcaa cacaaccagc acctgggtgg tgtacggcac   7860
ctgccatcat aagaaggggag aagccaggag aagcaggagg gctgtcacac tcccctccca   7920
ctccacaaga aagctgcaaa ccaggagcca gacctggctg gaaagcaggg agtacaccaa   7980
gcacctgatc agggtcgaga actggatctt caggaaccct ggattcgccc tcgccgctgc   8040
tgctattgcc tggctcctgg gctcctccac cagccaaaag gtgatctacc tggtgatgat   8100
cctcctgatc gcccccgcct acagcatcag gtgcatcggc gtgtccaata gggactttgt   8160
cgaaggaatg tccggcggca catgggtgga cgtcgtgctg gagcatggcg gctgtgtgac   8220
agtcatggcc caggacaaac ccaccgtgga tatcgagctg gtgacaacca cagtgtccaa   8280
catggccgag gtgaggagct actgctacga ggctagcatc agcgacatgg cttccgacag   8340
cagatgcccc acacagggcg aggcctacct cgacaaacag tccgacaccc agtacgtgtg   8400
caaaaggacc ctggtcgaca gaggatgggg caacggctgc ggcctgttcg gaaaaggaag   8460
cctggtcacc tgtgctaagt tcgcctgctc caagaagatg accggcaaga gcatccagcc   8520
```

```
cgagaacctc gagtacagga tcatgctctc cgtccatggc agccagcaca gcggaatgat   8580
cgtgaacgac accggccacg agaccgatga gaacagggcc aaggtggaaa tcacccccaa   8640
cagccctagg gctgaagcta ccctcggcgg atttggatcc ctgggcctgg attgtgaacc   8700
caggaccgga ctcgacttca gcgatctgta ctacctgacc atgaacaaca agcactggct   8760
ggtgcataag gagtggttcc atgatatccc cctgccctgg catgctggag ccgatacagg   8820
cacccctcac tggaacaaca aggaagccct ggtggagttc aaagatgccc acgccaagag   8880
acagacagtc gtcgtcctgg gcagccaaga gggcgctgtg catacagccc tggctggagc   8940
cctggaggcc gaaatggacg gcgccaaggg aaggctgtcc agcggacatc tgaagtgcag   9000
gctgaagatg gacaagctga ggctcaaggg cgtcagctac tccctgtgca ccgccgcctt   9060
tacctttaca aaaatccccg ccgagaccct ccacggcaca gtcacagtcg aggtgcagta   9120
cgctggaacc gacggacctt gtaaggtgcc cgcccaaatg gccgtggaca tgcagacact   9180
gacccctgtg ggcagactca tcacagccaa ccctgtgatc acagagtcca ccgagaacag   9240
caagatgatg ctcgagctgg atcctccttt cggcgacagc tacatcgtga tcggagtggg   9300
cgagaagaaa atcacccacc actggcacag gtccggcagc accattggca aagcctttga   9360
agccaccgtc agaggagcta aaaggatggc tgtgctgggc gacaccgctt gggacttcgg   9420
ctccgtggga ggagccctca actccctggg caagggcatt caccagattt tcggcgccgc   9480
tttcaagagc ctctttggcg gcatgtcctg gtttagccag attctcatcg gcacactgct   9540
gatgtggctg ggcctgaata ccaagaacgg cagcatcagc ctgatgtgtc tggccctggg   9600
aggcgtgctg atctttctgt ccaccgctgt cagcgccgac tgataaggcg cgcccaccca   9660
gcggccgcat acagcagcaa ttggcaagct gcttacatag aactcgcggc gattggcatg   9720
ccgccttaaa atttttattt tatttttctt ttcttttccg aatcggattt tgtttttaat   9780
atttcaaaaa aaaaaaaaaa aaaaaaaaaa aaaaaaaaaa aaaaagaaga gcgtttaaac   9840
acgtgatatc tggcctcatg ggccttcctt tcactgcccg ctttccagtc gggaaacctg   9900
tcgtgccagc tgcattaaca tggtcatagc tgtttccttg cgtattgggc gctctccgct   9960
tcctcgctca ctgactcgct gcgctcggtc gttcgggtaa agcctggggt gcctaatgag  10020
caaaaggcca gcaaaaggcc aggaaccgta aaaaggccgc gttgctggcg tttttccata  10080
ggctccgccc ccctgacgag catcacaaaa atcgacgctc aagtcagagg tggcgaaacc  10140
cgacaggact ataaagatac caggcgtttc cccctggaag ctccctcgtg cgctctcctg  10200
ttccgaccct gccgcttacc ggatacctgt ccgcctttct cccttcggga agcgtggcgc  10260
tttctcatag ctcacgctgt aggtatctca gttcggtgta ggtcgttcgc tccaagctgg  10320
gctgtgtgca cgaacccccc gttcagcccg accgctgcgc cttatccggt aactatcgtc  10380
ttgagtccaa cccggtaaga cacgacttat cgccactggc agcagccact ggtaacagga  10440
ttagcagagc gaggtatgta ggcggtgcta cagagttctt gaagtggtgg cctaactacg  10500
gctacactag aagaacagta tttggtatct gcgctctgct gaagccagtt accttcggaa  10560
aaagagttgg tagctcttga tccggcaaac aaaccaccgc tggtagcggt ggtttttttg  10620
tttgcaagca gcagattacg cgcagaaaaa aaggatctca agaagatcct ttgatctttt  10680
ctacggggtc tgacgctcag tggaacgaaa actcacgtta agggattttg gtcatgaata  10740
cacggtgcct gactgcgtta gcaatttaac tgtgataaac taccgcatta aagcttatcg  10800
atgataagct gtcaaacatg agaattctta gaaaaactca tcgagcatca aatgaaactg  10860
caatttattc atatcaggat tatcaatacc atatttttga aaagccgtt  tctgtaatga  10920
```

aggagaaaac tcaccgaggc agttccatag gatggcaaga tcctggtatc ggtctgcgat 10980
tccgactcgt ccaacatcaa tacaacctat taatttcccc tcgtcaaaaa taaggttatc 11040
aagtgagaaa tcaccatgag tgacgactga atccggtgag aatggcaaaa gcttatgcat 11100
ttctttccag acttgttcaa caggccagcc attacgctcg tcatcaaaat cactcgcatc 11160
aaccaaaccg ttattcattc gtgattgcgc ctgagcgaga cgaaatacgc gatcgctgtt 11220
aaaaggacaa ttacaaacag gaatcgaatg caaccggcgc aggaacactg ccagcgcatc 11280
aacaatattt tcacctgaat caggatattc ttctaatacc tggaatgctg ttttcccggg 11340
gatcgcagtg gtgagtaacc atgcatcatc aggagtacgg ataaaatgct tgatggtcgg 11400
aagaggcata aattccgtca gccagtttag tctgaccatc tcatctgtaa catcattggc 11460
aacgctacct ttgccatgtt tcagaaacaa ctctggcgca tcgggcttcc catacaatcg 11520
atagattgtc gcacctgatt gcccgacatt atcgcgagcc catttatacc catataaatc 11580
agcatccatg ttggaattta atcgcggcct cgagcaagac gtttcccgtt gaatatggct 11640
cataacaccc cttgtattac tgtttatgta agcagacagt tttattgttc atgagcggat 11700
acatatttga atgtatttag aaaaataaac aaataggggt tccgcgcaca tttccccgaa 11760
aagtgccacc taaattgtaa gcgttaatat tttgttaaaa ttcgcgttaa atttttgtta 11820
aatcagctca ttttttaacc aataggccga aatcggcaaa atcccttata aatcaaaaga 11880
atagaccgag atagggttga gtggccgcta cagggcgctc ccattcgcca ttcaggctgc 11940
gcaactgttg ggaagggcgt ttcggtgcgg gcctcttcgc tattacgcca gctggcgaaa 12000
gggggatgtg ctgcaaggcg attaagttgg gtaacgccag ggttttccca gtcacacgcg 12060
taatacgact cactatag 12078

<210> SEQ ID NO 65
<211> LENGTH: 12078
<212> TYPE: DNA
<213> ORGANISM: Zika virus

<400> SEQUENCE: 65
ataggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct cgccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540
ccaataaggg agttagagtc gcctactgga taggctttga caccacccct tttatgttta 600
agaacttggc tggagcatat ccatcatact ctaccaactg ggccgacgaa accgtgttaa 660
cggctcgtaa cataggccta tgcagctctg acgttatgga gcggtcacgt agagggatgt 720
ccattcttag aaagaagtat ttgaaaccat ccaacaatgt tctattctct gttggctcga 780
ccatctacca cgagaagagg gacttactga ggagctggca cctgccgtct gtatttcact 840
tacgtggcaa gcaaaattac acatgtcggt gtgagactat agttagttgc gacgggtacg 900

-continued

```
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
```

cgtcgcctaa catgtacggg ctgaataaag aagtggtccg tcagctctct cgcaggtacc 3360
cacaactgcc tcgggcagtt gccactggaa gagtctatga catgaacact ggtacactgc 3420
gcaattatga tccgcgcata aacctagtac ctgtaaacag aagactgcct catgctttag 3480
tcctccacca taatgaacac ccacagagtg acttttcttc attcgtcagc aaattgaagg 3540
gcagaactgt cctggtggtc ggggaaaagt tgtccgtccc aggcaaaatg gttgactggt 3600
tgtcagaccg gcctgaggct accttcagag ctcggctgga tttaggcatc ccaggtgatg 3660
tgcccaaata tgacataata tttgttaatg tgaggacccc atataaatac catcactatc 3720
agcagtgtga agaccatgcc attaagctta gcatgttgac caagaaagct tgtctgcatc 3780
tgaatcccgg cggaacctgt gtcagcatag gttatggtta cgctgacagg gccagcgaaa 3840
gcatcattgg tgctatagcg cggcagttca agttttcccg ggtatgcaaa ccgaaatcct 3900
cacttgaaga gacggaagtt ctgtttgtat tcattgggta cgatcgcaag gcccgtacgc 3960
acaatcctta caagctttca tcaaccttga ccaacattta tacaggttcc agactccacg 4020
aagccggatg tgcaccctca tatcatgtgg tgcgagggga tattgccacg gccaccgaag 4080
gagtgattat aaatgctgct aacagcaaag gacaacctgg cggagggg tg tgcggagcgc 4140
tgtataagaa attcccggaa agcttcgatt tacagccgat cgaagtagga aaagcgcgac 4200
tggtcaaagg tgcagctaaa catatcattc atgccgtagg accaaacttc aacaaagttt 4260
cggaggttga aggtgacaaa cagttggcag aggcttatga gtccatcgct aagattgtca 4320
acgataacaa ttacaagtca gtagcgattc cactgttgtc caccggcatc ttttccggga 4380
acaaagatcg actaacccaa tcattgaacc atttgctgac agctttagac accactgatg 4440
cagatgtagc catatactgc agggacaaga aatgggaaat gactctcaag gaagcagtgg 4500
ctaggagaga agcagtggag gagatatgca tatccgacga ctcttcagtg acagaacctg 4560
atgcagagct ggtgagggtg catccgaaga gttctttggc tggaaggaag ggctacagca 4620
caagcgatgg caaaactttc tcatatttgg aagggaccaa gtttcaccag gcggccaagg 4680
atatagcaga aattaatgcc atgtggcccg ttgcaacgga ggccaatgag caggtatgca 4740
tgtatatcct cggagaaagc atgagcagta ttaggtcgaa atgccccgtc gaagagtcgg 4800
aagcctccac accacctagc acgctgcctt gcttgtgcat ccatgccatg actccagaaa 4860
gagtacagcg cctaaaagcc tcacgtccag aacaaattac tgtgtgctca tcctttccat 4920
tgccgaagta tagaatcact ggtgtgcaga agatccaatg ctcccagcct atattgttct 4980
caccgaaagt gcctgcgtat attcatccaa ggaagtatct cgtggaaaca ccaccggtag 5040
acgagactcc ggagccatcg gcagagaacc aatccacaga ggggacacct gaacaaccac 5100
cacttataac cgaggatgag accaggacta gaacgcctga gccgatcatc atcgaagagg 5160
aagaagagga tagcataagt ttgctgtcag atggcccgac ccaccaggtg ctgcaagtcg 5220
aggcagacat tcacgggccg ccctctgtat ctagctcatc ctggtccatt cctcatgcat 5280
ccgactttga tgtggacagt ttatccatac ttgacaccct ggagggagct agcgtgacca 5340
gcggggcaac gtcagccgag actaactctt acttcgcaaa gagtatggag tttctggcgc 5400
gaccggtgcc tgcgcctcga acagtattca ggaaccctcc acatcccgct ccgcgcacaa 5460
gaacaccgtc acttgcaccc agcagggcct gctcgagaac cagcctagtt tccaccccgc 5520
caggcgtgaa tagggtgatc actagagagg agctcgaggc gcttaccccg tcacgcactc 5580
ctagcaggtc ggtctcgaga accagcctgg tctccaaccc gccaggcgta aatagggtga 5640

-continued

```
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga cccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gatgagagga gctgacacca gcgtgggcat tgtgggcctc ctgctgcccc aggcccaggc   7620
cgctgaggtc accagaagag gcagcgccta ctacatgtac ctggacagaa acgacgctgg   7680
cgaggctatt agcttcccca ccacactcgg catgaacaag tgttacatcc agatcatgga   7740
cctgggccac atgtgcgatg ccaccatgag ctacgaatgt cctatgctgg acgaaggcgt   7800
ggagcccgac gacgtggact gttggtgcaa cacaaccagc acctgggtgg tgtacggcac   7860
ctgccatcat aagaagggag aagccaggag aagcaggagg gctgtcacac tcccctccca   7920
ctccacaaga aagctgcaaa ccaggagcca gacctggctg gaaagcaggg agtacaccaa   7980
gcacctgatc agggtcgaga actggatctt caggaaccct ggattcgccc tcgccgctgc   8040
```

-continued

```
tgctattgcc tggctcctgg gctcctccac cagccaaaag gtgatctacc tggtgatgat   8100
cctcctgatc gcccccgcct acagcatcag gtgcatcggc gtgtccaata gggactttgt   8160
cgaaggaatg tccggcggca catgggtgga cgtcgtgctg gagcatggcg gctgtgtgac   8220
agtcatggcc caggacaaac ccaccgtgga tatcgagctg gtgacaacca cagtgtccaa   8280
catggccgag gtgaggagct actgctacga ggctagcatc agcgacatgg cttccgacag   8340
cagatgcccc acacagggcg aggcctacct cgacaaacag tccgacaccc agtacgtgtg   8400
caaaaggacc ctggtcgaca gaggatgggg caacggctgc ggcctgttcg gaaaaggaag   8460
cctggtcacc tgtgctaagt tcgcctgctc caagaagatg accggcaaga gcatccagcc   8520
cgagaacctc gagtacagga tcatgctctc cgtccatggc agccagcaca gcggaatgat   8580
cgtgaacgac accggccacg agaccgatga gaacagggcc aaggtggaaa tcacccccaa   8640
cagccctagg gctgaagcta ccctcggcgg atttggatcc ctgggcctgg attgtgaacc   8700
caggaccgga ctcgacttca gcgatctgta ctacctgacc atgaacaaca agcactggct   8760
ggtgcataag gagtggttcc atgatatccc cctgccctgg catgctggag ccgatacagg   8820
cacccctcac tggaacaaca aggaagccct ggtggagttc aaagatgccc acgccaagag   8880
acagacagtc gtcgtcctgg gcagccaaga gggcgctgtg catacagccc tggctggagc   8940
cctggaggcc gaaatggacg gcgccaaggg aaggctgtcc agcggacatc tgaagtgcag   9000
gctgaagatg gacaagctga ggctcaaggg cgtcagctac tccctgtgca ccgccgcctt   9060
tacctttaca aaaatccccg ccgagaccct ccacggcaca gtcacagtcg aggtgcagta   9120
cgctggaacc gacggacctt gtaaggtgcc cgcccaaatg gccgtggaca tgcagacact   9180
gacccctgtg ggcagactca tcacagccaa ccctgtgatc acagagtcca ccgagaacag   9240
caagatgatg ctcgagctgg atcctccttt cggcgacagc tacatcgtga tcggagtggg   9300
cgagaagaaa atcacccacc actggcacag gtccggcagc accattggca aagcctttga   9360
agccaccgtc agaggagcta aaaggatggc tgtgctgggc gacaccgctt gggacttcgg   9420
ctccgtggga ggagccctca actccctggg caagggcatt caccagattt tcggcgccgc   9480
tttcaagagc ctctttggcg gcatgtcctg gtttagccag attctcatcg gcacactgct   9540
gatgtggctg ggcctgaata ccaagaacgg cagcatcagc ctgatgtgtc tggccctggg   9600
aggcgtgctg atctttctgt ccaccgctgt cagcgccgac tgataaggcg cgcccaccca   9660
gcggccgcat acagcagcaa ttggcaagct gcttacatag aactcgcggc gattggcatg   9720
ccgccttaaa atttttattt tatttttctt ttcttttccg aatcggattt tgtttttaat   9780
atttcaaaaa aaaaaaaaaa aaaaaaaaaa aaaaaaaaaa aaaaagaaga gcgtttaaac   9840
acgtgatatc tggcctcatg ggccttcctt tcactgcccg ctttccagtc gggaaacctg   9900
tcgtgccagc tgcattaaca tggtcatagc tgtttccttg cgtattgggc gctctccgct   9960
tcctcgctca ctgactcgct gcgctcggtc gttcgggtaa agcctggggt gcctaatgag  10020
caaaaggcca gcaaaaggcc aggaaccgta aaaaggccgc gttgctggcg tttttccata  10080
ggctccgccc ccctgacgag catcacaaaa atcgacgctc aagtcagagg tggcgaaacc  10140
cgacaggact ataaagatac caggcgtttc cccctggaag ctccctcgtg cgctctcctg  10200
ttccgaccct gccgcttacc ggatacctgt ccgcctttct cccttcggga agcgtggcgc  10260
tttctcatag ctcacgctgt aggtatctca gttcggtgta ggtcgttcgc tccaagctgg  10320
gctgtgtgca cgaacccccc gttcagcccg accgctgcgc cttatccggt aactatcgtc  10380
```

```
ttgagtccaa cccggtaaga cacgacttat cgccactggc agcagccact ggtaacagga  10440
ttagcagagc gaggtatgta ggcggtgcta cagagttctt gaagtggtgg cctaactacg  10500
gctacactag aagaacagta tttggtatct gcgctctgct gaagccagtt accttcggaa  10560
aaagagttgg tagctcttga tccggcaaac aaaccaccgc tggtagcggt ggtttttttg  10620
tttgcaagca gcagattacg cgcagaaaaa aaggatctca agaagatcct ttgatctttt  10680
ctacggggtc tgacgctcag tggaacgaaa actcacgtta agggattttg gtcatgaata  10740
cacggtgcct gactgcgtta gcaatttaac tgtgataaac taccgcatta aagcttatcg  10800
atgataagct gtcaaacatg agaattctta gaaaaactca tcgagcatca aatgaaactg  10860
caatttattc atatcaggat tatcaatacc atatttttga aaaagccgtt tctgtaatga  10920
aggagaaaac tcaccgaggc agttccatag gatggcaaga tcctggtatc ggtctgcgat  10980
tccgactcgt ccaacatcaa tacaacctat taatttcccc tcgtcaaaaa taaggttatc  11040
aagtgagaaa tcaccatgag tgacgactga atccggtgag aatggcaaaa gcttatgcat  11100
ttctttccag acttgttcaa caggccagcc attacgctcg tcatcaaaat cactcgcatc  11160
aaccaaaccg ttattcattc gtgattgcgc ctgagcgaga cgaaatacgc gatcgctgtt  11220
aaaaggacaa ttacaaacag gaatcgaatg caaccggcgc aggaacactg ccagcgcatc  11280
aacaatattt tcacctgaat caggatattc ttctaatacc tggaatgctg ttttcccggg  11340
gatcgcagtg gtgagtaacc atgcatcatc aggagtacgg ataaaatgct tgatggtcgg  11400
aagaggcata aattccgtca gccagtttag tctgaccatc tcatctgtaa catcattggc  11460
aacgctacct ttgccatgtt tcagaaacaa ctctggcgca tcgggcttcc catacaatcg  11520
atagattgtc gcacctgatt gcccgacatt atcgcgagcc catttatacc catataaatc  11580
agcatccatg ttggaattta atcgcggcct cgagcaagac gtttcccgtt gaatatggct  11640
cataacaccc cttgtattac tgtttatgta agcagacagt tttattgttc atgagcggat  11700
acatatttga atgtatttag aaaaataaac aaataggggt tccgcgcaca tttccccgaa  11760
aagtgccacc taaattgtaa gcgttaatat tttgttaaaa ttcgcgttaa atttttgtta  11820
aatcagctca ttttttaacc aataggccga aatcggcaaa atcccttata aatcaaaaga  11880
atagaccgag atagggttga gtggccgcta cagggcgctc ccattcgcca ttcaggctgc  11940
gcaactgttg ggaagggcgt ttcggtgcgg gcctcttcgc tattacgcca gctggcgaaa  12000
gggggatgtg ctgcaaggcg attaagttgg gtaacgccag ggttttccca gtcacacgcg  12060
taatacgact cactatag                                                12078
```

<210> SEQ ID NO 66
<211> LENGTH: 12075
<212> TYPE: DNA
<213> ORGANISM: Zika virus

<400> SEQUENCE: 66

```
ataggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg gacaagaaaa tgaaggagct cgccgccgtc atgagcgacc    420
```

```
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg ttttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
```

-continued

```
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgaggggga tattgccacg gccaccgaag   4080
gagtgattat aaatgctgct aacagcaaag gacaacctgg cggagggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
```

aagaagagga tagcataagt ttgctgtcag atggcccgac ccaccaggtg ctgcaagtcg 5220
aggcagacat tcacgggccg ccctctgtat ctagctcatc ctggtccatt cctcatgcat 5280
ccgactttga tgtggacagt ttatccatac ttgacaccct ggagggagct agcgtgacca 5340
gcggggcaac gtcagccgag actaactctt acttcgcaaa gagtatggag tttctggcgc 5400
gaccggtgcc tgcgcctcga acagtattca ggaaccctcc acatcccgct ccgcgcacaa 5460
gaacaccgtc acttgcaccc agcagggcct gctcgagaac cagcctagtt tccaccccgc 5520
caggcgtgaa tagggtgatc actagagagg agctcgaggc gcttaccccg tcacgcactc 5580
ctagcaggtc ggtctcgaga accagcctgg tctccaaccc gccaggcgta aatagggtga 5640
ttacaagaga ggagtttgag gcgttcgtag cacaacaaca atgacggttt gatgcgggtg 5700
catacatctt ttcctccgac accggtcaag ggcatttaca acaaaaatca gtaaggcaaa 5760
cggtgctatc cgaagtggtg ttggagagga ccgaattgga gatttcgtat gccccgcgcc 5820
tcgaccaaga aaaagaagaa ttactacgca agaaattaca gttaaatccc acacctgcta 5880
acagaagcag ataccagtcc aggaaggtgg agaacatgaa agccataaca gctagacgta 5940
ttctgcaagg cctagggcat tatttgaagg cagaaggaaa agtggagtgc taccgaaccc 6000
tgcatcctgt tcctttgtat tcatctagtg tgaaccgtgc cttttcaagc cccaaggtcg 6060
cagtggaagc ctgtaacgcc atgttgaaag agaactttcc gactgtggct tcttactgta 6120
ttattccaga gtacgatgcc tatttggaca tggttgacgg agcttcatgc tgcttagaca 6180
ctgccagttt ttgccctgca aagctgcgca gctttccaaa gaaacactcc tatttggaac 6240
ccacaatacg atcggcagtg ccttcagcga tccagaacac gctccagaac gtcctggcag 6300
ctgccacaaa aagaaattgc aatgtcacgc aaatgagaga attgcccgta ttggattcgg 6360
cggcctttaa tgtggaatgc ttcaagaaat atgcgtgtaa taatgaatat tgggaaacgt 6420
ttaaagaaaa ccccatcagg cttactgaag aaaacgtggt aaattacatt accaaattaa 6480
aaggaccaaa agctgctgct ctttttgcga agacacataa tttgaatatg ttgcaggaca 6540
taccaatgga caggtttgta atggacttaa agagagacgt gaaagtgact ccaggaacaa 6600
aacatactga agaacggccc aaggtacagg tgatccaggc tgccgatccg ctagcaacag 6660
cgtatctgtg cggaatccac cgagagctgg ttaggagatt aaatgcggtc ctgcttccga 6720
acattcatac actgtttgat atgtcggctg aagactttga cgctattata gccgagcact 6780
tccagcctgg ggattgtgtt ctggaaactg acatcgcgtc gtttgataaa agtgaggacg 6840
acgccatggc tctgaccgcg ttaatgattc tggaagactt aggtgtggac gcagagctgt 6900
tgacgctgat tgaggcggct ttcggcgaaa tttcatcaat acatttgccc actaaaacta 6960
aatttaaatt cggagccatg atgaaatctg gaatgttcct cacactgttt gtgaacacag 7020
tcattaacat tgtaatcgca agcagagtgt tgagagaacg gctaaccgga tcaccatgtg 7080
cagcattcat tggagatgac aatatcgtga aaggagtcaa atcggacaaa ttaatggcag 7140
acaggtgcgc cacctggttg aatatggaag tcaagattat agatgctgtg gtgggcgaga 7200
aagcgcctta tttctgtgga gggtttattt tgtgtgactc cgtgaccggc acagcgtgcc 7260
gtgtggcaga ccccctaaaa aggctgttta agcttggcaa acctctggca gcagacgatg 7320
aacatgatga tgacaggaga agggcattgc atgaagagtc aacacgctgg aaccgagtgg 7380
gtattctttc agagctgtgc aaggcagtag aatcaaggta tgaaaccgta ggaacttcca 7440
tcatagttat ggccatgact actctagcta gcagtgttaa atcattcagc tacctgagag 7500

-continued

```
gggcccctat aactctctac ggctaacctg aatggactac gacatagtct agtccgccaa   7560
gatggagttc ggcctgagct gggtgttcct ggtggccatc ctggagggcg tgcattgcgc   7620
tgaggtcacc agaagaggca gcgcctacta catgtacctg gacagaaacg acgctggcga   7680
ggctattagc ttccccacca cactcggcat gaacaagtgt tacatccaga tcatggacct   7740
gggccacatg tgcgatgcca ccatgagcta cgaatgtcct atgctggacg aaggcgtgga   7800
gcccgacgac gtggactgtt ggtgcaacac aaccagcacc tgggtggtgt acggcacctg   7860
ccatcataag aagggagaag ccaggagaag caggagggct gtcacactcc cctcccactc   7920
cacaagaaag ctgcaaacca ggagccagac ctggctggaa agcagggagt acaccaagca   7980
cctgatcagg gtcgagaact ggatcttcag gaaccctgga ttcgccctcg ccgctgctgc   8040
tattgcctgg ctcctgggct cctccaccag ccaaaaggtg atctacctgg tgatgatcct   8100
cctgatcgcc cccgcctaca gcatcaggtg catcggcgtg tccaataggg actttgtcga   8160
aggaatgtcc ggcggcacat gggtggacgt cgtgctggag catggcggct gtgtgacagt   8220
catggcccag gacaaaccca ccgtggatat cgagctggtg acaaccacag tgtccaacat   8280
ggccgaggtg aggagctact gctacgaggc tagcatcagc gacatggctt ccgacagcag   8340
atgccccaca cagggcgagg cctacctcga caaacagtcc gacacccagt acgtgtgcaa   8400
aaggaccctg gtcgacagag gatggggcaa cggctgcggc ctgttcggaa aaggaagcct   8460
ggtcacctgt gctaagttcg cctgctccaa gaagatgacc ggcaagagca tccagcccga   8520
gaacctcgag tacaggatca tgctctccgt ccatggcagc cagcacagcg gaatgatcgt   8580
gaacgacacc ggccacgaga ccgatgagaa cagggccaag gtggaaatca cccccaacag   8640
ccctagggct gaagctaccc tcggcggatt tggatccctg ggcctggatt gtgaacccag   8700
gaccggactc gacttcagcg atctgtacta cctgaccatg aacaacaagc actggctggt   8760
gcataaggag tggttccatg atatccccct gccctggcat gctggagccg atacaggcac   8820
ccctcactgg aacaacaagg aagccctggt ggagttcaaa gatgcccacg ccaagagaca   8880
gacagtcgtc gtcctgggca gccaagaggg cgctgtgcat acagccctgg ctggagccct   8940
ggaggccgaa atggacggcg ccaagggaag gctgtccagc ggacatctga agtgcaggct   9000
gaagatggac aagctgaggc tcaagggcgt cagctactcc ctgtgcaccg ccgcctttac   9060
ctttacaaaa atccccgccg agaccctcca cggcacagtc acagtcgagg tgcagtacgc   9120
tggaaccgac ggaccttgta aggtgcccgc ccaaatggcc gtggacatgc agacactgac   9180
ccctgtgggc agactcatca cagccaaccc tgtgatcaca gagtccaccg agaacagcaa   9240
gatgatgctc gagctggatc ctcctttcgg cgacagctac atcgtgatcg gagtgggcga   9300
gaagaaaatc acccaccact ggcacaggtc cggcagcacc attggcaaag cctttgaagc   9360
caccgtcaga ggagctaaaa ggatggctgt gctgggcgac accgcttggg acttcggctc   9420
cgtgggagga gccctcaact ccctgggcaa gggcattcac cagattttcg gcgccgcttt   9480
caagagcctc tttggcggca tgtcctggtt tagccagatt ctcatcggca cactgctgat   9540
gtggctgggc ctgaatacca agaacggcag catcagcctg atgtgtctgg ccctgggagg   9600
cgtgctgatc tttctgtcca ccgctgtcag cgccgactga taaggcgcgc ccacccagcg   9660
gccgcataca gcagcaattg gcaagctgct tacatagaac tcgcggcgat tggcatgccg   9720
ccttaaaatt tttattttat ttttcttttc ttttccgaat cggattttgt ttttaatatt   9780
tcaaaaaaaa aaaaaaaaaa aaaaaaaaaa aaaaaaaaaa aagaagagcg tttaaacacg   9840
tgatatctgg cctcatgggc cttcctttca ctgcccgctt tccagtcggg aaacctgtcg   9900
```

```
tgccagctgc attaacatgg tcatagctgt ttccttgcgt attgggcgct ctccgcttcc   9960
tcgctcactg actcgctgcg ctcggtcgtt cgggtaaagc ctggggtgcc taatgagcaa  10020
aaggccagca aaaggccagg aaccgtaaaa aggccgcgtt gctggcgttt ttccataggc  10080
tccgcccccc tgacgagcat cacaaaaatc gacgctcaag tcagaggtgg cgaaacccga  10140
caggactata aagataccag gcgtttcccc ctggaagctc cctcgtgcgc tctcctgttc  10200
cgaccctgcc gcttaccgga tacctgtccg cctttctccc ttcgggaagc gtggcgcttt  10260
ctcatagctc acgctgtagg tatctcagtt cggtgtaggt cgttcgctcc aagctgggct  10320
gtgtgcacga accccccgtt cagcccgacc gctgcgcctt atccggtaac tatcgtcttg  10380
agtccaaccc ggtaagacac gacttatcgc cactggcagc agccactggt aacaggatta  10440
gcagagcgag gtatgtaggc ggtgctacag agttcttgaa gtggtggcct aactacggct  10500
acactagaag aacagtattt ggtatctgcg ctctgctgaa gccagttacc ttcggaaaaa  10560
gagttggtag ctcttgatcc ggcaaacaaa ccaccgctgg tagcggtggt ttttttgttt  10620
gcaagcagca gattacgcgc agaaaaaaag gatctcaaga agatcctttg atcttttcta  10680
cggggtctga cgctcagtgg aacgaaaact cacgttaagg gattttggtc atgaatacac  10740
ggtgcctgac tgcgttagca atttaactgt gataaactac cgcattaaag cttatcgatg  10800
ataagctgtc aaacatgaga attcttagaa aaactcatcg agcatcaaat gaaactgcaa  10860
tttattcata tcaggattat caataccata tttttgaaaa agccgtttct gtaatgaagg  10920
agaaaactca ccgaggcagt tccataggat ggcaagatcc tggtatcggt ctgcgattcc  10980
gactcgtcca acatcaatac aacctattaa tttcccctcg tcaaaaataa ggttatcaag  11040
tgagaaatca ccatgagtga cgactgaatc cggtgagaat ggcaaaagct tatgcatttc  11100
tttccagact tgttcaacag gccagccatt acgctcgtca tcaaaatcac tcgcatcaac  11160
caaaccgtta ttcattcgtg attgcgcctg agcgagacga aatacgcgat cgctgttaaa  11220
aggacaatta caaacaggaa tcgaatgcaa ccggcgcagg aacactgcca gcgcatcaac  11280
aatattttca cctgaatcag gatattcttc taatacctgg aatgctgttt tcccggggat  11340
cgcagtggtg agtaaccatg catcatcagg agtacggata aaatgcttga tggtcggaag  11400
aggcataaat tccgtcagcc agtttagtct gaccatctca tctgtaacat cattggcaac  11460
gctacctttg ccatgtttca gaaacaactc tggcgcatcg ggcttcccat acaatcgata  11520
gattgtcgca cctgattgcc cgacattatc gcgagcccat ttatacccat ataaatcagc  11580
atccatgttg gaatttaatc gcggcctcga gcaagacgtt tcccgttgaa tatggctcat  11640
aacacccctt gtattactgt ttatgtaagc agacagtttt attgttcatg agcggataca  11700
tatttgaatg tatttagaaa aataaacaaa taggggttcc gcgcacattt ccccgaaaag  11760
tgccacctaa attgtaagcg ttaatatttt gttaaaattc gcgttaaatt tttgttaaat  11820
cagctcattt tttaaccaat aggccgaaat cggcaaaatc ccttataaat caaaagaata  11880
gaccgagata gggttgagtg gccgctacag ggcgctccca ttcgccattc aggctgcgca  11940
actgttggga agggcgtttc ggtgcgggcc tcttcgctat tacgccagct ggcgaaaggg  12000
ggatgtgctg caaggcgatt aagttgggta acgccagggt tttcccagtc acacgcgtaa  12060
tacgactcac tatag                                                   12075
```

<210> SEQ ID NO 67
<211> LENGTH: 12384
<212> TYPE: DNA

<213> ORGANISM: Zika virus

<400> SEQUENCE: 67
ataggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct cgccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540
ccaataaggg agttagagtc gcctactgga taggctttga caccacccct tttatgttta 600
agaacttggc tggagcatat ccatcatact ctaccaactg ggccgacgaa accgtgttaa 660
cggctcgtaa cataggccta tgcagctctg acgttatgga gcggtcacgt agagggatgt 720
ccattcttag aaagaagtat ttgaaaccat ccaacaatgt tctattctct gttggctcga 780
ccatctacca cgagaagagg gacttactga ggagctggca cctgccgtct gtatttcact 840
tacgtggcaa gcaaaattac acatgtcggt gtgagactat agttagttgc gacgggtacg 900
tcgttaaaag aatagctatc agtccaggcc tgtatgggaa gccttcaggc tatgctgcta 960
cgatgcaccg cgagggattc ttgtgctgca aagtgacaga cacattgaac ggggagaggg 1020
tctcttttcc cgtgtgcacg tatgtgccag ctacattgtg tgaccaaatg actggcatac 1080
tggcaacaga tgtcagtgcg gacgacgcgc aaaaactgct ggttgggctc aaccagcgta 1140
tagtcgtcaa cggtcgcacc cagagaaaca ccaataccat gaaaaattac cttttgcccg 1200
tagtggccca ggcatttgct aggtgggcaa aggaatataa ggaagatcaa gaagatgaaa 1260
ggccactagg actacgagat agacagttag tcatggggtg ttgttgggct tttagaaggc 1320
acaagataac atctatttat aagcgcccgg atacccaaac catcatcaaa gtgaacagcg 1380
atttccactc attcgtgctg cccaggatag gcagtaacac attggagatc gggctgagaa 1440
caagaatcag gaaaatgtta gaggagcaca aggagccgtc acctctcatt accgccgagg 1500
acgtacaaga agctaagtgc gcagccgatg aggctaagga ggtgcgtgaa gccgaggagt 1560
tgcgcgcagc tctaccacct ttggcagctg atgttgagga gcccactctg gaagccgatg 1620
tcgacttgat gttacaagag gctggggccg gctcagtgga gacacctcgt ggcttgataa 1680
aggttaccag ctacgatggc gaggacaaga tcggctctta cgctgtgctt tctccgcagg 1740
ctgtactcaa gagtgaaaaa ttatcttgca tccaccctct cgctgaacaa gtcatagtga 1800
taacacactc tggccgaaaa gggcgttatg ccgtggaacc ataccatggt aaagtagtgg 1860
tgccagaggg acatgcaata cccgtccagg actttcaagc tctgagtgaa agtgccacca 1920
ttgtgtacaa cgaacgtgag ttcgtaaaca ggtacctgca ccatattgcc acacatggag 1980
gagcgctgaa cactgatgaa gaatattaca aaactgtcaa gcccagcgag cacgacggcg 2040
aatacctgta cgacatcgac aggaaacagt gcgtcaagaa agaactagtc actgggctag 2100
ggctcacagg cgagctggtg gatcctccct tccatgaatt cgcctacgag agtctgagaa 2160
cacgaccagc cgctccttac caagtaccaa ccataggggt gtatggcgtg ccaggatcag 2220
gcaagtctgg catcattaaa agcgcagtca ccaaaaaaga tctagtggtg agcgccaaga 2280

-continued

```
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
```

-continued

```
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
```

```
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gatgaagaat cctaagaaaa agtccggcgg attcaggatc gtgaatatgc tgaagagggg   7620
cgtggccagg gtctcccctt ttggaggcct gaaaaggctg cctgctggac tgctgctggg   7680
acacggcccc atcaggatgg tcctggccat cctcgccttc ctcagattca ccgccatcaa   7740
gccctccctc ggcctgatta acaggtgggg cagcgtcggc aagaaagaag ccatggaaat   7800
cattaagaag ttcaaaaaag acctggccgc catgctgagg atcatcaatg ccaggaagga   7860
gaagaagagg aggggagctg atacctccgt gggcatcgtg ggactgctgc tcaccacagc   7920
catggccgcc gaggtcacca gaagaggcag cgcttattac atgtacctgg acagaaatga   7980
cgccggcgaa gctatcagct tccctaccac cctgggcatg aacaagtgct acatccagat   8040
catggacctg ggccacatgt gcgatgccac catgtcctac gagtgcccca tgctcgacga   8100
aggagtggag cctgacgacg tggattgttg gtgcaacacc acctccacat gggtggtcta   8160
tggcacctgc catcacaaga aaggcgaagc caggaggtcc aggagggctg tgaccctgcc   8220
cagccactcc accaggaagc tgcaaacaag atcccagacc tggctggaat ccagggagta   8280
caccaagcac ctgatcaggg tggagaactg gattttcagg aatcccggct tcgccctggc   8340
cgctgccgcc atcgcttggc tgctcggcag cagcacctcc cagaaagtga tttacctggt   8400
gatgatcctg ctcatcgccc ccgcctacag catcagatgc atcggagtga gcaacaggga   8460
tttcgtggag ggcatgtccg gaggaacatg ggtggatgtg gtgctggaac atggcggctg   8520
cgtgacagtg atggcccagg acaagcccac agtggacatc gagctggtga ccaccacagt   8580
gtccaatatg gccgaggtca ggagctattg ctacgaggct agcatctccg acatggcttc   8640
cgacagcagg tgtcccacac agggcgaggc ttatctggac aagcagtccg atacccagta   8700
cgtgtgcaaa aggaccctgg tggatagagg atggggaaac ggctgtggcc tgttcggcaa   8760
gggctccctg gtgacctgtg ctaaatttgc ctgctccaag aagatgaccg gcaagtccat   8820
ccaacctgag aacctggagt acaggatcat gctgtccgtg cacggcagcc aacatagcgg   8880
catgatcgtg aatgacaccg gacacgaaac cgacgaaaac agggccaagg tggagattac   8940
ccccaatagc cccagagctg aggccacact gggcggcttt ggatccctcg gcctggattg   9000
tgagcccagg accggcctcg acttctccga tctgtattac ctgaccatga acaacaagca   9060
ttggctcgtg cacaaagagt ggtttcacga cattcccctg ccttggcacg ctggcgccga   9120
tacaggaacc ccccactgga acaacaagga ggctctggtc gaatttaaag acgcccatgc   9180
caaaagacag acagtcgtgg tgctgggctc ccaagaggga gccgtgcata cagccctggc   9240
cggagccctc gaggctgaaa tggacggagc taaaggcagg ctgtccagcg gacacctgaa   9300
gtgcaggctc aagatggaca agctcagact caagggagtg agctatagcc tgtgtacagc   9360
```

-continued

```
cgccttcaca ttcaccaaaa tccccgccga aaccctgcac ggcacagtga ccgtggaggt   9420
ccagtacgcc ggcacagacg gcccttgcaa agtgcccgcc cagatggctg tcgacatgca   9480
gacactgacc cctgtgggca ggctgattac cgctaacccc gtgattaccg agagcacaga   9540
gaacagcaag atgatgctgg agctggaccc tcctttcggc gattcctaca tcgtgatcgg   9600
agtgggcgag aaaaagatca cccaccattg gcacaggtcc ggctccacaa ttggcaaggc   9660
ctttgaggcc accgtgaggg gagctaagag gatggccgtg ctcggcgaca cagcctggga   9720
tttcggaagc gtgggaggcg ccctgaattc cctcggcaag ggcatccatc agatcttcgg   9780
cgctgccttc aagtccctct tcggaggcat gagctggttc agccagatcc tgatcggaac   9840
cctcctgatg tggctgggcc tgaacaccaa gaacggatcc attagcctga tgtgtctcgc   9900
cctgggcggc gtgctgatct tcctgtccac cgccgtgtcc gccgattgat aaggcgcgcc   9960
cacccagcgg ccgcatacag cagcaattgg caagctgctt acatagaact cgcggcgatt  10020
ggcatgccgc cttaaaattt ttattttatt tttctttct tttccgaatc ggattttgtt  10080
tttaatattt caaaaaaaaa aaaaaaaaaa aaaaaaaaaa aaaaaaaaaa agaagagcgt  10140
ttaaacacgt gatatctggc ctcatgggcc ttcctttcac tgcccgcttt ccagtcggga  10200
aacctgtcgt gccagctgca ttaacatggt catagctgtt tccttgcgta ttgggcgctc  10260
tccgcttcct cgctcactga ctcgctgcgc tcggtcgttc gggtaaagcc tggggtgcct  10320
aatgagcaaa aggccagcaa aaggccagga accgtaaaaa ggccgcgttg ctggcgtttt  10380
tccataggct ccgcccccct gacgagcatc acaaaaatcg acgctcaagt cagaggtggc  10440
gaaacccgac aggactataa agataccagg cgtttccccc tggaagctcc ctcgtgcgct  10500
ctcctgttcc gaccctgccg cttaccggat acctgtccgc ctttctccct tcgggaagcg  10560
tggcgctttc tcatagctca cgctgtaggt atctcagttc ggtgtaggtc gttcgctcca  10620
agctgggctg tgtgcacgaa ccccccgttc agcccgaccg ctgcgcctta tccggtaact  10680
atcgtcttga gtccaacccg gtaagacacg acttatcgcc actggcagca gccactggta  10740
acaggattag cagagcgagg tatgtaggcg gtgctacaga gttcttgaag tggtggccta  10800
actacggcta cactagaaga acagtatttg gtatctgcgc tctgctgaag ccagttacct  10860
tcggaaaaag agttggtagc tcttgatccg gcaaacaaac caccgctggt agcggtggtt  10920
tttttgtttg caagcagcag attacgcgca gaaaaaaagg atctcaagaa gatcctttga  10980
tcttttctac ggggtctgac gctcagtgga acgaaaactc acgttaaggg attttggtca  11040
tgaatacacg gtgcctgact gcgttagcaa tttaactgtg ataaactacc gcattaaagc  11100
ttatcgatga taagctgtca aacatgagaa ttcttagaaa aactcatcga gcatcaaatg  11160
aaactgcaat ttattcatat caggattatc aataccatat ttttgaaaaa gccgtttctg  11220
taatgaagga gaaaactcac cgaggcagtt ccataggatg gcaagatcct ggtatcggtc  11280
tgcgattccg actcgtccaa catcaataca acctattaat ttcccctcgt caaaaataag  11340
gttatcaagt gagaaatcac catgagtgac gactgaatcc ggtgagaatg gcaaaagctt  11400
atgcatttct ttccagactt gttcaacagg ccagccatta cgctcgtcat caaaatcact  11460
cgcatcaacc aaaccgttat tcattcgtga ttgcgcctga gcgagacgaa atacgcgatc  11520
gctgttaaaa ggacaattac aaacaggaat cgaatgcaac cggcgcagga acactgccag  11580
cgcatcaaca atattttcac ctgaatcagg atattcttct aatacctgga atgctgtttt  11640
cccggggatc gcagtggtga gtaaccatgc atcatcagga gtacggataa aatgcttgat  11700
ggtcggaaga ggcataaatt ccgtcagcca gtttagtctg accatctcat ctgtaacatc  11760
```

attggcaacg ctacctttgc catgtttcag aaacaactct ggcgcatcgg gcttcccata 11820
caatcgatag attgtcgcac ctgattgccc gacattatcg cgagcccatt tatacccata 11880
taaatcagca tccatgttgg aatttaatcg cggcctcgag caagacgttt cccgttgaat 11940
atggctcata acaccccttg tattactgtt tatgtaagca gacagtttta ttgttcatga 12000
gcggatacat atttgaatgt atttagaaaa ataaacaaat aggggttccg cgcacatttc 12060
cccgaaaagt gccacctaaa ttgtaagcgt taatattttg ttaaaattcg cgttaaattt 12120
ttgttaaatc agctcatttt ttaaccaata ggccgaaatc ggcaaaatcc cttataaatc 12180
aaaagaatag accgagatag ggttgagtgg ccgctacagg gcgctcccat tcgccattca 12240
ggctgcgcaa ctgttgggaa gggcgtttcg gtgcgggcct cttcgctatt acgccagctg 12300
gcgaaagggg gatgtgctgc aaggcgatta agttgggtaa cgccagggtt ttcccagtca 12360
cacgcgtaat acgactcact atag 12384

<210> SEQ ID NO 68
<211> LENGTH: 12384
<212> TYPE: DNA
<213> ORGANISM: Zika virus

<400> SEQUENCE: 68
ataggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct cgccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540
ccaataaggg agttagagtc gcctactgga taggctttga caccacccct tttatgttta 600
agaacttggc tggagcatat ccatcatact ctaccaactg ggccgacgaa accgtgttaa 660
cggctcgtaa cataggccta tgcagctctg acgttatgga gcggtcacgt agagggatgt 720
ccattcttag aaagaagtat ttgaaaccat ccaacaatgt tctattctct gttggctcga 780
ccatctacca cgagaagagg gacttactga ggagctggca cctgccgtct gtatttcact 840
tacgtggcaa gcaaaattac acatgtcggt gtgagactat agttagttgc gacgggtacg 900
tcgttaaaag aatagctatc agtccaggcc tgtatgggaa gccttcaggc tatgctgcta 960
cgatgcaccg cgagggattc ttgtgctgca aagtgacaga cacattgaac ggggagaggg 1020
tctcttttcc cgtgtgcacg tatgtgccag ctacattgtg tgaccaaatg actggcatac 1080
tggcaacaga tgtcagtgcg gacgacgcgc aaaaactgct ggttgggctc aaccagcgta 1140
tagtcgtcaa cggtcgcacc cagagaaaca ccaataccat gaaaaattac cttttgcccg 1200
tagtggccca ggcatttgct aggtgggcaa aggaatataa ggaagatcaa gaagatgaaa 1260
ggccactagg actacgagat agacagttag tcatggggtg ttgttgggct tttagaaggc 1320
acaagataac atctatttat aagcgcccgg atacccaaac catcatcaaa gtgaacagcg 1380
atttccactc attcgtgctg cccaggatag gcagtaacac attggagatc gggctgagaa 1440

-continued

```
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccatagggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
```

```
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
```

-continued

```
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gatgaagaat cccaagaaaa agagcggcgg cttcagaatc gtgaacatgc tgaagagggg   7620
agtggccaga gtgtcccccct ttggcggcct gaaaagactc cctgccggcc tgctcctggg   7680
acatggccct atcaggatgg tcctggccat tctggctttc ctgaggttca cagccatcaa   7740
gcctagcctg ggcctgatta acaggtgggg cagcgtcggc aagaaggaag ccatggagat   7800
tattaagaag ttcaagaaag acctcgctgc catgctgagg atcatcaatg ccaggaagga   7860
gaagaaaagg aggggcgctg acacaagcgt gggaatcgtg ggactgctgc tcccccaggc   7920
ccaggctgct gaagtgacca gaaggggctc cgcctactat atgtacctcg acaggaacga   7980
cgccggagag gccatcagct tccctaccac cctgggaatg aacaaatgct acatccagat   8040
catggacctc ggccacatgt gcgacgccac catgagctac gaatgcccca tgctggacga   8100
gggcgtggag cctgacgatg tggactgctg gtgcaacaca accagcacct gggtggtcta   8160
cggcacctgt caccacaaga aaggagaggc cagaaggtcc aggagggccg tcaccctgcc   8220
tagccacagc accagaaagc tgcagaccag gagccagacc tggctggaga gcagagagta   8280
caccaaacac ctcatcaggg tggagaactg gatttttagg aatcctggct ttgccctcgc   8340
tgccgccgct atcgcttggc tcctcggaag cagcaccagc cagaaggtca tctatctcgt   8400
gatgatcctg ctcatcgctc ccgcttactc catcaggtgc atcggcgtga gcaacagaga   8460
cttcgtggag ggaatgtccg gcggaacctg ggtggatgtg gtgctcgagc acggcggatg   8520
cgtcaccgtg atggcccaag ataagcctac cgtggacatc gaactggtga caacaaccgt   8580
```

```
gtccaacatg gccgaggtga gaagctactg ttacgaggcc tccatcagcg acatggcctc   8640
cgactccagg tgccctaccc agggagaggc ttacctggac aagcaatccg acacccagta   8700
cgtgtgtaag aggaccctgg tcgatagagg ctggggcaat ggctgtggac tgttcggcaa   8760
gggaagcctg gtgacctgcg ctaagttcgc ctgctccaaa aagatgaccg gcaagagcat   8820
ccagcccgag aacctggagt acagaatcat gctgtccgtg cacggcagcc agcacagcgg   8880
catgattgtg aacgacaccg gacacgaaac cgacgagaac agggccaaag tggagatcac   8940
ccccaatagc cccagggctg aagctacact gggaggattt ggcagcctgg gcctggattg   9000
tgagcctagg accggactgg atttcagcga tctgtactat ctgaccatga ataacaagca   9060
ctggctggtg cacaaggagt ggtttcacga catccctctg ccctggcacg ctggagccga   9120
tacaggcacc ccccactgga acaataagga ggccctcgtg gaattcaagg acgcccacgc   9180
caagagacaa accgtcgtgg tgctgggaag ccaggaaggc gccgtgcata ccgccctcgc   9240
cggcgctctc gaggctgaga tggacggagc caagggcaga ctgagcagcg gacatctcaa   9300
gtgcaggctg aagatggaca agctcaggct gaaaggagtc tcctacagcc tgtgcaccgc   9360
cgccttcaca tttaccaaaa tccccgccga gaccctccac ggaaccgtca cagtggaagt   9420
gcaatacgcc ggcacagatg gcccctgtaa ggtgcccgcc cagatggccg tggatatgca   9480
gaccctgacc cctgtcggca ggctgattac cgccaacccct gtgatcaccg agtccaccga   9540
gaacagcaaa atgatgctgg agctggatcc ccccttcggc gactcctaca ttgtgatcgg   9600
cgtgggcgag aagaaaatta cccatcactg gcatagaagc ggcagcacaa tcggcaaggc   9660
ctttgaggcc acagtgagag gcgccaaaag aatggccgtg ctgggagata cagcttggga   9720
ttttggatcc gtgggcggcg ccctgaactc cctgggcaaa ggaatccatc agatcttcgg   9780
cgctgctttc aagagcctct ttggcggcat gtcctggttc tcccaaatcc tgatcggcac   9840
actcctgatg tggctgggcc tcaacacaaa aaacggcagc atcagcctga tgtgcctcgc   9900
cctcggaggc gtgctgatct tcctgtccac cgctgtgagc gctgattgat aaggcgcgcc   9960
cacccagcgg ccgcatacag cagcaattgg caagctgctt acatagaact cgcggcgatt  10020
ggcatgccgc cttaaaattt ttattttatt tttctttttct tttccgaatc ggattttgtt  10080
tttaatattt caaaaaaaaa aaaaaaaaaa aaaaaaaaaa aaaaaaaaaa agaagagcgt  10140
ttaaacacgt gatatctggc ctcatgggcc ttcctttcac tgcccgcttt ccagtcggga  10200
aacctgtcgt gccagctgca ttaacatggt catagctgtt tccttgcgta ttgggcgctc  10260
tccgcttcct cgctcactga ctcgctgcgc tcggtcgttc gggtaaagcc tggggtgcct  10320
aatgagcaaa aggccagcaa aaggccagga accgtaaaaa ggccgcgttg ctggcgtttt  10380
tccataggct ccgcccccct gacgagcatc acaaaaatcg acgctcaagt cagaggtggc  10440
gaaacccgac aggactataa agataccagg cgtttccccc tggaagctcc ctcgtgcgct  10500
ctcctgttcc gaccctgccg cttaccggat acctgtccgc ctttctccct tcgggaagcg  10560
tggcgctttc tcatagctca cgctgtaggt atctcagttc ggtgtaggtc gttcgctcca  10620
agctgggctg tgtgcacgaa ccccccgttc agcccgaccg ctgcgcctta tccggtaact  10680
atcgtcttga gtccaacccg gtaagacacg acttatcgcc actggcagca gccactggta  10740
acaggattag cagagcgagg tatgtaggcg gtgctacaga gttcttgaag tggtggccta  10800
actacggcta cactagaaga acagtatttg gtatctgcgc tctgctgaag ccagttacct  10860
tcggaaaaag agttggtagc tcttgatccg gcaaacaaac caccgctggt agcggtggtt  10920
```

```
tttttgtttg caagcagcag attacgcgca gaaaaaaagg atctcaagaa gatcctttga  10980

tcttttctac ggggtctgac gctcagtgga acgaaaactc acgttaaggg attttggtca  11040

tgaatacacg gtgcctgact gcgttagcaa tttaactgtg ataaactacc gcattaaagc  11100

ttatcgatga taagctgtca aacatgagaa ttcttagaaa aactcatcga gcatcaaatg  11160

aaactgcaat ttattcatat caggattatc aataccatat ttttgaaaaa gccgtttctg  11220

taatgaagga gaaaactcac cgaggcagtt ccataggatg gcaagatcct ggtatcggtc  11280

tgcgattccg actcgtccaa catcaataca acctattaat ttcccctcgt caaaaataag  11340

gttatcaagt gagaaatcac catgagtgac gactgaatcc ggtgagaatg gcaaaagctt  11400

atgcatttct ttccagactt gttcaacagg ccagccatta cgctcgtcat caaaatcact  11460

cgcatcaacc aaaccgttat tcattcgtga ttgcgcctga gcgagacgaa atacgcgatc  11520

gctgttaaaa ggacaattac aaacaggaat cgaatgcaac cggcgcagga acactgccag  11580

cgcatcaaca atattttcac ctgaatcagg atattcttct aatacctgga atgctgtttt  11640

cccggggatc gcagtggtga gtaaccatgc atcatcagga gtacggataa aatgcttgat  11700

ggtcggaaga ggcataaatt ccgtcagcca gtttagtctg accatctcat ctgtaacatc  11760

attggcaacg ctacctttgc catgtttcag aaacaactct ggcgcatcgg gcttcccata  11820

caatcgatag attgtcgcac ctgattgccc gacattatcg cgagcccatt tatacccata  11880

taaatcagca tccatgttgg aatttaatcg cggcctcgag caagacgttt cccgttgaat  11940

atggctcata acaccccttg tattactgtt tatgtaagca gacagtttta ttgttcatga  12000

gcggatacat atttgaatgt atttagaaaa ataaacaaat aggggttccg cgcacatttc  12060

cccgaaaagt gccacctaaa ttgtaagcgt taatattttg ttaaaattcg cgttaaattt  12120

ttgttaaatc agctcatttt ttaaccaata ggccgaaatc ggcaaaatcc cttataaatc  12180

aaaagaatag accgagatag ggttgagtgg ccgctacagg gcgctcccat tcgccattca  12240

ggctgcgcaa ctgttgggaa gggcgtttcg gtgcgggcct cttcgctatt acgccagctg  12300

gcgaaagggg gatgtgctgc aaggcgatta agttgggtaa cgccagggtt ttcccagtca  12360

cacgcgtaat acgactcact atag                                         12384
```

<210> SEQ ID NO 69
<211> LENGTH: 12450
<212> TYPE: DNA
<213> ORGANISM: Zika virus

<400> SEQUENCE: 69

```
ataggcggcg catgagagaa gcccagacca attacctacc caaaatggag aaagttcacg     60

ttgacatcga ggaagacagc ccattcctca gagctttgca gcggagcttc ccgcagtttg    120

aggtagaagc caagcaggtc actgataatg accatgctaa tgccagagcg ttttcgcatc    180

tggcttcaaa actgatcgaa acggaggtgg acccatccga cacgatcctt gacattggaa    240

gtgcgcccgc ccgcagaatg tattctaagc acaagtatca ttgtatctgt ccgatgagat    300

gtgcggaaga tccggacaga ttgtataagt atgcaactaa gctgaagaaa aactgtaagg    360

aaataactga taaggaattg gacaagaaaa tgaaggagct cgccgccgtc atgagcgacc    420

ctgacctgga aactgagact atgtgcctcc acgacgacga gtcgtgtcgc tacgaagggc    480

aagtcgctgt ttaccaggat gtatacgcgg ttgacggacc gacaagtctc tatcaccaag    540

ccaataaggg agttagagtc gcctactgga taggctttga caccacccct tttatgttta    600

agaacttggc tggagcatat ccatcatact ctaccaactg ggccgacgaa accgtgttaa    660
```

-continued

```
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
```

-continued

```
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgaggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
```

gaccggtgcc tgcgcctcga acagtattca ggaaccctcc acatcccgct ccgcgcacaa 5460
gaacaccgtc acttgcaccc agcagggcct gctcgagaac cagcctagtt tccaccccgc 5520
caggcgtgaa tagggtgatc actagagagg agctcgaggc gcttaccccg tcacgcactc 5580
ctagcaggtc ggtctcgaga accagcctgg tctccaaccc gccaggcgta aatagggtga 5640
ttacaagaga ggagtttgag gcgttcgtag cacaacaaca atgacggttt gatgcgggtg 5700
catacatctt ttcctccgac accggtcaag ggcatttaca acaaaaatca gtaaggcaaa 5760
cggtgctatc cgaagtggtg ttggagagga ccgaattgga gatttcgtat gccccgcgcc 5820
tcgaccaaga aaaagaagaa ttactacgca agaaattaca gttaaatccc acacctgcta 5880
acagaagcag ataccagtcc aggaaggtgg agaacatgaa agccataaca gctagacgta 5940
ttctgcaagg cctagggcat tatttgaagg cagaaggaaa agtggagtgc taccgaaccc 6000
tgcatcctgt tcctttgtat tcatctagtg tgaaccgtgc cttttcaagc cccaaggtcg 6060
cagtggaagc ctgtaacgcc atgttgaaag agaactttcc gactgtggct tcttactgta 6120
ttattccaga gtacgatgcc tatttggaca tggttgacgg agcttcatgc tgcttagaca 6180
ctgccagttt ttgccctgca aagctgcgca gctttccaaa gaaacactcc tatttggaac 6240
ccacaatacg atcggcagtg ccttcagcga tccagaacac gctccagaac gtcctggcag 6300
ctgccacaaa aagaaattgc aatgtcacgc aaatgagaga attgcccgta ttggattcgg 6360
cggcctttaa tgtggaatgc ttcaagaaat atgcgtgtaa taatgaatat tgggaaacgt 6420
ttaaagaaaa ccccatcagg cttactgaag aaaacgtggt aaattacatt accaaattaa 6480
aaggaccaaa agctgctgct ctttttgcga agacacataa tttgaatatg ttgcaggaca 6540
taccaatgga caggtttgta atggacttaa agagagacgt gaaagtgact ccaggaacaa 6600
aacatactga agaacggccc aaggtacagg tgatccaggc tgccgatccg ctagcaacag 6660
cgtatctgtg cggaatccac cgagagctgg ttaggagatt aaatgcggtc ctgcttccga 6720
acattcatac actgtttgat atgtcggctg aagactttga cgctattata gccgagcact 6780
tccagcctgg ggattgtgtt ctggaaactg acatcgcgtc gtttgataaa agtgaggacg 6840
acgccatggc tctgaccgcg ttaatgattc tggaagactt aggtgtggac gcagagctgt 6900
tgacgctgat tgaggcggct ttcggcgaaa tttcatcaat acatttgccc actaaaacta 6960
aatttaaatt cggagccatg atgaaatctg gaatgttcct cacactgttt gtgaacacag 7020
tcattaacat tgtaatcgca agcagagtgt tgagagaacg gctaaccgga tcaccatgtg 7080
cagcattcat tggagatgac aatatcgtga aaggagtcaa atcggacaaa ttaatggcag 7140
acaggtgcgc cacctggttg aatatggaag tcaagattat agatgctgtg gtgggcgaga 7200
aagcgcctta tttctgtgga gggtttattt tgtgtgactc cgtgaccggc acagcgtgcc 7260
gtgtggcaga ccccctaaaa aggctgttta agcttggcaa acctctggca gcagacgatg 7320
aacatgatga tgacaggaga agggcattgc atgaagagtc aacacgctgg aaccgagtgg 7380
gtattctttc agagctgtgc aaggcagtag aatcaaggta tgaaaccgta ggaacttcca 7440
tcatagttat ggccatgact actctagcta gcagtgttaa atcattcagc tacctgagag 7500
gggcccctat aactctctac ggctaacctg aatggactac gacatagtct agtccgccaa 7560
gatgaagaac cccaagaaga aaagcggcgg attcaggatt gtgaacatgc tgaagagggg 7620
cgtggccagg gtgtcccctt ttggcggcct gaagagactg cctgctggac tgctcctggg 7680
ccacggacct atcaggatgg tgctcgccat cctggctttc ctcaggttta cagccatcaa 7740
acccagcctc ggcctgatca acagatgggg aagcgtgggc aagaaggagg ccatggagat 7800
catcaagaag tttaagaagg atctggccgc catgctgaga atcatcaacg ccaggaagga 7860
gaagaaaaga aggggctccg gagccacaaa cttcagcctg ctgaaacaag ccggcgacgt 7920
cgaagaaaat cccggccccg gcgctgacac ctccgtcgga atcgtgggcc tgctgctgac 7980
aaccgctatg gccgctgagg tgaccaggag aggctccgcc tactacatgt acctggatag 8040
aaatgacgcc ggcgaggcca tctcctttcc caccaccctc ggcatgaaca agtgctacat 8100
ccaaatcatg gacctcggcc atatgtgcga cgctaccatg agctacgaat gccctatgct 8160
ggacgagggc gtggagcctg atgacgtgga ctgttggtgc aataccacca gcacctgggt 8220
ggtgtatggc acatgccacc acaagaaagg cgaggccaga aggtccagga gggccgtgac 8280
actgcccagc cacagcacca gaaagctgca gacaagaagc cagacctggc tcgagagcag 8340
ggagtatacc aagcacctga ttagagtcga gaactggatc ttcagaaatc ccggcttcgc 8400
tctggctgct gccgccattg cttggctgct gggctccagc acctcccaga aggtgattta 8460
cctggtcatg atcctgctga tcgcccctgc ctactccatt agatgcatcg gcgtctccaa 8520
cagagacttc gtggaaggaa tgtccggcgg cacatgggtc gatgtggtgc tggagcacgg 8580
cggctgcgtg acagtcatgg cccaggacaa gcctaccgtg gacatcgagc tggtgacaac 8640
caccgtctcc aacatggccg aagtgaggtc ctactgctac gaggccagca tttccgacat 8700
ggcttccgac tccaggtgcc ctacccaggg cgaggcctac ctcgacaagc agagcgacac 8760
ccagtacgtc tgcaaaagaa ccctggtgga caggggctgg ggcaatggat gcggcctgtt 8820
tggcaagggc tccctcgtga catgtgccaa gttcgcttgc agcaagaaga tgaccggcaa 8880
gtccatccag cccgagaatc tcgagtacag gatcatgctc tccgtgcacg gcagccagca 8940
ctccggcatg attgtgaatg acacaggcca tgagaccgat gaaaataggg ccaaggtgga 9000
gatcacccct aacagcccta gggccgaagc tacactgggc ggattcggct ccctcggcct 9060
cgactgtgag cccaggacag gcctcgactt cagcgacctg tactacctca ccatgaataa 9120
taaacactgg ctggtgcaca aagagtggtt ccacgacatc cccctgccct ggcatgccgg 9180
agccgatacc ggaacacccc actggaacaa caaggaagcc ctggtcgagt tcaaggacgc 9240
ccacgccaag aggcaaaccg tggtggtgct gggatcccag gagggagccg tgcatacagc 9300
tctcgccggc gctctggagg ccgaaatgga cggagccaaa ggcaggctgt ccagcggcca 9360
cctgaaatgc aggctcaaga tggacaagct cagactgaag ggagtgtcct acagcctctg 9420
caccgccgcc tttacctta ccaagatccc cgccgagacc ctccacggaa ccgtgaccgt 9480
cgaagtccag tacgctggca cagacggccc ctgtaaggtg cctgcccaga tggccgtgga 9540
tatgcagacc ctgacacccg tgggcaggct gatcaccgct aaccctgtga tcaccgagag 9600
caccgagaat tccaagatga tgctggagct ggaccctccc ttcggcgaca gctatatcgt 9660
gatcggcgtc ggcgagaaga aaattaccca ccactggcac agaagcggca gcaccattgg 9720
caaggctttt gaggccacag tgagaggcgc taagagaatg gccgtgctgg gcgataccgc 9780
ctgggacttt ggcagcgtgg gcggagccct gaacagcctg ggcaaaggca tccaccagat 9840
ctttggcgcc gcctttaaga gcctcttcgg cggcatgtcc tggttcagcc agatcctgat 9900
cggcacactg ctgatgtggc tcggcctcaa taccaaaaat ggcagcatca gcctgatgtg 9960
cctcgctctc ggaggcgtgc tgattttcct gtccacagcc gtctccgctg attgataagg 10020
cgcgcccacc cagcggccgc atacagcagc aattggcaag ctgcttacat agaactcgcg 10080
gcgattggca tgccgcctta aaatttttat tttatttttc ttttcttttc cgaatcggat 10140

```
tttgttttta atatttcaaa aaaaaaaaaa aaaaaaaaaa aaaaaaaaaa aaaaaaagaa  10200
gagcgtttaa acacgtgata tctggcctca tgggccttcc tttcactgcc cgctttccag  10260
tcgggaaacc tgtcgtgcca gctgcattaa catggtcata gctgtttcct tgcgtattgg  10320
gcgctctccg cttcctcgct cactgactcg ctgcgctcgg tcgttcgggt aaagcctggg  10380
gtgcctaatg agcaaaaggc cagcaaaagg ccaggaaccg taaaaaggcc gcgttgctgg  10440
cgtttttcca taggctccgc ccccctgacg agcatcacaa aaatcgacgc tcaagtcaga  10500
ggtggcgaaa cccgacagga ctataaagat accaggcgtt tccccctgga agctccctcg  10560
tgcgctctcc tgttccgacc ctgccgctta ccggatacct gtccgccttt ctcccttcgg  10620
gaagcgtggc gctttctcat agctcacgct gtaggtatct cagttcggtg taggtcgttc  10680
gctccaagct gggctgtgtg cacgaacccc ccgttcagcc cgaccgctgc gccttatccg  10740
gtaactatcg tcttgagtcc aacccggtaa gacacgactt atcgccactg gcagcagcca  10800
ctggtaacag gattagcaga gcgaggtatg taggcggtgc tacagagttc ttgaagtggt  10860
ggcctaacta cggctacact agaagaacag tatttggtat ctgcgctctg ctgaagccag  10920
ttaccttcgg aaaaagagtt ggtagctctt gatccggcaa acaaaccacc gctggtagcg  10980
gtggtttttt tgtttgcaag cagcagatta cgcgcagaaa aaaaggatct caagaagatc  11040
ctttgatctt ttctacgggg tctgacgctc agtggaacga aaactcacgt taagggattt  11100
tggtcatgaa tacacggtgc ctgactgcgt tagcaattta actgtgataa actaccgcat  11160
taaagcttat cgatgataag ctgtcaaaca tgagaattct tagaaaaact catcgagcat  11220
caaatgaaac tgcaatttat tcatatcagg attatcaata ccatattttt gaaaaagccg  11280
tttctgtaat gaaggagaaa actcaccgag gcagttccat aggatggcaa gatcctggta  11340
tcggtctgcg attccgactc gtccaacatc aatacaacct attaatttcc cctcgtcaaa  11400
aataaggtta tcaagtgaga aatcaccatg agtgacgact gaatccggtg agaatggcaa  11460
aagcttatgc atttctttcc agacttgttc aacaggccag ccattacgct cgtcatcaaa  11520
atcactcgca tcaaccaaac cgttattcat tcgtgattgc gcctgagcga gacgaaatac  11580
gcgatcgctg ttaaaaggac aattacaaac aggaatcgaa tgcaaccggc gcaggaacac  11640
tgccagcgca tcaacaatat tttcacctga atcaggatat tcttctaata cctggaatgc  11700
tgttttcccg gggatcgcag tggtgagtaa ccatgcatca tcaggagtac ggataaaatg  11760
cttgatggtc ggaagaggca taaattccgt cagccagttt agtctgacca tctcatctgt  11820
aacatcattg gcaacgctac ctttgccatg tttcagaaac aactctggcg catcgggctt  11880
cccatacaat cgatagattg tcgcacctga ttgcccgaca ttatcgcgag cccatttata  11940
cccatataaa tcagcatcca tgttggaatt taatcgcggc ctcgagcaag acgtttcccg  12000
ttgaatatgg ctcataacac cccttgtatt actgtttatg taagcagaca gttttattgt  12060
tcatgagcgg atacatattt gaatgtattt agaaaaataa acaaataggg gttccgcgca  12120
catttccccg aaaagtgcca cctaaattgt aagcgttaat attttgttaa aattcgcgtt  12180
aaatttttgt taaatcagct cattttttaa ccaataggcc gaaatcggca aaatccctta  12240
taaatcaaaa gaatagaccg agatagggtt gagtggccgc tacagggcgc tcccattcgc  12300
cattcaggct gcgcaactgt tgggaagggc gtttcggtgc gggcctcttc gctattacgc  12360
cagctggcga aagggggatg tgctgcaagg cgattaagtt gggtaacgcc agggttttcc  12420
cagtcacacg cgtaatacga ctcactatag                                   12450
```

<210> SEQ ID NO 70
<211> LENGTH: 12078
<212> TYPE: RNA
<213> ORGANISM: Zika virus

<400> SEQUENCE: 70
auaggcggcg caugagagaa gcccagacca auuaccuacc caaaauggag aaaguucacg 60
uugacaucga ggaagacagc ccauuccuca gagcuuugca gcggagcuuc ccgcaguuug 120
agguagaagc caagcagguc acugauaaug accaugcuaa ugccagagcg uuuucgcauc 180
uggcuucaaa acugaucgaa acggaggugg acccauccga cacgauccuu gacauuggaa 240
gugcgcccgc ccgcagaaug uauucuaagc acaaguauca uuguaucugu ccgaugagau 300
gugcggaaga uccggacaga uuguauaagu augcaacuaa gcugaagaaa aacuguaagg 360
aaauaacuga uaaggaauug gacaagaaaa ugaaggagcu cgccgccguc augagcgacc 420
cugaccugga aacugagacu augugccucc acgacgacga gucgugucgc uacgaagggc 480
aagucgcugu uuaccaggau guauacgcgg uugacggacc gacaagucuc uaucaccaag 540
ccaauaaggg aguuagaguc gccuacugga uaggcuuuga caccaccccu uuuauguuua 600
agaacuuggc uggagcauau ccaucauacu cuaccaacug ggccgacgaa accguguuaa 660
cggcucguaa cauaggccua ugcagcucug acguuaugga gcggucacgu agagggaugu 720
ccauucuuag aaagaaguau uugaaaccau ccaacaaugu ucuauucucu guuggcucga 780
ccaucuacca cgagaagagg gacuuacuga ggagcuggca ccugccgucu guauuucacu 840
uacguggcaa gcaaaauuac acaugucggu gugagacuau aguuaguugc gacggguacg 900
ucguuaaaag aauagcuauc aguccaggcc uguaugggaa gccuucaggc uaugcugcua 960
cgaugcaccg cgagggauuc uugugcugca aagugacaga cacauugaac ggggagaggg 1020
ucucuuuucc cgugugcacg uaugugccag cuacauugug ugaccaaaug acuggcauac 1080
uggcaacaga ugucagugcg gacgacgcgc aaaaacugcu gguugggcuc aaccagcgua 1140
uagucgucaa cggucgcacc cagagaaaca ccaauaccau gaaaaauuac cuuuugcccg 1200
uaguggccca ggcauuugcu aggugggcaa aggaauauaa ggaagaucaa gaagaugaaa 1260
ggccacuagg acuacgagau agacaguuag ucauggggug uuguugggcu uuuagaaggc 1320
acaagauaac aucuauuuau aagcgcccgg auacccaaac caucaucaaa gugaacagcg 1380
auuuccacuc auucgugcug cccaggauag gcaguaacac auuggagauc gggcugagaa 1440
caagaaucag gaaaauguua gaggagcaca aggagccguc accucucauu accgccgagg 1500
acguacaaga agcuaagugc gcagccgaug aggcuaagga ggugcgugaa gccgaggagu 1560
ugcgcgcagc ucuaccaccu uuggcagcug auguugagga gcccacucug gaagccgaug 1620
ucgacuugau guuacaagag gcuggggccg gcucagugga gacaccucgu ggcuugauaa 1680
agguuaccag cuacgauggc gaggacaaga ucggcucuua cgcugugcuu ucuccgcagg 1740
cuguacucaa gagugaaaaa uuaucuugca uccacccucu cgcugaacaa gucauaguga 1800
uaacacacuc uggccgaaaa gggcguuaug ccguggaacc auaccauggu aaaguagugg 1860
ugccagaggg acaugcaaua cccguccagg acuuucaagc ucugagugaa agugccacca 1920
uuguguacaa cgaacgugag uucguaaaca gguaccugca ccauauugcc acacauggag 1980
gagcgcugaa cacugaugaa gaauauuaca aaacugucaa gcccagcgag cacgacggcg 2040
aauaccugua cgacaucgac aggaaacagu gcgucaagaa agaacuaguc acugggcuag 2100
ggcucacagg cgagcuggug gauccucccu uccaugaauu cgccuacgag agucugagaa 2160
cacgaccagc cgcuccuuac caaguaccaa ccauaggggu guauggcgug ccaggaucag 2220
gcaagucugg caucauuaaa agcgcaguca ccaaaaaaga ucuaguggug agcgccaaga 2280
aagaaaacug ugcagaaauu auaagggacg ucaagaaaau gaaagggcug gacgucaaug 2340
ccagaacugu ggacucagug cucuugaaug gaugcaaaca ccccguagag acccuguaua 2400
uugacgaagc uuuugcuugu caugcaggua cucucagagc gcucauagcc auuauaagac 2460
cuaaaaaggc agugcucugc ggggauccca aacagugcgg uuuuuuuaac augaugugcc 2520
ugaaagugca uuuuaaccac gagauuugca cacaagucuu ccacaaaagc aucucucgcc 2580
guugcacuaa aucugugacu ucggucgucu caaccuuguu uuacgacaaa aaaaugagaa 2640
cgacgaaucc gaaagagacu aagauuguga uugacacuac cggcaguacc aaaccuaagc 2700
aggacgaucu cauucucacu uguuucagag ggugggugaa gcaguugcaa auagauuaca 2760
aaggcaacga aauaaugacg gcagcugccu cucaagggcu gacccguaaa gguguguaug 2820
ccguucggua caaggugaau gaaaauccuc uguacgcacc caccucagaa caugugaacg 2880
uccuacugac ccgcacggag gaccgcaucg uguggaaaac acuagccggc gacccaugga 2940
uaaaaacacu gacugccaag uacccuggga auuucacugc cacgauagag gaguggcaag 3000
cagagcauga ugccaucaug aggcacaucu uggagagacc ggacccuacc gacgucuucc 3060
agaauaaggc aaacgugugu ugggccaagg cuuuagugcc ggugcugaag accgcuggca 3120
uagacaugac cacugaacaa uggaacacug uggauuauuu ugaaacggac aaagcucacu 3180
cagcagagau aguauugaac caacuaugcg ugagguucuu uggacucgau cuggacuccg 3240
gucuauuuuc ugcacccacu guuccguuau ccauuaggaa uaaucacugg gauaacuccc 3300
cgucgccuaa cauguacggg cugaauaaag aaguggucg ucagcucucu cgcagguacc 3360
cacaacugcc ucgggcaguu gccacuggaa gagucuauga caugaacacu gguacacugc 3420
gcaauuauga uccgcgcaua aaccuaguac cuguaaacag aagacugccu caugcuuuag 3480
uccuccacca uaaugaacac ccacagagug acuuuucuuc auucgucagc aaauugaagg 3540
gcagaacugu ccugguggu ggggaaaagu uguccguccc aggcaaaaug guugacuggu 3600
ugucagaccg gccugaggcu accuucagag cucggcugga uuuaggcauc ccaggugaug 3660
ugcccaaaua ugacauaaua uuuguuaaug ugaggacccc auauaaauac caucacuauc 3720
agcaguguga agaccaugcc auuaagcuua gcauguugac caagaaagcu ugucugcauc 3780
ugaaucccgg cggaaccugu gucagcauag guuaugguua cgcugacagg gccagcgaaa 3840
gcaucauugg ugcuauagcg cggcaguuca aguuuucccg gguaugcaaa ccgaaauccu 3900
cacuugaaga gacggaaguu cuguuuguau ucauugggua cgaucgcaag gcccguacgc 3960
acaauccuua caagcuuuca ucaaccuuga ccaacauuua uacagguucc agacuccacg 4020
aagccggaug ugcacccuca uaucaugugg ugcgagggga uauugccacg gccaccgaag 4080
gagugauuau aaaugcugcu aacagcaaag gacaaccugg cggagggggug ugcggagcgc 4140
uguauaagaa auucccggaa agcuucgauu uacagccgau cgaaguagga aaagcgcgac 4200
uggucaaagg ugcagcuaaa cauaucauuc augccguagg accaaacuuc aacaaaguuu 4260
cggagguuga aggugacaaa caguuggcag aggcuuauga guccaucgcu aagauuguca 4320
acgauaacaa uuacaaguca guagcgauuc cacuguuguc caccggcauc uuuuccggga 4380
acaaagaucg acuaacccaa ucauugaacc auuugcugac agcuuuagac accacugaug 4440
cagauguagc cauauacugc agggacaaga aaugggaaau gacucucaag gaagcagugg 4500

-continued

```
cuaggagaga agcaguggag gagauaugca uauccgacga cucuucagug acagaaccug   4560
augcagagcu ggugagggug cauccgaaga guucuuuggc uggaaggaag ggcuacagca   4620
caagcgaugg caaaacuuuc ucauauuugg aagggaccaa guuucaccag gcggccaagg   4680
auauagcaga aauuaaugcc auguggcccg uugcaacgga ggccaaugag cagguaugca   4740
uguauauccu cggagaaagc augagcagua uuaggucgaa augccccguc gaagagucgg   4800
aagccuccac accaccuagc acgcugccuu gcuugugcau ccaugccaug acuccagaaa   4860
gaguacagcg ccuaaaagcc ucacguccag aacaaauuac ugugugcuca uccuuuccau   4920
ugccgaagua uagaaucacu ggugugcaga agauccaaug cucccagccu auauuguucu   4980
caccgaaagu gccugcguau auucauccaa ggaaguaucu cguggaaaca ccaccgguag   5040
acgagacucc ggagccaucg gcagagaacc aauccacaga ggggacaccu gaacaaccac   5100
cacuuauaac cgaggaugag accaggacua gaacgccuga gccgaucauc aucgaagagg   5160
aagaagagga uagcauaagu uugcugucag auggcccgac ccaccaggug cugcaagucg   5220
aggcagacau ucacgggccg cccucuguau cuagcucauc cugguccauu ccucaugcau   5280
ccgacuuuga uguggacagu uuauccauac uugacacccu ggagggagcu agcgugacca   5340
gcggggcaac gucagccgag acuaacucuu acuucgcaaa gaguauggag uuucuggcgc   5400
gaccggugcc ugcgccucga acaguauuca ggaacccucc acaucccgcu ccgcgcacaa   5460
gaacaccguc acuugcaccc agcagggccu gcucgagaac cagccuaguu uccaccccgc   5520
caggcgugaa uagggugauc acuagagagg agcucgaggc gcuuaccccg ucacgcacuc   5580
cuagcagguc ggucucgaga accagccugg ucuccaaccc gccaggcgua aauaggguga   5640
uuacaagaga ggaguuugag gcguucguag cacaacaaca augacgguuu gaugcgggug   5700
cauacaucuu uuccuccgac accggucaag ggcauuuaca acaaaaauca guaaggcaaa   5760
cggugcuauc cgaaguggug uuggagagga ccgaauugga gauuucguau gccccgcgcc   5820
ucgaccaaga aaaagaagaa uuacuacgca agaaauuaca guuaaauccc acaccugcua   5880
acagaagcag auaccagucc aggaaggugg agaacaugaa agccauaaca gcuagacgua   5940
uucugcaagg ccuagggcau uauuugaagg cagaaggaaa aguggagugc uaccgaaccc   6000
ugcauccugu uccuuuguau ucaucuagug ugaaccgugc cuuuucaagc cccaaggucg   6060
caguggaagc cuguaacgcc auguugaaag agaacuuucc gacuguggcu ucuuacugua   6120
uuauuccaga guacgaugcc uauuuggaca ugguugacgg agcuucaugc ugcuuagaca   6180
cugccaguuu uugcccugca aagcugcgca gcuuuccaaa gaaacacucc uauuuggaac   6240
ccacaauacg aucggcagug ccuucagcga uccagaacac gcuccagaac guccuggcag   6300
cugccacaaa aagaaauugc aaugucacgc aaaugagaga auugcccgua uuggauucgg   6360
cggccuuuaa uguggaaugc uucaagaaau augcguguaa uaaugaauau ugggaaacgu   6420
uuaaagaaaa ccccaucagg cuuacugaag aaaacguggu aaauuacauu accaaauuaa   6480
aaggaccaaa agcugcugcu cuuuuugcga agacacauaa uuugaauaug uugcaggaca   6540
uaccaaugga cagguuugua auggacuuaa agagagacgu gaaagugacu ccaggaacaa   6600
aacauacuga agaacggccc aagguacagg ugauccaggc ugccgauccg cuagcaacag   6660
cguaucugug cggaauccac cgagagcugg uuaggagauu aaaugcgguc cugcuuccga   6720
acauucauac acuguuugau augucggcug aagacuuuga cgcuauuaua gccgagcacu   6780
uccagccugg ggauuguguu cuggaaacug acaucgcguc guuugauaaa agugaggacg   6840
acgccauggc ucugaccgcg uuaaugauuc uggaagacuu aggugugac gcagagcugu   6900
```

-continued

```
ugacgcugau ugaggcggcu uucggcgaaa uuucaucaau acauuugccc acuaaaacua   6960
aauuuaaauu cggagccaug augaaaucug gaauguuccu cacacuguuu gugaacacag   7020
ucauuaacau uguaaucgca agcagagugu ugagagaacg gcuaaccgga ucaccaugug   7080
cagcauucau uggagaugac aauaucguga aaggagucaa aucggacaaa uuaauggcag   7140
acaggugcgc caccugguug aauauggaag ucaagauuau agaugcugug gugggcgaga   7200
aagcgccuua uuucugugga ggguuuauuu ugugugacuc cgugaccggc acagcgugcc   7260
guguggcaga cccccuaaaa aggcuguuua agcuuggcaa accucuggca gcagacgaug   7320
aacaugauga ugacaggaga agggcauugc augaagaguc aacacgcugg aaccgagugg   7380
guauucuuuc agagcugugc aaggcaguag aaucaaggua ugaaaccgua ggaacuucca   7440
ucauaguuau ggccaugacu acucuagcua gcaguguuaa aucauucagc uaccugagag   7500
gggccccuau aacucucuac ggcuaaccug aauggacuac gacauagucu aguccgccaa   7560
gaugcgaggc gcagauacua gugucggaau uguuggccuc cugcugacca cagcuauggc   7620
agcggagguc acuagacgug ggagugcaua cuauauguac uuggacagaa acgaugcugg   7680
ggaggccaua ucuuuuccaa ccacauuggg gaugaauaag uguuauauac agaucaugga   7740
ucuuggacac augugugaug ccaccaugag cuaugaaugc ccuaugcugg augagggggu   7800
ggaaccagau gacgucgauu guuggugcaa cacgacguca acuuggguug uguacggaac   7860
cugccaucac aaaaaaggug aagcacggag aucuaggaga gcugugacgc uccccuccca   7920
uuccacuagg aagcugcaaa cgcggucgca aaccugguug gaaucaagag aauacacaaa   7980
gcacuugauu agagucgaaa auuggauauu caggaacccu ggcuucgcgu uagcagcagc   8040
ugccaucgcu uggcuuuugg gaagcucaac gagccaaaaa gucauauacu uggucaugau   8100
acugcugauu gccccggcau acagcaucag gugcauagga gucagcaaua gggacuuugu   8160
ggaagguaug ucagguggga cuuggguuga uguugucuug gaacauggag guugugucac   8220
cguaauggca caggacaaac cgacugucga cauagagcug guuacaacaa cagucagcaa   8280
cauggcggag guaagauccu acugcuauga ggcaucaaua ucagacaugg cuucggacag   8340
ccgcugccca acacaaggug aagccuaccu ugacaagcaa ucagacacuc aauaugucug   8400
caaaagaacg uuaguggaca gaggcugggg aaauggaugu ggacuuuuug gcaaagggag   8460
ccuggugaca ugcgcuaagu uugcaugcuc caagaaaaug accgggaaaa gcauccagcc   8520
agagaaucug gaguaccgga uaaugcuguc aguucauggc ucccagcaca gugggaugau   8580
cguuaaugac acaggacaug aaacugauga gaauagagcg aagguugaga uaacgcccaa   8640
uucaccaaga gccgaagcca cccugggggg uuuuggaagc cuaggacuug auugugaacc   8700
gaggacaggc cuugacuuuu cagauuugua uuacuugacu augaauaaca agcacugguu   8760
gguccacaag gagugguucc acgacauucc auuaccuugg cacgcugggg cagacaccgg   8820
aacuccacac uggaacaaca aagaagcacu gguagaguuc aaggacgcac augccaaaag   8880
gcaaacuguc gugguucuag ggagucaaga aggagcaguu cacacggccc uugcuggagc   8940
ucuggaggcu gagauggaug gugcaaaggg aaggcugucc ucuggccacu ugaaaugucg   9000
ccugaaaaug gauaaacuua gauugaaggg cgugucauac uccuugugua ccgcagcguu   9060
cacauucacc aagaucccgg cugaaacacu gcacgggaca gucacagugg agguacagua   9120
cgcagggaca gauggaccuu gcaagguucc agcucagaug gcgguggaca ugcaaacucu   9180
gaccccaguu gggagguuga uaaccgcuaa ccccguaauc acugaaagca cugagaacuc   9240
```

uaagaugaug cuggaacuug auccaccauu uggggacucu uacauuguca uaggagucgg 9300
ggagaagaag aucacccacc acuggcacag gaguggcagc accauuggaa aagcauuuga 9360
agccacugug agaggugcca agagaauggc agucuuggga gacacagccu gggacuuugg 9420
aucaguugga ggcgcucuca acucauuggg caagggcauc caucaaauuu uuggagcagc 9480
uuucaaauca uuguuuggag gaauguccug guucucacaa auccucauug gaacguugcu 9540
gaugugguug ggucugaaca caaagaaugg aucuauuucc cuuaugugcu uggccuuagg 9600
gggaguguug aucuucuuau ccacagccgu cucugcugau ugauaaggcg cgcccaccca 9660
gcggccgcau acagcagcaa uuggcaagcu gcuuacauag aacucgcggc gauuggcaug 9720
ccgccuuaaa auuuuuauuu uauuuuucuu uucuuuuccg aaucggauuu uguuuuuaau 9780
auuucaaaaa aaaaaaaaaa aaaaaaaaaa aaaaaaaaaa aaaaagaaga gcguuuaaac 9840
acgugauauc uggccucaug ggccuuccuu ucacugcccg cuuuccaguc gggaaaccug 9900
ucgugccagc ugcauuaaca uggucauagc uguuuccuug cguauugggc gcucuccgcu 9960
uccucgcuca cugacucgcu gcgcucgguc guucggguaa agccuggggu gccuaaugag 10020
caaaaggcca gcaaaaggcc aggaaccgua aaaaggccgc guugcuggcg uuuuuccaua 10080
ggcuccgccc cccugacgag caucacaaaa aucgacgcuc aagucagagg uggcgaaacc 10140
cgacaggacu auaaagauac caggcguuuc cccuggaag cucccucgug cgcucuccug 10200
uuccgacccu gccgcuuacc ggauaccugu ccgccuuucu cccuucggga agcguggcgc 10260
uuucucauag cucacgcugu agguaucuca guucggugua ggucguucgc uccaagcugg 10320
gcugugugca cgaacccccc guucagcccg accgcugcgc cuuauccggu aacuaucguc 10380
uugaguccaa cccgguaaga cacgacuuau cgccacuggc agcagccacu gguaacagga 10440
uuagcagagc gagguaugua ggcggugcua cagaguucuu gaagugguggg ccuaacuacg 10500 gcuacacuag aagaacagua uuugguaucu gcgcucugcu gaagccaguu accuucggaa 10560
aaagaguugg uagcucuuga uccggcaaac aaaccaccgc ugguagcggu gguuuuuuug 10620
uuugcaagca gcagauuacg cgcagaaaaa aaggaucuca agaagauccu uugaucuuuu 10680 cuacggggguc ugacgcucag uggaacgaaa acucacguua agggauuuug gucaugaaua 10740
cacggugccu gacugcguua gcaauuuaac ugugauaaac uaccgcauua aagcuuaucg 10800
augauaagcu gucaaacaug agaauucuua gaaaaacuca ucgagcauca aaugaaacug 10860
caauuuauuc auaucaggau uaucaauacc auauuuuuga aaaagccguu ucuguaauga 10920
aggagaaaac ucaccgaggc aguuccauag gauggcaaga uccugguauc ggucugcgau 10980
uccgacucgu ccaacaucaa uacaaccuau uaauuucccc ucgucaaaaa uaagguuauc 11040
aagugagaaa ucaccaugag ugacgacuga auccggugag aauggcaaaa gcuuaugcau 11100
uucuuuccag acuuguucaa caggccagcc auuacgcucg ucaucaaaau cacucgcauc 11160
aaccaaaccg uuauucauuc gugauugcgc cugagcgaga cgaaauacgc gaucgcuguu 11220
aaaaggacaa uuacaaacag gaaucgaaug caaccggcgc aggaacacug ccagcgcauc 11280
aacaauauuu ucaccugaau caggauauuc uucuaauacc uggaaugcug uuuucccggg 11340
gaucgcagug gugaguaacc augcaucauc aggaguacgg auaaaaugcu ugauggucgg 11400
aagaggcaua aauuccguca gccaguuuag ucugaccauc ucaucuguaa caucauuggc 11460
aacgcuaccu uugccauguu ucagaaacaa cucuggcgca ucgggcuucc cauacaaucg 11520
auagauuguc gcaccugauu gcccgacauu aucgcgagcc cauuuauacc cauauaaauc 11580
agcauccaug uuggaauuua aucgcggccu cgagcaagac guuucccguu gaauauggcu 11640
cauaacaccc cuuguauuac uguuuaugua agcagacagu uuuauuguuc augagcggau 11700
acauauuuga auguauuuag aaaaauaaac aaauaggggu uccgcgcaca uuuccccgaa 11760
aagugccacc uaaauuguaa gcguuaauau uuuguuaaaa uucgcguuaa auuuuuguua 11820
aaucagcuca uuuuuuaacc aauaggccga aaucggcaaa aucccuuaua aaucaaaaga 11880
auagaccgag auaggguuga guggccgcua cagggcgcuc ccauucgcca uucaggcugc 11940
gcaacuguug ggaagggcgu uucggugcgg gccucuucgc uauuacgcca gcuggcgaaa 12000
gggggaugug cugcaaggcg auuaaguugg guaacgccag gguuuuccca gucacacgcg 12060
uaauacgacu cacuauag 12078

<210> SEQ ID NO 71
<211> LENGTH: 12078
<212> TYPE: RNA
<213> ORGANISM: Zika virus

<400> SEQUENCE: 71
auaggcggcg caugagagaa gcccagacca auuaccuacc caaaauggag aaaguucacg 60
uugacaucga ggaagacagc ccauuccuca gagcuuugca gcggagcuuc ccgcaguuug 120
agguagaagc caagcagguc acugauaaug accaugcuaa ugccagagcg uuuucgcauc 180
uggcuucaaa acugaucgaa acggaggugg acccauccga cacgauccuu gacauuggaa 240
gugcgcccgc ccgcagaaug uauucuaagc acaaguauca uuguaucugu ccgaugagau 300
gugcggaaga uccggacaga uuguauaagu augcaacuaa gcugaagaaa aacuguaagg 360
aaauaacuga uaaggaauug gacaagaaaa ugaaggagcu cgccgccguc augagcgacc 420
cugaccugga aacugagacu augugccucc acgacgacga gucgugucgc uacgaagggc 480
aagucgcugu uuaccaggau guauacgcgg uugacggacc gacaagucuc uaucaccaag 540
ccaauaaggg aguuagaguc gccuacugga uaggcuuuga caccaccccu uuuauguuua 600
agaacuuggc uggagcauau ccaucauacu cuaccaacug ggccgacgaa accguguuaa 660
cggcucguaa cauaggccua ugcagcucug acguuaugga gcggucacgu agagggaugu 720
ccauucuuag aaagaaguau uugaaaccau ccaacaaugu ucuauucucu guuggcucga 780
ccaucuacca cgagaagagg gacuuacuga ggagcuggca ccugccgucu guauuucacu 840
uacguggcaa gcaaaauuac acaugucggu gugagacuau aguuaguugc gacggguacg 900
ucguuaaaag aauagcuauc aguccaggcc uguaugggaa gccuucaggc uaugcugcua 960
cgaugcaccg cgagggauuc uugugcugca aagugacaga cacauugaac ggggagaggg 1020
ucucuuuucc cgugugcacg uaugugccag cuacauugug ugaccaaaug acuggcauac 1080
uggcaacaga ugucagugcg gacgacgcgc aaaaacugcu gguugggcuc aaccagcgua 1140
uagucgucaa cggucgcacc cagagaaaca ccaauaccau gaaaaauuac cuuuugcccg 1200
uaguggccca ggcauuugcu aggugggcaa aggaauauaa ggaagaucaa gaagaugaaa 1260
ggccacuagg acuacgagau agacaguuag ucaugggggug uuguugggcu uuuagaaggc 1320
acaagauaac aucuauuuau aagcgcccgg auacccaaac caucaucaaa gugaacagcg 1380
auuuccacuc auucgugcug cccaggauag gcaguaacac auuggagauc gggcugagaa 1440
caagaaucag gaaaauguua gaggagcaca aggagccguc accucucauu accgccgagg 1500
acguacaaga agcuaagugc gcagccgaug aggcuaagga ggugcgugaa gccgaggagu 1560
ugcgcgcagc ucuaccaccu uuggcagcug auguugagga gcccacucug gaagccgaug 1620
ucgacuugau guuacaagag gcugggggccg gcucagugga gacaccucgu ggcuugauaa 1680
agguuaccag cuacgauggc gaggacaaga ucggcucuua cgcugugcuu ucuccgcagg 1740
cuguacucaa gagugaaaaa uuaucuugca uccacccucu cgcugaacaa gucauaguga 1800
uaacacacuc uggccgaaaa gggcguuaug ccguggaacc auaccauggu aaaguagugg 1860
ugccagaggg acaugcaaua cccguccagg acuuucaagc ucugagugaa agugccacca 1920
uuguguacaa cgaacgugag uucguaaaca gguaccugca ccauauugcc acacauggag 1980
gagcgcugaa cacugaugaa gaauauuaca aaacugucaa gcccagcgag cacgacggcg 2040
aauaccugua cgacaucgac aggaaacagu gcgucaagaa agaacuaguc acugggcuag 2100
ggcucacagg cgagcuggug gauccucccu uccaugaauu cgccuacgag agucugagaa 2160
cacgaccagc cgcuccuuac caaguaccaa ccauaggggu guauggcgug ccaggaucag 2220
gcaagucugg caucauuaaa agcgcaguca ccaaaaaaga ucuaguggug agcgccaaga 2280
aagaaaacug ugcagaaauu auaagggacg ucaagaaaau gaaagggcug gacgucaaug 2340
ccagaacugu ggacucagug cucuugaaug gaugcaaaca ccccguagag acccuguaua 2400
uugacgaagc uuuugcuugu caugcaggua cucucagagc gcucauagcc auuauaagac 2460
cuaaaaaggc agugcucugc ggggauccca aacagugcgg uuuuuuuaac augaugugcc 2520
ugaaagugca uuuuaaccac gagauuugca cacaagucuu ccacaaaagc aucucucgcc 2580
guugcacuaa aucugugacu ucggucgucu caaccuuguu uuacgacaaa aaaaugagaa 2640
cgacgaaucc gaaagagacu aagauuguga uugacacuac cggcaguacc aaaccuaagc 2700
aggacgaucu cauucucacu uguuucagag ggugggugaa gcaguugcaa auagauuaca 2760
aaggcaacga aauaaugacg gcagcugccu cucaagggcu gacccguaaa ggugguguaug 2820 ccguucggua caaggugaau gaaaauccuc uguacgcacc caccucagaa caugugaacg 2880
uccuacugac ccgcacggag gaccgcaucg uguggaaaac acuagccggc gacccaugga 2940
uaaaaacacu gacugccaag uacccuggga auuucacugc cacgauagag gaguggcaag 3000
cagagcauga ugccaucaug aggcacaucu uggagagacc ggacccuacc gacgucuucc 3060
agaauaaggc aaacgugugu ugggccaagg cuuuagugcc ggugcugaag accgcuggca 3120
uagacaugac cacugaacaa uggaacacug uggauuauuu ugaaacggac aaagcucacu 3180
cagcagagau aguauugaac caacuaugcg ugagguucuu uggacucgau cuggacuccg 3240
gucuauuuuc ugcacccacu guuccguuau ccauuaggaa uaaucacugg gauaacuccc 3300
cgucgccuaa cauguacggg cugaauaaag aaguggucccg ucagcucucu cgcagguacc 3360
cacaacugcc ucgggcaguu gccacuggaa gagucuauga caugaacacu gguacacugc 3420
gcaauuauga uccgcgcaua aaccuaguac cuguaaacag aagacugccu caugcuuuag 3480
uccuccacca uaaugaacac ccacagagug acuuuucuuc auucgucagc aaauugaagg 3540
gcagaacugu ccuggugguc ggggaaaagu uguccguccc aggcaaaaug guugacuggu 3600
ugucagaccg gccugaggcu accuucagag cucggcugga uuuaggcauc ccaggugaug 3660
ugcccaaaua ugacauaaua uuuguuaaug ugaggacccc auauaaauac caucacuauc 3720 agcagugua agaccaugcc auuaagcuua gcauguugac caagaaagcu ugucugcauc 3780
ugaaucccgg cggaaccugu gucagcauag guuaugguua cgcugacagg gccagcgaaa 3840
gcaucauugg ugcuauagcg cggcaguuca aguuuucccg gguaugcaaa ccgaaauccu 3900
cacuugaaga gacggaaguu cuguuuguau ucauugggua cgaucgcaag gcccguacgc 3960
acaauccuua caagcuuuca ucaaccuuga ccaacauuua uacagguucc agacuccacg 4020

-continued aagccggaug ugcacccuca uaucaugugg ugcgagggga uauugccacg gccaccgaag 4080
gagugauuau aaaugcugcu aacagcaaag gacaaccugg cggaggggug ugcggagcgc 4140
uguauaagaa auucccggaa agcuucgauu uacagccgau cgaaguagga aaagcgcgac 4200
uggucaaagg ugcagcuaaa cauaucauuc augccguagg accaaacuuc aacaaaguuu 4260
cggagguuga aggugacaaa caguuggcag aggcuuauga guccaucgcu aagauuguca 4320
acgauaacaa uuacaaguca guagcgauuc cacuguuguc caccggcauc uuuuccggga 4380
acaaagaucg acuaacccaa ucauugaacc auuugcugac agcuuuagac accacugaug 4440
cagauguagc cauauacugc agggacaaga aaugggaaau gacucucaag gaagcagugg 4500
cuaggagaga agcaguggag gagauaugca uauccgacga cucuucagug acagaaccug 4560
augcagagcu ggugagggug cauccgaaga guucuuuggc uggaaggaag ggcuacagca 4620
caagcgaugg caaaacuuuc ucauauuugg aagggaccaa guuucaccag gcggccaagg 4680
auauagcaga aauuaaugcc auguggcccg uugcaacgga ggccaaugag cagguaugca 4740
uguauauccu cggagaaagc augagcagua uuaggucgaa augccccguc gaagagucgg 4800
aagccuccac accaccuagc acgcugccuu gcuugugcau ccaugccaug acuccagaaa 4860
gaguacagcg ccuaaaagcc ucacguccag aacaaauuac ugugugcuca uccuuuccau 4920
ugccgaagua uagaaucacu ggugugcaga agauccaaug cucccagccu auauuguucu 4980
caccgaaagu gccugcguau auucauccaa ggaaguaucu cguggaaaca ccaccgguag 5040
acgagacucc ggagccaucg gcagagaacc aauccacaga ggggacaccu gaacaaccac 5100
cacuuauaac cgaggaugag accaggacua gaacgccuga gccgaucauc aucgaagagg 5160
aagaagagga uagcauaagu uugcugucag auggcccgac ccaccaggug cugcaagucg 5220
aggcagacau ucacgggccg cccucuguau cuagcucauc cugguccauu ccucaugcau 5280
ccgacuuuga uguggacagu uuauccauac uugacacccu ggagggagcu agcgugacca 5340
gcggggcaac gucagccgag acuaacucuu acuucgcaaa gaguauggag uuucuggcgc 5400
gaccggugcc ugcgccucga acaguauuca ggaacccucc acaucccgcu ccgcgcacaa 5460
gaacaccguc acuugcaccc agcagggccu gcucgagaac cagccuaguu uccaccccgc 5520
caggcgugaa uagggugauc acuagagagg agcucgaggc gcuuaccccg ucacgcacuc 5580
cuagcagguc ggucucgaga accagccugg ucuccaaccc gccaggcgua aauaggguga 5640
uuacaagaga ggaguuugag gcguucguag cacaacaaca augacgguuu gaugcgggug 5700
cauacaucuu uuccuccgac accggucaag ggcauuuaca acaaaaauca guaaggcaaa 5760
cggugcuauc cgaaguggug uuggagagga ccgaauugga gauuucguau gccccgcgcc 5820
ucgaccaaga aaaagaagaa uuacuacgca agaaauuaca guuaaauccc acaccugcua 5880
acagaagcag auaccagucc aggaaggugg agaacaugaa agccauaaca gcuagacgua 5940
uucugcaagg ccuagggcau uauuugaagg cagaaggaaa aguggagugc uaccgaaccc 6000
ugcauccugu uccuuuguau ucaucuagug ugaaccgugc cuuuucaagc cccaaggucg 6060
caguggaagc cuguaacgcc auguugaaag agaacuuucc gacuguggcu ucuuacugua 6120
uuauuccaga guacgaugcc uauuuggaca ugguugacgg agcuucaugc ugcuuagaca 6180
cugccaguuu uugcccugca aagcugcgca gcuuuccaaa gaaacacucc uauuuggaac 6240
ccacaauacg aucggcagug ccuucagcga uccagaacac gcuccagaac guccuggcag 6300
cugccacaaa aagaaauugc aaugucacgc aaaugagaga auugcccgua uuggauucgg 6360

-continued cggccuuuaa uguggaaugc uucaagaaau augcguguaa uaaugaauau ugggaaacgu 6420
uuaaagaaaa ccccaucagg cuuacugaag aaaacguggu aaauuacauu accaaauuaa 6480
aaggaccaaa agcugcugcu cuuuuugcga agacacauaa uuugaauaug uugcaggaca 6540
uaccaaugga cagguuugua auggacuuaa agagagacgu gaaagugacu ccaggaacaa 6600
aacauacuga agaacggccc aagguacagg ugauccaggc ugccgauccg cuagcaacag 6660
cguaucugug cggaauccac cgagagcugg uuaggagauu aaaugcgguc cugcuuccga 6720
acauucauac acuguuugau augucggcug aagacuuuga cgcuauuaua gccgagcacu 6780
uccagccugg ggauuguguu cuggaaacug acaucgcguc guuugauaaa agugaggacg 6840
acgccauggc ucugaccgcg uuaaugauuc uggaagacuu aggugugggac gcagagcugu 6900 ugacgcugau ugaggcggcu uucggcgaaa uuucaucaau acauuugccc acuaaaacua 6960
aauuuaaauu cggagccaug augaaaucug gaauguuccu cacacuguuu gugaacacag 7020
ucauuaacau uguaaucgca agcagagugu ugagagaacg gcuaaccgga ucaccaugug 7080
cagcauucau uggagaugac aauaucguga aaggagucaa aucggacaaa uuaauggcag 7140
acaggugcgc caccugguug aauauggaag ucaagauuau agaugcugug gugggcgaga 7200
aagcgccuua uuucugugga ggguuuauuu ugugugacuc cgugaccggc acagcgugcc 7260
guguggcaga cccccuaaaa aggcuguuua agcuuggcaa accucuggca gcagacgaug 7320
aacaugauga ugacaggaga agggcauugc augaagaguc aacacgcugg aaccgagugg 7380
guauucuuuc agagcugugc aaggcaguag aaucaaggua ugaaaccgua ggaacuucca 7440
ucauaguuau ggccaugacu acucuagcua gcaguguuaa aucauucagc uaccugagag 7500
gggccccuau aacucucuac ggcuaaccug aauggacuac gacauagucu aguccgccaa 7560
gaugagagga gcugacacca gcgugggcau ugugggccuc cugcugacaa ccgccauggc 7620
cgcugagguc accagaagag gcagcgccua cuacauguac cuggacagaa acgacgcugg 7680
cgaggcuauu agcuucccca ccacacucgg caugaacaag uguuacaucc agaucaugga 7740
ccugggccac augugcgaug ccaccaugag cuacgaaugu ccuaugcugg acgaaggcgu 7800
ggagcccgac gacguggacu guuggugcaa cacaaccagc accugggugg uguacggcac 7860
cugccaucau aagaagggag aagccaggag aagcaggagg gcugucacac uccccuccca 7920
cuccacaaga aagcugcaaa ccaggagcca gaccuggcug gaaagcaggg aguacaccaa 7980
gcaccugauc agggucgaga acuggaucuu caggaacccu ggauucgccc ucgccgcugc 8040
ugcuauugcc uggcuccugg gcuccuccac cagccaaaag gugaucuacc uggugaugau 8100
ccuccugauc gcccccgccu acagcaucag gugcaucggc guguccaaua gggacuuugu 8160
cgaaggaaug uccggcggca caugggugga cgucgugcug gagcauggcg gcugugugac 8220
agucauggcc caggacaaac ccaccgugga uaucgagcug gugacaacca caguguccaa 8280
cauggccgag gugaggagcu acugcuacga ggcuagcauc agcgacaugg cuuccgacag 8340
cagaugcccc acacagggcg aggccuaccu cgacaaacag uccgacaccc aguacgugug 8400
caaaaggacc cuggucgaca gaggaugggg caacggcugc ggccuguucg gaaaaggaag 8460
ccuggucacc ugugcuaagu ucgccugcuc caagaagaug accggcaaga gcauccagcc 8520
cgagaaccuc gaguacagga ucaugcucuc cguccauggc agccagcaca gcggaaugau 8580
cgugaacgac accggccacg agaccgauga gaacagggcc aagguggaaa ucacccccaa 8640
cagcccuagg gcugaagcua cccucggcgg auuuggaucc cugggccugg auugugaacc 8700
caggaccgga cucgacuuca gcgaucugua cuaccugacc augaacaaca agcacuggcu 8760

```
ggugcauaag gagugguucc augauauccc ccugcccugg caugcuggag ccgauacagg   8820
caccccucac uggaacaaca aggaagcccu gguggaguuc aaagaugccc acgccaagag   8880
acagacaguc gucguccugg gcagccaaga gggcgcugug cauacagccc uggcuggagc   8940
ccuggaggcc gaaauggacg gcgccaaggg aaggcugucc agcggacauc ugaagugcag   9000
gcugaagaug gacaagcuga ggcucaaggg cgucagcuac ucccugugca ccgccgccuu   9060
uaccuuuaca aaaauccccg ccgagacccu ccacggcaca gucacagucg aggugcagua   9120
cgcuggaacc gacggaccuu guaaggugcc cgcccaaaug gccguggaca ugcagacacu   9180
gaccccugug ggcagacuca ucacagccaa cccugugauc acagagucca ccgagaacag   9240
caagaugaug cucgagcugg auccuccuuu cggcgacagc uacaucguga ucggaguggg   9300
cgagaagaaa aucacccacc acuggcacag guccggcagc accauuggca aagccuuuga   9360
agccaccguc agaggagcua aaaggauggc ugugcugggc gacaccgcuu gggacuucgg   9420
cuccguggga ggagcccuca acucccuggg caagggcauu caccagauuu ucggcgccgc   9480
uuucaagagc cucuuuggcg gcauguccug guuuagccag auucucaucg gcacacugcu   9540
gauguggcug ggccugaaua ccaagaacgg cagcaucagc cugaugugucn uggcccuggg   9600
aggcgugcug aucuuucugu ccaccgcugu cagcgccgac ugauaaggcg cgcccaccca   9660
gcggccgcau acagcagcaa uuggcaagcu gcuuacauag aacucgcggc gauuggcaug   9720
ccgccuuaaa auuuuuauuu uauuuuucuu uucuuuuccg aaucggauuu uguuuuuaau   9780
auuucaaaaa aaaaaaaaaa aaaaaaaaaa aaaaaaaaaa aaaaagaaga gcguuuaaac   9840
acgugauauc uggccucaug ggccuuccuu ucacugcccg cuuuccaguc gggaaaccug   9900
ucgugccagc ugcauuaaca uggucauagc uguuuccuug cguauugggc gcucuccgcu   9960
uccucgcuca cugacucgcu gcgcucgguc guucggguaa agccuggggu gccuaaugag  10020
caaaaggcca gcaaaaggcc aggaaccgua aaaaggccgc guugcuggcg uuuuuccaua  10080
ggcuccgccc cccugacgag caucacaaaa aucgacgcuc aagucagagg uggcgaaacc  10140
cgacaggacu auaaagauac caggcguuuc cccccuggaag cucccucgug cgcucuccug  10200
uuccgacccu gccgcuuacc ggauaccugu ccgccuuucu cccuucggga agcguggcgc  10260
uuucucauag cucacgcugu agguaucuca guucggugua ggucguucgc uccaagcugg  10320
gcugugugca cgaacccccc guucagcccg accgcugcgc cuuauccggu aacuaucguc  10380
uugaguccaa cccgguaaga cacgacuuau cgccacuggc agcagccacu gguaacagga  10440
uuagcagagc gagguaugua ggcggugcua cagaguucuu gaagugguggg ccuaacuacg  10500
gcuacacuag aagaacagua uuugguaucu gcgcucugcu gaagccaguu accuucggaa  10560
aaagaguugg uagcucuuga uccggcaaac aaaccaccgc ugguagcggu gguuuuuuug  10620
uuugcaagca gcagauuacg cgcagaaaaa aaggaucuca agaagauccu uugaucuuuu  10680
cuacggggguc ugacgcucag uggaacgaaa acucacguua agggauuuug gucaugaaua  10740
cacggugccu gacugcguua gcaauuuaac ugugauaaac uaccgcauua aagcuuaucg  10800
augauaagcu gucaaacaug agaauucuua gaaaaacuca ucgagcauca aaugaaacug  10860
caauuuauuc auaucaggau uaucaauacc auauuuuuga aaaagccguu ucuguaauga  10920
aggagaaaac ucaccgaggc aguuccauag gauggcaaga uccugguauc ggucugcgau  10980
uccgacucgu ccaacaucaa uacaaccuau uaauuucccc ucgucaaaaa uaagguuauc  11040
aagugagaaa ucaccaugag ugacgacuga auccggugag aauggcaaaa gcuuaugcau  11100
```

uucuuuccag acuuguucaa caggccagcc auuacgcucg ucaucaaaau cacucgcauc 11160
aaccaaaccg uuauucauuc gugauugcgc cugagcgaga cgaaauacgc gaucgcuguu 11220
aaaaggacaa uuacaaacag gaaucgaaug caaccggcgc aggaacacug ccagcgcauc 11280
aacaauauuu ucaccugaau caggauauuc uucuaauacc uggaaugcug uuuucccggg 11340
gaucgcagug gugaguaacc augcaucauc aggaguacgg auaaaaugcu ugauggucgg 11400
aagaggcaua aauuccguca gccaguuuag ucugaccauc ucaucuguaa caucauuggc 11460
aacgcuaccu uugccauguu ucagaaacaa cucuggcgca ucgggcuucc cauacaaucg 11520
auagauuguc gcaccugauu gcccgacauu aucgcgagcc cauuuauacc cauauaaauc 11580
agcauccaug uuggaauuua aucgcggccu cgagcaagac guuucccguu gaauauggcu 11640
cauaacaccc cuuguauuac uguuuaugua agcagacagu uuuauuguuc augagcggau 11700
acauauuuga auguauuuag aaaaauaaac aaauaggggu uccgcgcaca uuuccccgaa 11760
aagugccacc uaaauuguaa gcguuaauau uuuguuaaaa uucgcguuaa auuuuuguua 11820
aaucagcuca uuuuuuaacc aauaggccga aaucggcaaa aucccuuaua aaucaaaaga 11880
auagaccgag auaggguuga guggccgcua cagggcgcuc ccauucgcca uucaggcugc 11940
gcaacuguug ggaagggcgu uucggugcgg gccucuucgc uauuacgcca gcuggcgaaa 12000
gggggaugug cugcaaggcg auuaaguugg guaacgccag gguuuuccca gucacacgcg 12060
uaauacgacu cacuauag 12078

<210> SEQ ID NO 72
<211> LENGTH: 12078
<212> TYPE: RNA
<213> ORGANISM: Zika virus

<400> SEQUENCE: 72
auaggcggcg caugagagaa gcccagacca auuaccuacc caaaauggag aaaguucacg 60
uugacaucga ggaagacagc ccauuccuca gagcuuugca gcggagcuuc ccgcaguuug 120
agguagaagc caagcagguc acugauaaug accaugcuaa ugccagagcg uuuucgcauc 180
uggcuucaaa acugaucgaa acggaggugg acccauccga cacgauccuu gacauuggaa 240
gugcgcccgc ccgcagaaug uauucuaagc acaaguauca uuguaucugu ccgaugagau 300
gugcggaaga uccggacaga uuguauaagu augcaacuaa gcugaagaaa aacuguaagg 360
aaauaacuga uaaggaauug gacaagaaaa ugaaggagcu cgccgccguc augagcgacc 420
cugaccugga aacugagacu augugccucc acgacgacga gucgugucgc uacgaagggc 480
aagucgcugu uuaccaggau guauacgcgg uugacggacc gacaagucuc uaucaccaag 540
ccaauaaggg aguuagaguc gccuacugga uaggcuuuga caccaccccu uuuauguuua 600
agaacuuggc uggagcauau ccaucauacu cuaccaacug ggccgacgaa accguguuaa 660
cggcucguaa cauaggccua ugcagcucug acguuaugga gcggucacgu agagggaugu 720
ccauucuuag aaagaaguau uugaaaccau ccaacaaugu ucuauucucu guuggcucga 780
ccaucuacca cgagaagagg gacuuacuga ggagcuggca ccugccgucu guauuucacu 840
uacguggcaa gcaaaauuac acaugucggu gugagacuau aguuaguugc gacggguacg 900
ucguuaaaag aauagcuauc aguccaggcc uguaugggaa gccuucaggc uaugcugcua 960
cgaugcaccg cgagggauuc uugugcugca aagugacaga cacauugaac ggggagaggg 1020
ucucuuuucc cgugugcacg uaugugccag cuacauugug ugaccaaaug acuggcauac 1080
uggcaacaga ugucagugcg gacgacgcgc aaaaacugcu gguugggcuc aaccagcgua 1140
uagucgucaa cggucgcacc cagagaaaca ccaauaccau gaaaaauuac cuuuugcccg 1200
uaguggccca ggcauuugcu aggugggcaa aggaauauaa ggaagaucaa gaagaugaaa 1260
ggccacuagg acuacgagau agacaguuag ucaugggug uuguugggcu uuuagaaggc 1320
acaagauaac aucuauuuau aagcgcccgg auacccaaac caucaucaaa gugaacagcg 1380
auuuccacuc auucgugcug cccaggauag gcaguaacac auuggagauc gggcugagaa 1440
caagaaucag gaaaauguua gaggagcaca aggagccguc accucucauu accgccgagg 1500
acguacaaga agcuaagugc gcagccgaug aggcuaagga ggugcgugaa gccgaggagu 1560
ugcgcgcagc ucuaccaccu uuggcagcug auguugagga gcccacucug gaagccgaug 1620
ucgacuugau guuacaagag gcuggggccg gcucagugga gacaccucgu ggcuugauaa 1680
agguuaccag cuacgauggc gaggacaaga ucggcucuua cgcugugcuu ucuccgcagg 1740
cuguacucaa gagugaaaaa uuaucuugca uccacccucu cgcugaacaa gucauaguga 1800
uaacacacuc uggccgaaaa gggcguuaug ccguggaacc auaccauggu aaaguagugg 1860
ugccagaggg acaugcaaua cccguccagg acuuucaagc ucugagugaa agugccacca 1920
uuguguacaa cgaacgugag uucguaaaca gguaccugca ccauauugcc acacauggag 1980
gagcgcugaa cacugaugaa gaauauuaca aaacugucaa gcccagcgag cacgacggcg 2040
aauaccugua cgacaucgac aggaaacagu gcgucaagaa agaacuaguc acugggcuag 2100
ggcucacagg cgagcuggug gauccucccu uccaugaauu cgccuacgag agucugagaa 2160
cacgaccagc cgcuccuuac caaguaccaa ccauaggggu guauggcgug ccaggaucag 2220
gcaagucugg caucauuaaa agcgcaguca ccaaaaaaga ucuaguggug agcgccaaga 2280
aagaaaacug ugcagaaauu auaagggacg ucaagaaaau gaaagggcug gacgucaaug 2340
ccagaacugu ggacucagug cucuugaaug gaugcaaaca ccccguagag acccuguaua 2400
uugacgaagc uuuugcuugu caugcaggua cucucagagc gcucauagcc auuauaagac 2460
cuaaaaaggc agugcucugc ggggauccca aacagugcgg uuuuuuuaac augaugugcc 2520
ugaaagugca uuuuaaccac gagauuugca cacaagucuu ccacaaaagc aucucucgcc 2580
guugcacuaa aucugugacu ucggucgucu caaccuuguu uuacgacaaa aaaaugagaa 2640
cgacgaaucc gaaagagacu aagauuguga uugacacuac cggcaguacc aaaccuaagc 2700
aggacgaucu cauucucacu uguuucagag ggugggugaa gcaguugcaa auagauuaca 2760
aaggcaacga aauaaugacg gcagcugccu cucaagggcu gacccguaaa ggguguguaug 2820
ccguucggua caaggugaau gaaaauccuc uguacgcacc caccucagaa caugugaacg 2880
uccuacugac ccgcacggag gaccgcaucg uguggaaaac acuagccggc gacccaugga 2940
uaaaaacacu gacugccaag uacccuggga auuucacugc cacgauagag gaguggcaag 3000
cagagcauga ugccaucaug aggcacaucu uggagagacc ggacccuacc gacgucuucc 3060
agaauaaggc aaacgugugu ugggccaagg cuuuagugcc ggugcugaag accgcuggca 3120
uagacaugac cacugaacaa uggaacacug uggauuauuu ugaaacggac aaagcucacu 3180
cagcagagau aguauugaac caacuaugcg ugagguucuu uggacucgau cuggacuccg 3240
gucuauuuuc ugcacccacu guuccguuau ccauuaggaa uaaucacugg gauaacuccc 3300
cgucgccuaa cauguacggg cugaauaaag aaguggaccg ucagcucucu cgcagguacc 3360
cacaacugcc ucgggcaguu gccacuggaa gagucuauga caugaacacu gguacacugc 3420
gcaauuauga uccgcgcaua aaccuaguac cuguaaacag aagacugccu caugcuuuag 3480
uccuccacca uaaugaacac ccacagagug acuuuucuuc auucgucagc aaauugaagg 3540
gcagaacugu ccuggugguc ggggaaaagu uguccguccc aggcaaaaug guugacuggu 3600
ugucagaccg gccugaggcu accuucagag cucggcugga uuuaggcauc ccaggugaug 3660
ugcccaaaua ugacauaaua uuuguuaaug ugaggacccc auauaaauac caucacuauc 3720
agcaguguga agaccaugcc auuaagcuua gcauguugac caagaaagcu ugucugcauc 3780
ugaaucccgg cggaaccugu gucagcauag guuaugguua cgcugacagg gccagcgaaa 3840
gcaucauugg ugcuauagcg cggcaguuca aguuuucccg gguaugcaaa ccgaaauccu 3900
cacuugaaga gacggaaguu cuguuuguau ucauugggua cgaucgcaag gcccguacgc 3960
acaauccuua caagcuuuca ucaaccuuga ccaacauuua uacagguucc agacuccacg 4020
aagccggaug ugcacccuca uaucaugugg ugcgagggga uauugccacg gccaccgaag 4080
gagugauuau aaaugcugcu aacagcaaag gacaaccugg cggagggggug ugcggagcgc 4140 uguauaagaa auucccggaa agcuucgauu uacagccgau cgaaguagga aaagcgcgac 4200
uggucaaagg ugcagcuaaa cauaucauuc augccguagg accaaacuuc aacaaaguuu 4260
cggagguuga aggugacaaa caguuggcag aggcuuauga guccaucgcu aagauuguca 4320
acgauaacaa uuacaaguca guagcgauuc cacuguuguc caccggcauc uuuuccggga 4380
acaaagaucg acuaacccaa ucauugaacc auuugcugac agcuuuagac accacugaug 4440
cagauguagc cauauacugc agggacaaga aaugggaaau gacucucaag gaagcagugg 4500
cuaggagaga agcaguggag gagauaugca uauccgacga cucuucagug acagaaccug 4560
augcagagcu ggugagggug cauccgaaga guucuuuggc uggaaggaag ggcuacagca 4620
caagcgaugg caaaacuuuc ucauauuugg aagggaccaa guuucaccag gcggccaagg 4680
auauagcaga aauuaaugcc auguggcccg uugcaacgga ggccaaugag cagguaugca 4740
uguauauccu cggagaaagc augagcagua uuaggucgaa augccccguc gaagagucgg 4800
aagccuccac accaccuagc acgcugccuu gcuugugcau ccaugccaug acuccagaaa 4860
gaguacagcg ccuaaaagcc ucacguccag aacaaauuac ugugugcuca uccuuuccau 4920
ugccgaagua uagaaucacu ggugugcaga agauccaaug cucccagccu auauuguucu 4980
caccgaaagu gccugcguau auucauccaa ggaaguaucu cguggaaaca ccaccgguag 5040
acgagacucc ggagccaucg gcagagaacc aauccacaga ggggacaccu gaacaaccac 5100
cacuuauaac cgaggaugag accaggacua gaacgccuga gccgaucauc aucgaagagg 5160
aagaagagga uagcauaagu uugcugucag auggcccgac ccaccaggug cugcaagucg 5220
aggcagacau ucacgggccg cccucuguau cuagcucauc cugguccauu ccucaugcau 5280
ccgacuuuga uguggacagu uuauccauac uugacacccu ggagggagcu agcgugacca 5340
gcggggcaac gucagccgag acuaacucuu acuucgcaaa gaguauggag uuucuggcgc 5400
gaccggugcc ugcgccucga acaguauuca ggaacccucc acaucccgcu ccgcgcacaa 5460
gaacaccguc acuugcaccc agcagggccu gcucgagaac cagccuaguu uccaccccgc 5520
caggcgugaa uagggugauc acuagagagg agcucgaggc gcuuaccccg ucacgcacuc 5580
cuagcagguc ggucucgaga accagccugg ucuccaaccc gccaggcgua aauagggug a 5640 uuacaagaga ggaguuugag gcguucguag cacaacaaca augacgguuu gaugcgggug 5700
cauacaucuu uuccuccgac accggucaag ggcauuuaca acaaaaauca guaaggcaaa 5760
cggugcuauc cgaaguggug uuggagagga ccgaauugga gauuucguau gccccgcgcc 5820
ucgaccaaga aaaagaagaa uuacuacgca agaaauuaca guuaaauccc acaccugcua 5880

-continued acagaagcag auaccagucc aggaaggugg agaacaugaa agccauaaca gcuagacgua 5940
uucugcaagg ccuagggcau uauuugaagg cagaaggaaa aguggagugc uaccgaaccc 6000
ugcauccugu uccuuuguau ucaucuagug ugaaccgugc cuuuucaagc cccaaggucg 6060
caguggaagc cuguaacgcc auguugaaag agaacuuucc gacuguggcu ucuuacugua 6120
uuauuccaga guacgaugcc uauuuggaca ugguugacgg agcuucaugc ugcuuagaca 6180
cugccaguuu uugcccugca aagcugcgca gcuuuccaaa gaaacacucc uauuuggaac 6240
ccacaauacg aucggcagug ccuucagcga uccagaacac gcuccagaac guccuggcag 6300
cugccacaaa aagaaauugc aaugucacgc aaaugagaga auugcccgua uuggauucgg 6360
cggccuuuaa uguggaaugc uucaagaaau augcguguaa uaaugaauau ugggaaacgu 6420
uuaaagaaaa ccccaucagg cuuacugaag aaaacguggu aaauuacauu accaaauuaa 6480
aaggaccaaa agcugcugcu cuuuuugcga agacacauaa uuugaauaug uugcaggaca 6540
uaccaaugga cagguuugua auggacuuaa agagagacgu gaaagugacu ccaggaacaa 6600
aacauacuga agaacggccc aagguacagg ugauccaggc ugccgauccg cuagcaacag 6660
cguaucugug cggaauccac cgagagcugg uuaggagauu aaaugcgguc cugcuuccga 6720
acauucauac acuguuugau augucggcug aagacuuuga cgcuauuaua gccgagcacu 6780
uccagccugg ggauuguguu cuggaaacug acaucgcguc guuugauaaa agugaggacg 6840
acgccauggc ucugaccgcg uuaaugauuc uggaagacuu aggugugga gcagagcugu 6900
ugacgcugau ugaggcggcu uucggcgaaa uuucaucaau acauuugccc acuaaaacua 6960
aauuuaaauu cggagccaug augaaaucug gaauguuccu cacacuguuu gugaacacag 7020
ucauuaacau uguaaucgca agcagagugu ugagagaacg gcuaaccgga ucaccaugug 7080
cagcauucau uggagaugac aauaucguga aaggagucaa aucggacaaa uuaauggcag 7140
acaggugcgc caccugguug aauauggaag ucaagauuau agaugcugug gugggcgaga 7200
aagcgccuua uuucugugga ggguuuauuu ugugugacuc cgugaccggc acagcgugcc 7260
guguggcaga cccccuaaaa aggcuguuua agcuuggcaa accucuggca gcagacgaug 7320
aacaugauga ugacaggaga agggcauugc augaagaguc aacacgcugg aaccgagugg 7380
guauucuuuc agagcugugc aaggcaguag aaucaaggua ugaaaccgua ggaacuucca 7440
ucauaguuau ggccaugacu acucuagcua gcaguguuaa aucauucagc uaccugagag 7500
gggccccuau aacucucuac ggcuaaccug aauggacuac gacauagucu aguccgccaa 7560
gaugagagga gcugacacca gcgugggcau ugugggccuc cugcugcccc aggcccaggc 7620
cgcugagguc accagaagag gcagcgccua cuacauguac cuggacagaa acgacgcugg 7680
cgaggcuauu agcuucccca ccacacucgg caugaacaag uguuacaucc agaucaugga 7740
ccugggccac augugcgaug ccaccaugag cuacgaaugu ccuaugcugg acgaaggcgu 7800
ggagcccgac gacguggacu guuggugcaa cacaaccagc accugggugg uguacggcac 7860
cugccaucau aagaagggag aagccaggag aagcaggagg gcugucacac uccccuccca 7920
cuccacaaga aagcugcaaa ccaggagcca gaccuggcug gaaagcaggg aguacaccaa 7980
gcaccugauc agggucgaga acuggaucuu caggaacccu ggauucgccc ucgccgcugc 8040
ugcuauugcc uggcuccugg gcuccuccac cagccaaaag gugaucuacc uggugaugau 8100
ccuccugauc gcccccgccu acagcaucag gugcaucggc guguccaaua gggacuuugu 8160
cgaaggaaug uccggcggca caugggugga cgucgugcug gagcauggcg gcugugugac 8220

-continued agucauggcc caggacaaac ccaccgugga uaucgagcug gugacaacca caguguccaa 8280
cauggccgag gugaggagcu acugcuacga ggcuagcauc agcgacaugg cuuccgacag 8340
cagaugcccc acacagggcg aggccuaccu cgacaaacag uccgacaccc aguacgugug 8400
caaaaggacc cuggucgaca gaggaugggg caacggcugc ggccuguucg gaaaaggaag 8460
ccuggucacc ugugcuaagu ucgccugcuc caagaagaug accggcaaga gcauccagcc 8520
cgagaaccuc gaguacagga ucaugcucuc cguccauggc agccagcaca gcggaaugau 8580
cgugaacgac accggccacg agaccgauga gaacagggcc aagguggaaa ucacccccaa 8640
cagcccuagg gcugaagcua cccucggcgg auuuggaucc cugggccugg auugugaacc 8700
caggaccgga cucgacuuca gcgaucugua cuaccugacc augaacaaca agcacuggcu 8760
ggugcauaag gagugguucc augauauccc ccugcccugg caugcuggag ccgauacagg 8820
caccccucac uggaacaaca aggaagcccu gguggaguuc aaagaugccc acgccaagag 8880
acagacaguc gucguccugg gcagccaaga gggcgcugug cauacagccc uggcuggagc 8940
ccuggaggcc gaaauggacg gcgccaaggg aaggcugucc agcggacauc ugaagugcag 9000
gcugaagaug gacaagcuga ggcucaaggg cgucagcuac ucccugugca ccgccgccuu 9060
uaccuuuaca aaaauccccg ccgagacccu ccacggcaca gucacagucg aggugcagua 9120
cgcuggaacc gacggaccuu guaaggugcc cgcccaaaug gccguggaca ugcagacacu 9180
gaccccugug ggcagacuca ucacagccaa cccugugauc acagagucca ccgagaacag 9240
caagaugaug cucgagcugg auccuccuuu cggcgacagc uacaucguga ucggaguggg 9300
cgagaagaaa aucacccacc acuggcacag guccggcagc accauuggca aagccuuuga 9360
agccaccguc agaggagcua aaaggauggc ugugcugggc gacaccgcuu gggacuucgg 9420
cuccguggga ggagcccuca acucccuggg caagggcauu caccagauuu ucggcgccgc 9480
uuucaagagc cucuuuggcg gcauguccug guuuagccag auucucaucg gcacacugcu 9540
gauguggcug ggccugaaua ccaagaacgg cagcaucagc cugaugugac uggcccuggg 9600
aggcgugcug aucuuucugu ccaccgcugu cagcgccgac ugauaaggcg cgcccaccca 9660
gcggccgcau acagcagcaa uuggcaagcu gcuuacauag aacucgcggc gauuggcaug 9720
ccgccuuaaa auuuuuauuu uauuuuucuu uucuuuuccg aaucggauuu uguuuuuaau 9780
auuucaaaaa aaaaaaaaaa aaaaaaaaaa aaaaaaaaaa aaaaagaaga gcguuuaaac 9840
acgugauauc uggccucaug ggccuuccuu ucacugcccg cuuuccaguc gggaaaccug 9900
ucgugccagc ugcauuaaca uggucauagc uguuuccuug cguauugggc gcucuccgcu 9960
uccucgcuca cugacucgcu gcgcucgguc guucggguaa agccuggggu gccuaaugag 10020
caaaaggcca gcaaaaggcc aggaaccgua aaaaggccgc guugcuggcg uuuuuccaua 10080
ggcuccgccc cccugacgag caucacaaaa aucgacgcuc aagucagagg uggcgaaacc 10140
cgacaggacu auaaagauac caggcguuuc cccccuggaag cucccucgug cgcucuccug 10200
uuccgacccu gccgcuuacc ggauaccugu ccgccuuucu cccuucggga agcguggcgc 10260
uuucucauag cucacgcugu agguaucuca guucggugua ggucguucgc uccaagcugg 10320
gcugugugca cgaacccccc guucagcccg accgcugcgc cuuauccggu aacuaucguc 10380
uugaguccaa cccgguaaga cacgacuuau cgccacuggc agcagccacu gguaacagga 10440
uuagcagagc gagguaugua ggcggugcua cagaguucuu gaaguggugg ccuaacuacg 10500
gcuacacuag aagaacagua uuugguaucu gcgcucugcu gaagccaguu accuucggaa 10560
aaagaguugg uagcucuuga uccggcaaac aaaccaccgc ugguagcggu gguuuuuuug 10620
uuugcaagca gcagauuacg cgcagaaaaa aaggaucuca agaagauccu uugaucuuuu 10680 cuacggggucugacgcucag uggaacgaaa acucacguua agggauuuug gucaugaaua 10740
cacggugccu gacugcguua gcaauuuaac ugugauaaac uaccgcauua aagcuuaucg 10800
augauaagcu gucaaacaug agaauucuua gaaaaacuca ucgagcauca aaugaaacug 10860
caauuuauuc auaucaggau uaucaauacc auauuuuuga aaaagccguu ucuguaauga 10920
aggagaaaac ucaccgaggc aguuccauag gauggcaaga uccugguauc ggucugcgau 10980
uccgacucgu ccaacaucaa uacaaccuau uaauuucccc ucgucaaaaa uaagguuauc 11040
aagugagaaa ucaccaugag ugacgacuga auccggugag aauggcaaaa gcuuaugcau 11100
uucuuuccag acuuguucaa caggccagcc auuacgcucg ucaucaaaau cacucgcauc 11160
aaccaaaccg uuauucauuc gugauugcgc cugagcgaga cgaaauacgc gaucgcuguu 11220
aaaaggacaa uuacaaacag gaaucgaaug caaccggcgc aggaacacug ccagcgcauc 11280
aacaauauuu ucaccugaau caggauauuc uucuaauacc uggaaugcug uuuucccggg 11340
gaucgcagug gugaguaacc augcaucauc aggaguacgg auaaaaugcu ugauggucgg 11400
aagaggcaua aauuccguca gccaguuuag ucugaccauc ucaucuguaa caucauuggc 11460
aacgcuaccu uugccauguu ucagaaacaa cucuggcgca ucgggcuucc cauacaaucg 11520
auagauuguc gcaccugauu gcccgacauu aucgcgagcc cauuuauacc cauauaaauc 11580
agcauccaug uuggaauuua aucgcggccu cgagcaagac guuucccguu gaauauggcu 11640
cauaacaccc cuuguauuac uguuuaugua agcagacagu uuuauuguuc augagcggau 11700
acauauuuga auguauuuag aaaaauaaac aaauaggggu uccgcgcaca uuuccccgaa 11760
aagugccacc uaaauuguaa gcguuaauau uuuguuaaaa uucgcguuaa auuuuuguua 11820
aaucagcuca uuuuuuaacc aauaggccga aaucggcaaa aucccuuaua aaucaaaaga 11880
auagaccgag auaggguuga guggccgcua cagggcgcuc ccauucgcca uucaggcugc 11940
gcaacuguug ggaagggcgu uucggugcgg gccucuucgc uauuacgcca gcuggcgaaa 12000
gggggaugug cugcaaggcg auuaaguugg guaacgccag gguuuuccca gucacacgcg 12060
uaauacgacu cacuauag 12078

<210> SEQ ID NO 73
<211> LENGTH: 12075
<212> TYPE: RNA
<213> ORGANISM: Zika virus

<400> SEQUENCE: 73
auaggcggcg caugagagaa gcccagacca auuaccuacc caaaauggag aaaguucacg 60
uugacaucga ggaagacagc ccauuccuca gagcuuugca gcggagcuuc ccgcaguuug 120
agguagaagc caagcagguc acugauaaug accaugcuaa ugccagagcg uuuucgcauc 180
uggcuucaaa acugaucgaa acggaggugg acccauccga cacgauccuu gacauuggaa 240
gugcgcccgc ccgcagaaug uauucuaagc acaaguauca uuguaucugu ccgaugagau 300
gugcggaaga uccggacaga uuguauaagu augcaacuaa gcugaagaaa aacuguaagg 360
aaauaacuga uaaggaauug gacaagaaaa ugaaggagcu cgccgccguc augagcgacc 420
cugaccugga aacugagacu augugccucc acgacgacga gucgugucgc uacgaagggc 480
aagucgcugu uuaccaggau guauacgcgg uugacggacc gacaagucuc uaucaccaag 540
ccaauaaggg aguuagaguc gccuacugga uaggcuuuga caccaccccu uuuauguuua 600

-continued

```
agaacuuggc uggagcauau ccaucauacu cuaccaacug ggccgacgaa accguguuaa    660
cggcucguaa cauaggccua ugcagcucug acguuaugga gcggucacgu agagggaugu    720
ccauucuuag aaagaaguau uugaaaccau ccaacaaugu ucuauucucu guuggcucga    780
ccaucuacca cgagaagagg gacuuacuga ggagcuggca ccugccgucu guauuucacu    840
uacguggcaa gcaaaauuac acaugucggu gugagacuau aguuaguugc gacggguacg    900
ucguuaaaag aauagcuauc aguccaggcc uguaugggaa gccuucaggc uaugcugcua    960
cgaugcaccg cgagggauuc uugugcugca aagugacaga cacauugaac ggggagaggg   1020
ucucuuuucc cgugugcacg uaugugccag cuacauugug ugaccaaaug acuggcauac   1080
uggcaacaga ugucagugcg gacgacgcgc aaaaacugcu gguugggcuc aaccagcgua   1140
uagucgucaa cggucgcacc cagagaaaca ccaauaccau gaaaaauuac cuuuugcccg   1200
uaguggccca ggcauuugcu aggugggcaa aggaauauaa ggaagaucaa gaagaugaaa   1260
ggccacuagg acuacgagau agacaguuag ucaugggggug uuguugggcu uuuagaaggc  1320
acaagauaac aucuauuuau aagcgcccgg auacccaaac caucaucaaa gugaacagcg   1380
auuuccacuc auucgugcug cccaggauag gcaguaacac auuggagauc gggcugagaa   1440
caagaaucag gaaaauguua gaggagcaca aggagccguc accucucauu accgccgagg   1500
acguacaaga agcuaagugc gcagccgaug aggcuaagga ggugcgugaa gccgaggagu   1560
ugcgcgcagc ucuaccaccu uuggcagcug auguugagga gcccacucug gaagccgaug   1620
ucgacuugau guuacaagag gcuggggccg gcucagugga gacaccucgu ggcuugauaa   1680
agguuaccag cuacgauggc gaggacaaga ucggcucuua cgcugugcuu ucuccgcagg   1740
cuguacucaa gagugaaaaa uuaucuugca uccacccucu cgcugaacaa gucauaguga   1800
uaacacacuc uggccgaaaa gggcguuaug ccguggaacc auaccauggu aaaguagugg   1860
ugccagaggg acaugcaaua cccguccagg acuuucaagc ucugagugaa agugccacca   1920
uuguguacaa cgaacgugag uucguaaaca gguaccugca ccauauugcc acacauggag   1980
gagcgcugaa cacugaugaa gaauauuaca aaacugucaa gcccagcgag cacgacggcg   2040
aauaccugua cgacaucgac aggaaacagu gcgucaagaa agaacuaguc acugggcuag   2100
ggcucacagg cgagcuggug gauccucccu uccaugaauu cgccuacgag agucugagaa   2160
cacgaccagc cgcuccuuac caaguaccaa ccauaggggu guauggcgug ccaggaucag   2220
gcaagucugg caucauuaaa agcgcaguca ccaaaaaaga ucuaguggug agcgccaaga   2280
aagaaaacug ugcagaaauu auaagggacg ucaagaaaau gaaagggcug gacgucaaug   2340
ccagaacugu ggacucagug cucuugaaug gaugcaaaca ccccguagag acccuguaua   2400
uugacgaagc uuuugcuugu caugcaggua cucucagagc gcucauagcc auuauaagac   2460
cuaaaaaggc agugcucugc ggggauccca aacagugcgg uuuuuuuaac augaugugcc   2520
ugaaagugca uuuuaaccac gagauuugca cacaagucuu ccacaaaagc aucucucgcc   2580
guugcacuaa aucugugacu ucggucgucu caaccuuguu uuacgacaaa aaaaugagaa   2640
cgacgaaucc gaaagagacu aagauuguga uugacacuac cggcaguacc aaaccuaagc   2700
aggacgaucu cauucucacu uguuucagag ggugggugaa gcaguugcaa auagauuaca   2760
aaggcaacga aauaaugacg gcagcugccu cucaagggcu gacccguaaa ggguguguaug  2820
ccguucggua caaggugaau gaaaauccuc uguacgcacc caccucagaa caugugaacg   2880
uccuacugac ccgcacggag gaccgcaucg uguggaaaac acuagccggc gacccaugga   2940
uaaaaacacu gacugccaag uacccuggga auuucacugc cacgauagag gaguggcaag   3000
```

cagagcauga ugccaucaug aggcacaucu uggagagacc ggacccuacc gacgucuucc 3060
agaauaaggc aaacgugugu ugggccaagg cuuuagugcc ggugcugaag accgcuggca 3120
uagacaugac cacugaacaa uggaacacug uggauuauuu ugaaacggac aaagcucacu 3180
cagcagagau aguauugaac caacuaugcg ugagguucuu uggacucgau cuggacuccg 3240
gucuauuuuc ugcacccacu guuccguuau ccauuaggaa uaaucacugg gauaacuccc 3300
cgucgccuaa cauguacggg cugaauaaag aaguggucug ucagcucucu cgcagguacc 3360
cacaacugcc ucgggcaguu gccacuggaa gagucuauga caugaacacu gguacacugc 3420
gcaauuauga uccgcgcaua aaccuaguac cuguaaacag aagacugccu caugcuuuag 3480
uccuccacca uaaugaacac ccacagagug acuuuucuuc auucgucagc aaauugaagg 3540
gcagaacugu ccugguggucc ggggaaaagu uguccguccc aggcaaaaug guugacuggu 3600
ugucagaccg gccugaggcu accuucagag cucggcugga uuuaggcauc ccaggugaug 3660
ugcccaaaua ugacauaaua uuuguuaaug ugaggacccc auauaaauac caucacuauc 3720
agcaguguga agaccaugcc auuaagcuua gcauguugac caagaaagcu ugucugcauc 3780
ugaaucccgg cggaaccugu gucagcauag guuaugguua cgcugacagg gccagcgaaa 3840
gcaucauugg ugcuauagcg cggcaguuca aguuuucccg gguaugcaaa ccgaaauccu 3900
cacuugaaga gacggaaguu cuguuuguau ucauugggua cgaucgcaag gcccguacgc 3960
acaauccuua caagcuuuca ucaaccuuga ccaacauuua uacagguucc agacuccacg 4020
aagccggaug ugcacccuca uaucaugugg ugcgagggga uauugccacg gccaccgaag 4080
gagugauuau aaaugcugcu aacagcaaag gacaaccugg cggagggggug ugcggagcgc 4140
uguauaagaa auucccggaa agcuucgauu uacagccgau cgaaguagga aaagcgcgac 4200
uggucaaagg ugcagcuaaa cauaucauuc augccguagg accaaacuuc aacaaaguuu 4260
cggagguuga aggugacaaa caguuggcag aggcuuauga guccaucgcu aagauuguca 4320
acgauaacaa uuacaaguca guagcgauuc cacuguuguc caccggcauc uuuuccggga 4380
acaaagaucg acuaacccaa ucauugaacc auuugcugac agcuuuagac accacugaug 4440
cagauguagc cauauacugc agggacaaga aaugggaaau gacucucaag gaagcagugg 4500
cuaggagaga agcaguggag gagauaugca uauccgacga cucuucagug acagaaccug 4560
augcagagcu ggugagggug cauccgaaga guucuuuggc uggaaggaag ggcuacagca 4620
caagcgaugg caaaacuuuc ucauauuugg aagggaccaa guuucaccag gcggccaagg 4680
auauagcaga aauuaaugcc auguggcccg uugcaacgga ggccaaugag cagguaugca 4740
uguauauccu cggagaaagc augagcagua uuaggucgaa augccccguc gaagagucgg 4800
aagccuccac accaccuagc acgcugccuu gcuugugcau ccaugccaug acuccagaaa 4860
gaguacagcg ccuaaaagcc ucacguccag aacaaauuac ugugugcuca uccuuuccau 4920
ugccgaagua uagaaucacu ggugugcaga agauccaaug cucccagccu auauuguucu 4980
caccgaaagu gccugcguau auucauccaa ggaaguaucu cguggaaaca ccaccgguag 5040
acgagacucc ggagccaucg gcagagaacc aauccacaga ggggacaccu gaacaaccac 5100
cacuuauaac cgaggaugag accaggacua gaacgccuga gccgaucauc aucgaagagg 5160
aagaagagga uagcauaagu uugcugucag auggcccgac ccaccaggug cugcaagucg 5220
aggcagacau ucacgggccg cccucuguau cuagcucauc cugguccauu ccucaugcau 5280
ccgacuuuga uguggacagu uuauccauac uugacacccu ggagggagcu agcgugacca 5340

-continued

```
gcggggcaac gucagccgag acuaacucuu acuucgcaaa gaguauggag uuucuggcgc   5400
gaccggugcc ugcgccucga acaguauuca ggaacccucc acaucccgcu ccgcgcacaa   5460
gaacaccguc acuugcaccc agcagggccu gcucgagaac cagccuaguu uccacccccgc  5520
caggcgugaa uagggugauc acuagagagg agcucgaggc gcuuaccccg ucacgcacuc   5580
cuagcagguc ggucucgaga accagccugg ucuccaaccc gccaggcgua aauaggguga   5640
uuacaagaga ggaguuugag gcguucguag cacaacaaca augacgguuu gaugcgggug   5700
cauacaucuu uuccuccgac accggucaag ggcauuuaca acaaaaauca guaaggcaaa   5760
cggugcuauc cgaaguggug uuggagagga ccgaauugga gauuucguau gccccgcgcc   5820
ucgaccaaga aaaagaagaa uuacuacgca agaaauuaca guuaaauccc acaccugcua   5880
acagaagcag auaccagucc aggaaggugg agaacaugaa agccauaaca gcuagacgua   5940
uucugcaagg ccuagggcau uauuugaagg cagaaggaaa aguggagugc uaccgaaccc   6000
ugcauccugu uccuuuguau ucaucuagug ugaaccgugc cuuuucaagc cccaaggucg   6060
caguggaagc cuguaacgcc auguugaaag agaacuuucc gacuguggcu ucuuacugua   6120
uuauuccaga guacgaugcc uauuuggaca ugguugacgg agcuucaugc ugcuuagaca   6180
cugccaguuu uugcccugca aagcugcgca gcuuuccaaa gaaacacucc uauuuggaac   6240
ccacaauacg aucggcagug ccuucagcga uccagaacac gcuccagaac guccuggcag   6300
cugccacaaa aagaaauugc aaugucacgc aaaugagaga auugcccgua uuggauucgg   6360
cggccuuuaa uguggaaugc uucaagaaau augcguguaa uaaugaauau ugggaaacgu   6420
uuaaagaaaa ccccaucagg cuuacugaag aaaacguggu aaauuacauu accaaauuaa   6480
aaggaccaaa agcugcugcu cuuuuugcga agacacauaa uuugaauaug uugcaggaca   6540
uaccaaugga cagguuugua auggacuuaa agagagacgu gaaagugacu ccaggaacaa   6600
aacauacuga agaacggccc aagguacagg ugauccaggc ugccgauccg cuagcaacag   6660
cguaucugug cggaauccac cgagagcugg uuaggagauu aaaugcgguc cugcuuccga   6720
acauucauac acuguuugau augucggcug aagacuuuga cgcuauuaua gccgagcacu   6780
uccagccugg ggauuguguu cuggaaacug acaucgcguc guuugauaaa agugaggacg   6840
acgccauggc ucugaccgcg uuaaugauuc uggaagacuu agguguggac gcagagcugu   6900
ugacgcugau ugaggcggcu uucggcgaaa uuucaucaau acauuugccc acuaaaacua   6960
aauuuaaauu cggagccaug augaaaucug gaauguuccu cacacuguuu gugaacacag   7020
ucauuaacau uguaaucgca agcagagugu ugagagaacg gcuaaccgga ucaccaugug   7080
cagcauucau uggagaugac aauaucguga aaggagucaa aucggacaaa uuaauggcag   7140
acaggugcgc caccugguug aauauggaag ucaagauuau agaugcugug gugggcgaga   7200
aagcgccuua uuucugugga ggguuuauuu ugugugacuc cgugaccggc acagcgugcc   7260
guguggcaga cccccuaaaa aggcuguuua agcuuggcaa accucuggca gcagacgaug   7320
aacaugauga ugacaggaga agggcauugc augaagaguc aacacgcugg aaccgagugg   7380
guauucuuuc agagcugugc aaggcaguag aaucaaggua ugaaaccgua ggaacuucca   7440
ucauaguuau ggccaugacu acucuagcua gcaguguuaa aucauucagc uaccugagag   7500
gggccccuau aacucucuac ggcuaaccug aauggacuac gacauagucu aguccgccaa   7560
gauggaguuc ggccugagcu ggguguuccu ggugcccauc cuggagggcg ugcauugcgc   7620
ugaggucacc agaagaggca gcgccuacua cauguaccug gacagaaacg acgcuggcga   7680
ggcuauuagc uuccccacca cacucggcau gaacaagugu uacauccaga ucauggaccu   7740
```

-continued gggccacaug ugcgaugcca ccaugagcua cgaauguccu augcuggacg aaggcgugga 7800
gcccgacgac guggacuguu ggugcaacac aaccagcacc uggguggugu acggcaccug 7860
ccaucauaag aagggagaag ccaggagaag caggagggcu gucacacucc ccucccacuc 7920
cacaagaaag cugcaaacca ggagccagac cuggcuggaa agcagggagu acaccaagca 7980
ccugaucagg gucgagaacu ggaucuucag gaacccugga uucgcccucg ccgcugcugc 8040
uauugccugg cuccugggcu ccuccaccag ccaaaaggug aucuaccugg ugaugauccu 8100
ccugaucgcc cccgccuaca gcaucaggug caucggcgug uccaauaggg acuuugucga 8160
aggaaugucc ggcggcacau ggguggacgu cgugcuggag cauggcggcu gugugacagu 8220
cauggcccag gacaaaccca ccguggauau cgagcuggug acaaccacag uguccaacau 8280
ggccgaggug aggagcuacu gcuacgaggc uagcaucagc gacauggcuu ccgacagcag 8340
augccccaca cagggcgagg ccuaccucga caaacagucc gacacccagu acgugugcaa 8400
aaggacccug gucgacagag gauggggcaa cggcugcggc cuguucggaa aaggaagccu 8460
ggucaccugu gcuaaguucg ccugcuccaa gaagaugacc ggcaagagca uccagcccga 8520
gaaccucgag uacaggauca ugcucuccgu ccauggcagc cagcacagcg gaaugaucgu 8580
gaacgacacc ggccacgaga ccgaugagaa cagggccaag guggaaauca cccccaacag 8640
cccuagggcu gaagcuaccc ucggcggauu uggaucccug ggccuggauu gugaacccag 8700
gaccggacuc gacuucagcg aucuguacua ccugaccaug aacaacaagc acuggcuggu 8760
gcauaaggag ugguuccaug auaucccccu gcccuggcau gcuggagccg auacaggcac 8820
cccucacugg aacaacaagg aagcccuggu ggaguucaaa gaugcccacg ccaagagaca 8880
gacagucguc guccugggca gccaagaggg cgcugugcau acagcccugg cuggagcccu 8940
ggaggccgaa auggacggcg ccaagggaag gcuguccagc ggacaucuga agugcaggcu 9000
gaagauggac aagcugaggc ucaagggcgu cagcuacucc cugugcaccg ccgccuuuac 9060
cuuuacaaaa auccccgccg agacccucca cggcacaguc acagucgagg ugcaguacgc 9120
uggaaccgac ggaccuugua aggugcccgc ccaaauggcc guggacaugc agacacugac 9180
cccugugggc agacucauca cagccaaccc ugugaucaca gaguccaccg agaacagcaa 9240
gaugaugcuc gagcuggauc cuccuuucgg cgacagcuac aucgugaucg gagugggcga 9300
gaagaaaauc acccaccacu ggcacagguc cggcagcacc auuggcaaag ccuuugaagc 9360
caccgucaga ggagcuaaaa ggauggcugu gcugggcgac accgcuuggg acuucggcuc 9420
cgugggagga gcccucaacu cccugggcaa gggcauucac cagauuuucg gcgccgcuuu 9480
caagagccuc uuuggcggca uguccugguu uagccagauu cucaucggca cacugcugau 9540
guggcugggc cugaauacca agaacggcag caucagccug augugucugg cccugggagg 9600
cgugcugauc uuucugucca ccgcugucag cgccgacuga uaaggcgcgc ccacccagcg 9660
gccgcauaca gcagcaauug gcaagcugcu uacauagaac ucgcggcgau uggcaugccg 9720
ccuuaaaauu uuuauuuuau uuuucuuuuc uuuuccgaau cggauuuugu uuuuaauauu 9780
ucaaaaaaaa aaaaaaaaaa aaaaaaaaaa aaaaaaaaaa aagaagagcg uuuaaacacg 9840
ugauaucugg ccucaugggc cuuccuuuca cugcccgcuu uccagucggg aaaccugucg 9900
ugccagcugc auuaacaugg ucauagcugu uuccuugcgu auugggcgcu cuccgcuucc 9960
ucgcucacug acucgcugcg cucggucguu cggguaaagc cuggggugcc uaaugagcaa 10020
aaggccagca aaaggccagg aaccguaaaa aggccgcguu gcuggcguuu uuccauaggc 10080
uccgcccccc ugacgagcau cacaaaaauc gacgcucaag ucagaggugg cgaaacccga 10140
caggacuaua aagauaccag gcguuucccc cuggaagcuc ccucgugcgc ucuccuguuc 10200
cgacccugcc gcuuaccgga uaccuguccg ccuuucuccc uucgggaagc guggcgcuuu 10260
cucauagcuc acgcuguagg uaucucaguu cgguguaggu cguucgcucc aagcugggcu 10320
gugugcacga accccccguu cagcccgacc gcugcgccuu auccgguaac uaucgucuug 10380
aguccaaccc gguaagacac gacuuaucgc cacuggcagc agccacuggu aacaggauua 10440
gcagagcgag guauguaggc ggugcuacag aguucuugaa gugguggccu aacuacggcu 10500
acacuagaag aacaguauuu gguaucugcg cucugcugaa gccaguuacc uucggaaaaa 10560
gaguugguag cucuugaucc ggcaaacaaa ccaccgcugg uagcggugguuuuuuuguuu 10620 gcaagcagca gauuacgcgc agaaaaaaag gaucucaaga agauccuuug aucuuuucua 10680
cggggucuga cgcucagugg aacgaaaacu cacguuaagg gauuuugguc augaauacac 10740
ggugccugac ugcguuagca auuuaacugu gauaaacuac cgcauuaaag cuuaucgaug 10800
auaagcuguc aaacaugaga auucuuagaa aaacucaucg agcaucaaau gaaacugcaa 10860
uuuauucaua ucaggauuau caauaccaua uuuuugaaaa agccguuucu guaaugaagg 10920
agaaaacuca ccgaggcagu uccauaggau ggcaagaucc ugguaucggu cugcgauucc 10980
gacucgucca acaucaauac aaccuauuaa uuuccccucg ucaaaaauaa gguuaucaag 11040
ugagaaauca ccaugaguga cgacugaauc cggugagaau ggcaaaagcu uaugcauuuc 11100
uuuccagacu uguucaacag gccagccauu acgcucguca ucaaaaucac ucgcaucaac 11160
caaaccguua uucauucgug auugcgccug agcgagacga aauacgcgau cgcuguuaaa 11220
aggacaauua caaacaggaa ucgaaugcaa ccggcgcagg aacacugcca gcgcaucaac 11280
aauauuuuca ccugaaucag gauauucuuc uaauaccugg aaugcuguuu ucccggggau 11340
cgcaguggug aguaaccaug caucaucagg aguacggaua aaaugcuuga uggucggaag 11400
aggcauaaau uccgucagcc aguuuagucu gaccaucuca ucuguaacau cauuggcaac 11460
gcuaccuuug ccauguuuca gaaacaacuc uggcgcaucg ggcuucccau acaaucgaua 11520
gauugucgca ccugauugcc cgacauuauc gcgagcccau uuauacccau auaaaucagc 11580
auccauguug gaauuuaauc gcggccucga gcaagacguu ucccguugaa uauggcucau 11640
aacaccccuu guauuacugu uuauguaagc agacaguuuu auuguucaug agcggauaca 11700
uauuugaaug uauuuagaaa aauaaacaaa uagggguucc gcgcacauuu ccccgaaaag 11760
ugccaccuaa auuguaagcg uuaauauuuu guuaaaauuc gcguuaaauu uuuguuaaau 11820
cagcucauuu uuuaaccaau aggccgaaau cggcaaaauc ccuuauaaau caaaagaaua 11880
gaccgagaua ggguugagug guccgcuacag ggcgcuccca uucgccauuc aggcugcgca 11940
acuguuggga agggcguuuc ggugcgggcc ucuucgcuau uacgccagcu ggcgaaaggg 12000
ggaugugcug caaggcgauu aaguugggua acgccagggu uuucccaguc acacgcguaa 12060
uacgacucac uauag 12075

<210> SEQ ID NO 74
<211> LENGTH: 12384
<212> TYPE: RNA
<213> ORGANISM: Zika virus

<400> SEQUENCE: 74
auaggcggcg caugagagaa gcccagacca auuaccuacc caaaauggag aaaguucacg 60
uugacaucga ggaagacagc ccauuccuca gagcuuugca gcggagcuuc ccgcaguuug 120

```
agguagaagc caagcagguc acugauaaug accaugcuaa ugccagagcg uuuucgcauc    180
uggcuucaaa acugaucgaa acggaggugg acccauccga cacgauccuu gacauuggaa    240
gugcgcccgc ccgcagaaug uauucuaagc acaaguauca uuguaucugu ccgaugagau    300
gugcggaaga uccggacaga uuguauaagu augcaacuaa gcugaagaaa aacuguaagg    360
aaauaacuga uaaggaauug gacaagaaaa ugaaggagcu cgccgccguc augagcgacc    420
cugaccugga aacugagacu augugccucc acgacgacga gucgugucgc uacgaagggc    480
aagucgcugu uuaccaggau guauacgcgg uugacggacc gacaagucuc uaucaccaag    540
ccaauaaggg aguuagaguc gccuacugga uaggcuuuga caccaccccu uuuauguuua    600
agaacuuggc uggagcauau ccaucauacu cuaccaacug ggccgacgaa accguguuaa    660
cggcucguaa cauaggccua ugcagcucug acguuaugga gcggucacgu agagggaugu    720
ccauucuuag aaagaaguau uugaaaccau ccaacaaugu ucuauucucu guuggcucga    780
ccaucuacca cgagaagagg gacuuacuga ggagcuggca ccugccgucu guauuucacu    840
uacguggcaa gcaaaauuac acaugucggu gugagacuau aguuaguugc gacggguacg    900
ucguuaaaag aauagcuauc aguccaggcc uguaugggaa gccuucaggc uaugcugcua    960
cgaugcaccg cgagggauuc uugugcugca aagugacaga cacauugaac ggggagaggg   1020
ucucuuuucc cgugugcacg uaugugccag cuacauugug ugaccaaaug acuggcauac   1080
uggcaacaga ugucagugcg gacgacgcgc aaaaacugcu gguugggcuc aaccagcgua   1140
uagucgucaa cggucgcacc cagagaaaca ccaauaccau gaaaaauuac cuuuugcccg   1200
uaguggccca ggcauuugcu aggugggcaa aggaauauaa ggaagaucaa gaagaugaaa   1260
ggccacuagg acuacgagau agacaguuag ucaugggggug uuguugggcu uuuagaaggc   1320
acaagauaac aucuauuuau aagcgcccgg auacccaaac caucaucaaa gugaacagcg   1380
auuuccacuc auucgugcug cccaggauag gcaguaacac auuggagauc gggcugagaa   1440
caagaaucag gaaaauguua gaggagcaca aggagccguc accucucauu accgccgagg   1500
acguacaaga agcuaagugc gcagccgaug aggcuaagga ggugcgugaa gccgaggagu   1560
ugcgcgcagc ucuaccaccu uuggcagcug auguugagga gcccacucug gaagccgaug   1620
ucgacuugau guuacaagag gcuggggccg gcucagugga gacaccucgu ggcuugauaa   1680
agguuaccag cuacgauggc gaggacaaga ucggcucuua cgcugugcuu ucuccgcagg   1740
cuguacucaa gagugaaaaa uuaucuugca uccacccucu cgcugaacaa gucauaguga   1800
uaacacacuc uggccgaaaa gggcguuaug ccguggaacc auaccauggu aaaguagugg   1860
ugccagaggg acaugcaaua cccguccagg acuuucaagc ucugagugaa agugccacca   1920
uuguguacaa cgaacgugag uucguaaaca gguaccugca ccauauugcc acacauggag   1980
gagcgcugaa cacugaugaa gaauauuaca aaacugucaa gcccagcgag cacgacggcg   2040
aauaccugua cgacaucgac aggaaacagu gcgucaagaa agaacuaguc acugggcuag   2100
ggcucacagg cgagcuggug gauccucccu uccaugaauu cgccuacgag agucugagaa   2160
cacgaccagc cgcuccuuac caaguaccaa ccauaggggu guauggcgug ccaggaucag   2220
gcaagucugg caucauuaaa agcgcaguca ccaaaaaaga ucuaguggug agcgccaaga   2280
aagaaaacug ugcagaaauu auaagggacg ucaagaaaau gaaagggcug gacgucaaug   2340
ccagaacugu ggacucagug cucuugaaug gaugcaaaca ccccguagag acccuguaua   2400
uugacgaagc uuuugcuugu caugcaggua cucucagagc gcucauagcc auuauaagac   2460
```

-continued

```
cuaaaaaggc agugcucugc ggggauccca aacagugcgg uuuuuuuaac augaugugcc   2520
ugaaagugca uuuuaaccac gagauuugca cacaagucuu ccacaaaagc aucucucgcc   2580
guugcacuaa aucugugacu ucggucgucu caaccuuguu uuacgacaaa aaaaugagaa   2640
cgacgaaucc gaaagagacu aagauuguga uugacacuac cggcaguacc aaaccuaagc   2700
aggacgaucu cauucucacu uguuucagag ggugggugaa gcaguugcaa auagauuaca   2760
aaggcaacga aauaaugacg gcagcugccu cucaagggcu gacccguaaa ggugugguaug  2820
ccguucggua caaggugaau gaaaauccuc uguacgcacc caccucagaa caugugaacg   2880
uccuacugac ccgcacggag gaccgcaucg uguggaaaac acuagccggc gacccaugga   2940
uaaaaacacu gacugccaag uacccuggga auuucacugc cacgauagag gaguggcaag   3000
cagagcauga ugccaucaug aggcacaucu uggagagacc ggacccuacc gacgucuucc   3060
agaauaaggc aaacgugugu ugggccaagg cuuuagugcc ggugcugaag accgcuggca   3120
uagacaugac cacugaacaa uggaacacug uggauuauuu ugaaacggac aaagcucacu   3180
cagcagagau aguauugaac caacuaugcg ugagguucuu uggacucgau cuggacuccg   3240
gucuauuuuc ugcacccacu guuccguuau ccauuaggaa uaaucacugg gauaacuccc   3300
cgucgccuaa cauguacggg cugaauaaag aaguggcccg ucagcucucu cgcagguacc   3360
cacaacugcc ucgggcaguu gccacuggaa gagucuauga caugaacacu gguacacugc   3420
gcaauuauga uccgcgcaua aaccuaguac cuguaaacag aagacugccu caugcuuuag   3480
uccuccacca uaaugaacac ccacagagug acuuuucuuc auucgucagc aaauugaagg   3540
gcagaacugu ccuggugguc ggggaaaagu uguccguccc aggcaaaaug guugacuggu   3600
ugucagaccg gccugaggcu accuucagag cucggcugga uuuaggcauc ccaggugaug   3660
ugcccaaaua ugacauaaua uuuguuaaug ugaggacccc auauaaauac caucacuauc   3720
agcaguguga agaccaugcc auuaagcuua gcauguugac caagaaagcu ugucugcauc   3780
ugaaucccgg cggaaccugu gucagcauag guuaugguua cgcugacagg gccagcgaaa   3840
gcaucauugg ugcuauagcg cggcaguuca aguuucccg gguaugcaaa ccgaaauccu   3900
cacuugaaga gacggaaguu cuguuuguau ucauugggua cgaucgcaag gcccguacgc   3960
acaauccuua caagcuuuca ucaaccuuga ccaacauuua uacagguucc agacuccacg   4020
aagccggaug ugcacccuca uaucaugugg ugcgagggga uauugccacg gccaccgaag   4080
gagugauuau aaaugcugcu aacagcaaag gacaaccugg cggagggggug ugcggagcgc  4140
uguauaagaa auucccggaa agcuucgauu uacagccgau cgaaguagga aaagcgcgac   4200
uggucaaagg ugcagcuaaa cauaucauuc augccguagg accaaacuuc aacaaaguuu   4260
cggagguuga aggugacaaa caguuggcag aggcuuauga guccaucgcu aagauuguca   4320
acgauaacaa uuacaaguca guagcgauuc cacuguuguc caccggcauc uuuuccggga   4380
acaaagaucg acuaacccaa ucauugaacc auuugcugac agcuuuagac accacugaug   4440
cagauguagc cauauacugc agggacaaga aaugggaaau gacucucaag gaagcagugg   4500
cuaggagaga agcaguggag gagauaugca uauccgacga cucuucagug acagaaccug   4560
augcagagcu ggugagggug cauccgaaga guucuuuggc uggaaggaag ggcuacagca   4620
caagcgaugg caaaacuuuc ucauauuugg aagggaccaa guuucaccag gcggccaagg   4680
auauagcaga aauuaaugcc auguggcccg uugcaacgga ggccaaugag cagguaugca   4740
uguauauccu cggagaaagc augagcagua uuaggucgaa augccccguc gaagagucgg   4800
aagccuccac accaccuagc acgcugccuu gcuugugcau ccaugccaug acuccagaaa   4860
```

gaguacagcg ccuaaaagcc ucacguccag aacaaauuac ugugugcuca uccuuuccau 4920
ugccgaagua uagaaucacu ggugugcaga agauccaaug cucccagccu auauuguucu 4980
caccgaaagu gccugcguau auucauccaa ggaaguaucu cguggaaaca ccaccgguag 5040
acgagacucc ggagccaucg gcagagaacc aauccacaga ggggacaccu gaacaaccac 5100
cacuuauaac cgaggaugag accaggacua gaacgccuga gccgaucauc aucgaagagg 5160
aagaagagga uagcauaagu uugcugucag auggcccgac ccaccaggug cugcaagucg 5220
aggcagacau ucacgggccg cccucuguau cuagcucauc cugguccauu ccucaugcau 5280
ccgacuuuga uguggacagu uuauccauac uugacacccu ggagggagcu agcgugacca 5340
gcggggcaac gucagccgag acuaacucuu acuucgcaaa gaguauggag uuucuggcgc 5400
gaccggugcc ugcgccucga acaguauuca ggaacccucc acaucccgcu ccgcgcacaa 5460
gaacaccguc acuugcaccc agcagggccu gcucgagaac cagccuaguu uccaccccgc 5520
caggcgugaa uagggugauc acuagagagg agcucgaggc gcuuaccccg ucacgcacuc 5580
cuagcagguc ggucucgaga accagccugg ucuccaaccc gccaggcgua aauaggguga 5640
uuacaagaga ggaguuugag gcguucguag cacaacaaca augacgguuu gaugcgggug 5700
cauacaucuu uuccuccgac accggucaag ggcauuuaca acaaaaauca guaaggcaaa 5760
cggugcuauc cgaaguggug uuggagagga ccgaauugga gauuucguau gccccgcgcc 5820
ucgaccaaga aaaagaagaa uuacuacgca agaaauuaca guuaaauccc acaccugcua 5880
acagaagcag auaccagucc aggaaggugg agaacaugaa agccauaaca gcuagacgua 5940
uucugcaagg ccuagggcau uauuugaagg cagaaggaaa aguggagugc uaccgaaccc 6000
ugcauccugu uccuuuguau ucaucuagug ugaaccgugc cuuuucaagc cccaaggucg 6060
caguggaagc cuguaacgcc auguugaaag agaacuuucc gacuguggcu ucuuacugua 6120
uuauuccaga guacgaugcc uauuuggaca ugguugacgg agcuucaugc ugcuuagaca 6180
cugccaguuu uugcccugca aagcugcgca gcuuuccaaa gaaacacucc uauuuggaac 6240
ccacaauacg aucggcagug ccuucagcga uccagaacac gcuccagaac guccuggcag 6300
cugccacaaa aagaaauugc aaugucacgc aaaugagaga auugcccgua uuggauucgg 6360
cggccuuuaa uguggaaugc uucaagaaau augcguguaa uaaugaauau ugggaaacgu 6420
uuaaagaaaa ccccaucagg cuuacugaag aaaacguggu aaauuacauu accaaauuaa 6480
aaggaccaaa agcugcugcu cuuuuugcga agacacauaa uuugaauaug uugcaggaca 6540
uaccaaugga cagguuugua auggacuuaa agagagacgu gaaagugacu ccaggaacaa 6600
aacauacuga agaacggccc aagguacagg ugauccaggc ugccgauccg cuagcaacag 6660
cguaucugug cggaauccac cgagagcugg uuaggagauu aaaugcgguc cugcuuccga 6720
acauucauac acuguuugau augucggcug aagacuuuga cgcuauuaua gccgagcacu 6780
uccagccugg ggauuguguu cuggaaacug acaucgcguc guuugauaaa agugaggacg 6840
acgccauggc ucugaccgcg uuaaugauuc uggaagacuu aggugugggac gcagagcugu 6900 ugacgcugau ugaggcggcu uucggcgaaa uuucaucaau acauuugccc acuaaaacua 6960
aauuuaaauu cggagccaug augaaaucug gaauguuccu cacacuguuu gugaacacag 7020
ucauuaacau uguaaucgca agcagagugu ugagagaacg gcuaaccgga ucaccaugug 7080
cagcauucau uggagaugac aauaucguga aaggagucaa aucggacaaa uuaauggcag 7140
acaggugcgc caccugguug aauauggaag ucaagauuau agaugcugug gugggcgaga 7200

-continued

```
aagcgccuua uuucugugga ggguuuauuu ugugugacuc cgugaccggc acagcgugcc   7260
guguggcaga cccccuaaaa aggcuguuua agcuuggcaa accucuggca gcagacgaug   7320
aacaugauga ugacaggaga agggcauugc augaagaguc aacacgcugg aaccgagugg   7380
guauucuuuc agagcugugc aaggcaguag aaucaaggua ugaaaccgua ggaacuucca   7440
ucauaguuau ggccaugacu acucuagcua gcaguguuaa aucauucagc uaccugagag   7500
gggccccuau aacucucuac ggcuaaccug aauggacuac gacauagucu aguccgccaa   7560
gaugaagaau ccuaagaaaa aguccggcgg auucaggauc gugaauaugc ugaagagggg   7620
cguggccagg gucuccccuu uuggaggccu gaaaaggcug ccugcuggac ugcugcuggg   7680
acacggcccc aucaggaugg uccuggccau ccucgccuuc cucagauuca ccgccaucaa   7740
gcccucccuc ggccugauua acaggugggg cagcgucggc aagaaagaag ccauggaaau   7800
cauuaagaag uucaaaaaag accuggccgc caugcugagg aucaucaaug ccaggaagga   7860
gaagaagagg aggggagcug auaccuccgu gggcaucgug ggacugcugc ucaccacagc   7920
cauggccgcc gaggucacca gaagaggcag cgcuuauuac auguaccugg acagaaauga   7980
cgccggcgaa gcuaucagcu ucccuaccac ccugggcaug aacaagugcu acauccagau   8040
cauggaccug ggccacaugu gcgaugccac cauguccuac gagugcccca ugcucgacga   8100
aggaguggag ccugacgacg uggauuguug gugcaacacc accuccacau ggguggucua   8160
uggcaccugc caucacaaga aaggcgaagc caggaggucc aggagggcug ugacccugcc   8220
cagccacucc accaggaagc ugcaaacaag aucccagacc uggcuggaau ccagggagua   8280
caccaagcac cugaucaggg uggagaacug gauuuucagg aaucccggcu ucgcccuggc   8340
cgcugccgcc aucgcuuggc ugcucggcag cagcaccucc cagaaaguga uuuaccuggu   8400
gaugauccug cucaucgccc ccgccuacag caucagaugc aucggaguga gcaacaggga   8460
uuucguggag ggcauguccg gaggaacaug gguggaugug gugcuggaac auggcggcug   8520
cgugacagug auggcccagg acaagcccac aguggacauc gagcugguga ccaccacagu   8580
guccaauaug gccgagguca ggagcuauug cuacgaggcu agcaucuccg acauggcuuc   8640
cgacagcagg ugucccacac agggcgaggc uuaucuggac aagcaguccg auacccagua   8700
cgugugcaaa aggacccugg uggauagagg auggggaaac ggcuguggcc uguucggcaa   8760
gggcucccug gugaccugug cuaaauuugc cugcuccaag aagaugaccg gcaaguccau   8820
ccaaccugag aaccuggagu acaggaucau gcuguccgug cacggcagcc aacauagcgg   8880
caugaucgug aaugacaccg gacacgaaac cgacgaaaac agggccaagg uggagauuac   8940
ccccaauagc cccagagcug aggccacacu gggcggcuuu ggaucccucg gccuggauug   9000
ugagcccagg accggccucg acuucuccga ucuguauuac cugaccauga acaacaagca   9060
uuggcucgug cacaaagagu gguuucacga cauuccccug ccuuggcacg cuggcgccga   9120
uacaggaacc ccccacugga acaacaagga ggcucugguc gaauuuaaag acgcccaugc   9180
caaaagacag acagucgugg ugcugggcuc ccaagaggga gccgugcaua cagcccuggc   9240
cggagcccuc gaggcugaaa uggacggagc uaaaggcagg cuguccagcg gacaccugaa   9300
gugcaggcuc aagauggaca agcucagacu caagggagug agcuauagcc uguguacagc   9360
cgccuucaca uucaccaaaa uccccgccga aacccugcac ggcacaguga ccguggaggu   9420
ccaguacgcc ggcacagacg gcccuugcaa agugcccgcc cagauggcug ucgacaugca   9480
gacacugacc ccugugggca ggcugauuac cgcuaacccc gugauuaccg agagcacaga   9540
gaacagcaag augaugcugg agcuggaccc uccuuucggc gauuccuaca ucgugaucgg   9600
```

```
agugggcgag aaaaagauca cccaccauug gcacaggucc ggcuccacaa uuggcaaggc   9660
cuuugaggcc accgugaggg gagcuaagag gauggccgug cucggcgaca cagccuggga   9720
uuucggaagc gugggaggcg cccugaauuc ccucggcaag ggcauccauc agaucuucgg   9780
cgcugccuuc aagucccucu ucggaggcau gagcugguuc agccagaucc ugaucggaac   9840
ccuccugaug uggcugggcc ugaacaccaa gaacggaucc auuagccuga ugugucucgc   9900
ccugggcggc gugcugaucu uccuguccac cgccgugucc gccgauugau aaggcgcgcc   9960
cacccagcgg ccgcauacag cagcaauugg caagcugcuu acauagaacu cgcggcgauu  10020
ggcaugccgc cuuaaaauuu uuauuuuauu uuucuuuucu uuuccgaauc ggauuuuguu  10080
uuuaauauuu caaaaaaaaa aaaaaaaaaa aaaaaaaaaa aaaaaaaaaa agaagagcgu  10140
uuaaacacgu gauaucuggc cucaugggcc uuccuuucac ugcccgcuuu ccagucggga  10200
aaccugucgu gccagcugca uuaacauggu cauagcuguu uccuugcgua uugggcgcuc  10260
uccgcuuccu cgcucacuga cucgcugcgc ucggucguuc ggguaaagcc uggggugccu  10320
aaugagcaaa aggccagcaa aaggccagga accguaaaaa ggccgcguug cuggcguuuu  10380
uccauaggcu ccgccccccu gacgagcauc acaaaaaucg acgcucaagu cagagguggc  10440
gaaacccgac aggacuauaa agauaccagg cguuuccccc uggaagcucc cucgugcgcu  10500
cuccuguucc gacccugccg cuuaccggau accuguccgc cuuucucccu ucgggaagcg  10560
uggcgcuuuc ucauagcuca cgcuguaggu aucucaguuc gguguagguc guucgcucca  10620
agcugggcug ugugcacgaa ccccccguuc agcccgaccg cugcgccuua uccgguaacu  10680
aucgucuuga guccaacccg guaagacacg acuuaucgcc acuggcagca gccacuggua  10740
acaggauuag cagagcgagg uauguaggcg gugcuacaga guucuugaag ugguggccua  10800
acuacggcua cacuagaaga acaguauuug guaucugcgc ucugcugaag ccaguuaccu  10860
ucggaaaaag aguugguagc ucuugauccg gcaaacaaac caccgcuggu agcggugguu  10920
uuuuuguuug caagcagcag auuacgcgca gaaaaaaagg aucucaagaa gauccuuuga  10980
ucuuuucuac ggggucugac gcucagugga acgaaaacuc acguuaaggg auuuugguca  11040
ugaauacacg gugccugacu gcguuagcaa uuuaacugug auaaacuacc gcauuaaagc  11100
uuaucgauga uaagcuguca aacaugagaa uucuuagaaa aacucaucga gcaucaaaug  11160
aaacugcaau uuauucauau caggauuauc aauaccauau uuuugaaaaa gccguuucug  11220
uaaugaagga gaaaacucac cgaggcaguu ccauaggaug gcaagauccu gguaucgguc  11280
ugcgauuccg acucguccaa caucaauaca accuauuaau uuccccucgu caaaaauaag  11340
guuaucaagu gagaaaucac caugagugac gacugaaucc ggugagaaug gcaaaagcuu  11400
augcauuucu uuccagacuu guucaacagg ccagccauua cgcucgucau caaaaucacu  11460
cgcaucaacc aaaccguuau ucauucguga uugcgccuga gcgagacgaa auacgcgauc  11520
gcuguuaaaa ggacaauuac aaacaggaau cgaaugcaac cggcgcagga acacugccag  11580
cgcaucaaca auauuuucac cugaaucagg auauucuucu aauaccugga augcuguuuu  11640
cccggggauc gcagugguga guaaccaugc aucaucagga guacggauaa aaugcuugau  11700
ggucggaaga ggcauaaauu ccgucagcca guuuagucug accaucucau cuguaacauc  11760
auuggcaacg cuaccuuugc cauguuucag aaacaacucu ggcgcaucgg gcuucccaua  11820
caaucgauag auugucgcac cugauugccc gacauuaucg cgagcccauu uauacccaua  11880
uaaaucagca uccauguugg aauuuaaucg cggccucgag caagacguuu cccguugaau  11940
```

auggcucaua acaccccuug uauuacuguu uauguaagca gacaguuuua uuguucauga 12000
gcggauacau auuugaaugu auuuagaaaa auaaacaaau agggguuccg cgcacauuuc 12060
cccgaaaagu gccaccuaaa uuguaagcgu uaauauuuug uuaaaauucg cguuaaauuu 12120
uuguuaaauc agcucauuuu uuaaccaaua ggccgaaauc ggcaaaaucc cuuauaaauc 12180
aaaagaauag accgagauag gguugagugg ccgcuacagg gcgcucccau ucgccauuca 12240
ggcugcgcaa cuguugggaa gggcguuucg gugcgggccu cuucgcuauu acgccagcug 12300
gcgaaagggg gaugugcugc aaggcgauua aguuggguaa cgccagggu uucccaguca 12360 cacgcguaau acgacucacu auag 12384

<210> SEQ ID NO 75
<211> LENGTH: 12384
<212> TYPE: RNA
<213> ORGANISM: Zika virus

<400> SEQUENCE: 75
auaggcggcg caugagagaa gcccagacca auuaccuacc caaaauggag aaaguucacg 60
uugacaucga ggaagacagc ccauuccuca gagcuuugca gcggagcuuc ccgcaguuug 120
agguagaagc caagcagguc acugauaaug accaugcuaa ugccagagcg uuuucgcauc 180
uggcuucaaa acugaucgaa acggaggugg acccauccga cacgauccuu gacauuggaa 240
gugcgcccgc ccgcagaaug uauucuaagc acaaguauca uuguaucugu ccgaugagau 300
gugcggaaga uccggacaga uuguauaagu augcaacuaa gcugaagaaa aacuguaagg 360
aaauaacuga uaaggaauug gacaagaaaa ugaaggagcu cgccgccguc augagcgacc 420
cugaccugga aacugagacu augugccucc acgacgacga gucgugucgc uacgaagggc 480
aagucgcugu uuaccaggau guauacgcgg uugacggacc gacaagucuc uaucaccaag 540
ccaauaaggg aguuagaguc gccuacugga uaggcuuuga caccaccccu uuuauguuua 600
agaacuuggc uggagcauau ccaucauacu cuaccaacug ggccgacgaa accguguuaa 660
cggcucguaa cauaggccua ugcagcucug acguuaugga gcggucacgu agagggaugu 720
ccauucuuag aaagaaguau uugaaaccau ccaacaaugu ucuauucucu guuggcucga 780
ccaucuacca cgagaagagg gacuuacuga ggagcuggca ccugccgucu guauuucacu 840
uacguggcaa gcaaaauuac acaugucggu gugagacuau aguuaguugc gacggguacg 900
ucguuaaaag aauagcuauc aguccaggcc uguaugggaa gccuucaggc uaugcugcua 960
cgaugcaccg cgagggauuc uugugcugca aagugacaga cacauugaac ggggagaggg 1020
ucucuuuucc cgugugcacg uaugugccag cuacauugug ugaccaaaug acuggcauac 1080
uggcaacaga ugucagugcg gacgacgcgc aaaaacugcu gguugggcuc aaccagcgua 1140
uagucgucaa cggucgcacc cagagaaaca ccaauaccau gaaaaauuac cuuuugcccg 1200
uaguggccca ggcauuugcu aggugggcaa aggaauauaa ggaagaucaa gaagaugaaa 1260
ggccacuagg acuacgagau agacaguuag ucaugggggug uuguugggcu uuuagaaggc 1320
acaagauaac aucuauuuau aagcgcccgg auacccaaac caucaucaaa gugaacagcg 1380
auuuccacuc auucgugcug cccaggauag gcaguaacac auuggagauc gggcugagaa 1440
caagaaucag gaaaauguua gaggagcaca aggagccguc accucucauu accgccgagg 1500
acguacaaga agcuaagugc gcagccgaug aggcuaagga ggugcgugaa gccgaggagu 1560
ugcgcgcagc ucuaccaccu uuggcagcug auguugagga gcccacucug gaagccgaug 1620
ucgacuugau guuacaagag gcuggggccg gcucagugga gacaccucgu ggcuugauaa 1680
agguuaccag cuacgauggc gaggacaaga ucggcucuua cgcugugcuu ucuccgcagg 1740
cuguacucaa gagugaaaaa uuaucuugca uccacccucu cgcugaacaa gucauaguga 1800
uaacacacuc uggccgaaaa gggcguuaug ccguggaacc auaccauggu aaaguagugg 1860
ugccagaggg acaugcaaua cccguccagg acuuucaagc ucugagugaa agugccacca 1920
uuguguacaa cgaacgugag uucguaaaca gguaccugca ccauauugcc acacauggag 1980
gagcgcugaa cacugaugaa gaauauuaca aaacugucaa gcccagcgag cacgacggcg 2040
aauaccugua cgacaucgac aggaaacagu gcgucaagaa agaacuaguc acugggcuag 2100
ggcucacagg cgagcuggug gauccucccu uccaugaauu cgccuacgag agucugagaa 2160
cacgaccagc cgcuccuuac caaguaccaa ccauaggggu guauggcgug ccaggaucag 2220
gcaagucugg caucauuaaa agcgcaguca ccaaaaaaga ucuaguggug agcgccaaga 2280
aagaaaacug ugcagaaauu auaagggacg ucaagaaaau gaaagggcug gacgucaaug 2340
ccagaacugu ggacucagug cucuugaaug gaugcaaaca ccccguagag acccuguaua 2400
uugacgaagc uuuugcuugu caugcaggua cucucagagc gcucauagcc auuauaagac 2460
cuaaaaaggc agugcucugc ggggauccca aacagugcgg uuuuuuuaac augaugugcc 2520
ugaaagugca uuuuaaccac gagauuugca cacaagucuu ccacaaaagc aucucucgcc 2580
guugcacuaa aucugugacu ucggucgucu caaccuuguu uuacgacaaa aaaaugagaa 2640
cgacgaaucc gaaagagacu aagauuguga uugacacuac cggcaguacc aaaccuaagc 2700
aggacgaucu cauucucacu uguuucagag gguggguaaa gcaguugcaa auagauuaca 2760
aaggcaacga aauaaugacg gcagcugccu cucaagggcu gacccguaaa gguguguaug 2820
ccguucggua caaggugaau gaaaauccuc uguacgcacc caccucagaa caugugaacg 2880
uccuacugac ccgcacggag gaccgcaucg uguggaaaac acuagccggc gacccaugga 2940
uaaaaacacu gacugccaag uacccuggga auuucacugc cacgauagag gaguggcaag 3000
cagagcauga ugccaucaug aggcacaucu uggagagacc ggacccuacc gacgucuucc 3060
agaauaaggc aaacgugugu ugggccaagg cuuuagugcc ggugcugaag accgcuggca 3120
uagacaugac cacugaacaa uggaacacug uggauuauuu ugaaacggac aaagcucacu 3180
cagcagagau aguauugaac caacuaugcg ugagguucuu uggacucgau cuggacuccg 3240
gucuauuuuc ugcacccacu guuccguuau ccauuaggaa uaaucacugg gauaacuccc 3300
cgucgccuaa cauguacggg cugaauaaag aaguggucccg ucagcucucu cgcagguacc 3360
cacaacugcc ucgggcaguu gccacuggaa gagucuauga caugaacacu gguacacugc 3420
gcaauuauga uccgcgcaua aaccuaguac cuguaaacag aagacugccu caugcuuuag 3480
uccuccacca uaaugaacac ccacagagug acuuuucuuc auucgucagc aaauugaagg 3540
gcagaacugu ccuggugguc ggggaaaagu uguccguccc aggcaaaaug guugacuggu 3600
ugucagaccg gccugaggcu accuucagag cucggcugga uuuaggcauc ccaggugaug 3660
ugcccaaaua ugacauaaua uuuguuaaug ugaggacccc auauaaauac caucacuauc 3720
agcaguguga agaccaugcc auuaagcuua gcauguugac caagaaagcu ugucugcauc 3780
ugaaucccgg cggaaccugu gucagcauag guuaugguua cgcugacagg gccagcgaaa 3840
gcaucauugg ugcuauagcg cggcaguuca aguuucccg gguaugcaaa ccgaaauccu 3900
cacuugaaga gacggaaguu cuguuuguau ucauugggua cgaucgcaag gcccguacgc 3960
acaauccuua caagcuuuca ucaaccuuga ccaacauuua uacagguucc agacuccacg 4020

-continued aagccggaug ugcacccuca uaucaugugg ugcgagggga uauugccacg gccaccgaag 4080
gagugauuau aaaugcugcu aacagcaaag gacaaccugg cggagggggug ugcggagcgc 4140
uguauaagaa auucccggaa agcuucgauu uacagccgau cgaaguagga aaagcgcgac 4200
uggucaaagg ugcagcuaaa cauaucauuc augccguagg accaaacuuc aacaaaguuu 4260
cggagguuga aggugacaaa caguuggcag aggcuuauga guccaucgcu aagauuguca 4320
acgauaacaa uuacaaguca guagcgauuc cacuguuguc caccggcauc uuuuccggga 4380
acaaagaucg acuaacccaa ucauugaacc auuugcugac agcuuuagac accacugaug 4440
cagauguagc cauauacugc agggacaaga aaugggaaau gacucucaag gaagcagugg 4500
cuaggagaga agcaguggag gagauaugca uauccgacga cucuucagug acagaaccug 4560
augcagagcu ggugagggug cauccgaaga guucuuuggc uggaaggaag ggcuacagca 4620
caagcgaugg caaaacuuuc ucauauuugg aagggaccaa guuucaccag gcggccaagg 4680
auauagcaga aauuaaugcc auguggcccg uugcaacgga ggccaaugag cagguaugca 4740
uguauauccu cggagaaagc augagcagua uuaggucgaa augccccguc gaagagucgg 4800
aagccuccac accaccuagc acgcugccuu gcuugugcau ccaugccaug acuccagaaa 4860
gaguacagcg ccuaaaagcc ucacguccag aacaaauuac ugugugcuca uccuuuccau 4920
ugccgaagua uagaaucacu ggugugcaga agauccaaug cucccagccu auauuguucu 4980
caccgaaagu gccugcguau auucauccaa ggaaguaucu cguggaaaca ccaccgguag 5040
acgagacucc ggagccaucg gcagagaacc aauccacaga ggggacaccu gaacaaccac 5100
cacuuauaac cgaggaugag accaggacua gaacgccuga gccgaucauc aucgaagagg 5160
aagaagagga uagcauaagu uugcugucag auggcccgac ccaccaggug cugcaagucg 5220
aggcagacau ucacgggccg cccucuguau cuagcucauc cugguccauu ccucaugcau 5280
ccgacuuuga uguggacagu uuauccauac uugacacccu ggagggagcu agcgugacca 5340
gcggggcaac gucagccgag acuaacucuu acuucgcaaa gaguauggag uuucuggcgc 5400
gaccggugcc ugcgccucga acaguauuca ggaacccucc acaucccgcu ccgcgcacaa 5460
gaacaccguc acuugcaccc agcagggccu gcucgagaac cagccuaguu uccaccccgc 5520
caggcgugaa uagggugauc acuagagagg agcucgaggc gcuuaccccg ucacgcacuc 5580
cuagcagguc ggucucgaga accagccugg ucuccaaccc gccaggcgua aauaggguga 5640
uuacaagaga ggaguuugag gcguucguag cacaacaaca augacgguuu gaugcgggug 5700
cauacaucuu uuccuccgac accggucaag ggcauuuaca acaaaaauca guaaggcaaa 5760
cggugcuauc cgaagguggug uuggagagga ccgaauugga gauuucguau gccccgcgcc 5820
ucgaccaaga aaaagaagaa uuacuacgca agaaauuaca guuaaauccc acaccugcua 5880
acagaagcag auaccagucc aggaaggugg agaacaugaa agccauaaca gcuagacgua 5940
uucugcaagg ccuagggcau uauuugaagg cagaaggaaa aguggagugc uaccgaaccc 6000
ugcauccugu uccuuuguau ucaucuagug ugaaccgugc cuuuucaagc cccaaggucg 6060
caguggaagc cuguaacgcc auguugaaag agaacuuucc gacuguggcu ucuuacugua 6120
uuauuccaga guacgaugcc uauuuggaca ugguugacgg agcuucaugc ugcuuagaca 6180
cugccaguuu uugcccugca aagcugcgca gcuuuccaaa gaaacacucc uauuuggaac 6240
ccacaauacg aucggcagug ccuucagcga uccagaacac gcuccagaac guccuggcag 6300
cugccacaaa aagaaauugc aaugucacgc aaaugagaga auugcccgua uuggauucgg 6360
cggccuuuaa uguggaaugc uucaagaaau augcguguaa uaaugaauau ugggaaacgu 6420
uuaaagaaaa ccccaucagg cuuacugaag aaaacguggu aaauuacauu accaaauuaa 6480
aaggaccaaa agcugcugcu cuuuuugcga agacacauaa uuugaauaug uugcaggaca 6540
uaccaaugga cagguuugua auggacuuaa agagagacgu gaaagugacu ccaggaacaa 6600
aacauacuga agaacggccc aagguacagg ugauccaggc ugccgauccg cuagcaacag 6660
cguaucugug cggaauccac cgagagcugg uuaggagauu aaaugcgguc cugcuuccga 6720
acauucauac acuguuugau augucggcug aagacuuuga cgcuauuaua gccgagcacu 6780
uccagccugg ggauuguguu cuggaaacug acaucgcguc guuugauaaa agugaggacg 6840
acgccauggc ucugaccgcg uuaaugauuc uggaagacuu aggugugac gcagagcugu 6900
ugacgcugau ugaggcggcu uucggcgaaa uuucaucaau acauuugccc acuaaaacua 6960
aauuuaaauu cggagccaug augaaaucug gaauguuccu cacacuguuu gugaacacag 7020
ucauuaacau uguaaucgca agcagagugu ugagagaacg gcuaaccgga ucaccaugug 7080
cagcauucau uggagaugac aauaucguga aaggagucaa aucggacaaa uuaauggcag 7140
acaggugcgc caccugguug aauauggaag ucaagauuau agaugcugug gugggcgaga 7200
aagcgccuua uuucugugga ggguuuauuu ugugugacuc cgugaccggc acagcgugcc 7260
guguggcaga cccccuaaaa aggcuguuua agcuuggcaa accucuggca gcagacgaug 7320
aacaugauga ugacaggaga agggcauugc augaagaguc aacacgcugg aaccgagugg 7380
guauucuuuc agagcugugc aaggcaguag aaucaaggua ugaaaccgua ggaacuucca 7440
ucauaguuau ggccaugacu acucuagcua gcaguguuaa aucauucagc uaccugagag 7500
gggccccuau aacucucuac ggcuaaccug aauggacuac gacauagucu aguccgccaa 7560
gaugaagaau cccaagaaaa agagcggcgg cuucagaauc gugaacaugc ugaagagggg 7620
aguggccaga gugucccccu uuggcggccu gaaaagacuc ccugccggcc ugcuccuggg 7680
acauggcccu aucaggaugg uccuggccau ucuggcuuuc cugagguuca cagccaucaa 7740
gccuagccug ggccugauua acaggugggg cagcgucggc aagaaggaag ccauggagau 7800
uauuaagaag uucaagaaag accucgcugc caugcugagg aucaucaaug ccaggaagga 7860
gaagaaaagg aggggcgcug acacaagcgu gggaaucgug ggacugcugc ucccccaggc 7920
ccaggcugcu gaagugacca gaaggggcuc cgccuacuau auguaccucg acaggaacga 7980
cgccggagag gccaucagcu ucccuaccac ccugggaaug aacaaaugcu acauccagau 8040
cauggaccuc ggccacaugu gcgacgccac caugagcuac gaaugcccca ugcuggacga 8100
gggcguggag ccugacgaug uggacugcug gugcaacaca accagcaccu ggguggucua 8160
cggcaccugu caccacaaga aaggagaggc cagaaggucc aggagggccg ucacccugcc 8220
uagccacagc accagaaagc ugcagaccag gagccagacc uggcuggaga gcagagagua 8280
caccaaacac cucaucaggg uggagaacug gauuuuuagg aauccuggcu uugcccucgc 8340
ugccgccgcu aucgcuuggc uccucggaag cagcaccagc cagaagguca ucuaucucgu 8400
gaugauccug cucaucgcuc ccgcuuacuc caucaggugc aucggcguga gcaacagaga 8460
cuucguggag ggaauguccg gcggaaccug gguggaugug gugcucgagc acggcggaug 8520
cgucaccgug auggcccaag auaagccuac cguggacauc gaacugguga caacaaccgu 8580
guccaacaug gccgagguga gaagcuacug uuacgaggcc uccaucagcg acauggccuc 8640
cgacuccagg ugcccuaccc agggagaggc uuaccuggac aagcaauccg acacccagua 8700
cgugugaag aggacccugg ucgauagagg cuggggcaau ggcuguggac uguucggcaa 8760

-continued

```
gggaagccug gugaccugcg cuaaguucgc cugcuccaaa aagaugaccg gcaagagcau   8820
ccagcccgag aaccuggagu acagaaucau gcuguccgug cacggcagcc agcacagcgg   8880
caugauugug aacgacaccg gacacgaaac cgacgagaac agggccaaag uggagaucac   8940
ccccaauagc cccagggcug aagcuacacu gggaggauuu ggcagccugg gccuggauug   9000
ugagccuagg accggacugg auuucagcga ucuguacuau cugaccauga auaacaagca   9060
cuggcuggug cacaaggagu gguuucacga caucccucug cccuggcacg cuggagccga   9120
uacaggcacc ccccacugga acaauaagga ggcccucgug gaauucaagg acgcccacgc   9180
caagagacaa accgucgugg ugcugggaag ccaggaaggc gccgugcaua ccgcccucgc   9240
cggcgcucuc gaggcugaga uggacggagc caagggcaga cugagcagcg gacaucucaa   9300
gugcaggcug aagauggaca agcucaggcu gaaaggaguc uccuacagcc ugugcaccgc   9360
cgccuucaca uuuaccaaaa uccccgccga gacccuccac ggaaccguca caguggaagu   9420
gcaauacgcc ggcacagaug gccccuguaa ggugcccgcc cagauggccg uggauaugca   9480
gacccugacc ccugucggca ggcugauuac cgccaacccu gugaucaccg aguccaccga   9540
gaacagcaaa augaugcugg agcuggaucc ccccuucggc gacuccuaca uugugaucgg   9600
cgugggcgag aagaaaauua cccaucacug gcauagaagc ggcagcacaa ucggcaaggc   9660
cuuugaggcc acagugagag gcgccaaaag aauggccgug cugggagaua cagcuuggga   9720
uuuuggaucc gugggcggcg cccugaacuc ccugggcaaa ggaauccauc agaucuucgg   9780
cgcugcuuuc aagagccucu uuggcggcau guccugguuc ucccaaaucc ugaucggcac   9840
acuccugaug uggcugggcc ucaacacaaa aaacggcagc aucagccuga ugugccucgc   9900
ccucggaggc gugcugaucu uccuguccac cgcugugagc gcugauugau aaggcgcgcc   9960
cacccagcgg ccgcauacag cagcaauugg caagcugcuu acauagaacu cgcggcgauu  10020
ggcaugccgc cuuaaaauuu uuauuuuauu uuucuuuucu uuuccgaauc ggauuuuguu  10080
uuuaauauuu caaaaaaaaa aaaaaaaaaa aaaaaaaaaa aaaaaaaaaa agaagagcgu  10140
uuaaacacgu gauaucuggc cucaugggcc uuccuuucac ugcccgcuuu ccagucggga  10200
aaccugucgu gccagcugca uuaacauggu cauagcuguu uccuugcgua uugggcgcuc  10260
uccgcuuccu cgcucacuga cucgcugcgc ucggucguuc ggguaaagcc uggggugccu  10320
aaugagcaaa aggccagcaa aaggccagga accguaaaaa ggccgcguug cuggcguuuu  10380
uccauaggcu ccgcccccu gacgagcauc acaaaaaucg acgcucaagu cagagguggc  10440
gaaacccgac aggacuauaa agauaccagg cguuuccccc uggaagcucc cucgugcgcu  10500
cuccuguucc gacccugccg cuuaccggau accuguccgc cuuucucccu ucgggaagcg  10560
uggcgcuuuc ucauagcuca cgcuguaggu aucucaguuc gguguagguc guucgcucca  10620
agcugggcug ugugcacgaa ccccccguuc agcccgaccg cugcgccuua uccgguaacu  10680
aucgucuuga guccaacccg guaagacacg acuuaucgcc acuggcagca gccacuggua  10740
acaggauuag cagagcgagg uauguaggcg gugcuacaga guucuugaag ugguggccua  10800
acuacggcua cacuagaaga acaguauuug guaucugcgc ucugcugaag ccaguuaccu  10860
ucggaaaaag aguugguagc ucuugauccg gcaaacaaac caccgcuggu agcgguggu u  10920
uuuuuguuug caagcagcag auuacgcgca gaaaaaaagg aucucaagaa gauccuuuga  10980
ucuuuucuac ggggucugac gcucagugga acgaaaacuc acguuaaggg auuuugguca  11040
ugaauacacg gugccugacu gcguuagcaa uuuaacugug auaaacuacc gcauuaaagc  11100
uuaucgauga uaagcuguca aacaugagaa uucuuagaaa aacucaucga gcaucaaaug  11160
```

aaacugcaau uuauucauau caggauuauc aauaccauau uuuugaaaaa gccguuucug 11220
uaaugaagga gaaaacucac cgaggcaguu ccauaggaug gcaagauccu gguaucgguc 11280
ugcgauuccg acucguccaa caucaauaca accuauuaau uuccccucgu caaaaauaag 11340
guuaucaagu gagaaaucac caugagugac gacugaaucc ggugagaaug gcaaaagcuu 11400
augcauuucu uuccagacuu guucaacagg ccagccauua cgcucgucau caaaaucacu 11460
cgcaucaacc aaaccguuau ucauucguga uugcgccuga gcgagacgaa auacgcgauc 11520
gcuguuaaaa ggacaauuac aaacaggaau cgaaugcaac cggcgcagga acacugccag 11580
cgcaucaaca auauuuucac cugaaucagg auauucuucu aauaccugga augcuguuuu 11640
cccggggauc gcaguggug a guaaccaugc aucaucagga guacggauaa aaugcuugau 11700
ggucggaaga ggcauaaauu ccgucagcca guuuagucug accaucucau cuguaacauc 11760
auuggcaacg cuaccuuugc cauguuucag aaacaacucu ggcgcaucgg gcuucccaua 11820
caaucgauag auugucgcac cugauugccc gacauuaucg cgagcccauu uauacccaua 11880
uaaaucagca uccauguugg aauuuaaucg cggccucgag caagacguuu cccguugaau 11940
auggcucaua acaccccuug uauuacuguu uauguaagca gacaguuuua uuguucauga 12000
gcggauacau auuugaaugu auuuagaaaa auaaacaaau agggguuccg cgcacauuuc 12060
cccgaaaagu gccaccuaaa uuguaagcgu uaauauuuug uuaaaauucg cguuaaauuu 12120
uuguuaaauc agcucauuuu uuaaccaaua ggccgaaauc ggcaaaaucc cuuauaaauc 12180
aaaagaauag accgagauag gguugagugg ccgcuacagg gcgcucccau ucgccauuca 12240
ggcugcgcaa cuguugggaa gggcguuucg gugcgggccu cuucgcuauu acgccagcug 12300
gcgaaagggg gaugugcugc aaggcgauua aguugggu aa cgccagggu u uucccaguca 12360 cacgcguaau acgacucacu auag 12384

<210> SEQ ID NO 76
<211> LENGTH: 12450
<212> TYPE: RNA
<213> ORGANISM: Zika virus

<400> SEQUENCE: 76
auaggcggcg caugagagaa gcccagacca auuaccuacc caaaauggag aaaguucacg 60
uugacaucga ggaagacagc ccauuccuca gagcuuugca gcggagcuuc ccgcaguuug 120
agguagaagc caagcagguc acugauaaug accaugcuaa ugccagagcg uuuucgcauc 180
uggcuucaaa acugaucgaa acggaggugg acccauccga cacgauccuu gacauuggaa 240
gugcgcccgc ccgcagaaug uauucuaagc acaaguauca uuguaucugu ccgaugagau 300
gugcggaaga uccggacaga uuguauaagu augcaacuaa gcugaagaaa aacuguaagg 360
aaauaacuga uaaggaauug gacaagaaaa ugaaggagcu cgccgccguc augagcgacc 420
cugaccugga aacugagacu augugccucc acgacgacga gucgugucgc uacgaagggc 480
aagucgcugu uuaccaggau guauacgcgg uugacggacc gacaagucuc uaucaccaag 540
ccaauaaggg aguuagaguc gccuacugga uaggcuuuga caccaccccu uuuauguuua 600
agaacuuggc uggagcauau ccaucauacu cuaccaacug ggccgacgaa accguguuaa 660
cggcucguaa cauaggccua ugcagcucug acguuaugga gcggucacgu agagggaugu 720
ccauucuuag aaagaaguau uugaaaccau ccaacaaugu ucuauucucu guuggcucga 780
ccaucuacca cgagaagagg gacuuacuga ggagcuggca ccugccgucu guauuucacu 840

-continued

```
uacguggcaa gcaaaauuac acaugucggu gugagacuau aguuaguugc gacggguacg    900
ucguuaaaag aauagcuauc aguccaggcc uguaugggaa gccuucaggc uaugcugcua    960
cgaugcaccg cgagggauuc uugugcugca aagugacaga cacauugaac ggggagaggg   1020
ucucuuuucc cgugugcacg uaugugccag cuacauugug ugaccaaaug acuggcauac   1080
uggcaacaga ugucagugcg gacgacgcgc aaaaacugcu gguugggcuc aaccagcgua   1140
uagucgucaa cggucgcacc cagagaaaca ccaauaccau gaaaaauuac cuuuugcccg   1200
uaguggccca ggcauuugcu aggugggcaa aggaauauaa ggaagaucaa gaagaugaaa   1260
ggccacuagg acuacgagau agacaguuag ucauggggug uuguugggcu uuuagaaggc   1320
acaagauaac aucuauuuau aagcgcccgg auacccaaac caucaucaaa gugaacagcg   1380
auuuccacuc auucgugcug cccaggauag gcaguaacac auuggagauc gggcugagaa   1440
caagaaucag gaaaauguua gaggagcaca aggagccguc accucucauu accgccgagg   1500
acguacaaga agcuaagugc gcagccgaug aggcuaagga ggugcgugaa gccgaggagu   1560
ugcgcgcagc ucuaccaccu uuggcagcug auguugagga gcccacucug gaagccgaug   1620
ucgacuugau guuacaagag gcuggggccg gcucagugga gacaccucgu ggcuugauaa   1680
agguuaccag cuacgauggc gaggacaaga ucggcucuua cgcugugcuu ucuccgcagg   1740
cuguacucaa gagugaaaaa uuaucuugca uccacccucu cgcugaacaa gucauaguga   1800
uaacacacuc uggccgaaaa gggcguuaug ccguggaacc auaccauggu aaaguagugg   1860
ugccagaggg acaugcaaua cccguccagg acuuucaagc ucugagugaa agugccacca   1920
uuguguacaa cgaacgugag uucguaaaca gguaccugca ccauauugcc acacauggag   1980
gagcgcugaa cacugaugaa gaauauuaca aaacugucaa gcccagcgag cacgacggcg   2040
aauaccugua cgacaucgac aggaaacagu gcgucaagaa agaacuaguc acugggcuag   2100
ggcucacagg cgagcuggug gauccucccu uccaugaauu cgccuacgag agucugagaa   2160
cacgaccagc cgcuccuuac caaguaccaa ccauaggggu guauggcgug ccaggaucag   2220
gcaagucugg caucauuaaa agcgcaguca ccaaaaaaga ucuaguggug agcgccaaga   2280
aagaaaacug ugcagaaauu auaagggacg ucaagaaaau gaaagggcug gacgucaaug   2340
ccagaacugu ggacucagug cucuugaaug gaugcaaaca ccccguagag acccuguaua   2400
uugacgaagc uuuugcuugu caugcaggua cucucagagc gcucauagcc auuauaagac   2460
cuaaaaaggc agugcucugc ggggauccca aacagugcgg uuuuuuuaac augaugugcc   2520
ugaaagugca uuuuaaccac gagauuugca cacaagucuu ccacaaaagc aucucucgcc   2580
guugcacuaa aucugugacu ucggucgucu caaccuuguu uuacgacaaa aaaaugagaa   2640
cgacgaaucc gaaagagacu aagauuguga uugacacuac cggcaguacc aaaccuaagc   2700
aggacgaucu cauucucacu uguuucagag ggugggugaa gcaguugcaa auagauuaca   2760
aaggcaacga aauaaugacg gcagcugccu cucaagggcu gacccguaaa ggguguguaug   2820
ccguucggua caaggugaau gaaaauccuc uguacgcacc caccucagaa caugugaacg   2880
uccuacugac ccgcacggag gaccgcaucg uguggaaaac acuagccggc gacccaugga   2940
uaaaaacacu gacugccaag uacccuggga auuucacugc cacgauagag gaguggcaag   3000
cagagcauga ugccaucaug aggcacaucu uggagagacc ggacccuacc gacgucuucc   3060
agaauaaggc aaacgugugu ugggccaagg cuuuagugcc ggugcugaag accgcuggca   3120
uagacaugac cacugaacaa uggaacacug uggauuauuu ugaaacggac aaagcucacu   3180
cagcagagau aguauugaac caacuaugcg ugagguucuu uggacucgau cuggacuccg   3240
```

gucuauuuuc ugcacccacu guuccguuau ccauuaggaa uaaucacugg gauaacuccc 3300
cgucgccuaa cauguacggg cugaauaaag aaguggucg ucagcucucu cgcagguacc 3360
cacaacugcc ucgggcaguu gccacuggaa gagucuauga caugaacacu gguacacugc 3420
gcaauuauga uccgcgcaua aaccuaguac cuguaaacag aagacugccu caugcuuuag 3480
uccuccacca uaaugaacac ccacagagug acuuuucuuc auucgucagc aaauugaagg 3540
gcagaacugu ccuggugguc ggggaaaagu uguccguccc aggcaaaaug guugacuggu 3600
ugucagaccg gccugaggcu accuucagag cucggcugga uuuaggcauc ccaggugaug 3660
ugcccaaaua ugacauaaua uuuguuaaug ugaggacccc auauaaauac caucacuauc 3720
agcaguguga agaccaugcc auuaagcuua gcauguugac caagaaagcu ugucugcauc 3780
ugaaucccgg cggaaccugu gucagcauag guuaugguua cgcugacagg gccagcgaaa 3840
gcaucauugg ugcuauagcg cggcaguuca aguuuucccg gguaugcaaa ccgaaauccu 3900
cacuugaaga gacggaaguu cuguuuguau ucauugggua cgaucgcaag gcccguacgc 3960
acaauccuua caagcuuuca ucaaccuuga ccaacauuua uacagguucc agacuccacg 4020
aagccggaug ugcacccuca uaucaugugg ugcgagggga uauugccacg gccaccgaag 4080
gagugauuau aaaugcugcu aacagcaaag gacaaccugg cggaggggug ugcggagcgc 4140
uguauaagaa auucccggaa agcuucgauu uacagccgau cgaaguagga aaagcgcgac 4200
uggucaaagg ugcagcuaaa cauaucauuc augccguagg accaaacuuc aacaaaguuu 4260
cggagguuga aggugacaaa caguuggcag aggcuuauga guccaucgcu aagauuguca 4320
acgauaacaa uuacaaguca guagcgauuc cacuguuguc caccggcauc uuuuccggga 4380
acaaagaucg acuaacccaa ucauugaacc auuugcugac agcuuuagac accacugaug 4440
cagauguagc cauauacugc agggacaaga aaugggaaau gacucucaag gaagcagugg 4500
cuaggagaga agcaguggag gagauaugca uauccgacga cucuucagug acagaaccug 4560
augcagagcu ggugagggug cauccgaaga guucuuuggc uggaaggaag ggcuacagca 4620
caagcgaugg caaaacuuuc ucauauuugg aagggaccaa guuucaccag gcggccaagg 4680
auauagcaga aauuaaugcc auguggcccg uugcaacgga ggccaaugag cagguaugca 4740
uguauauccu cggagaaagc augagcagua uuaggucgaa augccccguc gaagagucgg 4800
aagccuccac accaccuagc acgcugccuu gcuugugcau ccaugccaug acuccagaaa 4860
gaguacagcg ccuaaaagcc ucacguccag aacaaauuac ugugugcuca uccuuuccau 4920
ugccgaagua uagaaucacu ggugugcaga agauccaaug cucccagccu auauuguucu 4980
caccgaaagu gccugcguau auucauccaa ggaaguaucu cguggaaaca ccaccgguag 5040
acgagacucc ggagccaucg gcagagaacc aauccacaga ggggacaccu gaacaaccac 5100
cacuuauaac cgaggaugag accaggacua gaacgccuga gccgaucauc aucgaagagg 5160
aagaagagga uagcauaagu uugcugucag auggcccgac ccaccaggug cugcaagucg 5220
aggcagacau ucacgggccg cccucuguau cuagcucauc cugguccauu ccucaugcau 5280
ccgacuuuga uguggacagu uuauccauac uugacacccu ggagggagcu agcgugacca 5340
gcggggcaac gucagccgag acuaacucuu acuucgcaaa gaguauggag uuucuggcgc 5400
gaccggugcc ugcgccucga acaguauuca ggaacccucc acaucccgcu ccgcgcacaa 5460
gaacaccguc acuugcaccc agcagggccu gcucgagaac cagccuaguu uccaccccgc 5520
caggcgugaa uagggugauc acuagagagg agcucgaggc gcuuaccccg ucacgcacuc 5580
cuagcagguc ggucucgaga accagccugg ucuccaaccc gccaggcgua aauaggguga 5640
uuacaagaga ggaguuugag gcguucguag cacaacaaca augacgguuu gaugcgggug 5700
cauacaucuu uuccuccgac accggucaag ggcauuuaca acaaaaauca guaaggcaaa 5760
cggugcuauc cgaaguggug uuggagagga ccgaauugga gauuucguau gccccgcgcc 5820
ucgaccaaga aaaagaagaa uuacuacgca agaaauuaca guuaaauccc acaccugcua 5880
acagaagcag auaccagucc aggaaggugg agaacaugaa agccauaaca gcuagacgua 5940
uucugcaagg ccuagggcau uauuugaagg cagaaggaaa aguggagugc uaccgaaccc 6000
ugcauccugu uccuuuguau ucaucuagug ugaaccgugc cuuuucaagc cccaaggucg 6060
caguggaagc cuguaacgcc auguugaaag agaacuuucc gacuguggcu ucuuacugua 6120
uuauuccaga guacgaugcc uauuuggaca ugguugacgg agcuucaugc ugcuuagaca 6180
cugccaguuu uugcccugca aagcugcgca gcuuuccaaa gaaacacucc uauuuggaac 6240
ccacaauacg aucggcagug ccuucagcga uccagaacac gcuccagaac guccuggcag 6300
cugccacaaa aagaaauugc aaugucacgc aaaugagaga auugcccgua uuggauucgg 6360
cggccuuuaa uguggaaugc uucaagaaau augcguguaa uaaugaauau ugggaaacgu 6420
uuaaagaaaa ccccaucagg cuuacugaag aaaacguggu aaauuacauu accaaauuaa 6480
aaggaccaaa agcugcugcu cuuuuugcga agacacauaa uuugaauaug uugcaggaca 6540
uaccaaugga cagguuugua auggacuuaa agagagacgu gaaagugacu ccaggaacaa 6600
aacauacuga agaacggccc aagguacagg ugauccaggc ugccgauccg cuagcaacag 6660
cguaucugug cggaauccac cgagagcugg uuaggagauu aaaugcgguc cugcuuccga 6720
acauucauac acuguuugau augucggcug aagacuuuga cgcuauuaua gccgagcacu 6780
uccagccugg ggauuguguu cuggaaacug acaucgcguc guuugauaaa agugaggacg 6840
acgccauggc ucugaccgcg uuaaugauuc uggaagacuu agguguggac gcagagcugu 6900
ugacgcugau ugaggcggcu uucggcgaaa uuucaucaau acauuugccc acuaaaacua 6960
aauuuaaauu cggagccaug augaaaucug gaauguuccu cacacuguuu gugaacacag 7020
ucauuaacau uguaaucgca agcagagugu ugagagaacg gcuaaccgga ucaccaugug 7080
cagcauucau uggagaugac aauaucguga aaggagucaa aucggacaaa uuaauggcag 7140
acaggugcgc caccugguug aauauggaag ucaagauuau agaugcugug gugggcgaga 7200
aagcgccuua uuucugugga ggguuuauuu ugugugacuc cgugaccggc acagcgugcc 7260
guguggcaga cccccuaaaa aggcuguuua agcuuggcaa accucuggca gcagacgaug 7320
aacaugauga ugacaggaga agggcauugc augaagaguc aacacgcugg aaccgagugg 7380
guauucuuuc agagcugugc aaggcaguag aaucaaggua ugaaaccgua ggaacuucca 7440
ucauaguuau ggccaugacu acucuagcua gcaguguuaa aucauucagc uaccugagag 7500
gggccccuau aacucucuac ggcuaaccug aauggacuac gacauagucu aguccgccaa 7560
gaugaagaac ccccaagaaga aaagcggcgg auucaggauu gugaacaugc ugaagagggg 7620
cguggccagg guguccccuu uuggcggccu gaagagacug ccugcuggac ugcuccuggg 7680
ccacggaccu aucaggaugg ugcucgccau ccuggcuuuc cucagguuua cagccaucaa 7740
acccagccuc ggccugauca acagaugggg aagcgugggc aagaaggagg ccauggagau 7800
caucaagaag uuuaagaagg aucuggccgc caugcugaga aucaucaacg ccaggaagga 7860
gaagaaaaga aggggcuccg gagccacaaa cuucagccug cugaaacaag ccggcgacgu 7920
cgaagaaaau cccggccccg gcgcugacac cuccgucgga aucgugggcc ugcugcugac 7980
aaccgcuaug gccgcugagg ugaccaggag aggcuccgcc uacuacaugu accuggauag 8040
aaaugacgcc ggcgaggcca ucuccuuucc caccacccuc ggcaugaaca agugcuacau 8100
ccaaaucaug gaccucggcc auaugugcga cgcuaccaug agcuacgaau gcccuaugcu 8160
ggacgagggc guggagccug augacgugga cuguuggugc aauaccacca gcaccugggu 8220
gguguauggc acaugccacc acaagaaagg cgaggccaga agguccagga gggccgugac 8280
acugcccagc cacagcacca gaaagcugca gacaagaagc cagaccuggc ucgagagcag 8340
ggaguauacc aagcaccuga uuagagucga gaacuggauc uucagaaauc ccggcuucgc 8400
ucuggcugcu gccgccauug cuuggcugcu gggcuccagc accucccaga aggugauuua 8460
ccuggucaug auccugcuga ucgccccugc cuacuccauu agaugcaucg gcgucuccaa 8520
cagagacuuc guggaaggaa uguccggcgg cacaugggue gauguggugc uggagcacgg 8580
cggcugcgug acagucaugg cccaggacaa gccuaccgug gacaucgagc uggugacaac 8640
caccgucucc aacauggccg aagugagguc cuacugcuac gaggccagca uuuccgacau 8700
ggcuuccgac uccaggugcc cuacccaggg cgaggccuac cucgacaagc agagcgacac 8760
ccaguacguc ugcaaaagaa cccuggugga caggggcugg ggcaauggau gcggccuguu 8820
uggcaagggc ucccucguga caugugccaa guucgcuugc agcaagaaga ugaccggcaa 8880
guccauccag cccgagaauc ucgaguacag gaucaugcuc uccgugcacg gcagccagca 8940
cuccggcaug auugugaaug acacaggcca ugagaccgau gaaaauaggg ccaaggugga 9000
gaucaccccu aacagcccua gggccgaagc uacacugggc ggauucggcu cccucggccu 9060
cgacugugag cccaggacag gccucgacuu cagcgaccug uacuaccuca ccaugaauaa 9120
uaaacacugg cuggugcaca aagagugguu ccacgacauc cccugcccu ggcaugccgg 9180
agccgauacc ggaacacccc acuggaacaa caaggaagcc cuggucgagu ucaaggacgc 9240
ccacgccaag aggcaaaccg ugguggugcu gggaucccag gagggagccg ugcauacagc 9300
ucucgccggc gcucuggagg ccgaaaugga cggagccaaa ggcaggcugu ccagcggcca 9360
ccugaaaugc aggcucaaga uggacaagcu cagacugaag ggagugucu acagccucug 9420
caccgccgcc uuuaccuuua ccaagauccc cgccgagacc cuccacggaa ccgugaccgu 9480
cgaaguccag uacgcuggca cagacggccc cuguaaggug ccugcccaga uggccgugga 9540
uaugcagacc cugacacccg ugggcaggcu gaucaccgcu aacccuguga ucaccgagag 9600
caccgagaau uccaagauga ugcuggagcu ggacccuccc uucggcgaca gcuauaucgu 9660
gaucggcguc ggcgagaaga aaauuaccca ccacuggcac agaagcggca gcaccauugg 9720
caaggcuuuu gaggccacag ugagaggcgc uaagagaaug gccgugcugg gcgauaccgc 9780
cugggacuuu ggcagcgugg gcggagcccu gaacagccug ggcaaaggca uccaccagau 9840
cuuuggcgcc gccuuuaaga gccucuucgg cggcaugucc ugguucagcc agauccugau 9900
cggcacacug cugauguggc ucggccucaa uaccaaaaau ggcagcauca gccugaugug 9960
ccucgcucuc ggaggcgugc ugauuuuccu guccacagcc gucuccgcug auugauaagg 10020
cgcgcccacc cagcggccgc auacagcagc aauuggcaag cugcuuacau agaacucgcg 10080
gcgauuggca ugccgccuua aaauuuuuau uuuauuuuuc uuuucuuuuc cgaaucggau 10140
uuuguuuuua auauuucaaa aaaaaaaaaa aaaaaaaaaa aaaaaaaaaa aaaaaaagaa 10200
gagcguuuaa acacgugaua ucuggccuca ugggccuucc uuucacugcc cgcuuuccag 10260
ucgggaaacc ugucgugcca gcugcauuaa cauggucaua gcuguuuccu ugcguauugg 10320

-continued gcgcucuccg cuuccucgcu cacugacucg cugcgcucgg ucguucgggu aaagccuggg 10380
gugccuaaug agcaaaaggc cagcaaaagg ccaggaaccg uaaaaaggcc gcguugcugg 10440
cguuuuucca uaggcuccgc ccccccugacg agcaucacaa aaaucgacgc ucaagucaga 10500
gguggcgaaa cccgacagga cuauaaagau accaggcguu ucccccugga agcucccucg 10560
ugcgcucucc uguuccgacc cugccgcuua ccggauaccu guccgccuuu cucccuucgg 10620
gaagcguggc gcuuucucau agcucacgcu guagguaucu caguucggug uaggucguuc 10680
gcuccaagcu gggcugugug cacgaacccc ccguucagcc cgaccgcugc gccuuauccg 10740
guaacuaucg ucuugagucc aacccgguaa gacacgacuu aucgccacug gcagcagcca 10800
cugguaacag gauuagcaga gcgagguaug uaggcggugc uacagaguuc uugaaguggu 10860
ggccuaacua cggcuacacu agaagaacag uauuugguau cugcgcucug cugaagccag 10920
uuaccuucgg aaaaagaguu gguagcucuu gauccggcaa acaaaccacc gcugguagcg 10980
gugguuuuuu uguuugcaag cagcagauua cgcgcagaaa aaaaggaucu caagaagauc 11040
cuuugaucuu uucuacgggg ucugacgcuc aguggaacga aaacucacgu uaagggauuu 11100
uggucaugaa uacacggugc cugacugcgu uagcaauuua acugugauaa acuaccgcau 11160
uaaagcuuau cgaugauaag cugucaaaca ugagaauucu uagaaaaacu caucgagcau 11220
caaaugaaac ugcaauuuau ucauaucagg auuaucaaua ccauauuuuu gaaaaagccg 11280
uuucuguaau gaaggagaaa acucaccgag gcaguuccau aggauggcaa gauccuggua 11340
ucggucugcg auuccgacuc guccaacauc aauacaaccu auuaauuucc ccucgucaaa 11400
aauaagguua ucaagugaga aaucaccaug agugacgacu gaauccggug agaauggcaa 11460
aagcuuaugc auuucuuucc agacuuguuc aacaggccag ccauuacgcu cgucaucaaa 11520
aucacucgca ucaaccaaac cguuauucau ucgugauugc gccugagcga gacgaaauac 11580
gcgaucgcug uuaaaaggac aauuacaaac aggaaucgaa ugcaaccggc gcaggaacac 11640
ugccagcgca ucaacaauau uuucaccuga aucaggauau ucuucuaaua ccuggaaugc 11700
uguuuucccg gggaucgcag uggugaguaa ccaugcauca ucaggaguac ggauaaaaug 11760
cuugaugguc ggaagaggca uaaauuccgu cagccaguuu agucugacca ucucaucugu 11820
aacaucauug gcaacgcuac cuuugccaug uuucagaaac aacucuggcg caucgggcuu 11880
cccauacaau cgauagauug ucgcaccuga uugcccgaca uuaucgcgag cccauuuaua 11940
cccauauaaa ucagcaucca uguuggaauu uaaucgcggc cucgagcaag acguuucccg 12000
uugaauaugg cucauaacac cccuuguauu acuguuuaug uaagcagaca guuuuauugu 12060
ucaugagcgg auacauauuu gaauguauuu agaaaaauaa acaaauaggg guuccgcgca 12120
cauuuccccg aaaagugcca ccuaaauugu aagcguuaau auuuuguuaa aauucgcguu 12180
aaauuuuugu uaaaucagcu cauuuuuuaa ccaauaggcc gaaaucggca aaaucccuua 12240
uaaaucaaaa gaauagaccg agauaggguu gaguggccgc uacagggcgc ucccauucgc 12300
cauucaggcu gcgcaacugu ugggaagggc guuucggugc gggccucuuc gcuauuacgc 12360
cagcuggcga aagggggaug ugcugcaagg cgauuaaguu ggguaacgcc aggguuuucc 12420
cagucacacg cguaauacga cucacuauag 12450

<210> SEQ ID NO 77
<211> LENGTH: 2079
<212> TYPE: RNA
<213> ORGANISM: Zika virus

<400> SEQUENCE: 77

-continued

```
augcgaggcg cagauacuag ugucggaauu guuggccucc ugcugaccac agcuauggca     60

gcggagguca cuagacgugg gagugcauac uauauguacu uggacagaaa cgaugcuggg    120

gaggccauau cuuuuccaac cacauugggg augaauaagu guuauauaca gaucauggau    180

cuuggacaca ugugugaugc caccaugagc uaugaaugcc cuaugcugga ugaggggggug    240

gaaccagaug acgucgauug uuggugcaac acgacgucaa cuuggguugu guacggaacc    300

ugccaucaca aaaaagguga agcacggaga ucuaggagag cugugacgcu ccccucccau    360

uccacuagga agcugcaaac gcggucgcaa accugguugg aaucaagaga auacacaaag    420

cacuugauua gagucgaaaa uuggauauuc aggaacccug gcuucgcguu agcagcagcu    480

gccaucgcuu ggcuuuuggg aagcucaacg agccaaaaag ucauauacuu ggucaugaua    540

cugcugauug ccccggcaua cagcaucagg ugcauaggag ucagcaauag ggacuuugug    600

gaagguaugu caggugggac uuggguugau guugucuugg aacauggagg uugugucacc    660

guaauggcac aggacaaacc gacugucgac auagagcugg uuacaacaac agucagcaac    720

auggcggagg uaagauccua cugcuaugag gcaucaauau cagacauggc uucggacagc    780

cgcugcccaa cacaagguga agccuaccuu gacaagcaau cagacacuca auaugucugc    840

aaaagaacgu uaguggacag aggcugggga aauggaugug gacuuuuugg caaagggagc    900

cuggugacau gcgcuaaguu ugcaugcucc aagaaaauga ccgggaaaag cauccagcca    960

gagaaucugg aguaccggau aaugcuguca guucauggcu cccagcacag ugggaugauc   1020

guuaaugaca caggacauga aacugaugag aauagagcga agguugagau aacgcccaau   1080

ucaccaagag ccgaagccac ccuggggggu uuuggaagcc uaggacuuga uugugaaccg   1140

aggacaggcc uugacuuuuc agauuuguau uacuugacua ugaauaacaa gcacugguug   1200

guccacaagg aguggguucca cgacauucca uuaccuuggc acgcuggggc agacaccgga   1260

acuccacacu ggaacaacaa agaagcacug guagaguuca aggacgcaca ugccaaaagg   1320

caaacugucg ugguucuagg gagucaagaa ggagcaguuc acacggcccu ugcuggagcu   1380

cuggaggcug agauggaugg ugcaaaggga aggcuguccu cuggccacuu gaaaugucgc   1440

cugaaaaugg auaaacuuag auugaagggc gugucauacu ccuuguguac cgcagcguuc   1500

acauucacca agaucccggc ugaaacacug cacgggacag ucacagugga gguacaguac   1560

gcagggacag auggaccuug caagguucca gcucagaugg cgguggacau gcaaacucug   1620

accccaguug ggagguugau aaccgcuaac cccguaauca cugaaagcac ugagaacucu   1680

aagaugaugc uggaacuuga uccaccauuu ggggacucuu acauugucau aggagucggg   1740

gagaagaaga ucacccacca cuggcacagg aguggcagca ccauuggaaa agcauuugaa   1800

gccacuguga gaggugccaa gagaauggca gucuugggag acacagccug ggacuuugga   1860

ucaguuggag gcgcucucaa cucauugggc aagggcaucc aucaaauuuu uggagcagcu   1920

uucaaaucau uguuuggagg aauguccugg uucucacaaa uccucauugg aacguugcug   1980

auguguugg gucugaacac aaagaaugga ucuauuuccc uuaugugcuu ggccuuaggg   2040

ggaguguuga ucuucuuauc cacagccguc ucugcugau                           2079
```

<210> SEQ ID NO 78
<211> LENGTH: 2079
<212> TYPE: RNA
<213> ORGANISM: Zika virus

<400> SEQUENCE: 78

```
augagaggag cugacaccag cgugggcauu gugggccucc ugcugacaac cgccauggcc     60

gcugagguca ccagaagagg cagcgccuac uacauguacc uggacagaaa cgacgcuggc    120

gaggcuauua gcuuccccac cacacucggc augaacaagu guuacaucca gaucauggac    180

cugggccaca ugugcgaugc caccaugagc uacgaauguc cuaugcugga cgaaggcgug    240

gagcccgacg acguggacug uuggugcaac acaaccagca ccugggugu guacggcacc     300

ugccaucaua agaagggaga agccaggaga agcaggaggg cugucacacu ccccucccac    360

uccacaagaa agcugcaaac caggagccag accuggcugg aaagcaggga guacaccaag    420

caccugauca gggucgagaa cuggaucuuc aggaacccug gauucgcccu cgccgcugcu    480

gcuauugccu ggcuccuggg cuccuccacc agccaaaagg ugaucuaccu ggugaugauc    540

cuccugaucg cccccgccua cagcaucagg ugcaucggcg uguccaauag ggacuuuguc    600

gaaggaaugu ccggcggcac augggugac gucgugcugg agcauggcgg cugugugaca     660

gucauggccc aggacaaacc caccguggau aucgagcugg ugacaaccac aguguccaac    720

auggccgagg ugaggagcua cugcuacgag gcuagcauca gcgacauggc uuccgacagc    780

agaugcccca cacagggcga ggccuaccuc gacaaacagu ccgacaccca guacgugugc    840

aaaaggaccc uggucgacag aggaugggc aacggcugcg gccuguucgg aaaaggaagc     900

cuggucaccu gugcuaaguu cgccugcucc aagaagauga ccggcaagag cauccagccc    960

gagaaccucg aguacaggau caugcucucc guccauggca gccagcacag cggaaugauc   1020

gugaacgaca ccggccacga gaccgaugag aacagggcca agguggaaau cacccccaac   1080

agcccuaggg cugaagcuac ccucggcgga uuuggauccc ugggccugga uugugaaccc   1140

aggaccggac ucgacuucag cgaucuguac uaccugacca ugaacaacaa gcacuggcug   1200

gugcauaagg agugguucca ugauaucccc cugcccuggc augcuggagc cgauacaggc   1260

accccucacu ggaacaacaa ggaagcccug guggaguuca aagaugccca cgccaagaga   1320

cagacagucg ucguccuggg cagccaagag ggcgcugugc auacagcccu ggcuggagcc   1380

cuggaggccg aaauggacgg cgccaaggga aggcugucca gcggacaucu gaagugcagg   1440

cugaagaugg acaagcugag gcucaagggc gucagcuacu cccugugcac cgccgccuuu   1500

accuuuacaa aaauccccgc cgagacccuc cacggcacag ucacagucga ggugcaguac   1560

gcuggaaccg acggaccuug uaaggugccc gcccaaaugg ccguggacau gcagacacug   1620

accccugugg gcagacucau cacagccaac ccugugauca cagaguccac cgagaacagc   1680

aagaugaugc ucgagcugga ucccucuuuc ggcgacagcu acaucgugau cggaguggc    1740

gagaagaaaa ucacccacca cuggcacagg uccggcagca ccauuggcaa agccuuugaa   1800

gccaccguca gaggagcuaa aaggauggcu gugcugggcg acaccgcuug ggacuucggc   1860

uccgugggag gagcccucaa cucccugggc aagggcauuc accagauuuu cggcgccgcu   1920

uucaagagcc ucuuuggcgg cauguccugg uuuagccaga uucucaucgg cacacugcug   1980

auguggcugg gccugaauac caagaacggc agcaucagcc ugaugugucu ggcccuggga   2040

ggcgugcuga ucuuucuguc caccgcuguc agcgccgac                          2079
```

<210> SEQ ID NO 79
<211> LENGTH: 2079
<212> TYPE: RNA
<213> ORGANISM: Zika virus

<400> SEQUENCE: 79

```
augagaggag cugacaccag cgugggcauu gugggccucc ugcugcccca ggcccaggcc     60
```

gcugagguca ccagaagagg cagcgccuac uacauguacc uggacagaaa cgacgcuggc 120
gaggcuauua gcuuccccac cacacucggc augaacaagu guuacaucca gaucauggac 180
cugggccaca ugugcgaugc caccaugagc uacgaauguc cuaugcugga cgaaggcgug 240
gagcccgacg acguggacug uuggugcaac acaaccagca ccuggguggu guacggcacc 300
ugccaucaua agaagggaga agccaggaga agcaggaggg cugucacacu ccccucccac 360
uccacaagaa agcugcaaac caggagccag accuggcugg aaagcaggga guacaccaag 420
caccugauca gggucgagaa cuggaucuuc aggaacccug gauucgcccu cgccgcugcu 480
gcuauugccu ggcuccuggg cuccuccacc agccaaaagg ugaucuaccu ggugaugauc 540
cuccugaucg cccccgccua cagcaucagg ugcaucggcg uguccaauag ggacuuuguc 600
gaaggaaugu ccggcggcac augggugac gucgugcugg agcauggcgg cugugugaca 660
gucauggccc aggacaaacc caccguggau aucgagcugg ugacaaccac aguguccaac 720
auggccgagg ugaggagcua cugcuacgag gcuagcauca gcgacauggc uuccgacagc 780
agaugcccca cacagggcga ggccuaccuc gacaaacagu ccgacaccca guacgugugc 840
aaaaggaccc uggucgacag aggauggggc aacggcugcg gccuguucgg aaaaggaagc 900
cuggucaccu gugcuaaguu cgccugcucc aagaagauga ccggcaagag cauccagccc 960
gagaaccucg aguacaggau caugcucucc guccauggca gccagcacag cggaaugauc 1020
gugaacgaca ccggccacga gaccgaugag aacagggcca agguggaaau cacccccaac 1080
agcccuaggg cugaagcuac ccucggcgga uuuggauccc ugggccugga uugugaaccc 1140
aggaccggac ucgacuucag cgaucuguac uaccugacca ugaacaacaa gcacuggcug 1200
gugcauaagg agugguucca ugauaucccc cugcccuggc augcuggagc cgauacaggc 1260
accccucacu ggaacaacaa ggaagcccug guggaguuca aagaugccca cgccaagaga 1320
cagacagucg ucguccuggg cagccaagag ggcgcugugc auacagcccu ggcuggagcc 1380
cuggaggccg aaauggacgg cgccaaggga aggcugucca gcggacaucu gaagugcagg 1440
cugaagaugg acaagcugag gcucaagggc gucagcuacu cccugugcac cgccgccuuu 1500
accuuuacaa aaauccccgc cgagacccuc cacggcacag ucacagucga ggugcaguac 1560
gcuggaaccg acggaccuug uaaggugccc gcccaaaugg ccguggacau gcagacacug 1620
accccugugg gcagacucau cacagccaac ccugugauca cagaguccac cgagaacagc 1680
aagaugaugc ucgagcugga uccuccuuuc ggcgacagcu acaucgugau cggagugggc 1740
gagaagaaaa ucacccacca cuggcacagg uccggcagca ccauuggcaa agccuuugaa 1800
gccaccguca gaggagcuaa aaggauggcu gugcugggcg acaccgcuug ggacuucggc 1860
uccgugggag gagcccucaa cucccugggc aagggcauuc accagauuuu cggcgccgcu 1920
uucaagagcc ucuuuggcgg cauguccugg uuuagccaga uucucaucgg cacacugcug 1980
auguggcugg gccugaauac caagaacggc agcaucagcc ugaugugucu ggcccuggga 2040
ggcgugcuga ucuuucuguc caccgcuguc agcgccgac 2079

<210> SEQ ID NO 80
<211> LENGTH: 2076
<212> TYPE: RNA
<213> ORGANISM: Zika virus

<400> SEQUENCE: 80
auggaguucg gccugagcug gguguuccug guggccaucc uggagggcgu gcauugcgcu 60
gaggucacca gaagaggcag cgccuacuac auguaccugg acagaaacga cgcuggcgag 120
gcuauuagcu uccccaccac acucggcaug aacaagugu acauccagau cauggaccug 180
ggccacaugu gcgaugccac caugagcuac gaauguccua ugcuggacga aggcguggag 240
cccgacgacg uggacuguug gugcaacaca accagcaccu ggguggugua cggcaccugc 300
caucauaaga agggagaagc caggagaagc aggagggcug ucacacuccc cucccacucc 360
acaagaaagc ugcaaaccag gagccagacc uggcuggaaa gcagggagua caccaagcac 420
cugaucaggg ucgagaacug gaucuucagg aacccuggau ucgcccucgc cgcugcugcu 480
auugccuggc uccugggcuc cuccaccagc caaaagguga ucuaccuggu gaugauccuc 540
cugaucgccc ccgccuacag caucaggugc aucggcgugu ccaauaggga cuuugucgaa 600
ggaauguccg gcggcacaug gguggacguc gugcuggagc auggcggcug ugugacaguc 660
auggcccagg acaaacccac cguggauauc gagcugguga caaccacagu guccaacaug 720
gccgagguga ggagcuacug cuacgaggcu agcaucagcg acauggcuuc cgacagcaga 780
ugccccacac agggcgaggc cuaccucgac aaacaguccg acacccagua cgugugcaaa 840
aggacccugg ucgacagagg auggggcaac ggcugcggcc uguucggaaa aggaagccug 900
gucaccugug cuaaguucgc cugcuccaag aagaugaccg gcaagagcau ccagcccgag 960
aaccucgagu acaggaucau gcucuccguc cauggcagcc agcacagcgg aaugaucgug 1020
aacgacaccg gccacgagac cgaugagaac agggccaagg uggaaaucac ccccaacagc 1080
ccuagggcug aagcuacccu cggcggauuu ggaucccugg gccuggauug ugaacccagg 1140
accggacucg acuucagcga ucuguacuac cugaccauga acaacaagca cuggcuggug 1200
cauaaggagu gguuccauga uaucccccug cccuggcaug cuggagccga uacaggcacc 1260
ccucacugga acaacaagga agcccuggug gaguucaaag augcccacgc caagagacag 1320
acagucgucg uccugggcag ccaagagggc gcugugcaua cagcccuggc uggagcccug 1380
gaggccgaaa uggacggcgc caagggaagg cuguccagcg gacaucugaa gugcaggcug 1440
aagauggaca agcugaggcu caagggcguc agcuacuccc ugugcaccgc cgccuuuacc 1500
uuuacaaaaa uccccgccga gacccuccac ggcacaguca cagucgaggu gcaguacgcu 1560
ggaaccgacg gaccuuguaa ggugcccgcc caaauggccg uggacaugca gacacugacc 1620
ccugugggca gacucaucac agccaacccu gugaucacag aguccaccga gaacagcaag 1680
augaugcucg agcuggaucc uccuuucggc gacagcuaca ucgugaucgg agugggcgag 1740
aagaaaauca cccaccacug gcacaggucc ggcagcacca uuggcaaagc cuuugaagcc 1800
accgucagag gagcuaaaag gauggcugug cugggcgaca ccgcuuggga cuucggcucc 1860
gugggaggag cccucaacuc ccugggcaag ggcauucacc agauuuucgg cgccgcuuuc 1920
aagagccucu uuggcggcau guccugguuu agccagauuc ucaucggcac acugcugaug 1980
uggcugggcc ugaauaccaa gaacggcagc aucagccuga ugugucuggc ccugggaggc 2040
gugcugaucu uucuguccac cgcugucagc gccgac 2076

<210> SEQ ID NO 81
<211> LENGTH: 2391
<212> TYPE: RNA
<213> ORGANISM: Zika virus

<400> SEQUENCE: 81
augaagaauc cuaagaaaaa guccggcgga uucaggaucg ugaauaugcu gaagaggggc 60
guggccaggg ucuccccuuu uggaggccug aaaaggcugc cugcuggacu gcugcuggga 120

```
cacggcccca ucaggauggu ccuggccauc cucgccuucc ucagauucac cgccaucaag    180
cccucccucg gccugauuaa caggugggge agcgucggca agaaagaagc cauggaaauc    240
auuaagaagu ucaaaaaaga ccuggccgcc augcugagga ucaucaaugc caggaaggag    300
aagaagagga ggggagcuga uaccuccgug ggcaucgugg gacugcugcu caccacagcc    360
auggccgccg aggucaccag aagaggcagc gcuuauuaca uguaccugga cagaaaugac    420
gccggcgaag cuaucagcuu cccuaccacc cugggcauga acaagugcua cauccagauc    480
auggaccugg gccacaugug cgaugccacc auguccuacg agugccccau gcucgacgaa    540
ggaguggagc cugacgacgu ggauuguugg ugcaacacca ccuccacaug gguggucuau    600
ggcaccugcc aucacaagaa aggcgaagcc aggaggucca ggagggcugu gacccugccc    660
agccacucca ccaggaagcu gcaaacaaga ucccagaccu ggcuggaauc cagggaguac    720
accaagcacc ugaucagggu ggagaacugg auuuucagga aucccggcuu cgcccuggcc    780
gcugccgcca ucgcuuggcu gcucggcagc agcaccuccc agaaagugau uuaccuggug    840
augauccugc ucaucgcccc cgccuacagc aucagaugca ucggagugag caacagggau    900
uucguggagg gcauguccgg aggaacaugg guggaugugg ugcuggaaca uggcggcugc    960
gugacaguga uggcccagga caagcccaca guggacaucg agcuggugac caccacagug   1020
uccaauaugg ccgaggucag gagcuauugc uacgaggcua gcaucuccga cauggcuucc   1080
gacagcaggu gucccacaca gggcgaggcu uaucuggaca agcaguccga uacccaguac   1140
gugugcaaaa ggacccuggu ggauagagga uggggaaacg gcuguggccu guucggcaag   1200
ggcucccugg ugaccugugc uaaauuugcc ugcuccaaga agaugaccgg caaguccauc   1260
caaccugaga accuggagua caggaucaug cuguccgugc acggcagcca acauagcggc   1320
augaucguga augacaccgg acacgaaacc gacgaaaaca gggccaaggu ggagauuacc   1380
cccaauagcc ccagagcuga ggccacacug ggcggcuuug gaucccucgg ccuggauugu   1440
gagcccagga ccggccucga cuucuccgau cuguauuacc ugaccaugaa caacaagcau   1500
uggcucgugc acaaagagug guuucacgac auuccccugc cuuggcacgc uggcgccgau   1560
acaggaaccc cccacuggaa caacaaggag gcucuggucg aauuuaaaga cgcccaugcc   1620
aaaagacaga cagucguggu gcugggcucc caagagggag ccgugcauac agcccuggcc   1680
ggagcccucg aggcugaaau ggacggagcu aaaggcaggc uguccagcgg acaccugaag   1740
ugcaggcuca agauggacaa gcucagacuc aagggaguga gcuauagccu guguacagcc   1800
gccuucacau ucaccaaaau ccccgccgaa acccugcacg gcacagugac cguggagguc   1860
caguacgccg gcacagacgg cccuugcaaa gugcccgccc agauggcugu cgacaugcag   1920
acacugaccc cugugggcag gcugauuacc gcuaaccccg ugauuaccga gagcacagag   1980
aacagcaaga ugaugcugga gcuggacccu ccuuucggcg auuccuacau cgugaucgga   2040
gugggcgaga aaaagaucac ccaccauugg cacagguccg gcuccacaau uggcaaggcc   2100
uuugaggcca ccgugagggg agcuaagagg auggccgugc ucggcgacac agccugggau   2160
uucggaagcg ugggaggcgc ccugaauucc cucggcaagg gcauccauca gaucuucggc   2220
gcugccuuca agucccucuu cggaggcaug agcugguuca gccagauccu gaucggaacc   2280
cuccugaugu ggcugggccu gaacaccaag aacggaucca uuagccugau gugucucgcc   2340
cugggcggcg ugcugaucuu ccuguccacc gccguguccg ccgauugaua a            2391
```

<210> SEQ ID NO 82

<211> LENGTH: 2391
<212> TYPE: RNA
<213> ORGANISM: Zika virus

<400> SEQUENCE: 82
augaagaauc ccaagaaaaa gagcggcggc uucagaaucg ugaacaugcu gaagagggga 60
guggccagag uguccccuu uggcggccug aaaagacucc cugccggccu gcuccuggga 120
cauggcccua ucaggauggu ccuggccauu cuggcuuucc ugagguucac agccaucaag 180
ccuagccugg gccugauuaa cagguggggc agcgucggca agaaggaagc cauggagauu 240
auuaagaagu ucaagaaaga ccucgcugcc augcugagga ucaucaaugc caggaaggag 300
aagaaaagga ggggcgcuga cacaagcgug ggaaucgugg gacugcugcu cccccaggcc 360
caggcugcug aagugaccag aaggggcucc gccuacuaua uguaccucga caggaacgac 420
gccggagagg ccaucagcuu cccuaccacc cugggaauga acaaaugcua cauccagauc 480
auggaccucg gccacaugug cgacgccacc augagcuacg aaugccccau gcuggacgag 540
ggcguggagc cugacgaugu ggacugcugg ugcaacacaa ccagcaccug gguggucuac 600
ggcaccuguc accacaagaa aggagaggcc agaaggucca ggagggccgu cacccugccu 660
agccacagca ccagaaagcu gcagaccagg agccagaccu ggcuggagag cagagaguac 720
accaaacacc ucaucagggu ggagaacugg auuuuuagga auccuggcuu ugcccucgcu 780
gccgccgcua ucgcuuggcu ccucggaagc agcaccagcc agaaggucau cuaucucgug 840
augauccugc ucaucgcucc cgcuuacucc aucaggugca ucggcgugag caacagagac 900
uucguggagg gaauguccgg cggaaccugg guggaugugg ugcucgagca cggcggaugc 960
gucaccguga uggcccaaga uaagccuacc guggacaucg aacuggugac aacaaccgug 1020
uccaacaugg ccgaggugag aagcuacugu uacgaggccu ccaucagcga cauggccucc 1080
gacuccaggu gcccuaccca gggagaggcu uaccuggaca agcaauccga cacccaguac 1140
guguguaaga ggacccuggu cgauagaggc uggggcaaug gcuguggacu guucggcaag 1200
ggaagccugg ugaccugcgc uaaguucgcc ugcuccaaaa agaugaccgg caagagcauc 1260
cagcccgaga accuggagua cagaaucaug cuguccgugc acggcagcca gcacagcggc 1320
augauuguga acgacaccgg acacgaaacc gacgagaaca gggccaaagu ggagaucacc 1380
cccaauagcc ccagggcuga agcuacacug ggaggauuug gcagccuggg ccuggauugu 1440
gagccuagga ccggacugga uuucagcgau cuguacuauc ugaccaugaa uaacaagcac 1500
uggcuggugc acaaggagug guuucacgac aucccucugc ccuggcacgc uggagccgau 1560
acaggcaccc cccacuggaa caauaaggag gcccucgugg aauucaagga cgcccacgcc 1620
aagagacaaa ccgucgugguu gcugggaagc caggaaggcg ccgugcauac cgcccucgcc 1680
ggcgcucucg aggcugagau ggacggagcc aagggcagac ugagcagcgg acaucucaag 1740
ugcaggcuga agauggacaa gcucaggcug aaaggagucu ccuacagccu gugcaccgcc 1800
gccuucacau uuaccaaaau ccccgccgag acccuccacg gaaccgucac aguggaagug 1860
caauacgccg gcacagaugg ccccuguaag gugcccgccc agauggccgu ggauaugcag 1920
acccugaccc cugucggcag gcugauuacc gccaacccug ugaucaccga guccaccgag 1980
aacagcaaaa ugaugcugga gcuggauccc cccuucggcg acuccuacau ugugaucggc 2040
gugggcgaga agaaaauuac ccaucacugg cauagaagcg gcagcacaau cggcaaggcc 2100
uuugaggcca cagugagagg cgccaaaaga auggccgugc ugggagauac agcuugggau 2160
uuuggauccg ugggcggcgc ccugaacucc cugggcaaag gaauccauca gaucuucggc 2220
gcugcuuuca agagccucuu uggcggcaug uccugguucu cccaaauccu gaucggcaca 2280
cuccugaugu ggcugggccu caacacaaaa aacggcagca ucagccugau gugccucgcc 2340
cucggaggcg ugcugaucuu ccuguccacc gcugugagcg cugauugaua a 2391

<210> SEQ ID NO 83
<211> LENGTH: 2457
<212> TYPE: RNA
<213> ORGANISM: Zika virus

<400> SEQUENCE: 83
augaagaacc ccaagaagaa aagcggcgga uucaggauug ugaacaugcu gaagaggggc 60
guggccaggg uguccccuuu uggcggccug aagagacugc cugcuggacu gcuccugggc 120
cacggaccua ucaggauggu gcucgccauc cuggcuuucc ucagguuuac agccaucaaa 180
cccagccucg gccugaucaa cagaugggga agcgugggca agaaggaggc cauggagauc 240
aucaagaagu uuaagaagga ucuggccgcc augcugagaa ucaucaacgc caggaaggag 300
aagaaaagaa ggggcuccgg agccacaaac uucagccugc ugaaacaagc cggcgacguc 360
gaagaaaauc ccggccccgg cgcugacacc uccgucggaa ucgugggccu gcugcugaca 420
accgcuaugg ccgcugaggu gaccaggaga ggcuccgccu acuacaugua ccuggauaga 480
aaugacgccg gcgaggccau cuccuuuccc accacccucg gcaugaacaa gugcuacauc 540
caaaucaugg accucggcca uaugugcgac gcuaccauga gcuacgaaug cccuaugcug 600
gacgagggcg uggagccuga ugacguggac uguuggugca auaccaccag caccugggug 660
guguauggca caugccacca caagaaaggc gaggccagaa gguccaggag ggccgugaca 720
cugcccagcc acagcaccag aaagcugcag acaagaagcc agaccuggcu cgagagcagg 780
gaguauacca agcaccugau uagagucgag aacuggaucu ucagaaaucc cggcuucgcu 840
cuggcugcug ccgccauugc uuggcugcug ggcuccagca ccucccagaa ggugauuuac 900
cuggucauga uccugcugau cgccccugcc uacuccauua gaugcaucgg cgucuccaac 960
agagacuucg uggaaggaau guccggcggc acaugggucg auguggugcu ggagcacggc 1020
ggcugcguga cagucauggc ccaggacaag ccuaccgugg acaucgagcu ggugacaacc 1080
accgucucca acauggccga agugaggucc uacugcuacg aggccagcau uuccgacaug 1140
gcuuccgacu ccaggugccc uacccagggc gaggccuacc ucgacaagca gagcgacacc 1200
caguacgucu gcaaaagaac ccugguggac aggggcuggg gcaauggaug cggccuguuu 1260
ggcaagggcu cccucgugac augugccaag uucgcuugca gcaagaagau gaccggcaag 1320
uccauccagc ccgagaaucu cgaguacagg aucaugcucu ccgugcacgg cagccagcac 1380
uccggcauga uugugaauga cacaggccau gagaccgaug aaaauagggc caagguggag 1440
aucaccccua acagcccuag ggccgaagcu acacugggcg gauucggcuc ccucggccuc 1500
gacugugagc ccaggacagg ccucgacuuc agcgaccugu acuaccucac caugaauaau 1560
aaacacuggc uggugcacaa agagugguuc cacgacaucc cccugcccug gcaugccgga 1620
gccgauaccg gaacacccca cuggaacaac aaggaagccc uggucgaguu caaggacgcc 1680
cacgccaaga ggcaaaccgu gguggugcug ggaucccagg agggagccgu gcauacagcu 1740
cucgccggcg cucuggaggc cgaaauggac ggagccaaag gcaggcuguc cagcggccac 1800
cugaaaugca ggcucaagau ggacaagcuc agacugaagg gaguguccua cagccucugc 1860
accgccgccu uuaccuuuac caagaucccc gccgagaccc uccacggaac cgugaccguc 1920

-continued

| | |
|---|---|
| gaaguccagu acgcuggcac agacggcccc uguaaggugc cugcccagau ggccguggau | 1980 |
| augcagaccc ugacacccgu gggcaggcug aucaccgcua acccugugau caccgagagc | 2040 |
| accgagaauu ccaagaugau gcuggagcug gacccucccu ucggcgacag cuauaucgug | 2100 |
| aucggcgucg gcgagaagaa aauuacccac cacuggcaca gaagcggcag caccauuggc | 2160 |
| aaggcuuuug aggccacagu gagaggcgcu aagagaaugg ccgugcuggg cgauaccgcc | 2220 |
| ugggacuuug gcagcguggg cggagcccug aacagccugg gcaaaggcau ccaccagauc | 2280 |
| uuuggcgccg ccuuuaagag ccucuucggc ggcauguccu gguucagcca gauccugauc | 2340 |
| ggcacacugc ugauguggcu cggccucaau accaaaaaug gcagcaucag ccugaugugc | 2400 |
| cucgcucucg gaggcgugcu gauuuuccug uccacagccg ucuccgcuga uugauaa | 2457 |